United States Patent
Nadal-Ginard

(10) Patent No.: US 10,526,581 B2
(45) Date of Patent: Jan. 7, 2020

(54) MODULATION OF CARDIAC STEM-PROGENITOR CELL DIFFERENTIATION, ASSAYS AND USES THEREOF

(71) Applicant: Bernardo Nadal-Ginard, Chestnut Hill, MA (US)

(72) Inventor: Bernardo Nadal-Ginard, Chestnut Hill, MA (US)

( * ) Notice: Subject to any disclaimer, the term of this patent is extended or adjusted under 35 U.S.C. 154(b) by 0 days.

(21) Appl. No.: 14/762,760

(22) PCT Filed: Jan. 24, 2014

(86) PCT No.: PCT/EP2014/000193
§ 371 (c)(1),
(2) Date: Jul. 22, 2015

(87) PCT Pub. No.: WO2014/114465
PCT Pub. Date: Jul. 31, 2014

(65) Prior Publication Data
US 2015/0368618 A1    Dec. 24, 2015

Related U.S. Application Data

(60) Provisional application No. 61/756,328, filed on Jan. 24, 2013, provisional application No. 61/756,305, filed on Jan. 24, 2013.

(51) Int. Cl.
| | | |
|---|---|---|
| C12N 5/071 | (2010.01) | |
| C12N 5/074 | (2010.01) | |
| C12N 5/077 | (2010.01) | |
| C12N 5/0775 | (2010.01) | |
| A61K 9/00 | (2006.01) | |
| A61K 35/34 | (2015.01) | |
| A61K 45/06 | (2006.01) | |
| G01N 33/50 | (2006.01) | |

(52) U.S. Cl.
CPC .......... *C12N 5/0692* (2013.01); *A61K 9/0019* (2013.01); *A61K 35/34* (2013.01); *A61K 45/06* (2013.01); *C12N 5/0607* (2013.01); *C12N 5/0657* (2013.01); *C12N 5/0668* (2013.01); *G01N 33/5073* (2013.01); *C12N 2501/15* (2013.01); *C12N 2501/155* (2013.01); *C12N 2501/415* (2013.01)

(58) Field of Classification Search
CPC .. C12N 5/0692; C12N 5/0607; C12N 5/0657; C12N 5/0668; C12N 2501/15; C12N 2501/155; C12N 2501/415; A61K 9/0019; A61K 35/34; A61K 45/06; G01N 33/5073
USPC ........................................................ 424/93.7
See application file for complete search history.

(56) References Cited

FOREIGN PATENT DOCUMENTS

| EP | 1 857 544 A1 | 11/2007 | |
|---|---|---|---|
| WO | WO-2008/058216 A2 | 5/2008 | |
| WO | WO-2009/136283 | 11/2009 | |
| WO | WO 2010/015665 | * 2/2010 | ............... A61K 9/14 |

OTHER PUBLICATIONS

Hare et al., A Randomized, Double-Blind Placebo-Controlled, Dose-Escalation Study of Intravenous Adult Human Mesenchymal Stem Cells (Prochymal) After Acute Myocardial Infarction, Journal of the American College of Cardiology, (2009), 54(24): pp. 2277-2286.*
Examination Report for EP 14707641.8 dated Jun. 10, 2016.
Akashi, et al., Takotsubo cardiomyopathy: a new form of acute, reversible heart failure. Circulation. 2008, 118, 2754-2762.
Askari, et al., "Effect of stromal-cell-derived factor-I on stem cell homing and tissue regeneration in ischemic cardiomyopathy.", 2003, Lancet 362, 697-703.
Beltrami, et al., "Evidence that human cardiac myocytes divide after myocardial infarction.", N. Engl J Med. 2001 ;344:1750-7.
Bergmann, et al. Evidence for cardiomyocyte renewal in humans. Science, 2009, 324, 98-102.
Brooks, et al., "Isoproterenol-induced myocardial injury and diastolic dysfunction in mice: structural and functional correlates." Comp Med. 59, 339-343. (2009).
Buckingham, et al., "Building the mammalian heart from two sources of myocardial cells." Nat Rev Genet. 2005;6:826-35.
Cairns, et al., "Kit regulatory elements required for expression in developing hematopoietic and germ cell lineages.", Blood, 2003, 102, 3954-3962.
Chong, et al., "Adult cardiac-resident MSC-like stem cells with a proepicardial origin.", Cell Stem Cell. 2011;9:527-40.
Cohen, et al., "Wnt/beta-catenin signaling promotes expansion of Isl-l-positive cardiac progenitor cells through regulation of FGF signaling.", J Clin Invest. 2007;117: 1794-804.

(Continued)

*Primary Examiner* — Jennifer M.H. Tichy
(74) *Attorney, Agent, or Firm* — Foley & Lardner LLP

(57) ABSTRACT

The present invention relates to endogenous cardiac stem-progenitor cells (eCSCs). Provided herein are c-kitpos CD166pos eCSCs that are negative for the hematopoietic marker, CD45 and the mast cell marker, Tryptase. These single cell derived eCSCs can differentiate into a variety of specific cell types corresponding to the derivatives of the three germ layers. Also provided herein is a stage-specific TGF-P-Family/Wnt-Inhibitor cocktail for modulating in vitro myogenic specification and maturation of c-kitpos eCSCs. Also provided herein are methods of modulating eCSCs clonal expansion and differentiation. Also provided herein are screening assays for small organic molecules that modulate early cardiomyogenic progenitor cells. The invention further relates to the use of these modulated cells in prophylactic and therapeutic methods, including in pharmaceutical compositions of such cells, growth factors and/or small organic compounds. Finally, the invention relates to the use of such differentiated cells in transplantation and medical treatments.

17 Claims, 131 Drawing Sheets

Figure 1A:
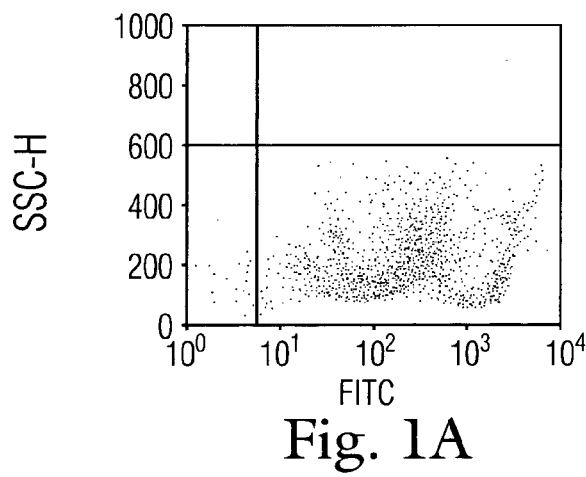
Figure 1B:
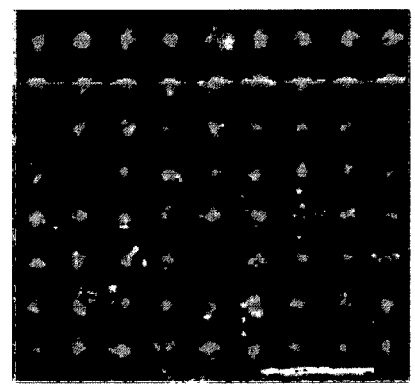

Specification includes a Sequence Listing.

(56) References Cited

OTHER PUBLICATIONS

Czechowicz, et al., "Efficient transplantation via antibody-based clearance of hematopoietic stem cell niches.", Science, 2007, 318, 1296-1299.

Diez, C., et al. "Gene expression in rod shaped cardiac myocytes, sorted by flow cytometry." Cardiovasc Res. 40, 530-7. (1998).

Dong, et al., "Myocardial CXCR4 expression is required for mesenchymal stem cell mediated repair following acute myocardial infarction." Circulation, 2012, 126, 314-24.

Du P, et al. "lumi: a pipeline for processing Illumina microarray." Bioinformatics 24, 1547-1548 (2008).

Ellison, et al., "Acute beta-adrenergic overload produces myocyte damage through calcium leakage from the ryanodine receptor 2 but spares cardiac stem cells.", J Biol Chem. 2007;282:11397-409.

Ellison, et al., "Cardiac stem and progenitor cell identification: different markers for the same cell?", Front Biosci (Schol Ed). 2010, 2, 641-652.

Ellison, et al., "Myocyte death and renewal: modern concepts of cardiac cellular homeostasis." Nat Clin Pract Cardiovasc, 2007, Med 4 Suppl 1, S52-59.

Ellison, et al., "Physiological cardiac remodelling in response to endurance exercise training: cellular and molecular mechanisms.", Heart. 2012; 98: 5-10.

Epstein, et al., "Cardiac development and implications for heart disease.", N Engl J Med. 2010;363:1638-47.

Guenechea, et al., "Delayed engraftment of nonobese diabetic/severe combined immunodeficient mice transplanted with ex vivo-expanded human CD34(+) cord blood cells." Blood, 1993, 93, 1097-1105.

Hsieh, et al., "Evidence from a genetic fate-mapping study that stem cells refresh adult mammalian cardiomyocytes after injury." Nat Med. 2007;13:970-4.

Huang et al., "Systemic and integrative analysis of large gene lists using DAVID bioinformatics resources," Protocol, vol. 4, No. 1, 2009.

Jaiswal, et al., Stem Cells In Vitro. "Osteogenic Differentiation of Purified, Culture-Expanded Human Mesenchymal.", Journal of Cellular Biochemistry 1997;64:295-312.

Jesty, et al., "c-kit+ precursors support postinfarction myogenesis in the neonatal, but not adult, heart.", Proc Natl Acad Sci 2012; 109:13380-5.

Kajstura, et al., "Cardiomyogenesis in the aging and failing human heart." Circulation, 2012, 126, 1869-1881 (Retracted).

Kattman, et al., "Multipotent flk-1+ cardiovascular progenitor cells give rise to the cardiomyocyte, endothelial, and vascular smooth muscle lineages.", Dev Cell. 2006; 11:723-32.

Kawaguchi, et al. "c-kitpos GATA-4 high rat cardiac stem cells foster adult cardiomyocyte survival through IGF-1 paracrine signalling." PLoS One. 5, e14297. (2010).

Keyte, et al., "The neural crest in cardiac congenital anomalies.", Differentiation. 2012;84:25-40.

Klaus, et al., "Wnt/β-catenin and Bmp signals control distinct sets of transcription factors in cardiac progenitor cells.", Proc Natl Acad Sci U S A. 2012;109:10921-6.

Kuroda, et al., "Unique multipotent cells in adult human mesenchymal cell populations.", Proc Natl Acad Sci U S A. May 11, 2010;107(19):8639-43.

Laflamme, et al., "Cardiomyocytes derived from human embryonic stem cells in pro-survival factors enhance function of infarcted rat hearts.", Nat Biotechnol. 2007;25:1015-24.

Laugwitz, et al., "Postnatal isl1 + cardioblasts enter fully differentiated cardiomyocyte lineages." Nature. 2005;433:647-53.

Lin, H.H., et al. "Heme oxygenase-1 promotes neovascularization in ischemic heart by coinduction of VEGF and SDF-1.", J Mol Cell Cardiol. 45, 44-55. (2008).

Loffredo, et al., "Bone marrow-derived cell therapy stimulates endogenous cardiomyocyte progenitors and promotes cardiac repair." Cell Stem Cell, 2011, 8, 389-398.

Lompre, et al.. "Expression of the cardiac ventricular alpha- and beta-myosin heavy chain genes is developmentally and hormonally regulated.", J Biol Chem., 1984, 259, 6437-6446.

Matsuura, et al., "Adult cardiac Sca-I-positive cells differentiate into beating cardiomyocytes.", J Biol Chem. 2004; 279: 11384-91.

Mercola, et al., "Cardiac muscle regeneration: lessons from development. ", Genes Dev. 2011 ;25:299-309.

Messina, et al., "Isolation and expansion of adult cardiac stem cells from human and murine heart.", Circ Res. 2004;9:911-21.

Montarras, et al."Direct isolation of satellite cells for skeletal muscle regeneration.", Science, 2005, 309, 2064-2067.

Noseda, et al., "Cardiopoietic factors: extracellular signals for cardiac lineage commitment.", Circ Res. 2011;108:129-52.

Oh, et al., "Cardiac progenitor cells from adult myocardium: homing, differentiation, and fusion after infarction.", Proc Natl Acad Sci 2003. 100, 12313-12318.

Orford, et al., "Deconstructing stem cell self-renewal: genetic insights into cell-cycle regulation." Nat Rev Genet. 2008. 9, 115-128.

Orlic, et al., "Bone marrow cells regenerate infarcted myocardium. ", Nature 2001, 410, 701-705.

Oshimori, et al., "The Harmonies Played by TGF-β in Stem Cell Biology." Cell Stem Cell. 2012;11 :751-64.

Oyama, et al. Cardiac side population cells have a potential to migrate and differentiate into cardiomyocytes in vitro and in vivo. J Cell Biol. 2007; 176: 329-41.

Priori, et al., "Induced pluripotent stem cell-derived cardiomyocytes in studies of inherited arrhythmias.", J Clin Invest. 2013;123:84-91.

Qian, et al., "In vivo reprogramming of murine cardiac fibroblasts into induced cardiomyocytes." Nature, 2012, 485, 593-598.

Qyang, et al., "The renewal and differentiation of Isl 1+ cardiovascular progenitors are controlled by a Wnt/beta-catenin pathway.", Cell Stem Cell. 2007; 1:165-79.

Riley, et al., "Vascularizing the heart.", Cardiovasc Res. Jul. 15, 2011;91(2):260-8.

Rossi, et al. "Stems cells and the pathways to aging and cancer." Cell. 2008, 132, 681-696.

Sata, et al. "Hematopoietic stem cells differentiate into vascular cells that participate in the pathogenesis of atherosclerosis." Nat. Med. 2002, 8, 403-409.

Schneider, J.W., et al., "Reversal of terminal differentiation mediated by p 107 in Rb-/-muscle cells." Science. 1994, 264, 1467-71.

Schuijers J, et al., Adult mammalian stem cells: the role of Wnt, Lgr5 and R-spondins. EMBO J. 2012;31 :2685-96.

Senyo, et al., "Mammalian heart renewal by pre-existing cardiomyocytes." Nature. 2013, 493, 433-6.

Shao, et al. "A mouse model reveals an important role for catecholamine-induced lipotoxicity in the pathogenesis of stress-induced cardiomyopathy." Eur J Heart Fail. 15, 9-22. (2013).

Smart, et al. "De novo cardiomyocytes from within the activated adult heart after injury." Nature 2011, 474, 640-644.

Smits, et al., "Human cardiomyocyte progenitor cells differentiate into functional mature cardiomyocytes: an in vitro model for studying human cardiac physiology and pathophysiology.", Nat Protoc. 2009;4:232-43.

Sohal, D.S., et al., "Temporally regulated and tissue-specific gene manipulations in the adult and embryonic heart using a tamoxifen-inducible Cre protein." Circ Res 89, 20-25. (2001).

Song, et al. "Heart repair by reprogramming non-myocytes with cardiac transcription factors." Nature 2012, 485, 599-604.

Song, et al., "Efficient generation of hepatocyte-like cells from human induced pluripotent stem cells.", Cell Res. 2009;19: 1233-42.

Takeuchi, et al. "Directed transdifferentiation of mouse mesoderm to heart tissue by defined factors." Nature 2009, 459, 708-711.

Tallini, et al., "c-kit expression identifies cardiovascular precursors in the neonatal heart." Proc Natl Acad Sci 2009, 106, 1808-1813.

Torella, D., et al. "Cardiac stem cell and myocyte aging, heart failure, and insulin-like growth factor-I overexpression." Circ Res. 94, 514-524. (2004).

Urbanek, et al., "Intense myocyte formation from cardiac stem cells in human cardiac hypertrophy.", Proc Natl Acad Sci U S A. 2003;100:10440-5.

(56) References Cited

OTHER PUBLICATIONS

Urbanek. et al., "Myocardial regeneration by activation of multipotent cardiac stem cells in ischemic heart failure.", Proc Natl Acad Sci U S A. 2005;102:8692-7.
Vincent, et al., "How to make a heart: the origin and regulation of cardiac progenitor cells.", Curr Top Dev Biol. 2010;90: 1-41.
Waring, C.D., et al. "The adult heart responds to increased workload with physiologic hypertrophy, cardiac stem cell activation, and new myocyte formation." Eur Heart J. Oct. 25, 2012. [Epub ahead of print]. doi: 10.1093/eurheartj/ehs338. (2012).
Weissman, LL., "Translating stem and progenitor cell biology to the clinic: barriers and opportunities." Science 287, 1442-1446 (2000).
Wilson, A., et al., "Hematopoietic stem cells reversibly switch from dormancy to self-renewal during homeostasis and repair." Cell 135, 1118-1129. (2008).
Wray et al., "WNTing embryonic stem cells," Trends in Cell Biology, Mar. 2012, vol. 22, No. 3.
Yamanaka, et al., "Nuclear reprogramming to a pluripotent state by three approaches.", Nature. 2010;465:704-12.
Yoon, et al., "Mechanism of improved cardiac function after bone marrow mononuclear cell therapy: role of cardiovascular lineage commitment." Circulation. 121, 2001-2011. (2010).
Zaruba, et al., "Cardiomyogenic potential of C-kit(+)-expressing cells derived from neonatal and adult mouse hearts.", Circulation. 2010;121 :1992-2000.
Zhang, et al., "A PEGylated fibrin patch for mesenchymal stem cell delivery." Tissue Eng. 12, 9-19. (2006).
Beltrami, et al., "Adult cardiac stem cells are multipotent and support myocardial regeneration", Cell, Cell Press, US, vol. 114, No. 6, Sep. 19, 2003, pp. 763-776, XP002689419.
Ellison et al., "Adult c-kitpos Cardiac Stem Cells Are Necessary and Sufficient for Functional Cardiac Regeneration and Repair", Cell, vol. 154, No. 4, Aug. 1, 2013, pp. 827-842, XP055110202.
Ellison et al., "Optimizing Cardiac Repair and Regeneration Through activation of the Endogenous Cardiac Stem Cell Compartment", Journal of Cardiovascular Translational Research, Springer US, Boston, vol. 5, No. 5, Jun. 12, 2012, pp. 667-677, XP035114732.
Ellison, et al.,"Endogenous Cardiac Stem Cell Activation by Insulin-Like Growth Factor-1/Hepatocyte Growth Factor Intracoronary Injection Fosters Survival and Regeneration of the Infarcted Pig Heart", Journal of the American College of Cardiology, Elsevier, New York, NY, US, vol. 58, No. 9, May 24, 2011, pp. 977-986, XP28266059.
International Search Report for PCT/EP2014/000193 dated Apr. 11, 2014.
Leinonen et al., "Left Atrial Appendages from Adult Hearts Contain a Reservoir of Diverse Cardiac Progenitor Cells", PLOS ONE, vol. 8, No. 3, Mar. 1, 2013, p. e59228, XP055111133.
Miyamoto et al., "Characterization of Long-Term Cultured c-kit Cardiac Stem Cells Derived From Adult Rat Hearts", Stem Cells and Development, vol. 19, No. 1, Jan. 1, 2010, pp. 105-116, XP55111176.
Pouly et al., "Cardiac stem cells in the real world", Journal of Thoracic and cardiovascular surgery, Mosby Year Book, Inc., St. Louis, MO, US, vol. 35, No. 3, Mar. 7, 2008, pp. 6736-678, XP022506876.
Sandstedt, et al., "C-kit CD45a cells found in the adult human heart represent a population of the endothelial progenitor cells", Basic Research in Cardiology, Steinkopff-Verlag, DA, vol. 105, No. 4, Feb. 2, 2010, pp. 545-556, XP019846779.
Sandstedt, et al., "Human C-kit CD45—cardiac stem cells are heterogenous and display both cardiac and endothelial commitment by single-cell qPCR analysis", Biochemical and Biophysical Research Communications, vol. 443, No. 1, Jan. 1, 2014, pp. 234-238, XP055111186.
Tomita et al., "Cardiac neural crest cells contribute to the dormant multipotent stem cell in the mammalian heart", The Journal of Cell Biology: JCB, The Rockefeller University Press, US, vol. 170, No. 7, Sep. 26, 2005, pp. 1135-1146, XP008122588.
Torella, et al., "Cardiovascular development: towards biomedical applicability; Resident cardiac stem cells", CMLS Cellular and Molecular Life Sciences, Birkhauser-Verlag, BA, vol. 64, No. 6, Feb. 13, 2007, pp. 661-673, XP019488192.
Zhou et al., "CD117-positive Cells of the Heart: Progenitor Cells or Mast Cells?", Journal of Histochemistry & Cytochemistry, vol. 58, No. 4, Dec. 21, 2009, pp. 309-316, XP055111185.
European Office Action, dated Jun. 18, 2018, issued in corresponding European Patent Appln. No. 14707641.8.
Australian First Examination Report, issued in Australian Patent Application No. 2014210181, 3 pages (dated Feb. 5, 2019).
European Examination Report, issued in European Patent Application No. 14707641.8, 4 pages (dated Feb. 8, 2019).

* cited by examiner

Flow Cytometry Data

Rat Oct 4. apa from 692 to 823
Alignment to
tubo2, reampli, subcloned colonia 2.ape from 1 to 175

Matches (|) : 132
Mismatches (#):0
Gaps( ) :43
Unattempted (.) : 0

```
692      agaaccgtgtgaggtggaactggagaacatgtttctgcagtgcccgaagccctccctgcagcagagatcactagcattgcc 771
              |||||||||||||||||                    ||||||||||||||||||||||||||||||||||||||||||||
         agaaccgtgtgaggtggaac
  1 GTGTGCTGGAATTCGCCCTTAGAACGTGTGAGGTGGAACCTGGAGAACATGTTTCTGCAGTGCCCGAAGCCCTCCCTGCAGCAGAGATCACTAGCATTGCC 100
    TOPO vector 772 aagcagcttgggctggagagggatgtggttccatgtggttctgtaaccggc~~~~~~~~~~~~~~~~~~~~~~ 823
    |||||||||||||||||||||||||||||||||||||||||||||||||||                        TOPO vector
101 AAGCAGCTTGGGCTGGAGAGGGATGTGGTTCGAGTGTGGTTCTGTAACCGGCCAAGGGGCGAATTCTTCAGATATCC 175
```

Fig. 10B

CTRL HGF　　　　CTRL IGF-1　　　　CTRL FGF-2

CTRL BMP-4　　　CTRL Wnt-3a　　　CTRL Wnt-5a

BrdU α-sarc act DAPI

ISO 28d

YFP  BrdU  αSA  DAPI

ISO 28d

BM<sup>GFP</sup>+ISO 28d

ISO+5+FU+CSCs^GFP (56d)

ISO+5-FU+CSCs^GFP (84d)

ISO+5-FU+CSCs^GFP (84d)

Figure 21A:
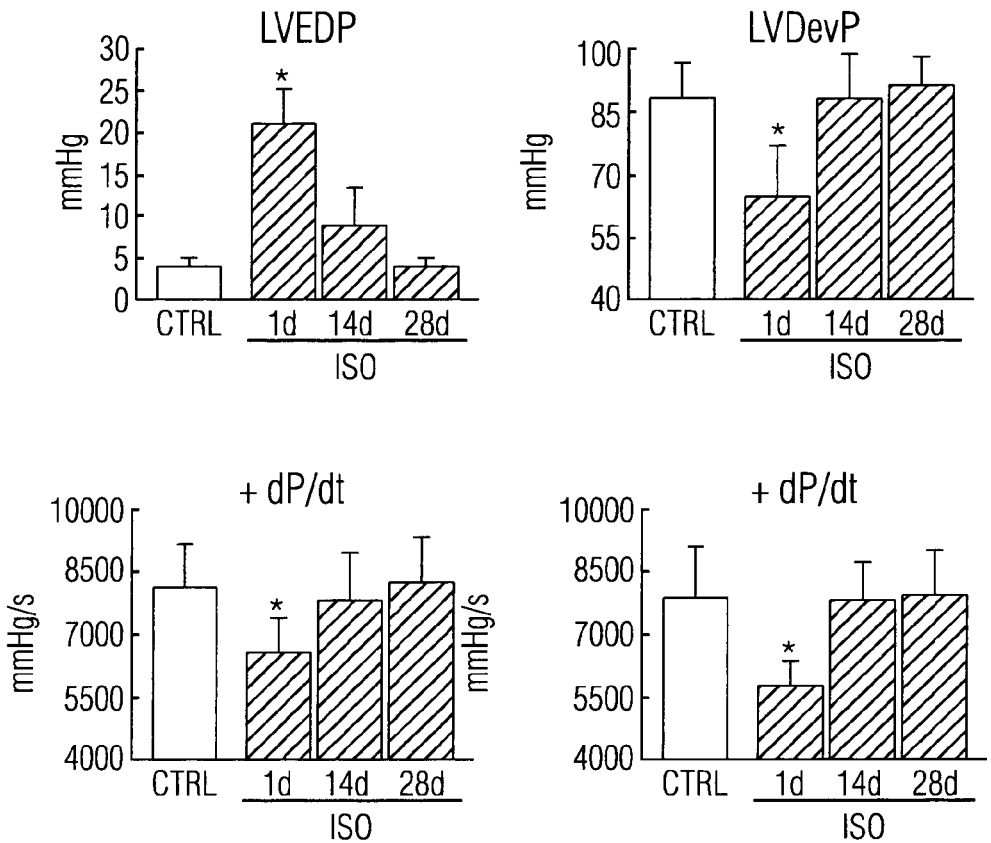
Figure 21B:
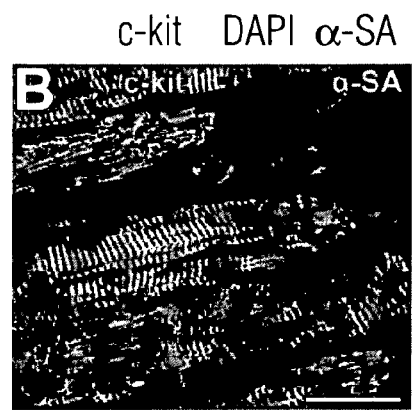
Figure 21C:
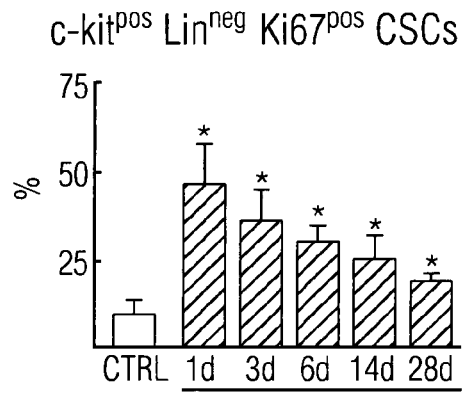
Figure 21G:
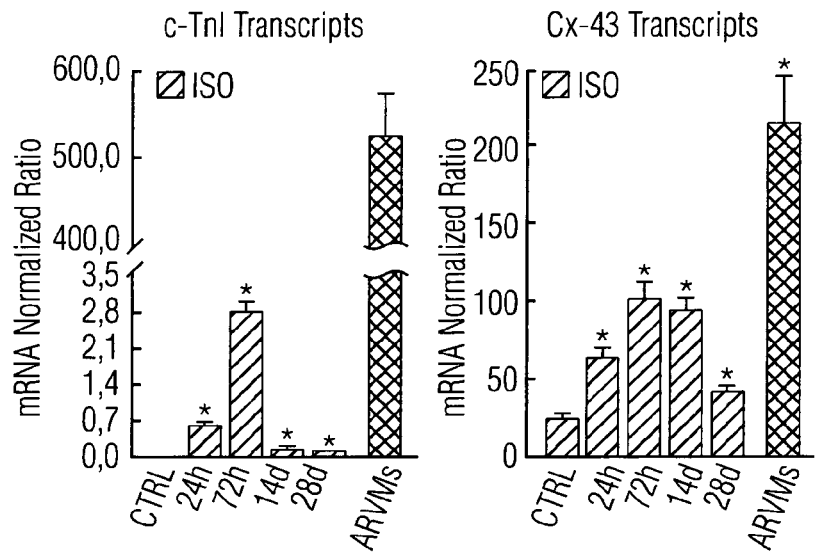
Figure 21H:
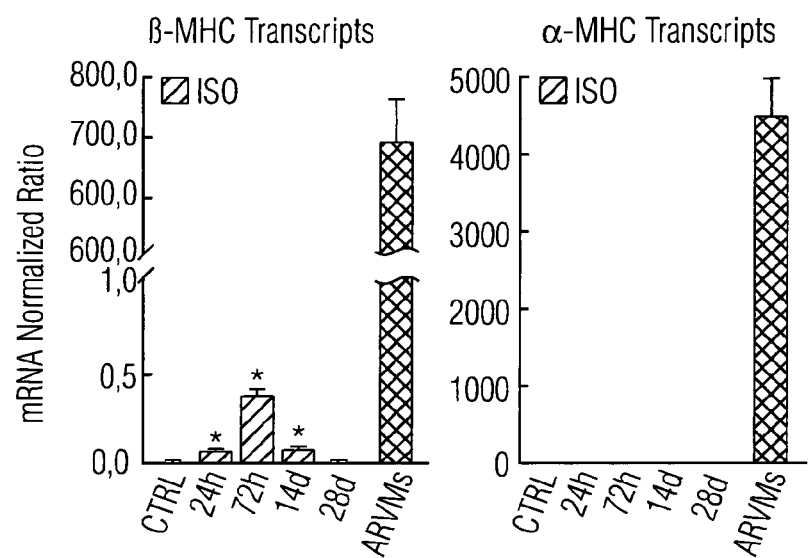
Figure 21I:
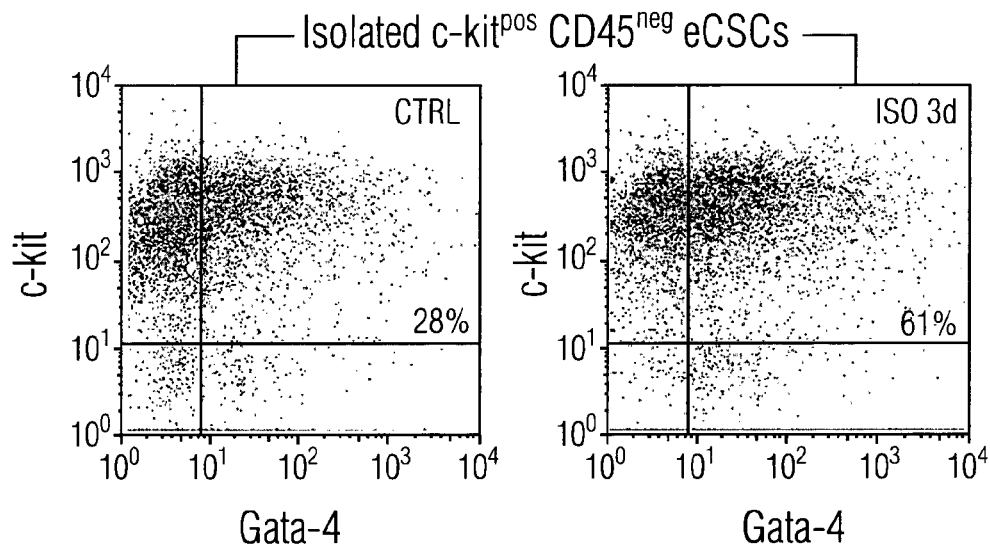
Figure 21J:
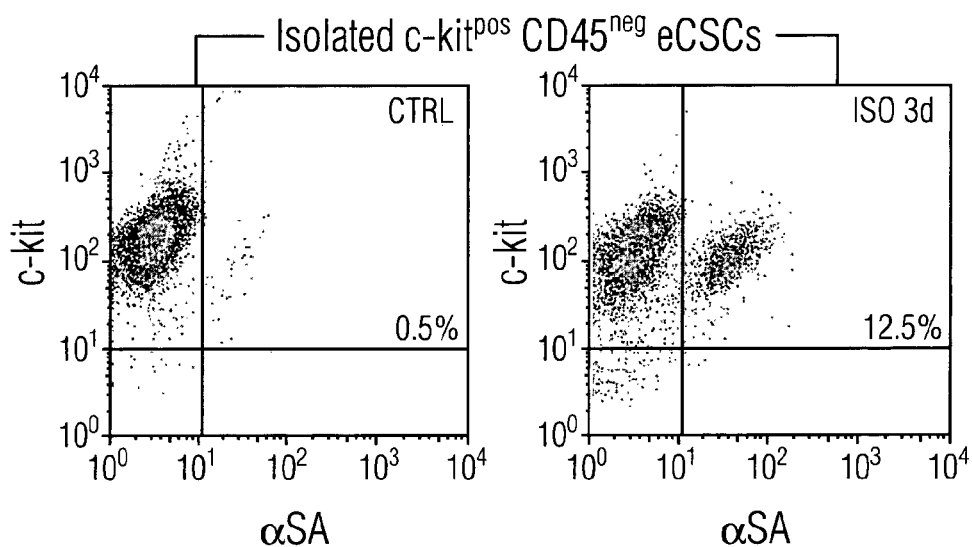
Figure 21K:
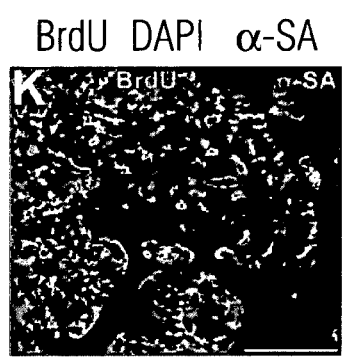

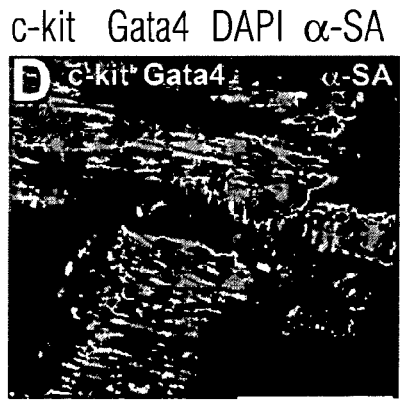
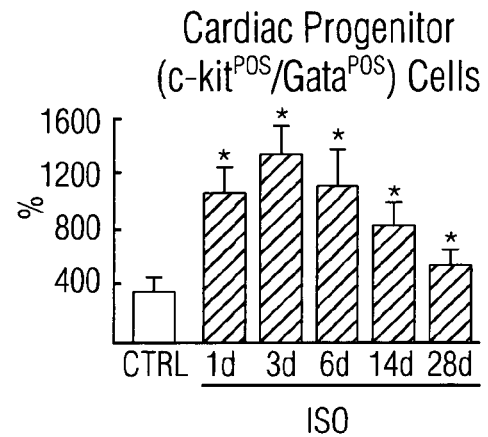
Fig. 21D    Fig. 21E
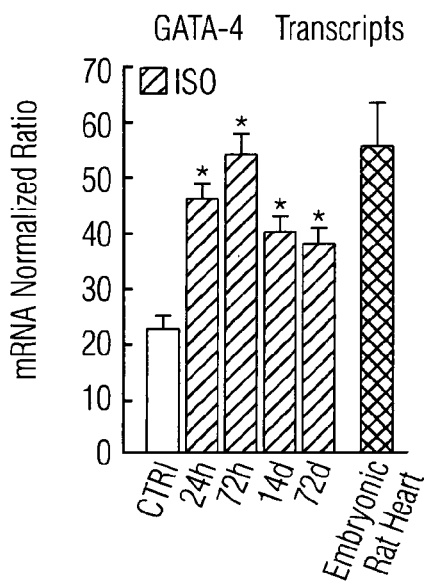
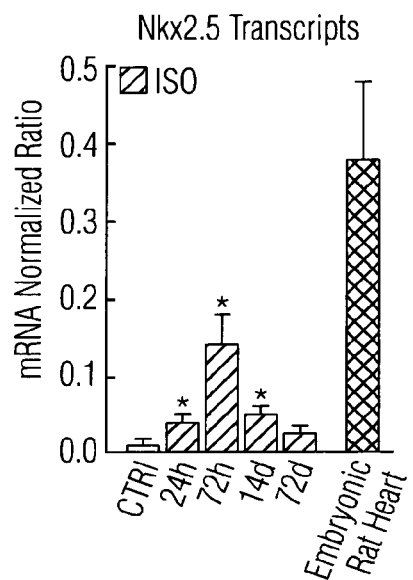
Fig. 21F

BrdU DAPI α-SA

Figure 22A:
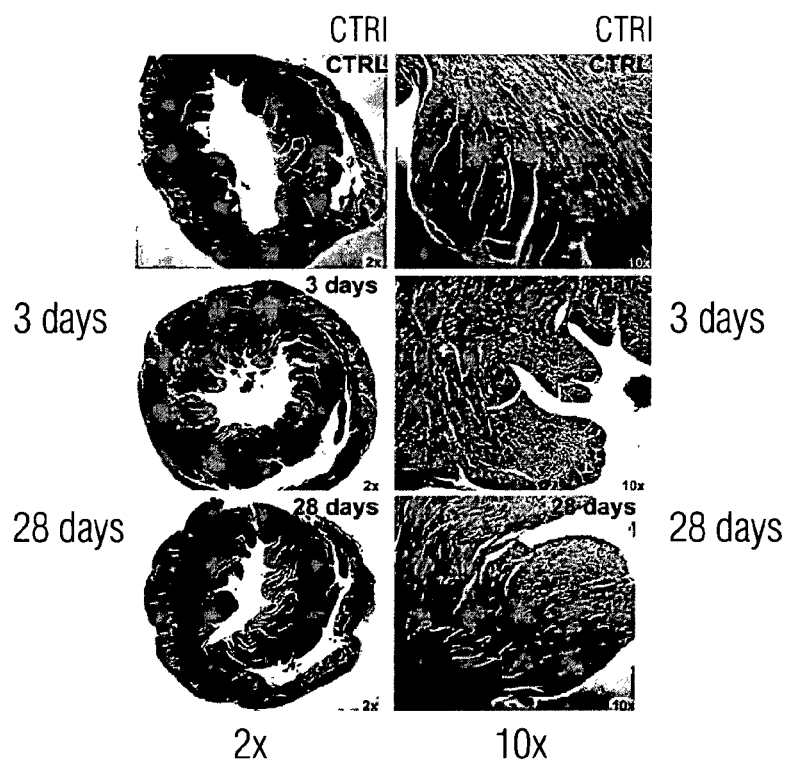
Figure 22B:
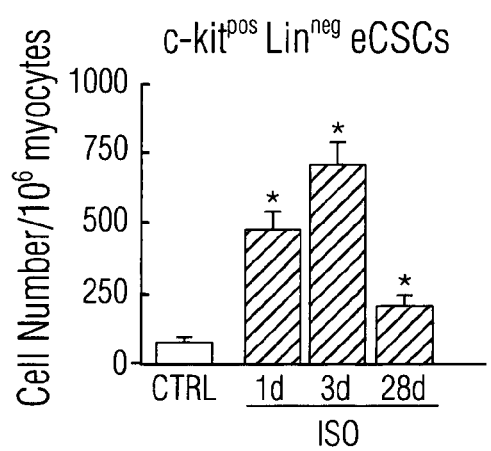
Figure 22C:
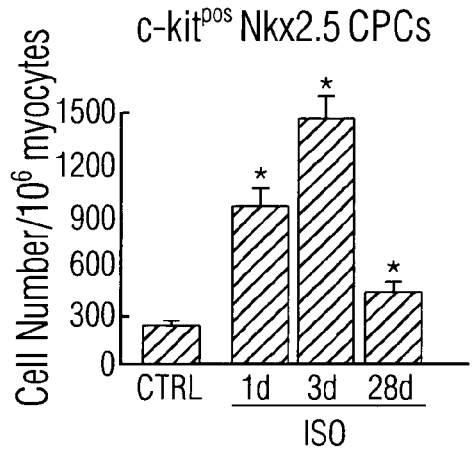
Figures 22G, 22H:
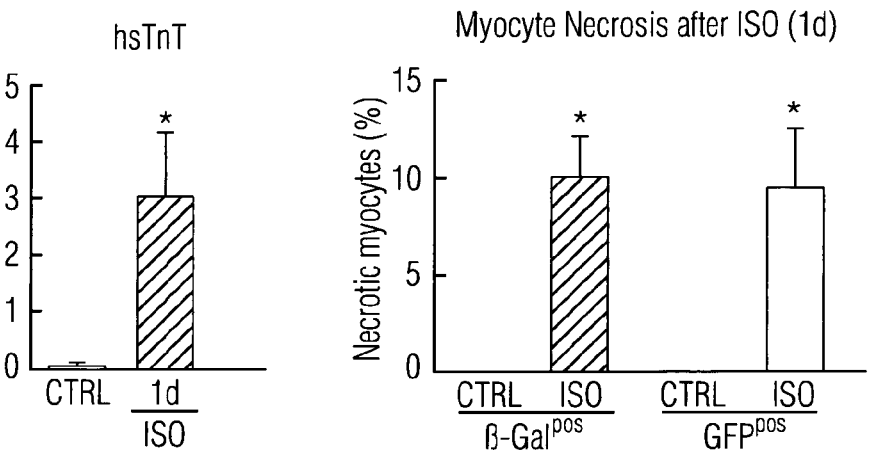
Figure 22I:
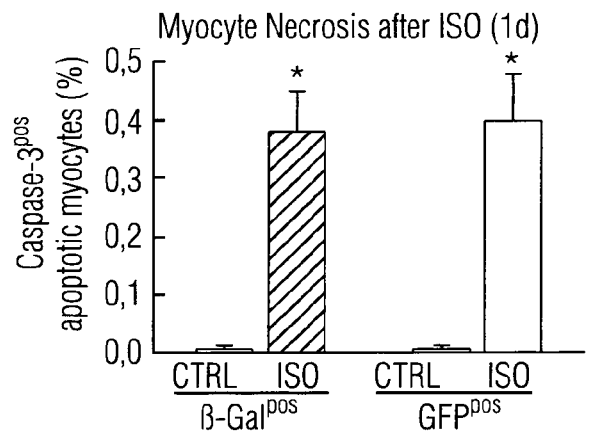
Figure 22J:
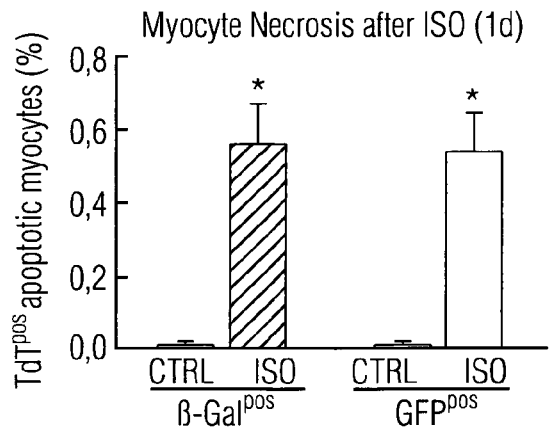
Figure 23A:
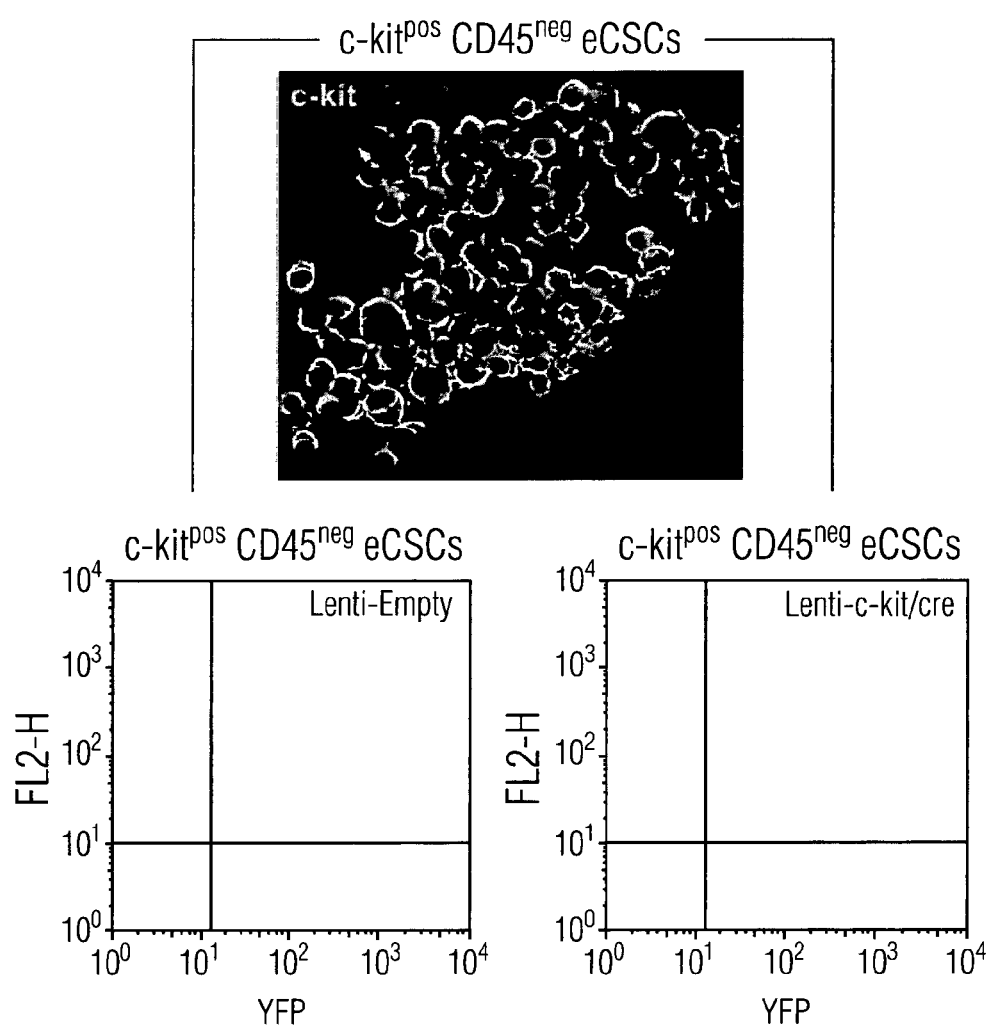
Figure 23B:
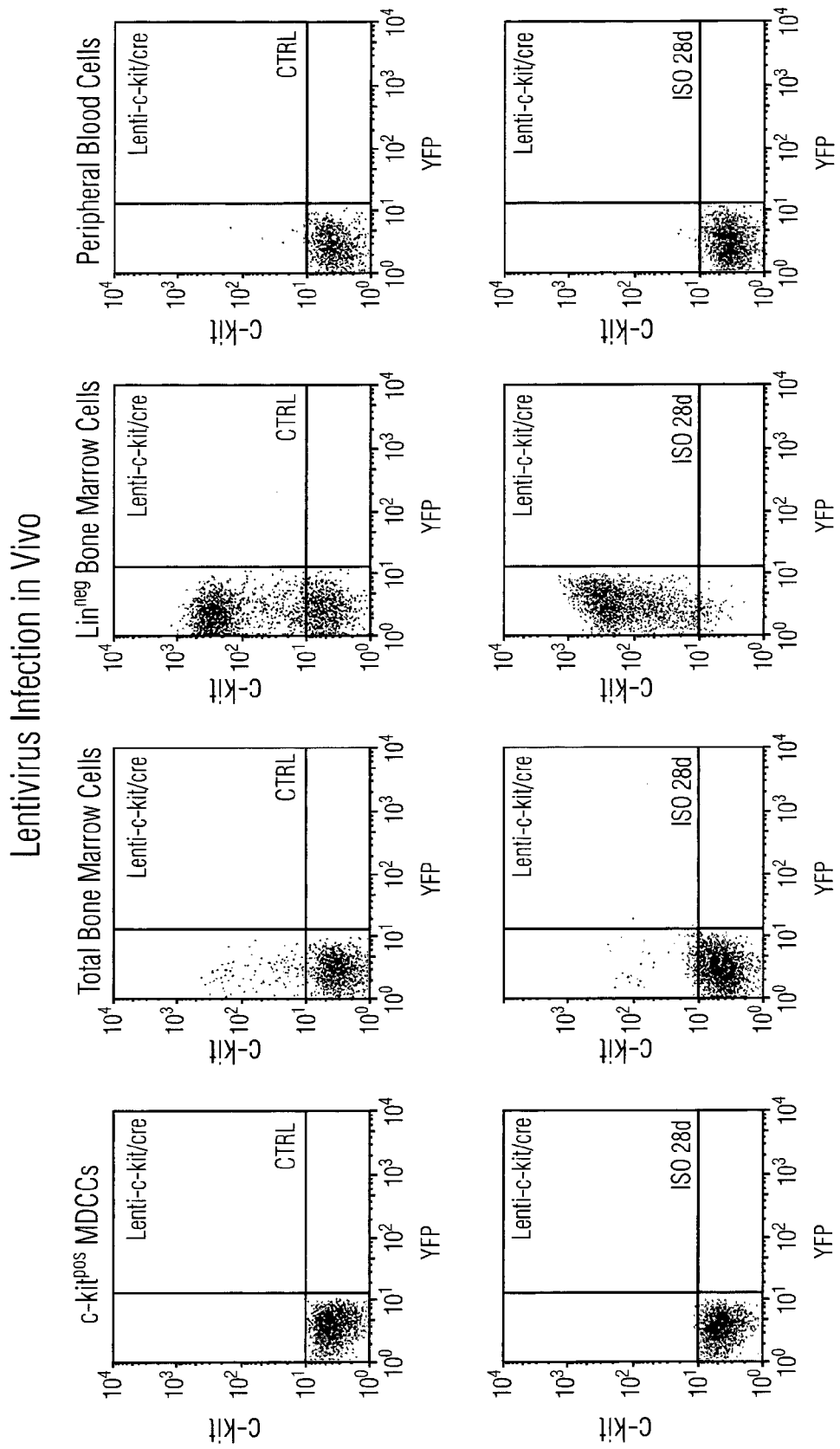
Figure 23C:
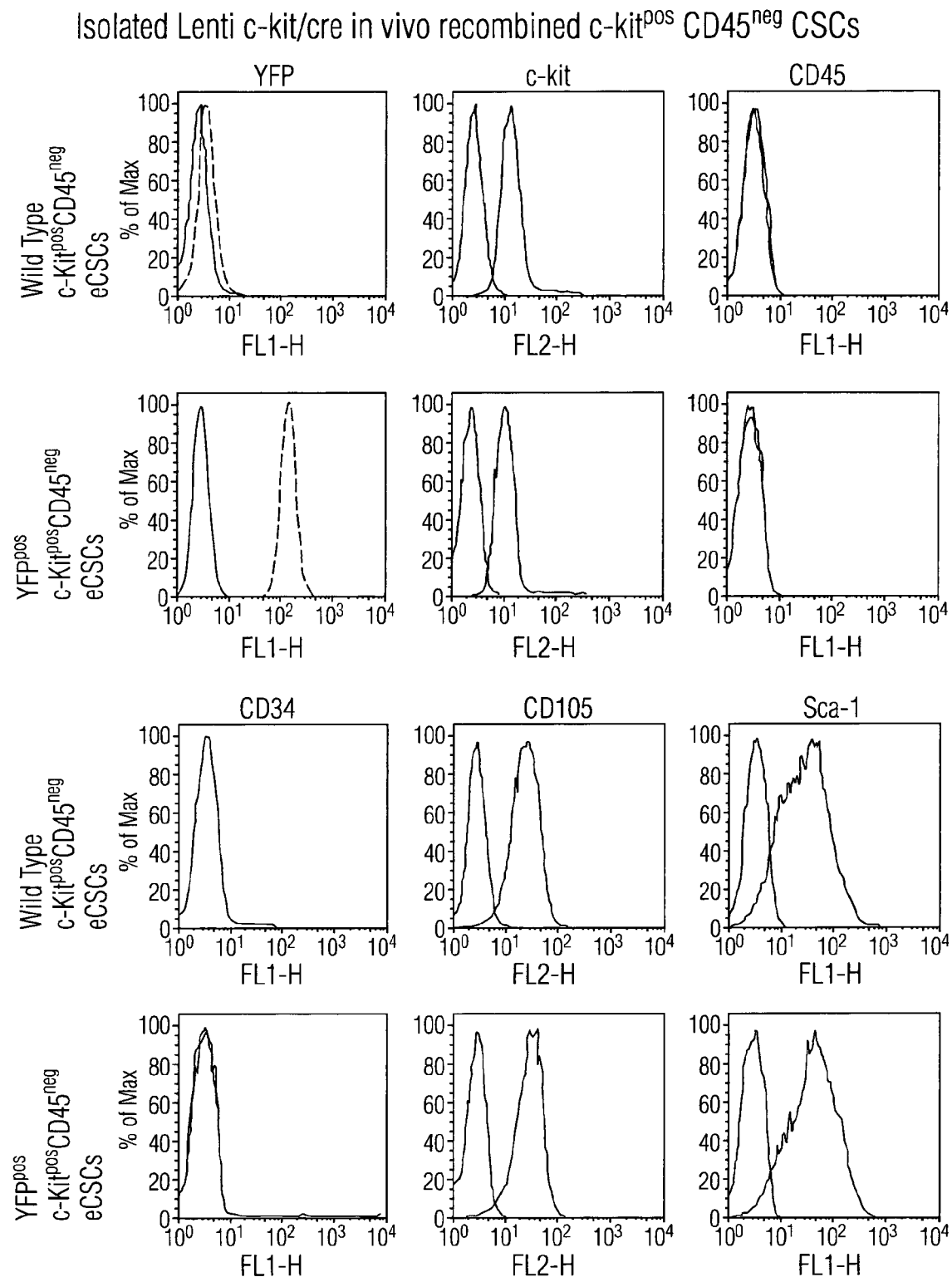
Figure 23D:
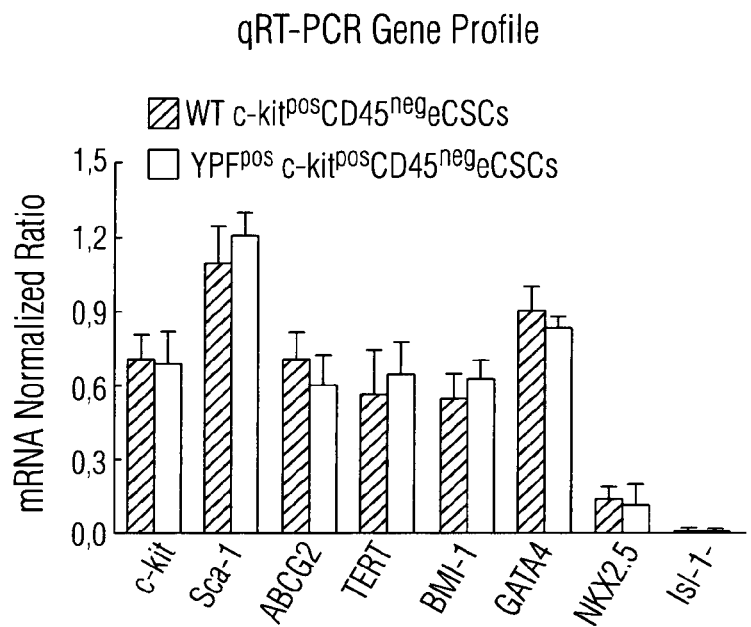
Figure 23E:
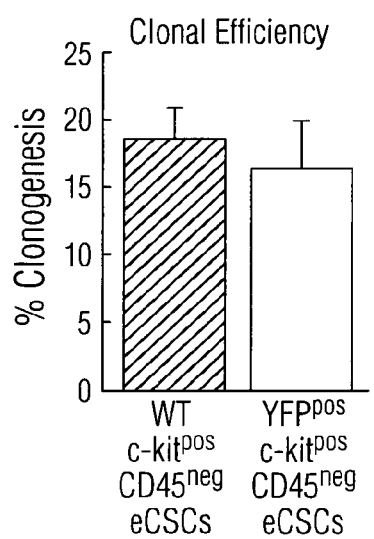
Figure 23F:
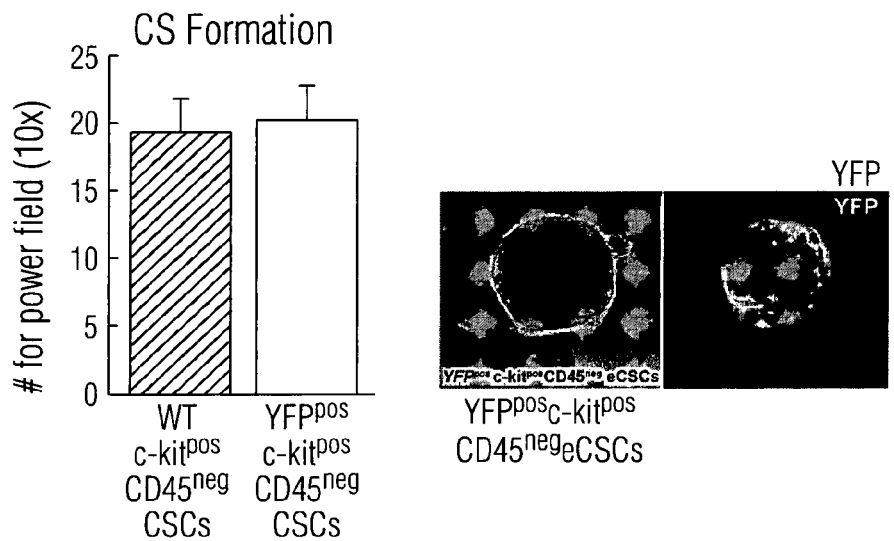
Figure 23G:
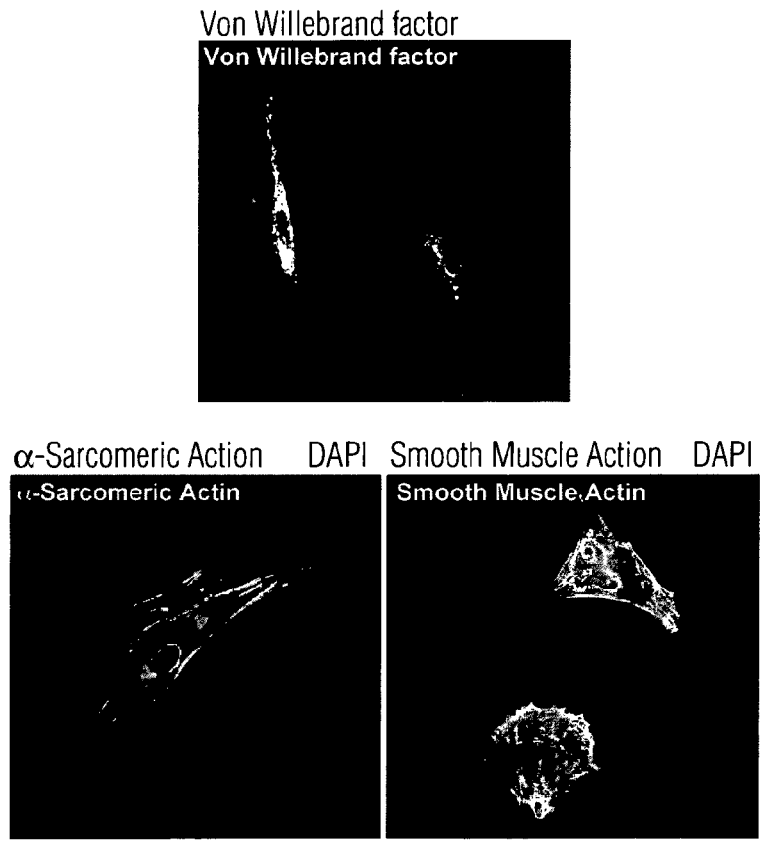
Figure 24A:
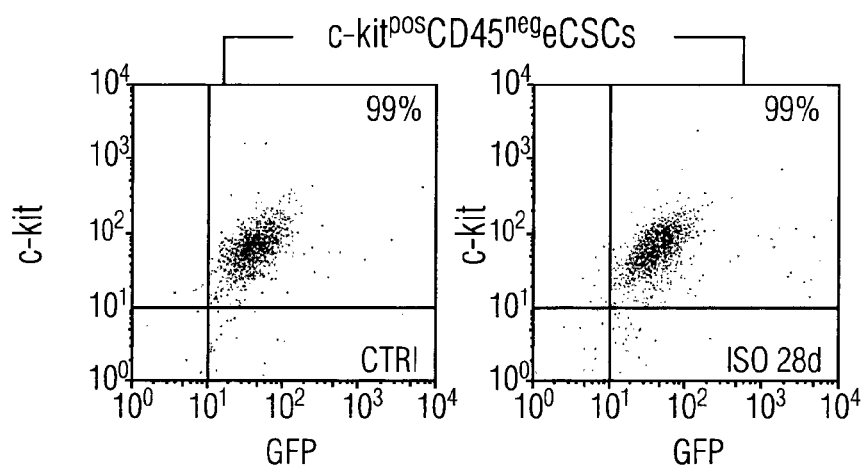
Figure 24B:
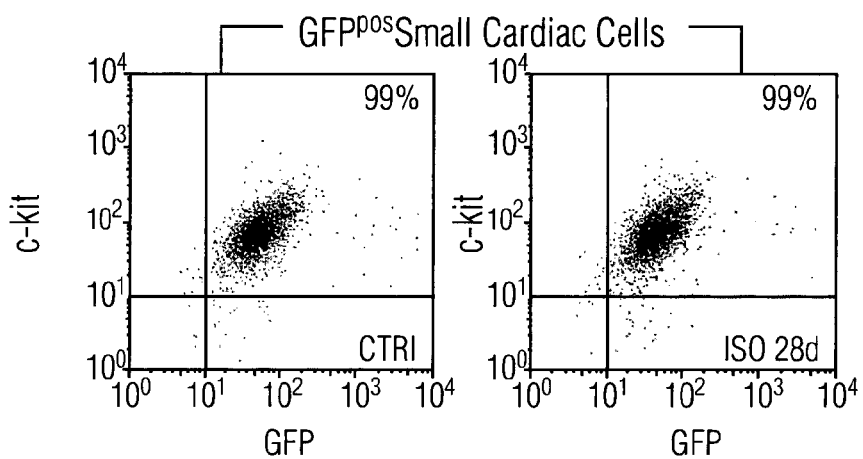
Figures 24C, 24D:
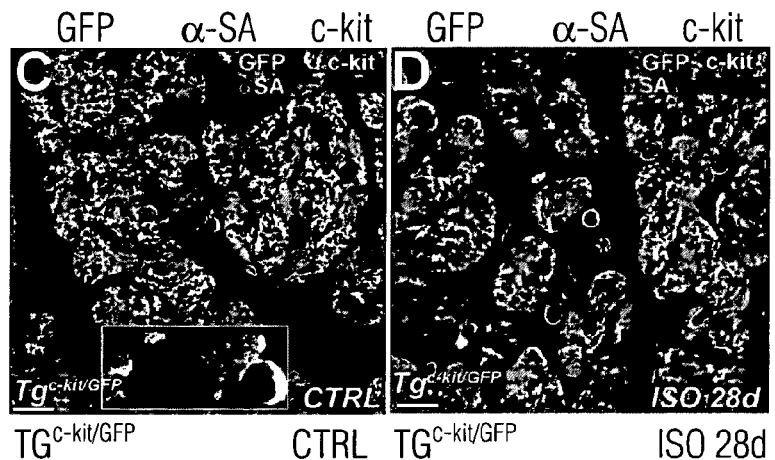
Figures 24E, 24F:
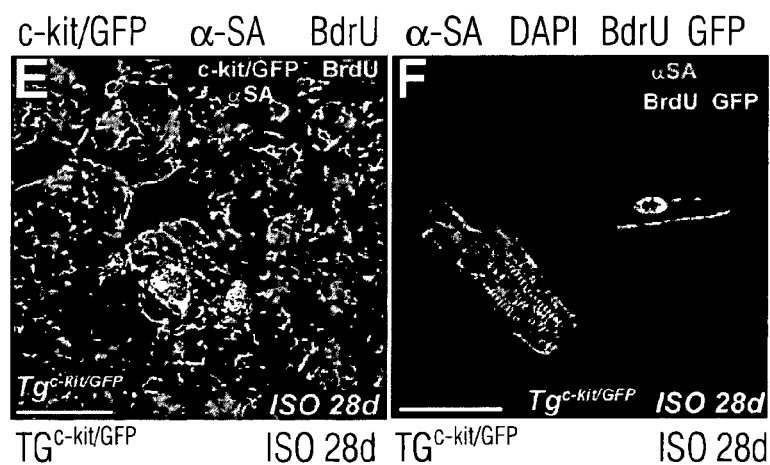
Figure 24G:
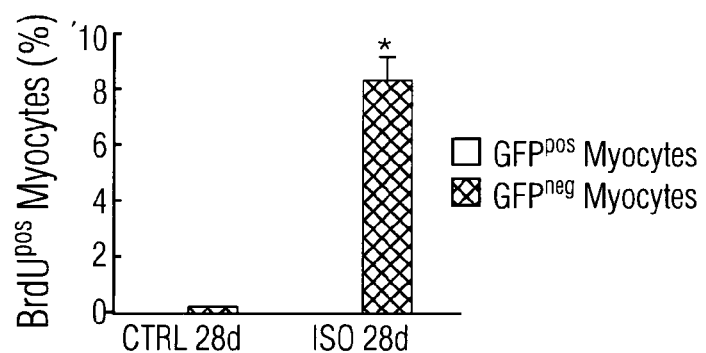
Figure 24H:
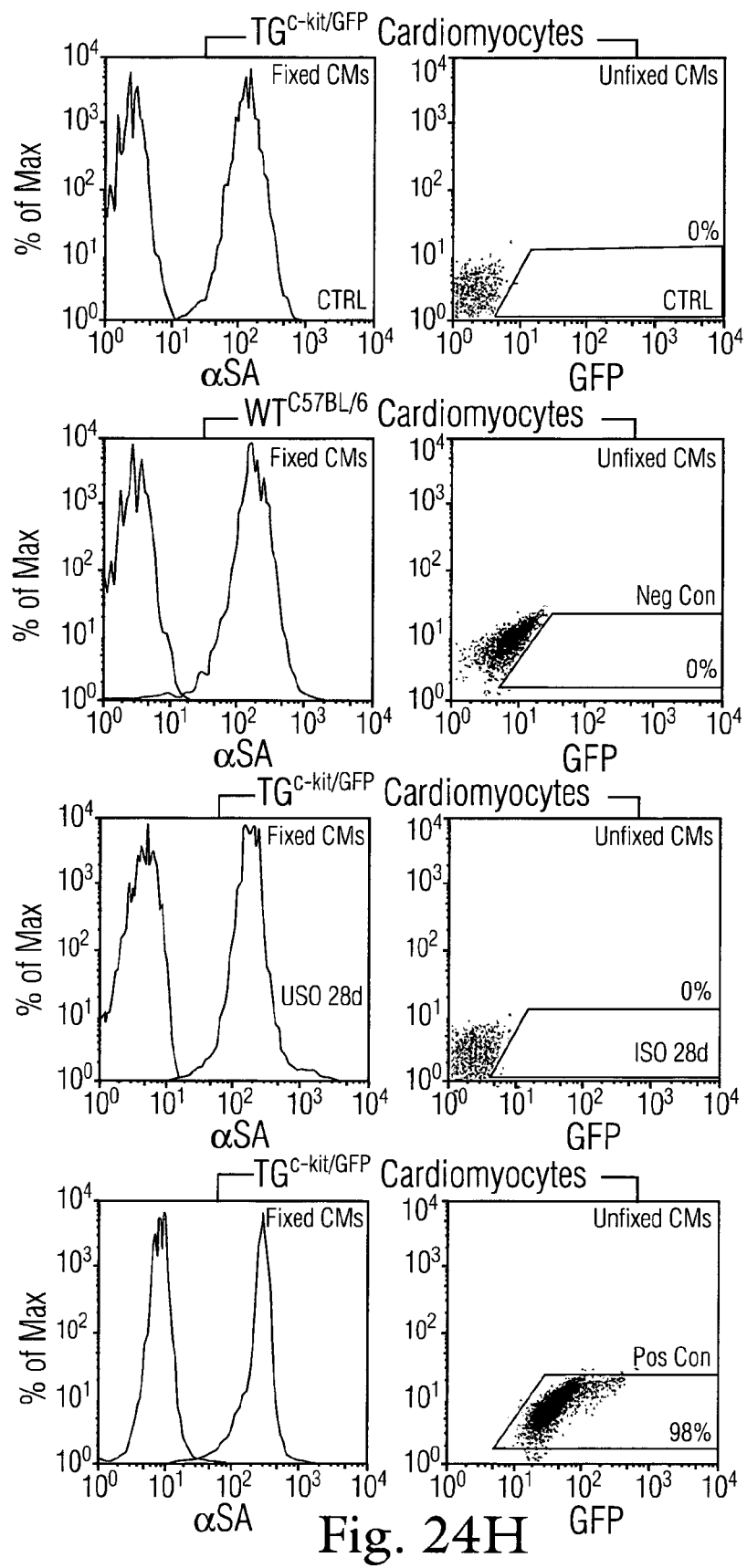
Figure 24I:
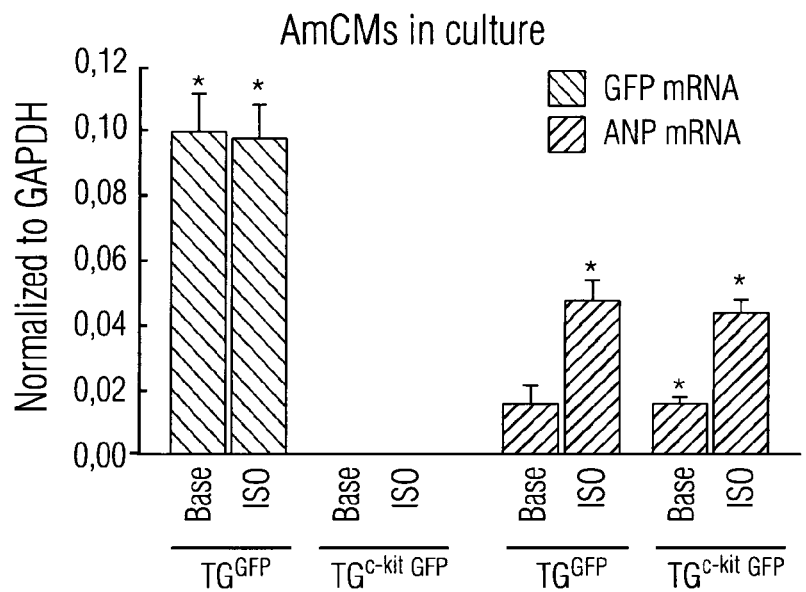
Figure 24J:
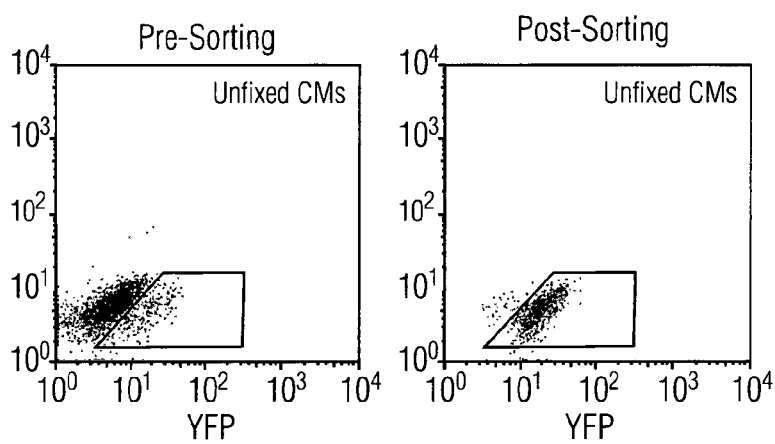
Figure 24K:
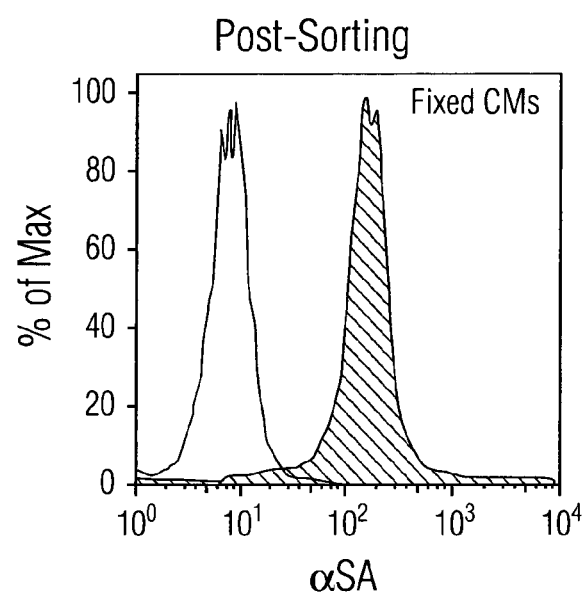
Figure 24L:
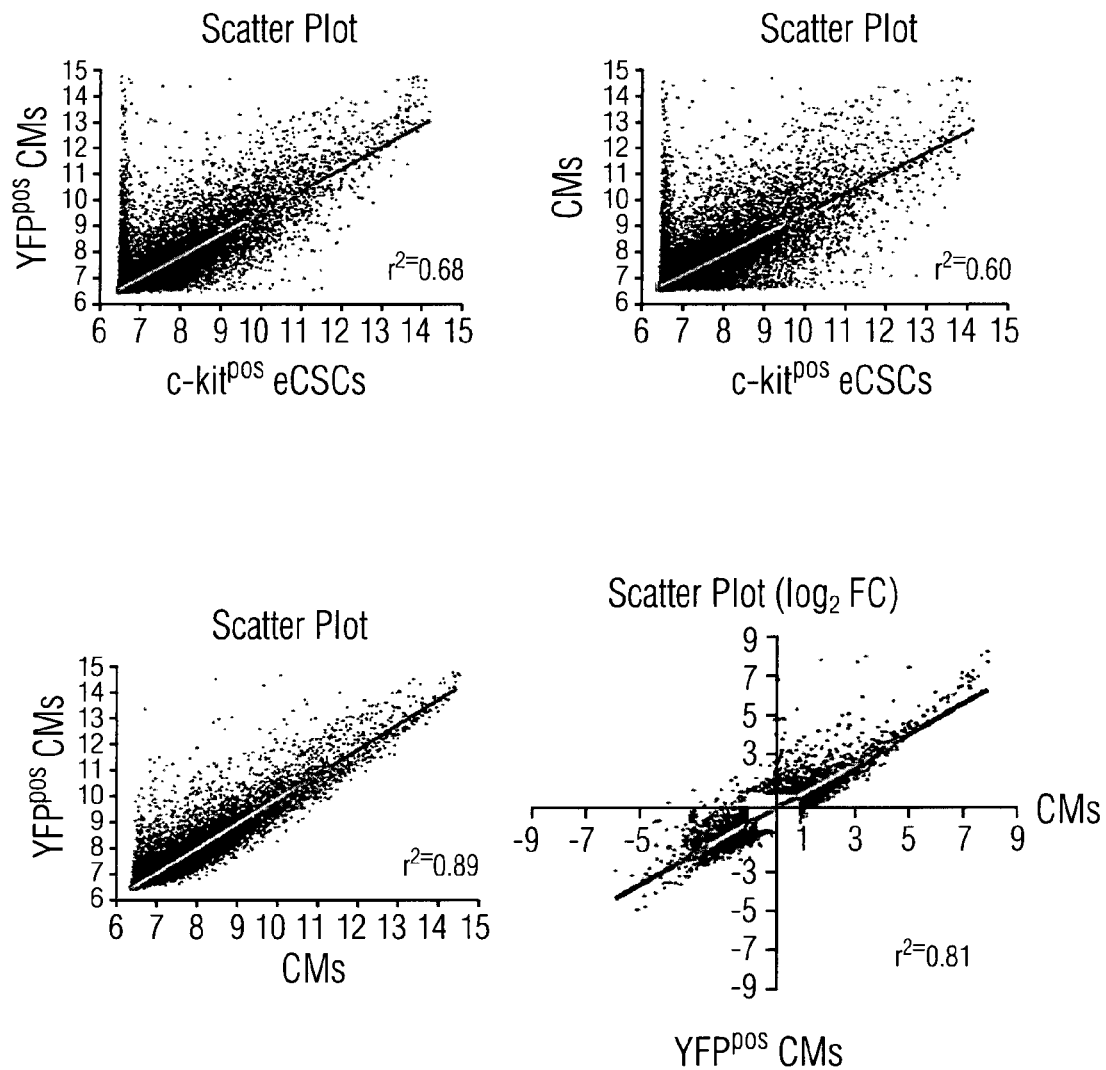
Figure 25A:
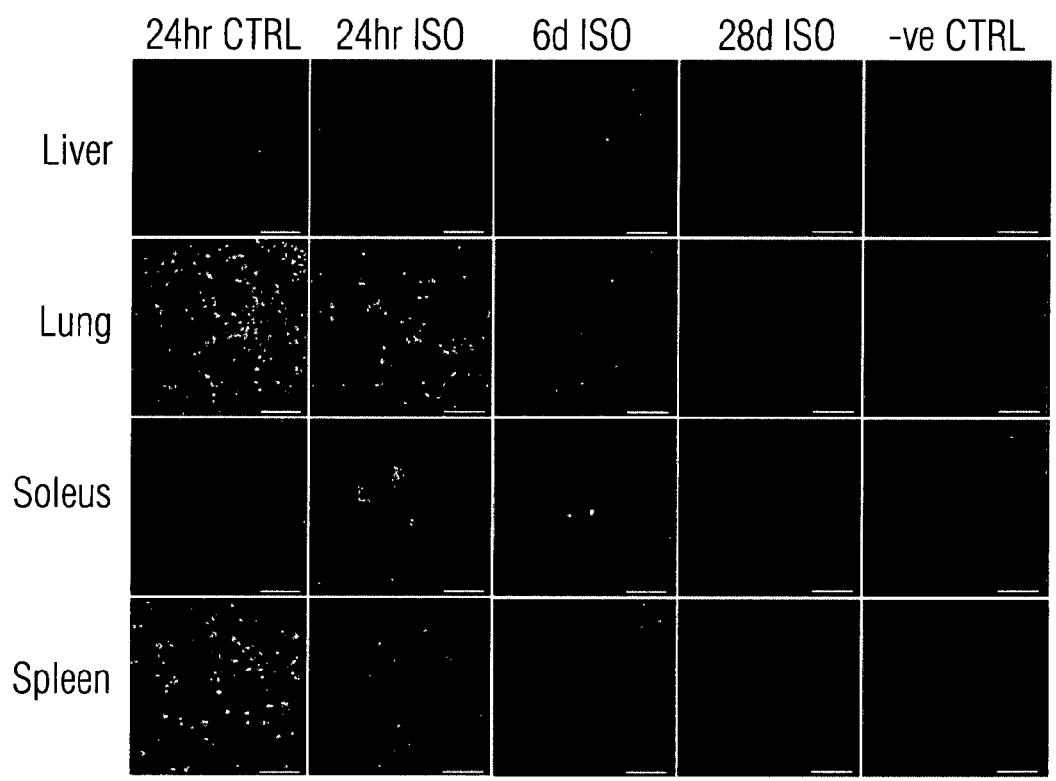
Figure 25B:
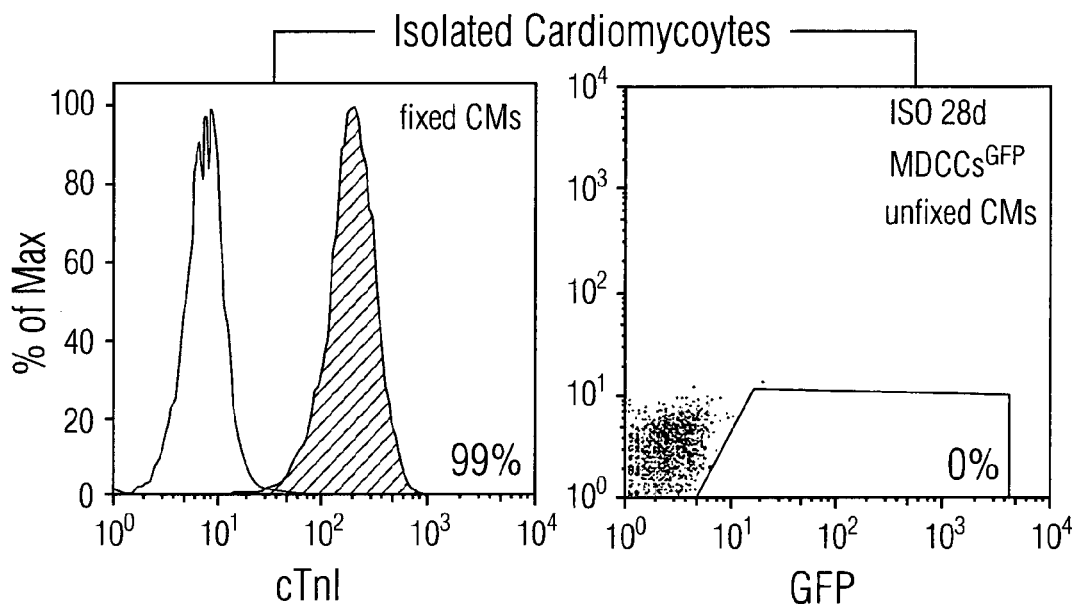
Figure 25C:
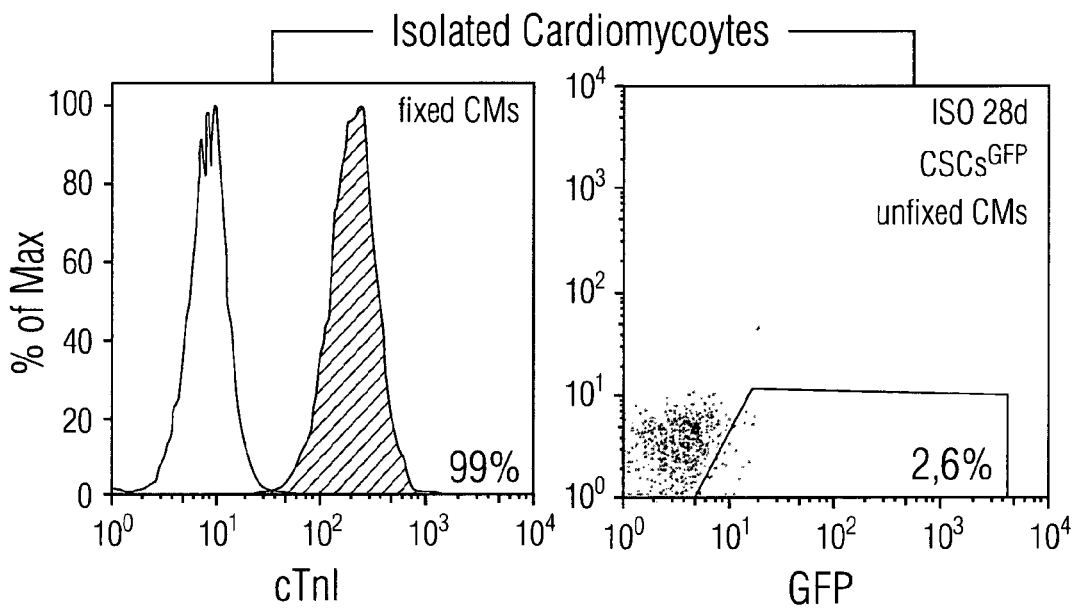
Figure 25D:
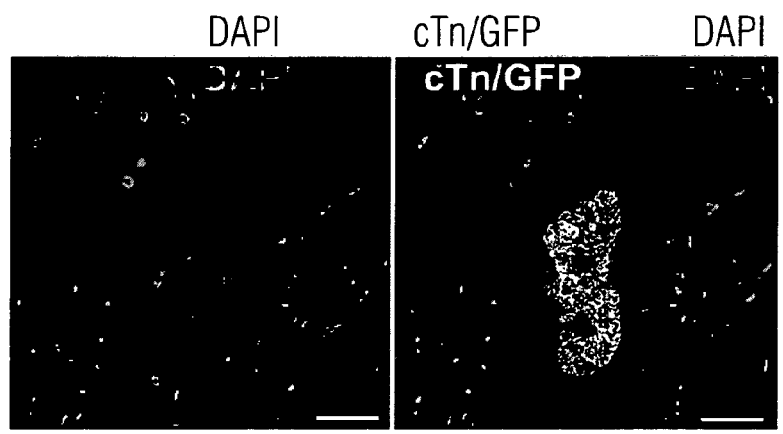
Figure 25D:
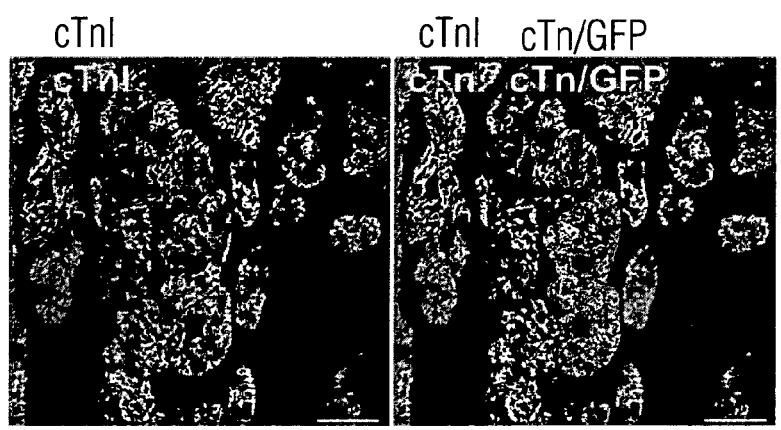
Figure 25E:
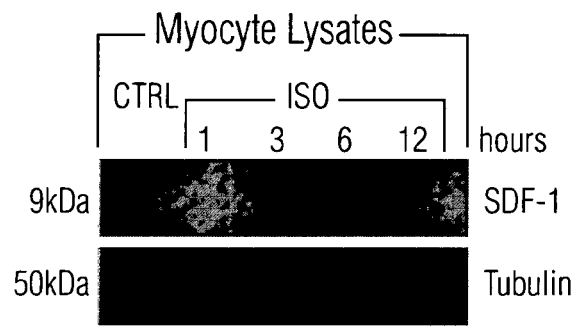
Figure 25F:
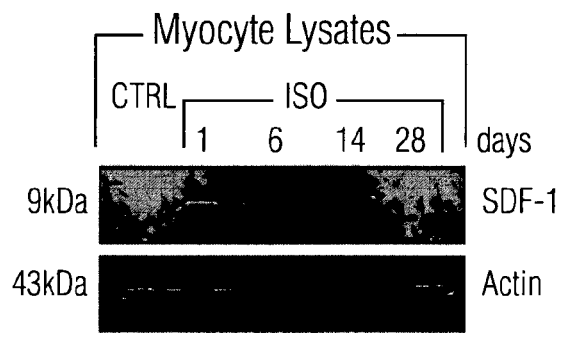
Figure 25G:
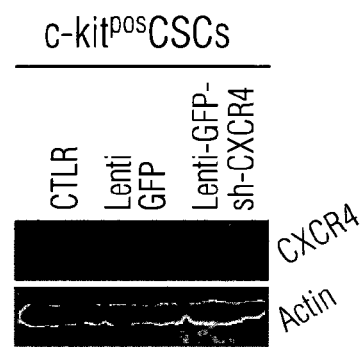
Figure 26A:
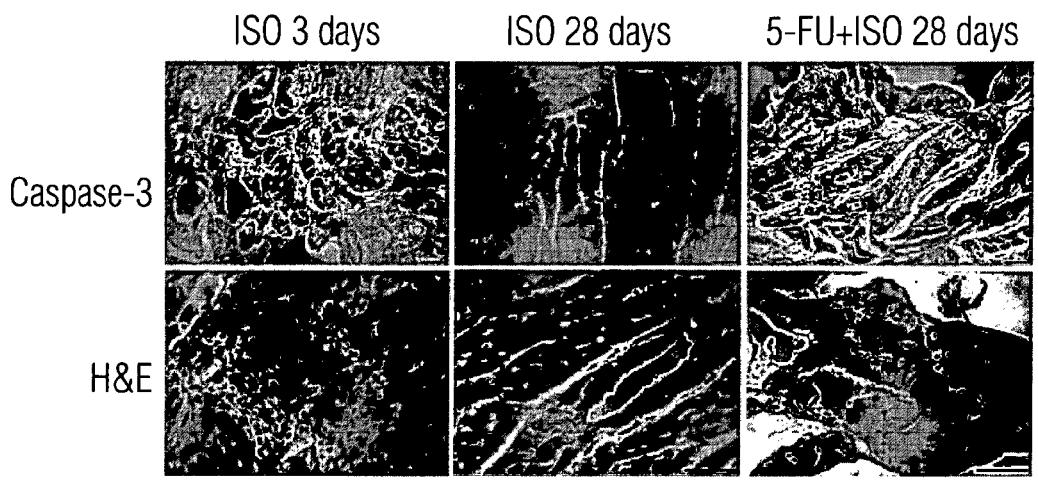
Figure 26B:
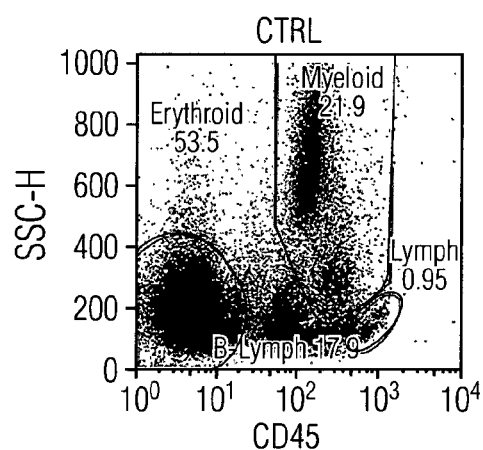
Figure 26B:
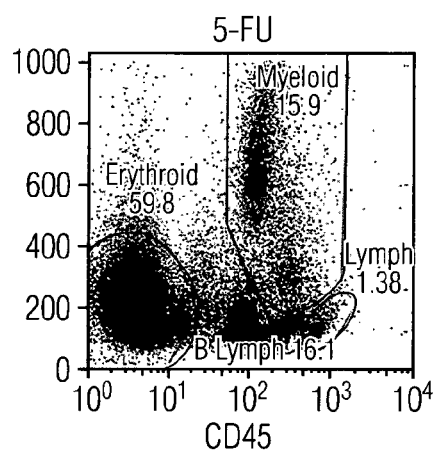
Figure 26C:
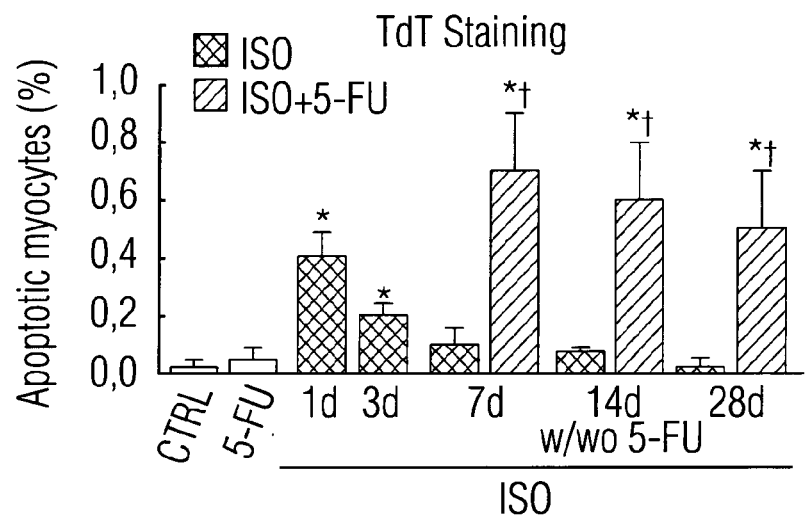
Figure 26D:
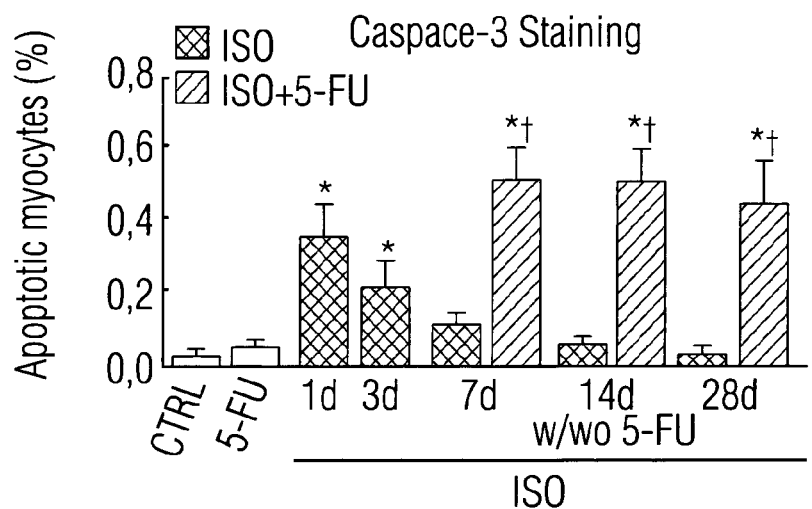
Figure 26E:
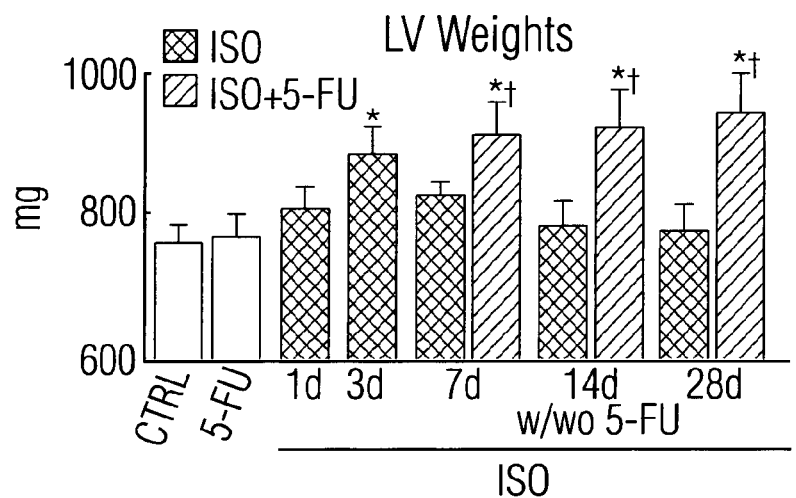
Figure 26F:
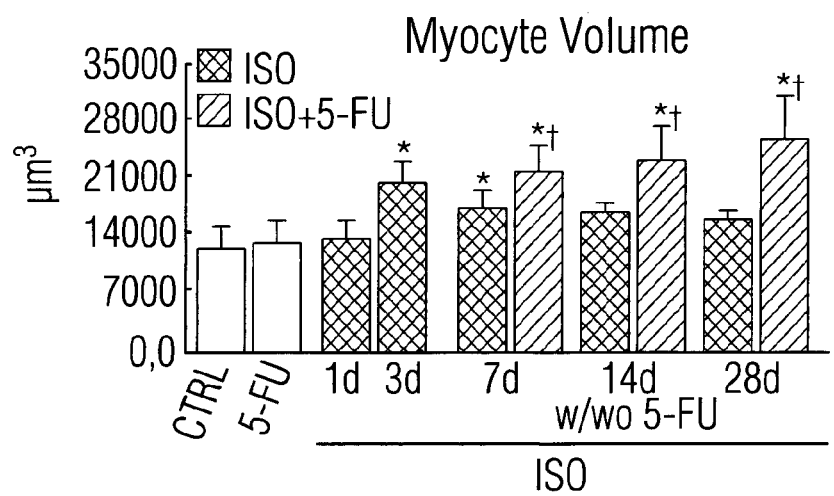
Figure 26G:
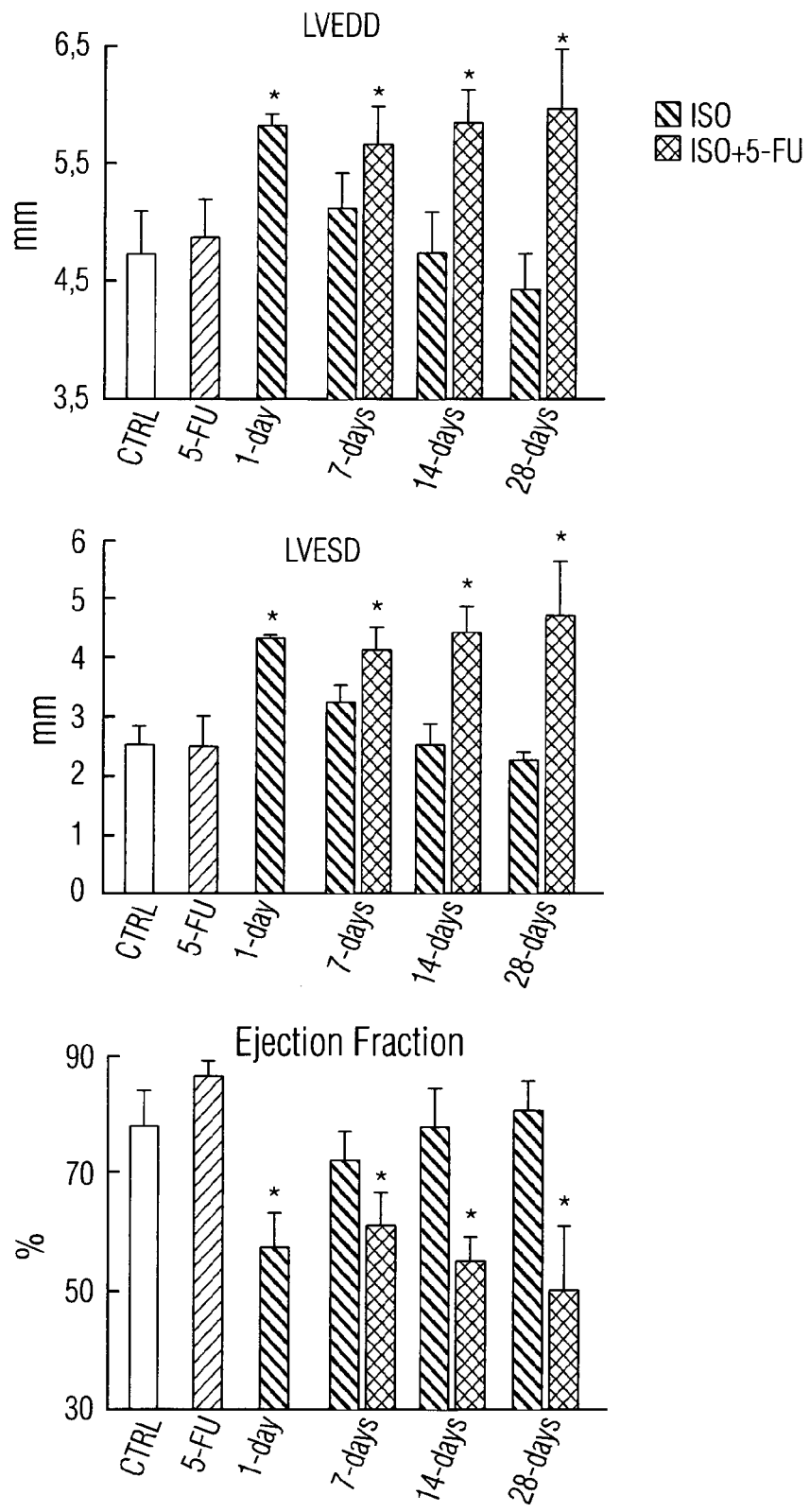
Figure 27A:
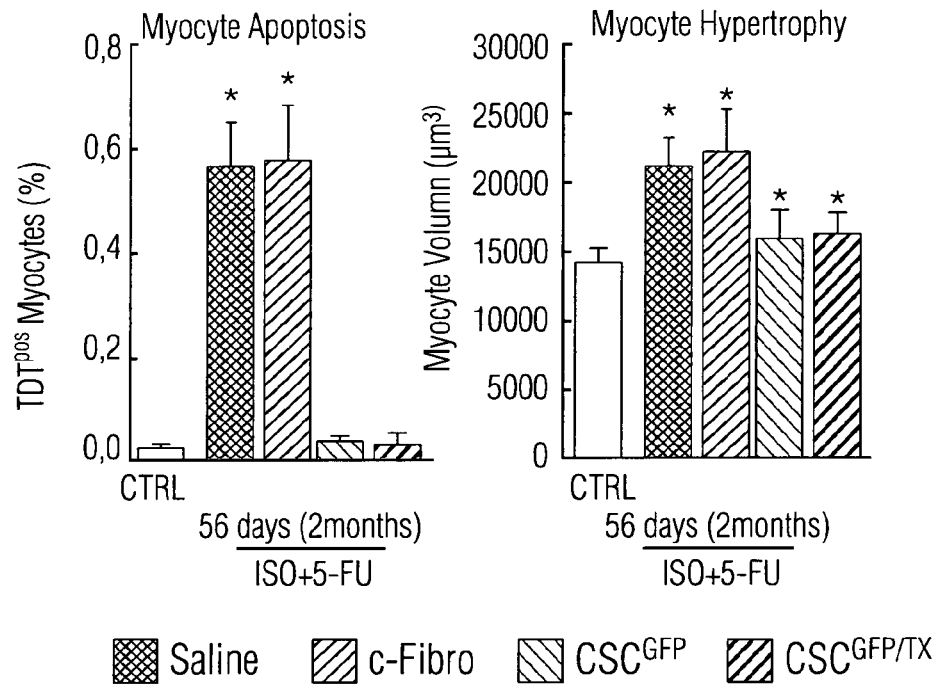
Figure 27B:
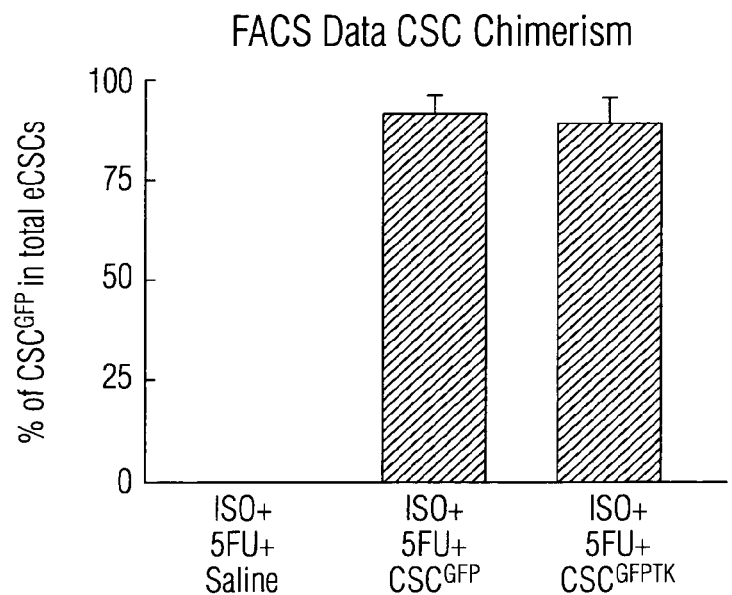
Figure 27C:
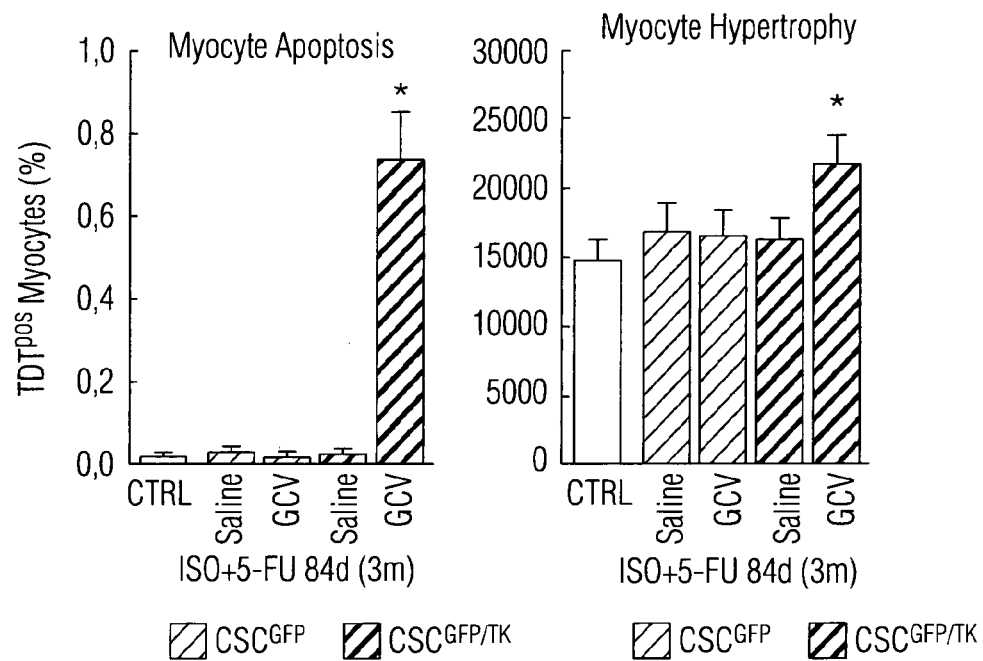
Figure 27D:
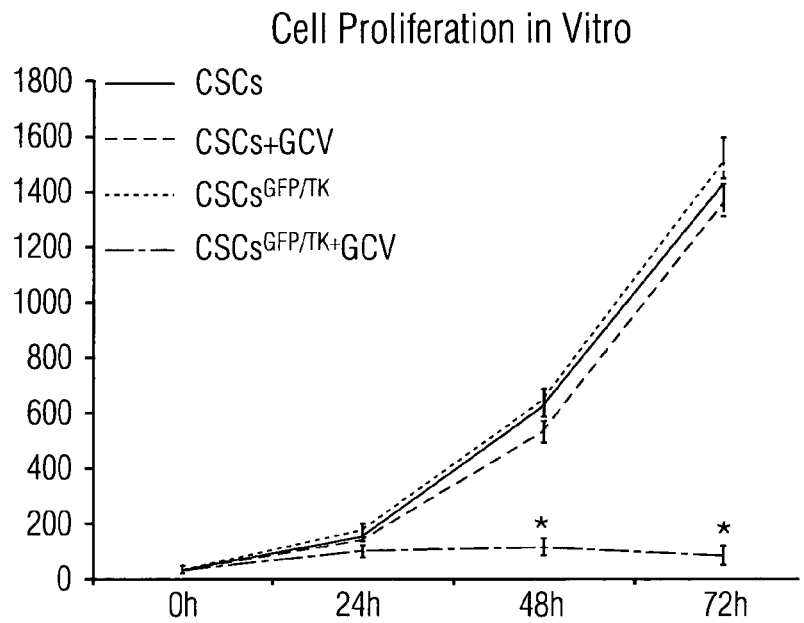
Figure 27E:
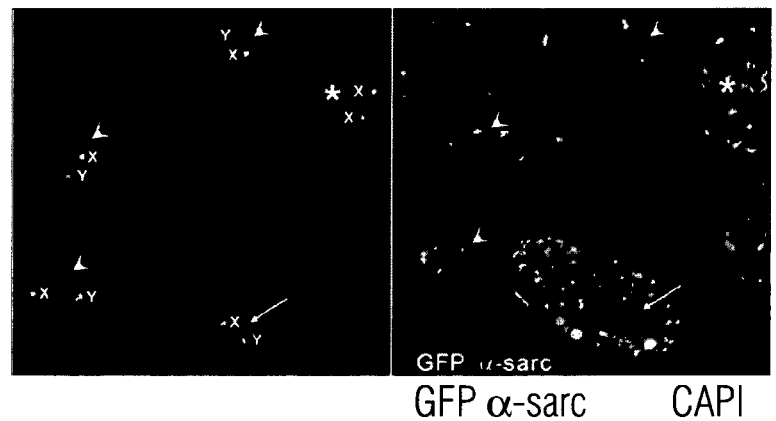
Figure 27F:
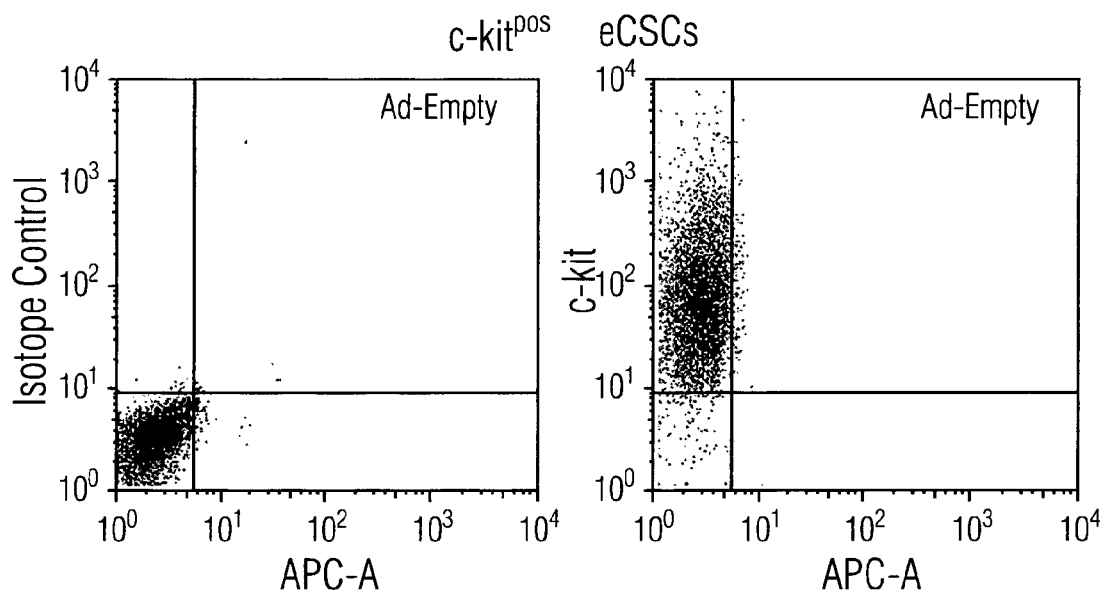
Figure 27G:
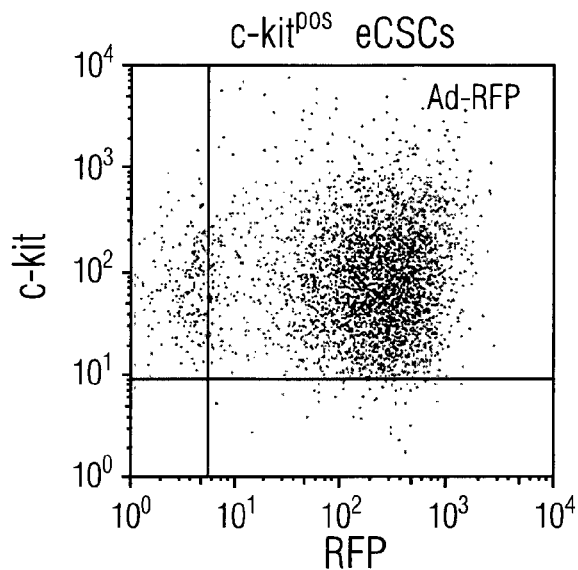
Figure 27H:
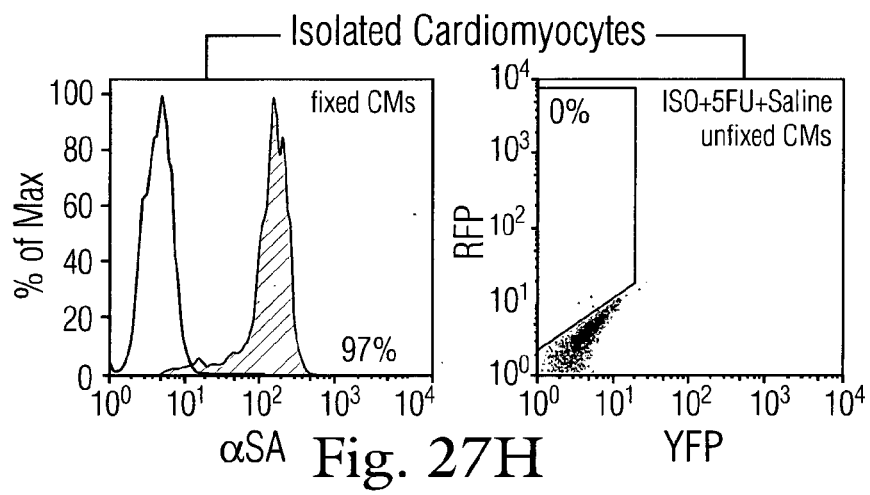
Figure 27I:
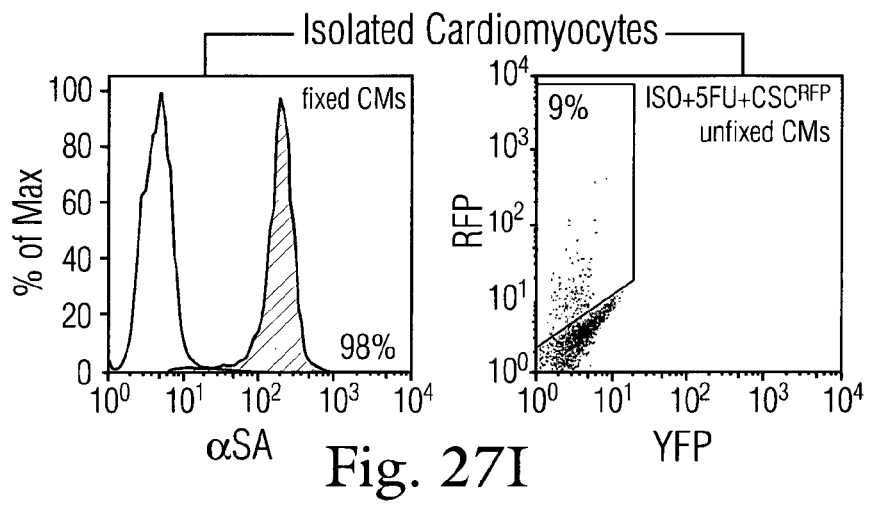
Figure 28A:
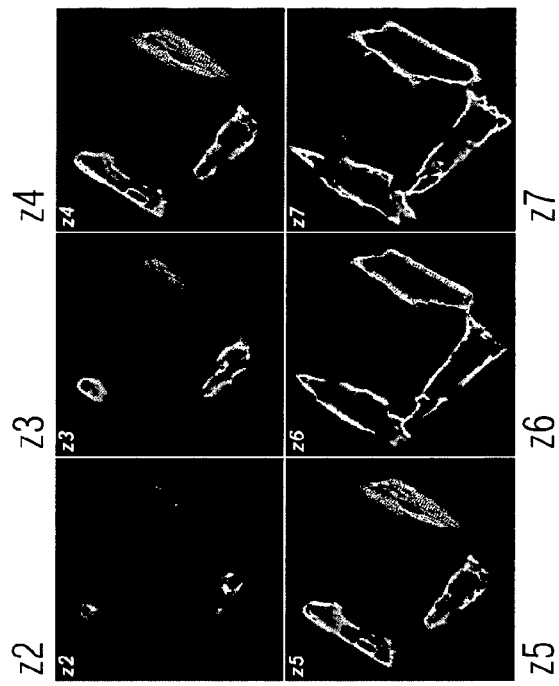
Figure 28B:
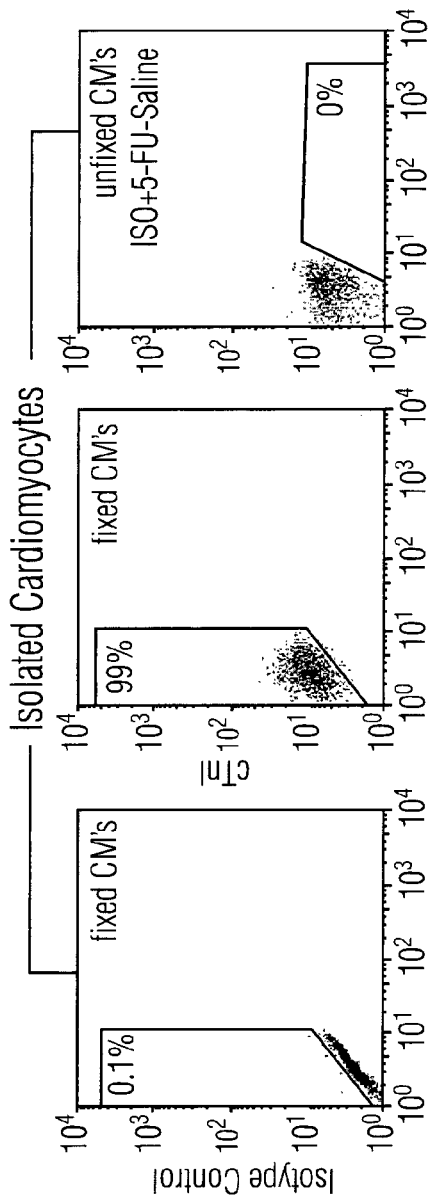
Figure 28C:
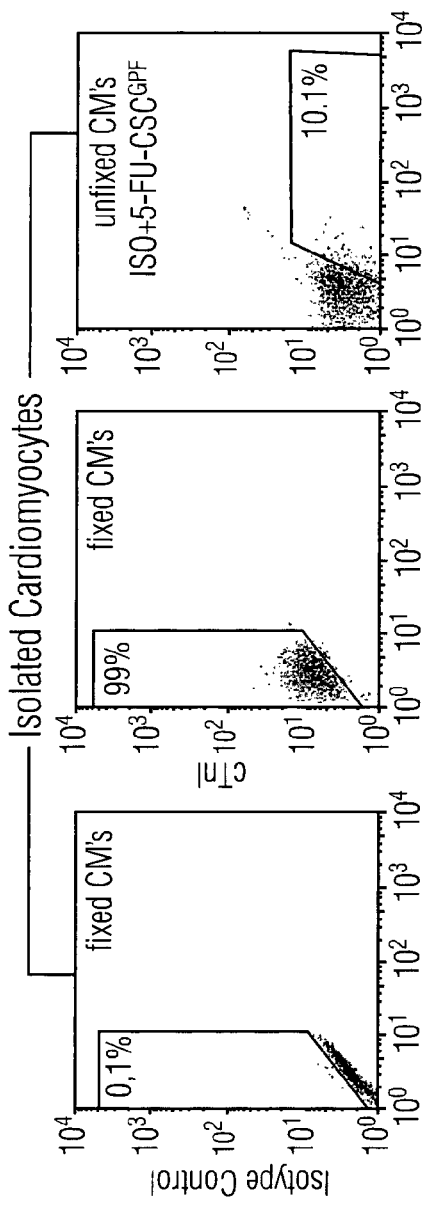
Figure 28D:
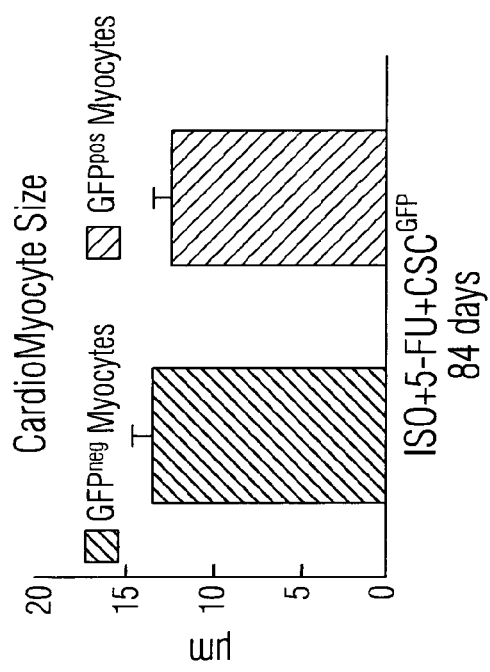
Figure 28E:
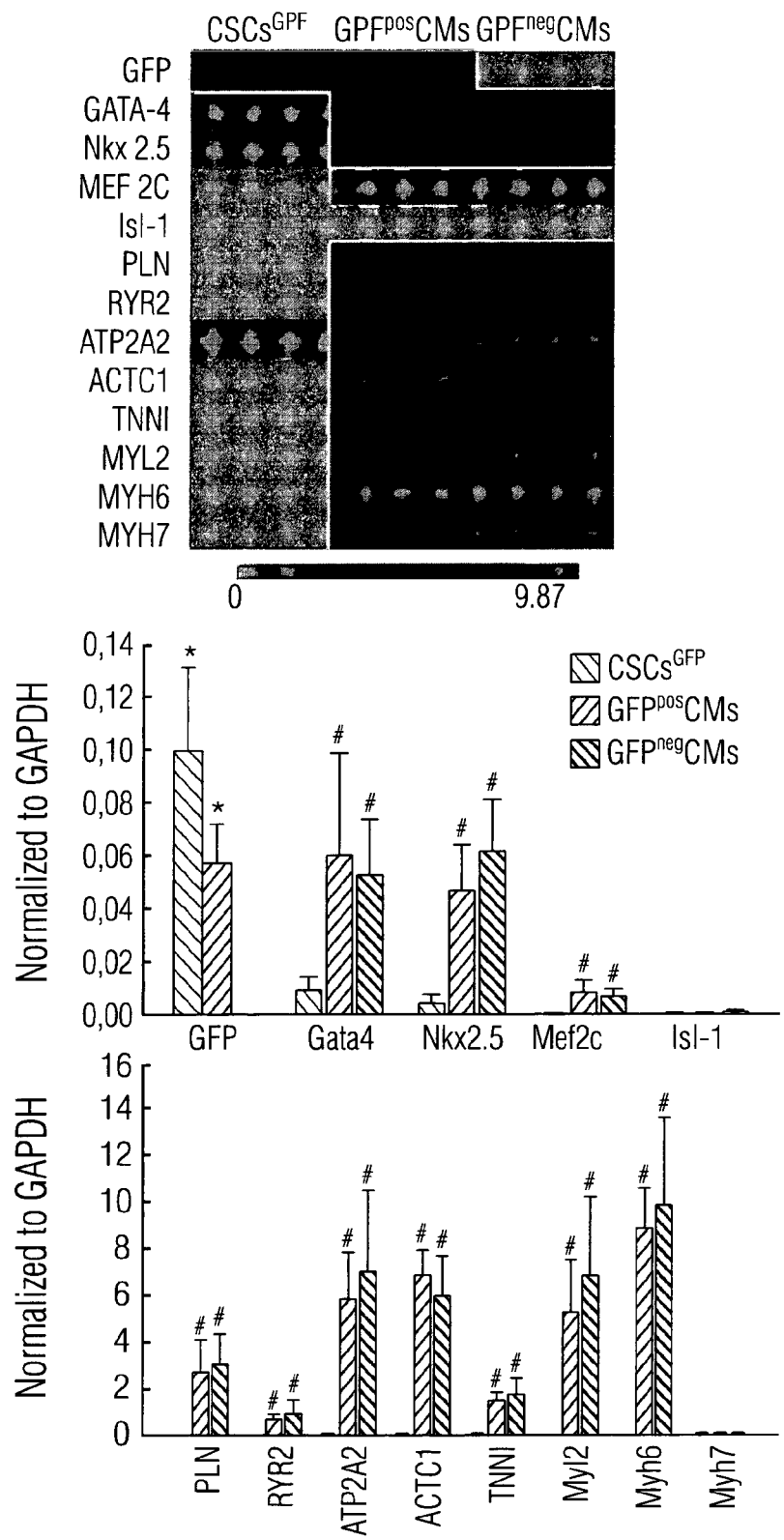
Figure 28F:
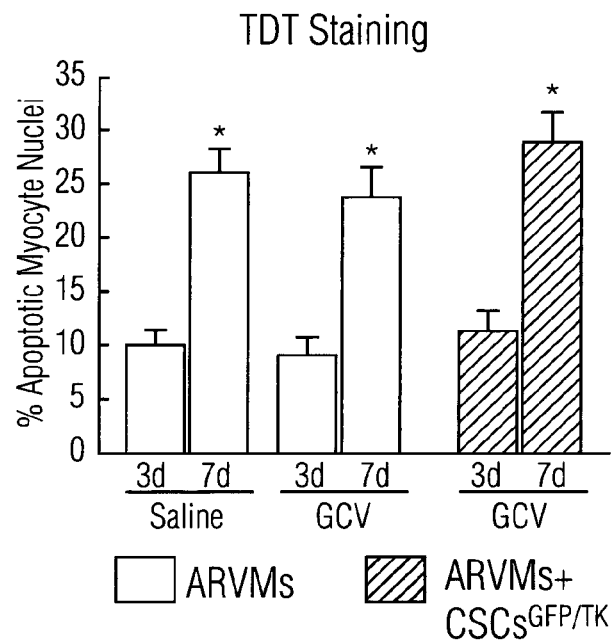
Figure 28F:
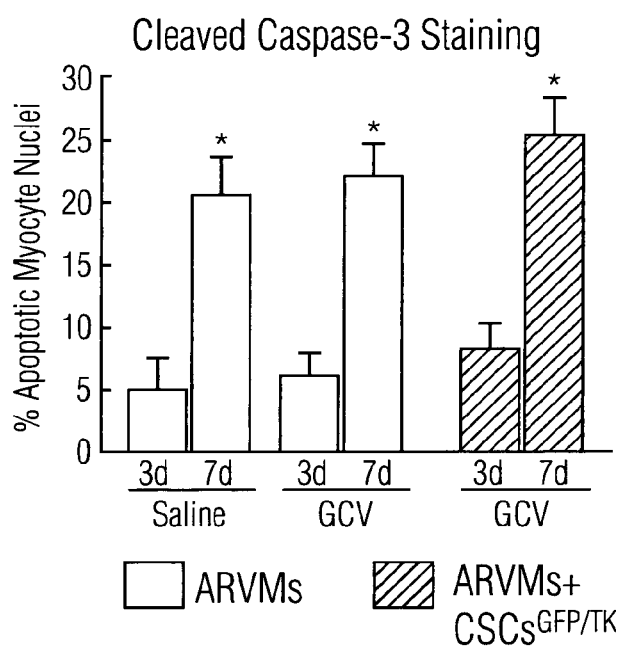

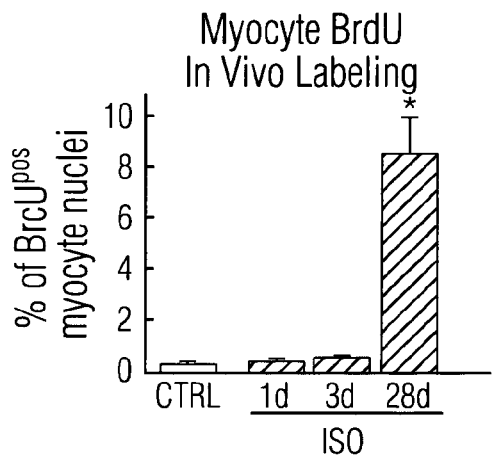
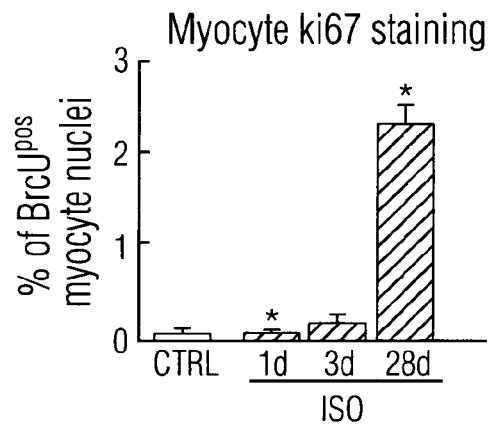
Fig. 22D          Fig. 22E
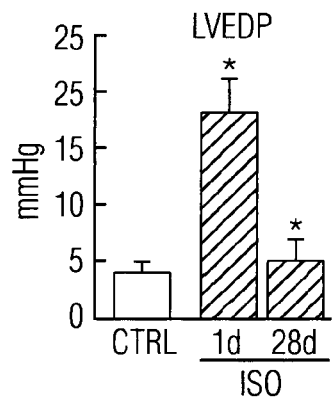
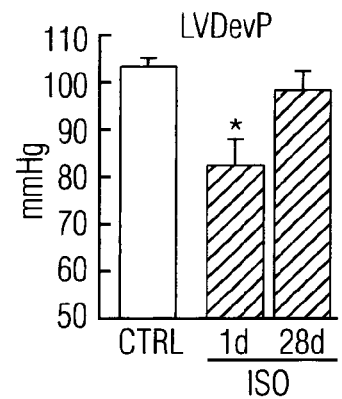
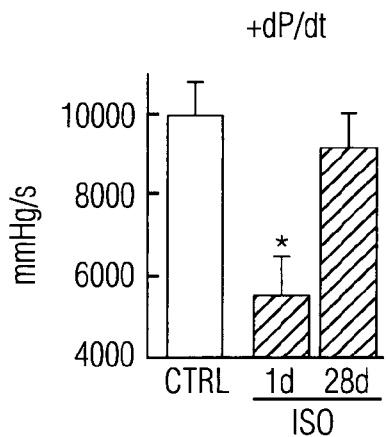
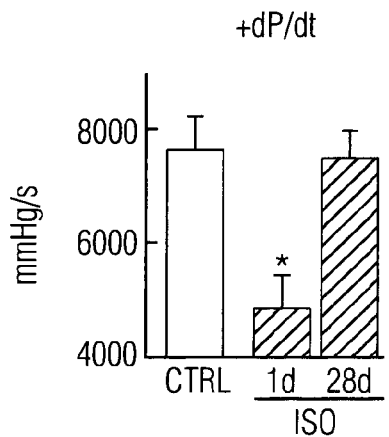
Fig. 22F YFP$^{pos}$ c-kit$^{pos}$ CD45$^{neg}$ eCSCs Tri-lineage Differentiation in vitro

| Genes Over-Expressed in | | | |
|---|---|---|---|
| Differentiated vs. Undifferentiated pCSCs | | | |
| Position | Gene Symbol | Fold Regulation | p-value |
| A04 | BMP2 | 4.1989 | 0.000727 |
| B12 | NOGGIN | 3.3326 | 0.002358 |
| C04 | GDF9 | 2.8089 | 0.031078 |
| C06 | GDF15 | 4.801 | 0.003233 |
| C11 | IGF2 | 3.302 | 0.182151 |
| D03 | PDGFRc | 2.0405 | 0.129537 |
| D05 | IL1A | 2.1189 | 0.02994 |
| D09 | IL8 | 2.0186 | 0.023874 |
| E04 | JAG2 | 2.639 | 0.035079 |
| E06 | LIF | 2.4509 | 0.006239 |
| F06 | SPP1 | 3.1023 | 0.000083 |
| F11 | TGFB3 | 8.5347 | 0.000596 |
| G09 | TIMP2 | 2.8812 | 0.00501 |

| Genes Under-Expressed in | | | |
|---|---|---|---|
| Differentiated vs. Undifferentiated pCSCs | | | |
| Position | Gene Symbol | Fold Regulation | p-value |
| A10 | HGF | -2.362 | 0.061775 |
| A11 | KITLG | -3.0314 | 0.001784 |
| C07 | POSTN | -4.8568 | 0.024854 |
| D02 | PDGFRa | -4.2673 | 0.000011 |
| D08 | IL6 | -7.8899 | 0.035898 |
| D11 | IL33 | -10.1965 | 0.023282 |
| F01 | Neuregulin 2 | -2.308 | 0.268521 |
| F03 | NTF3 | -25082 | 0.002924 |
| F04 | PGF | -7.3615 | 0.002044 |
| F05 | FST | -5.0164 | 0.066429 |

Fig. 30C

Genetic Stability of Human eCSCs After 68 Passages

|     | Pig 02 |      | Pig 03 |      | Pig 04 |      |
| --- | ---    | ---  | ---    | ---  | ---    | ---  |
|     | 25     | 100  | 25     | 100  | 25     | 100  |
| T0  | 0,9    | 1,77 | 1,55   | 8,53 | 0,99   | 4,23 |
| T3  | 9,3    | 17,2 | 18,3   | 19,3 | 1,26   | 1,66 |
| T4  | 5,0    | 7,35 | 18,2   | 7,53 | 1,91   | 2,86 |
| T5  | 8,7    | 15,7 | 31,3   | 15,7 | 3,87   | 6,18 |
| T6  | 56,0   | 31,2 | 53,3   | 24,8 | 46,1   | 66,5 |
| T7  | 43,4   | 21,1 | 59,1   | 35,7 | 34,2   | 23,5 |
| T8  | 36,2   | 18,6 | 53     | 49,6 | 22,2   | 40,4 |
Fig. 33A
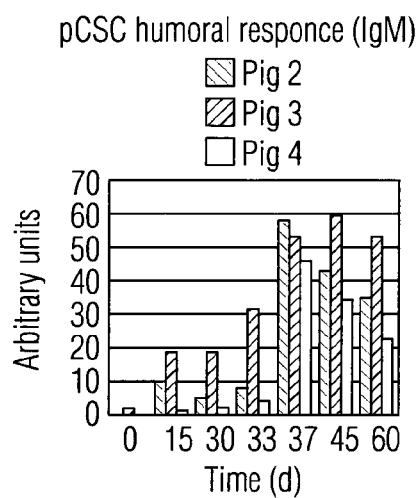
Fig. 33B
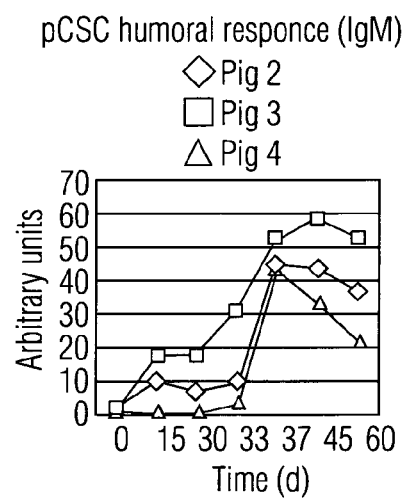
Fig. 33C

|    | Pig 02 |      | Pig 03 |      | Pig 04 |      |
|----|--------|------|--------|------|--------|------|
|    | 25     | 100  | 25     | 100  | 25     | 100  |
| T0 | 1,75   | 1,5  | 1,9    | 1,41 | 2,2    | 1,94 |
| T3 | 2,27   | 1,93 | 2,01   | 1,7  | 18,6   | 1,85 |
| T4 | 6,72   | 2,31 | 3,11   | 2,89 | 1,77   | 2,14 |
| T5 | 9,25   | 3,82 | 4,6    | 5,32 | 1,67   | 2,48 |
| T6 | 43,1   | 12,4 | 23,4   | 17,3 | 8,87   | 5,16 |
| T7 | 54,3   | 16,7 | 47,4   | 24,2 | 16,6   | 7,26 |
| T8 | 54,8   | 39,3 | 48,3   | 27   | 12,9   | 7,48 |
Fig. 34A
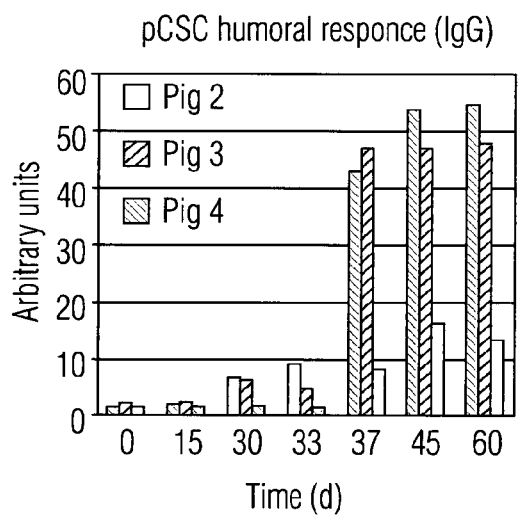
Fig. 34B
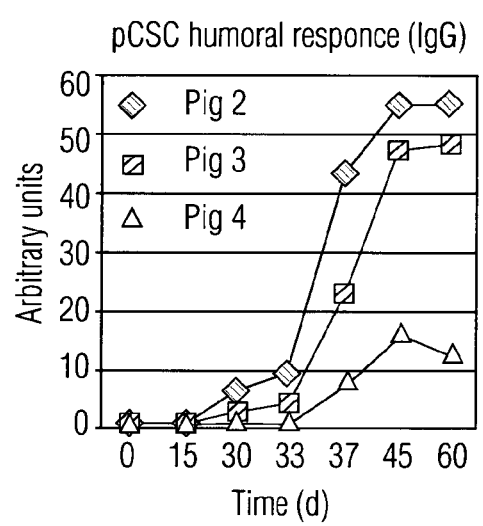
Fig. 34C BrdU  α-sarc  DAPI BrdU  vWF  DAPI

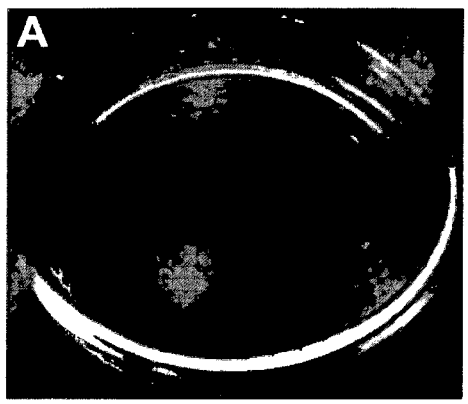 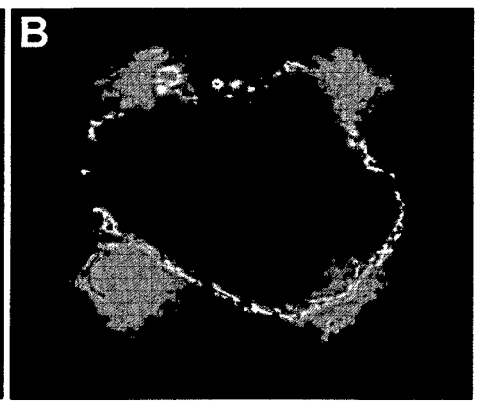
Fig. 40A  Fig. 40B
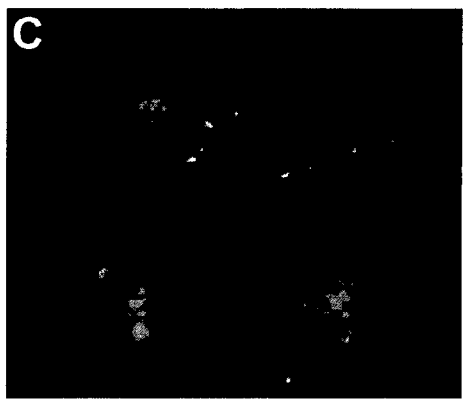 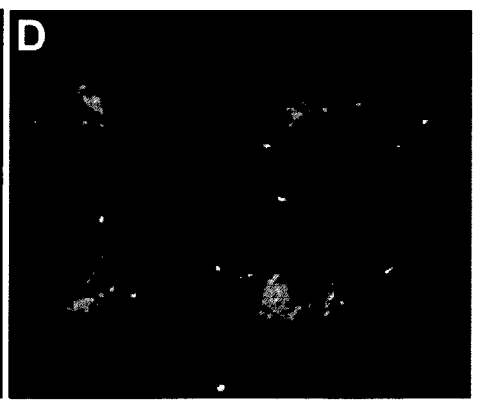
Fig. 40C  Fig. 40D
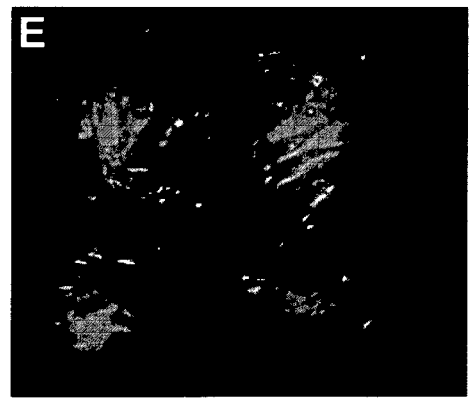 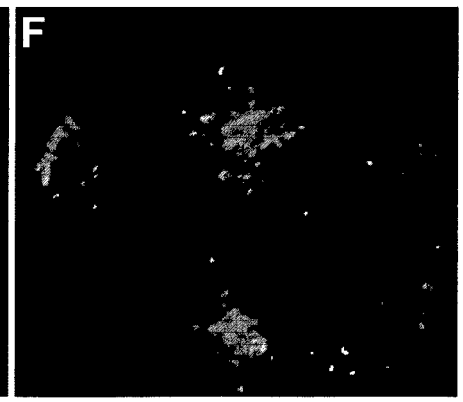
Fig. 40E  Fig. 40F

MODULATION OF CARDIAC STEM-PROGENITOR CELL DIFFERENTIATION, ASSAYS AND USES THEREOF

RELATED APPLICATIONS

This application is a U.S. National Stage under 35 U.S.C. § 371 of International Application No. PCT/EP2014/000193. Entitled "MODULATION OF CARDIAC STEM-PROGENITOR CELL DIFFERENTIATION, ASSAYS AND USES THEREOF," filed Jan. 24, 2014, which in turn claims the benefit of U.S. provisional application Ser. No. 61/756,328, filed Jan. 24, 2013 and U.S. provisional application Ser. No. 61/756,305, filed Jan. 24, 2013, which are hereby incorporated by reference in their entireties.

SEQUENCE LISTING

The instant application contains a Sequence Listing which has been filed electronically in ASCII format and is hereby incorporated by reference in its entirety. Said ASCII copy, created on Aug. 23, 2019, is named 111209-0102_SL.txt and is 13,049 bytes in size.

1. INTRODUCTION

The present invention relates to isolated endogenous cardiac stem-progenitor cells (eCSCs). Provided herein are c-kit$^{pos}$eCSCs that are negative for the hematopoietic marker, CD45 and the mast cell marker, Tryptase. Also provided herein are isolated c-kit$^{pos}$ eCSCs express at different levels, CD90, PDGFrα, CXCR4, Nestin, CD146, CD 166 and Flk-1 and do not express Wilms Tumor-1 (Wt1).

Also provided herein are clonal population of c-kit$^{pos}$ eCSCs from single cell derivation, that expresses the pluripotency genes, Oct-4, Klf-4, Nanog and Sox-2. These single cell derived eCSCs can differentiate into a variety of specific cell types corresponding to the derivatives of the three germ layers. Also provided herein is a stage-specific TGF-β-Family/Wnt-Inhibitor cocktail for modulating in vitro myogenic specification and maturation of c-kit$^{pos}$ eCSCs.

Also provided herein are methods of modulating eCSCs clonal expansion, growth and differentiation. Provided herein are methods that can be employed to regulate and control the differentiation and maturation of mammalian, particularly human, eCSCs. Also provided herein are screening assays for small organic molecules that modulate the differentiation and maturation of mammalian eCSCs or the modulation of early cardiomyogenic progenitor cells along a specific differentiation pathway. The invention also relates to the temporal aspects of cardiac stem-progenitor cell development, and in vitro models based upon these temporal aspects. The invention further relates to the use of these modulated cells in prophylactic and therapeutic methods, including in pharmaceutical compositions of such cells and/or small organic compounds. Finally, the invention relates to the use of such differentiated cells in transplantation and other medical treatments.

2. BACKGROUND

During embryonic development, normal adult heart cell homeostasis and in response to cardiac injury, cardiogenesis requires the formation of muscle and non-muscle cell lineages within the myocardial tissue (1-5). Cardiac tissue development is orchestrated by the expansion and differential specification of cardiac multipotent progenitor/precursor cells (1-4). On the other hand, maintenance of cardiac cell diversity during adulthood, in response to normal wear and tear or following minor or major damages, appears to be mainly due to the activity of cardiac stem/progenitor cells (5,6). Indeed, the adult heart harbours resident and tissue-specific endogenous cardiac stem-progenitor cells (eCSCs), even though several phenotypically different cell populations with dissimilar regenerative potential have been described so far (5,7). Understanding how embryonic progenitor/precursor and adult stem/progenitor cells generate and control the formation of pacemaker, atrial and ventricular muscle cell lineages, or smooth muscle and endothelial vascular cell lineages is of fundamental importance in unravelling the molecular cues that underlie both cardiovascular development and myocardial regeneration. In particular, while a number of molecules and signalling pathways driving heart cell specification in embryonic life have been established, whether the same mechanisms (or different) are operative on adult eCSCs is largely unknown (8,9). Elucidation of factors and signalling pathways that govern eCSC self-renewal and differentiation and their mode of action, in addition to providing a better understanding of adult myocardial biology, could also make feasible the design of a cocktail of growth factors and activating molecules which could stimulate in situ the expansion and maturation of these regenerative cells (10).

To date, no one has described isolated and enriched c-kit$^{pos}$eCSCs, that are CD45$^{neg}$, and Tryptase$^{neg}$. No one has described a reproducible method to isolate and enrich these cells to generate amounts large enough to be suitable for therapeutic purposes. The enriched population contains more than 98% of eCSCs that have these properties. No one has described the use of compositions discussed below, in the growth and differentiation of eCSCs. In particular, no one has demonstrated the use of such composition to modulate the differentiation of c-kit$^{pos}$eCSCs, that are CD 166$^{pos}$, CD45$^{neg}$, and Tryptase$^{neg}$. Likewise, no one has described the use of the compounds described herein to expand the eCSCs populations so as to produce a pharmaceutical composition containing such cells. Such expanded eCSCs cell cultures would be useful in the treatment of damaged cardiacmyogenic tissues. Because control over cardiac stem-precursor cell differentiation can produce cell populations that are therapeutically useful, there is a need for the ability to control and regulate the differentiation of cells of cardiacmyogenic lineage.

3. SUMMARY

Provided herein are eCSCs populations, and methods of culturing, proliferating and expanding the same. Also provided herein are methods of differentiating the eCSCs. Also provided herein are methods of using the eCSCs in assays and for transplanting into the myocardium. Also provided herein is clonal c-kit$^{pos}$ eCSCs that express multipotency genes and can give rise to cells of the 3 germ layers. Also provided are compositions containing factors, molecule(s), and a stage-specific method for inducing myocyte growth and specification of c-kit$^{pos}$ eCSCs.

Provided herein are isolated eCSCs, and cell populations comprising such cells, wherein the eCSCs are present in, and isolatable from cardiac tissues of different mammalian species, including human. The eCSCs exhibit one or more characteristics of a stem cell (e.g., exhibit markers associated with stem cells, replicate at least 10-20 times in culture in an undifferentiated state, differentiate into adult cells representative of the three germ layers, etc.), and can adhere to a tissue culture substrate (e.g., tissue culture plastic such as the surface of a tissue culture dish or multiwell plate).

The present invention relates to endogenous cardiac stem-progenitor cells (eCSCs). In certain embodiments, provided herein are c-kit$^{pos}$ eCSCs that are negative for the hematopoietic marker, CD45 and the mast cell marker, Tryptase. Also provided herein are isolated c-kit$^{pos}$ eCSCs express at different levels, CD90, PDGFrα, CXCR4, Nestin, CD146, CD166 and Flk-1 and do not express Wilms Tumor-1 (Wt1). Also provided herein are clonal population of c-kit$^{pos}$ eCSCs from single cell derivation that expresses the pluripotency genes, Oct-4, Klf-4, Nanog and Sox-2. These single cell derived eCSCs can differentiate into a variety of specific cell types corresponding to the derivatives of the three germ layers. Provided herein are the cells that are produced by the above methods that are useful as pharmaceutical compositions. In another embodiment, provided herein is a population of isolated stem-progenitor cells comprising, e.g., that is enriched for, eCSCs. In various embodiments, at least 10%, at least 20%, at least 30%, at least 40%, at least 50% at least 60%, at least 70%, at least 80%, at least 90%, or at least 95% or more of said isolated eCSCs are c-kit$^{pos}$eCSCs that are negative for the hematopoietic marker, CD45 and the mast cell marker, Tryptase. In certain embodiments, at least 10%, at least 20%, at least 30%, at least 40%, at least 50% at least 60%, at least 70%, at least 80%, at least 90%, or at least 95% or more of said isolated eCSCs expresses the pluripotency genes, Oct-4, Klf-4, Nanog and Sox-2. In certain embodiments, said population has been expanded, e.g., passaged at least once, at least three times, at least five times, at least 10 times, at least 15 times, or at least 20 times. In certain embodiments, said population forms contractile myocytes when cultured under conditions that allow formation of contractile myocytes.

Provided herein is an isolated population of the eCSCs described herein that is produced according to a method described herein.

In certain embodiments, provided herein is a composition comprising a stem cell described herein. In certain embodiments, the composition comprises eCSCs.

In another specific embodiment, any of the foregoing compositions comprises a matrix. In a more specific embodiment, said matrix is a three-dimensional scaffold. In another more specific embodiment, said matrix comprises collagen, gelatin, laminin, fibronectin, pectin, ornithine, or vitronectin. In another more specific embodiment, said matrix comprises an extracellular membrane protein. In another more specific embodiment, said matrix comprises a synthetic compound. In another more specific embodiment, said matrix comprises a bioactive compound. In another more specific embodiment, said bioactive compound is a growth factor, cytokine, antibody, or organic molecule of less than 5,000 daltons.

In another embodiment, provided herein is a composition comprising medium conditioned by any of the foregoing stem cells, or any of the foregoing stem cell populations. In a specific embodiment, any such composition comprises a stem cell that is not derived from cardiac tissues.

The eCSCs, as modulated by a composition as disclosed herein, are useful for transplantation (i.e., cardiomyogenic reconstitution), and may be used in regenerative medicine as a renewable source of replacement cells and tissues (including cardiac muscle cells) to treat normal senescence, injury or diseases such as heart disease, stroke, Parkinson's disease, cardiotoxicity produced by certain antioncogenic drugs (e.g. Herceptin and Doxorubicine) and Alzheimer's disease. The cells will also be useful in the determination of the intracellular biochemical pathways that mediate the action of the composition as provided herein. These cells may also be useful for the screening of new drugs and toxins, for example, to determine potential anti-cancer drugs, to understand the origins of birth defects, determine the cardiac toxicity of different therapeutic compounds, etc. Provided herein is the transplantation of pretreated eCSCs to treat or prevent disease. In one embodiment, a patient in need of transplantation is also administered a composition as disclosed herein before, during and/or after transplantation. In other embodiments, provided herein is the control or regulation of eCSCs in vivo by the administration of both eCSCs and a small molecule compound as disclosed herein to a patient in need thereof.

Also provided herein is a method for the isolation and expansion of human cardiac stem-progenitor cells from a myocardial biopsy obtained from a biopsy catheter, direct sampling during cardiac surgery or a cadaver. In certain embodiments, the method comprises enzymatic digestion. In certain embodiments, the method comprises cardiac tissue culturing.

Also provided herein is a stage-specific TGF-β-Family/Wnt-Inhibitor composition for modulating in vitro myogenic specification and maturation of c-kit$^{pos}$ eCSCs. In certain embodiments, the composition comprises Wnt/β-catenin. In certain embodiments, the composition comprises Wnt-3a. In certain embodiments, the composition comprises Dkk-1. In certain embodiments, the composition comprises β-catenin$^{shrna}$. In certain embodiments, the composition comprises Dkk-1/β-catenin$^{shrna}$. In certain embodiments, the composition comprises TGF-β1/Smad2. In certain embodiments, the composition comprises BMP-2, BMP-4 and TGF-β1. In certain embodiments, the composition comprises Smad2$^{shrna}$. In certain embodiments, the composition comprises TGF-β family/Wnt-inhibitor. In certain embodiments, the composition comprises BMP-2, BMP-4, TGF-β1 and Dkk-1. Provided herein is a composition comprising one or more cardiopoietic growth factors. In certain embodiments, the composition comprises IGF-1, Wnt3a, FGF-2, HGF or a combination thereof. In certain embodiments, the composition comprises TGF-β, Wnt5a, BMP-2 or BMP-4 or a combination thereof. In one embodiment, provided herein is a pharmaceutical composition comprising eCSCs as described herein that have been contacted with one or more growth factors as described herein, particularly one that regulate the activity of Wnt, β-catenin or TGF-β, in the first six days of culture, under conditions that promote proliferation and differentiation of said progenitor cells, and a pharmaceutically-acceptable carrier. In a specific embodiment, the pharmaceutical composition includes cells that have been collected and cryopreserved after six days of culture. In another specific embodiment, the cells of the pharmaceutical composition are c-kit$^{pos}$eCSCs and are negative for the hematopoietic marker, CD45 and the mast cell marker, Tryptase. In certain embodiments, the cells of the pharmaceutical composition are c-kit$^{pos}$eCSCs, and expresses CD90, PDGFrα, CXCR4, Nestin, CD146, CD166 and Flk-1. In certain embodiments, the cells of the pharmaceutical composition are c-kit$^{pos}$eCSCs and do not express Wilms Tumor-1 (Wt1). In certain embodiments, the cells of the pharmaceutical composition are c-kit$^{pos}$eCSCs that expresses Oct-4, Klf-4, Nanog and Sox-2.

In another embodiment, the invention also provides for method of making a pharmaceutical composition, comprising contacting eCSCs with a compound that regulates the activity of Wnt, β-catenin or TGF-β, wherein said eCSCs are cultured for six days in a culture medium under culture conditions that allow proliferation and differentiation of said eCSCs; collecting said cells after six days of culture; and combining said cells with a pharmaceutically-acceptable carrier. In a specific embodiment, said contacting is performed on the first day of culture. In another specific embodiment, said contacting is performed at least twice during said six days of culture. In another specific embodiment of this method, said cells are cryopreserved after said collecting. In certain embodiments, provided herein are eCSCs wherein said cells have been cryopreserved, wherein said population is contained within a container. In a specific embodiment of any of the foregoing cryopreserved populations, said container is a bag. In various specific embodiments, said population comprises about, at least, or at most $1\times10^6$ said stem cells, $5\times10^6$ said stem cells, $1\times10^7$ said stem cells, $5\times10^7$ said stem cells, $1\times10^8$ said stem cells, $5\times10^8$ said stem cells, $1\times10^9$ said stem cells, $5\times10^9$ said stem cells, or $1\times10^{10}$ said stem cells. In other specific embodiments of any of the foregoing cryopreserved populations, said stem cells have been passaged about, at least, or no more than 5 times, no more than 10 times, no more than 15 times, no more than 20 times or no more than 30 times or no more than 40 times. In another specific embodiment of any of the foregoing cryopreserved populations, said stem cells have been expanded within said container.

Provided herein is a method for expanding a eCSCs population in a mammalian subject, comprising administering a therapeutically effective amount of eCSCs to said recipient mammalian subject. In specific embodiment of this method, said eCSCs are differentiated in the recipient mammalian subject. In another specific embodiment of this method, said eCSCs are administered to said subject in a cell preparation that is substantially free of non-eCSCs cells. In another specific embodiment of this method, said eCSCs are administered to the recipient mammalian subject in a cell preparation that comprises growth factors or small molecules that are described herein. In another specific embodiment of this method, said eCSCs are administered to the recipient mammalian subject in conjunction with a carrier. In another specific embodiment of this method, the eCSCs express incorporated genetic material of interest.

The cells can be administered to the same subjects or to a different subject from whom/which the cells were originally isolated. In certain embodiments, the transplant is autologous. In certain embodiments, the transplant is allogeneic. The transplant is allogeneic if administered to recipients of the same species but to individuals other than from the donor. In certain embodiments, the transplant is to recipients of another family, genus or species.

In yet other embodiments, the invention encompasses methods of conditioning eCSCs, following cryopreservation and thawing, to counteract the deleterious effects of cryopreservation and exposure to cryopreservatives on the stem cells. In certain embodiments, the invention provides methods of conditioning stem cells following cryopreservation and thawing, to counteract the deleterious effects of exposure to cryopreservatives (e.g., DMSO) on the proliferative and migratory capacity of stem cells.

Also provided herein are methods of modulating eCSCs clonal expansion, growth and differentiation. Provided herein are methods that can be employed to regulate and control the differentiation and maturation of mammalian, particularly human, eCSCs. The methods include regulating the activity of Wnt, β-catenin or TGF-β. The method comprises providing the composition described herein. The disclosure further contemplated administration of these compositions to eCSCs at specific times to modulate their differentiation in specific ways.

It has been discovered that the timing of the administration of the compositions described herein have a profound impact upon the growth and/or differentiation of eCSCs. Thus, in one embodiment, differentiation of eCSCs into myocytes is delayed or suppressed by a method comprising contacting the eCSCs on the first day of culture with a composition disclosed herein. In another embodiment, the development of eCSCs is reduced or prevented by a method comprising contacting said eCSCs with a composition on the first day of culture. In another embodiment, the persistence of a clonal eCSCs cell population derived from eCSCs progenitor cells is increased by contacting said progenitor cells with a composition after culturing said progenitor cells for six days in the absence of said composition.

The present invention also encompasses methods of modulating the differentiation of eCSCs, comprising contacting the progenitor cells at various times during the proliferative and differentiative phases with one or more of the compositions as disclosed herein. Thus, in one embodiment, the method of modulating the differentiation of the progenitor cells comprising contacting said cells with one or more compositions on the first day of culture only. In another embodiment, said cells are contacted with said composition in one dose on any day between the first day and the twelfth day of culture. In another embodiment, said cells are contacted at least two times with said composition, on different days, between days 0-12, inclusive. In yet another embodiment, said cells are contacted with one or more composition twice a day, once a day, or once every other day during the proliferative and/or differentiation phases. In another embodiment, said contacting is performed in vitro. In yet another embodiment, said contacting is performed in vivo in a subject. In a more specific embodiment, said subject is a human, a non-human mammal, an bird or a reptile.

Also provided herein are methods to induce eCSCs to produce contractile myocytes comprising: (i) adding oxytocin to a culture medium to form cardiospheres and culture cells for a period of time; (ii) adding BMP-2, BMP-4, TGF-β1 and Dkk-1 and culture cells for a period of time; (iii) removing BMP-2, BMP-4, TGF-β1 and culture cells for a period of time; and (iv) adding Dkk-1 and culture cells for a period of time.

Also provided herein are screening assays for small organic molecules that modulate the differentiation and maturation of mammalian eCSCs or the modulation of cardiomyocyte development. Provided herein are screening assays for small molecules that modulate the differentiation and maturation of early cardiomyogenic progenitor cells along a specific differentiation pathway. The invention also relates to the temporal aspects of cardiac stem-progenitor cell development, and in vitro models based upon these temporal aspects. The invention further relates to the use of these modulated cells in prophylactic and therapeutic methods, including in pharmaceutical compositions of such cells and/or small organic compounds. Finally, the invention relates to the use of such differentiated cells in transplantation and other medical treatments.

3.1 Definitions

As used herein, the term "endogenous cell" refers to a "non-foreign" cell, i.e., a "self" or autologous cell, that is derived from the heart.

As used herein, the term "autologous transplantation" refers to the transplantation of isolated cells into the blood or solid tissues of the donor.

As used herein, the term "allogeneic transplantation" refers to the transplantation of cells isolated from one particular donor and either expanded in vitro or not, are transplanted into a recipient or recipients of the same species but others than the donor.

As used herein, the term "multipotent cell" refers to a cell that has the capacity to grow into any of subset of the mammalian body's approximately 260 cell types. Unlike a pluripotent cell, a multipotent cell does not have the capacity to form all of the cell types.

As used herein, the term "pluripotent cell" refers to a cell that has complete differentiation versatility, i.e., the capacity to grow into any of the mammalian body's approximately 260 cell types. A pluripotent cell can be self-renewing, and can remain dormant or quiescent within a tissue. Unlike a totipotent cell (e.g., a fertilized, diploid egg cell), a pluripotent cell cannot usually form a new blastocyst to give raise to a whole embryo.

As used herein, the term "progenitor cell" refers to a cell that is committed to differentiate into a specific type of cell or to form a specific type of tissue.

As used herein, the term "stem cell" refers to a master cell that can reproduce indefinitely to form the specialized cells of tissues and organs. A stem cell is a developmentally pluripotent or multipotent cell. A stem cell can divide to produce two daughter stem cells, or one daughter stem cell and one progenitor ("transit") cell, which then proliferates into the tissue's mature, fully formed cells.

As used herein, the term "isolated stem-progenitor cell" or "isolated eCSC" means a stem-progenitor cell or eCSC that is substantially separated from other, non-stem-progenitor cells, non-eCSCs of the tissue, e.g., heart, from which the stem-progenitor cell is derived. A stem-progenitor cell is "isolated" if at least 50%, 60%, 70%, 80%, 90%, 95%, or at least 99% of the non-stem-progenitor cells with which the stem-progenitor cell is naturally associated, or stem-progenitor cells displaying a different marker profile, are removed from the stem-progenitor cell, e.g., during collection and/or culture of the stem-progenitor cell.

As used herein, the term "population of isolated cells" means a population of cells that is substantially separated from other cells of the tissue, e.g., heart, from which the population of cells is derived. A stem cell is "isolated" if at least 50%, 60%, 70%, 80%, 90%, 95%, or at least 99% of the cells with which the population of cells, or cells from which the population of cells is derived, is naturally associated, i.e., stem cells displaying a different marker profile, are removed from the stem cell, e.g., during collection and/or culture of the stem cell.

As used herein, the term "stem-progenitor cell" refers to a stem-progenitor cell that is derived from a mammalian heart, regardless of morphology, cell surface markers, or the number of passages after a primary culture. The term "stem-progenitor cell" as used herein does not, however, refer to a trophoblast. A cell is considered a "stem-progenitor cell" if the cell retains at least one attribute of a stem-progenitor cell, e.g., a marker or gene expression profile associated with one or more types of stem-progenitor cells; the ability to replicate at least 10-40 times in culture, the ability to differentiate into cells of all three germ layers; the lack of adult (i.e., differentiated) cell characteristics, or the like.

As used herein, a stem-progenitor cell is "positive" for a particular marker when that marker is detectable above background in comparison to, e.g., an isotype control. A cell is also positive for a marker when that marker can be used to distinguish the cell from at least one other cell type, or can be used to select or isolate the cell when present or expressed by the cell. In the context of, e.g., antibody-mediated detection, "positive," as an indication a particular cell surface marker is present, means that the marker is detectable using an antibody, e.g., a fluorescently-labeled antibody, specific for that marker or using RT-PCR; "positive" also means that a cell bears that marker in a amount that produces a signal, e.g., in a cytometer, that is detectably above background. Conversely, "negative" in the same context means that the cell surface marker is not detectable using an antibody specific for that marker compared to background or using RT-PCR.

4. DESCRIPTION OF THE FIGURES

FIGS. 1(A-F). Adult c-kit$^{pos}$ CD45$^{neg}$ eCSCs are clonogenic and express pluripotency markers (A) Representative scatter plot showing the purity of immunomagnetic bead sorted c-kit$^{pos}$ (CD45$^{neg}$) eCSCs from a normal adult rat heart. (B) A single c-kit$^{pos}$ CD45$^{neg}$ eCSC (B; top panel) gives rise to a clone of eCSCs (B; bottom panel; Bar=100 µm). (C) The eCSCs have a clonal efficiency of ~21%. *P<0.05 vs. ckit$^{neg}$; †P<0.01 vs. total c-kit$^{pos}$ cell population. Data are Mean±SD of 10 plates/population. (D) Immuno-fluorescent staining of cloned c-kit$^{pos}$ (green) eCSCs at Passage 0 (P0) for expression of pluripotent and cardiac markers (red). Nuclei are stained in blue by DAPI. Bar=20 µm. (E) qRT-PCR confirms that cloned c-kit$^{pos}$ eCSCs express pluripotent transcripts, similar to expression in rat ICM at embryonic stage 4 (E4; CTRL). Data are Mean±SD of 5 clones/gene at P0. *P<0.01 vs. c-kit$^{pos}$ eCSCs (F) Representative western blot confirm expression of Oct-4 and Nanog in clonal c-kit$^{pos}$ eCSCs at P0.

FIG. 2(A-D). Phenotype of adult c-kit$^{pos}$ CD45$^{neg}$ eCSCs and are cardiac multipotent. (A-B) Phenotyping of clonal c-kit$^{pos}$ CD45$^{neg}$ eCSCs shows expression of PDGFrα, CXCR4, Nestin, Flk-1, and CD146. c-kit$^{pos}$ CD45$^{neg}$ eCSCs are negative for Wt1 (C) Sub-cloning efficiency of a clone of c-kit$^{pos}$ eCSC tested at every 10th passage show maintained and increased their clonogenicity. *P<0.01 vs. P0. (D) Sub-clones of c-kit$^{pos}$ eCSCs, generated at P1, P25 and P50 of the original clone, maintained their expression of pluripotent and cardiac potential genes. (I) Cardiospheres generated from clonal c-kit$^{pos}$ (green) eCSCs differentiate into the cardiomyocyte (cTnI, red), smooth muscle (SMA, red) and endothelial (vWF, red) cell lineages. Nuclei are stained in blue by DAPI. Bar=50 µm.

FIGS. 3(A-F). Adult myocardium produces cardiopoietic factors acting on the specific receptors of c-kit$^{pos}$ eCSCs in vivo (A) c-kit$^{pos}$ eCSCs express the receptors for BMP-2 (BMP-RII), FGF-2 (FGF-R1), Wnts (Fzd5 and LRP6), TGF-β1 (TGFβ-R1 and RII), IGF (IGF-1R), and HGF (c-met). (B) qRT-PCR data confirming c-kit$^{pos}$ eCSCs express the transcripts for different growth factor receptors. (C-D) Representative western blots for activation of IGF-1 and TGF-β1 receptors and their downstream signaling, on c-kit$^{pos}$ CD45$^{neg}$ eCSCs after ISO-induced damage in vivo. (E) Histochemical staining for different cardiopoietic growth factors (DAB, Brown) of LV sections from 24 hr ISO-injured rats. Bar=100 µm. (F) Representative western blots of the cardiopoietic growth factors in cardiomyocytes after ISO.

FIGS. 4(A-E). Adult myocardium produces cardiopoietic factors acting on the specific receptors of c-kit$^{pos}$ eCSCs in vivo (A-C) Effect of growth factors and cytokines on c-kit$^{pos}$ eCSC proliferation (A), clonogenicity (B), and cardiomyocyte differentiation (C) which was measured as percentage of cardiac troponin I (cTnI) expressing cells after 14 days in culture. *P<0.05 vs. CTRL. (D) Representative immunostaining of cardiac troponin I (cTnI; red) positive eCSC-derived cells following supplementation with IGF-1 (left panel) or TGF-β1 (right panel). Nuclei were identified by DAPI in blue. Bar=50 μm. (E) qRT-PCR analysis showing the fold change of c-kit, Oct-4, Gata-4, Nkx2.5 and cTnI mRNAs following 14 days in base differentiation medium (CTRL) and base differentiation medium supplemented with IGF-1 or TGF-β1, compared to cloned c-kit$^{pos}$ eCSCs at P0 (Base). *P<0.05 vs. CTRL. †P<0.05 vs. IGF-1. Data are Mean±SD of n=6/condition.

FIGS. 5(A-F). Cardiopoietic factors determining c-kit$^{pos}$ eCSC fate in vitro (A) Representative immunoprecipitation and western blot show stimulation of c-kit$^{pos}$ CSCs with Wnt-3a drives canonical pathway activation as shown by β-catenin nuclear translocation and binding to TCF (B) Western blot shows the lentiviral vector for β-catenin shRNA significantly reduced its specific target. (C-E) Effect of canonical Wnt pathway activation on c-kit$^{pos}$ CSC proliferation (C), clonogenicity (D) and cardiomyocyte differentiation (E). *P<0.05 vs. BASE; †P<0.05 vs. the respective treatment. (F) qRT-PCR analysis showing the fold change of Oct-4, c-kit, Gata-4, Nkx2.5 and cTnI mRNAs following 14 days in base differentiation medium (CTRL) and base differentiation medium supplemented with Wnt-3a-CM or Dkk-1, compared to cloned c-kit$^{pos}$ CSCs (Base). *P<0.05 vs. CTRL. †P<0.05 vs. Wnt-3a-CM FIGS. 6(A-F). The Effects of Canonical Wnt and TGF-β1/SMAD-2 pathways on eCSC fate (A) Representative western blot shows TGFβ-1 activates the canonical Smad-2 pathway in c-kit$^{pos}$ CSCs as shown by the phosphorylation of SMAD-2. (B) The specific lenti shRNA significantly reduced Smad2 protein in c-kit$^{pos}$ CSCs. (C-E) Effect of TGF-β1 and BMP 2 and 4 on c-kit$^{pos}$ eCSC proliferation (C), clonogenicity (D) and cardiomyocyte differentiation (E). *P<0.05 vs. BASE; †P<0.05 vs. the respective treatment. (F) qRT-PCR analysis showing the fold change of Oct-4, c-kit, Gata-4, Nkx2.5 and cTnI mRNAs following 14 days in base differentiation medium (CTRL), TGF-β1 or Smad2$^{shRNA}$+TGF-β1, compared to cloned c-kit$^{pos}$ eCSCs (Base). *P<0.05 vs. CTRL. †P<0.05 vs. Smad2shRNA+TGF-b1.

FIGS. 7(A-F). A stage-specific TGF-β-Family/Wnt Inhibitor cocktail induces c-kit$^{pos}$ eCSC cardiospheres to differentiate with high efficiency into spontaneously rhythmic beating cardiomyocytes in vitro. (A) c-kit$^{pos}$ (green) eCSC cardiospheres express pluripotent stemness markers (red). Nuclei are stained in blue by DAPI. Bar=50 μm. (B) Schematic timeline of the stage-specific protocol used for the differentiation of c-kit$^{pos}$ eCSC cardiospheres into functional, rhythmic beating cardiomyocytes in vitro. (C) Frequency of cTnI positive cells and percentage of beating cells (hatched bars) after manipulation of the TGF-β/Wnt signalling pathways, as indicated. *P<0.05 vs. all. (D) At days 8-14, eCSC cardiosphere cells stain positive for the cardiomyocyte lineage (S-Actinin, green), exhibiting sarcomeric structures (z lines and dots) and gap junction formation (Cnx-43; red) between cells. Bar=50 μm. (E) PCR products and (F) qRT-PCR analysis following the stage-specific cardiomyocyte differentiation protocol, revealed the change in transcripts for Oct-4, c-kit, Sox-2, Tert, Nkx2.5, Gata-4, β-MHC and cTnI in the differentiated cardiosphere eCSCs, relative to 0 days (undifferentiated cells). Data are Mean±.SD of 3 assays.

FIGS. 8(A-C). Multilineage differentiation of eCSCs. (A-C) c-kit$^{pos}$ eCSCs give rise to osteogenic (A), hepatic (B) and neurogenic (C) cell types.

FIGS. 9(A-D). (A) Representative scatter plots from flow cytometry analysis show that about 50% of the freshly isolated c-kit$^{pos}$ cardiac cells express the hematopoietic lineage marker, CD45. (B) Immunostaining of cytospin preparations of freshly isolated c-kit$^{pos}$ cardiac cells revealed that a significant fraction (about 50%) of c-kit$^{pos}$ cardiac cells are tryptase positive, identifying cardiac mast cells. Bar=20 μm. (C-D) Representative scatter plots show that about 15% and 10% of the freshly isolated c-kit$^{pos}$ cardiac cells express CD34 (hematopoietic and endothelial cell marker) and CD90 (mesenchymal cell marker), respectively. (E-F) The total c-kit$^{pos}$ cardiac cells were depleted of CD45 (see methods) and cytospin immunostaining showed high enrichment for c-kit and also through depletion of CD45$^{pos}$ cells, the depletion of tryptase positive cells (more than 90% of cardiac mast cells are CD45 positive, data not shown and see Sperr et al. 1994). Bar=20 μm. (G-H) 3% and 20% of the sorted c-kit$^{pos}$ CD45$^{neg}$ cardiac cells were positive for CD34 and CD90, respectively.

FIGS. 10(A-B). Representative gels showing PCR products with the corresponding bp length from qRT-PCR for Oct-4, Nanog, Sox-2 and Klf4 of clonogenic c-kit$^{pos}$ CSCs and E4 rat inner cell mass (ICM), which shows similar transcript levels between the two. ARVMs were used as a negative control. (B) Oct-4 gene sequencing shows perfect alignment of Oct-4 cDNA amplified from c-kit$^{pos}$ CSCs over the designed rat Oct-4 primer sequence (NM001009178).

Figure 11:
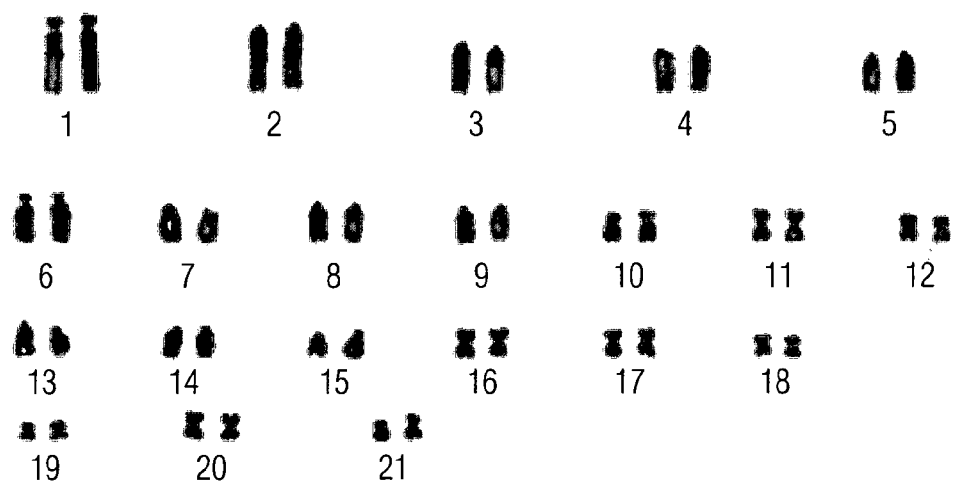

FIG. 11. Representative karyotype of cloned c-kit$^{pos}$ rat CSCs after 65 passages.

FIGS. 12(A-C). (A) The procedure used for the isolation of adult rat cardiomyocytes yielded a high purity of rod shaped cardiomyocytes. (B) Representative light microscope images of staining for the different cardiopoietic growth factors (HGF, IGF-1, FGF-2, BMP-4, Wnt-3a, Wnt-5a) on LV sections of CTRL rats. (c) qRT-PCR analysis of different growth factors and cytokines mRNAs in the surviving myocytes isolated from rats up to 72 hours after ISO-treatment. *P<0.05 vs. CTRL. Data are Mean±SD of n=5/group.

Figure 13:
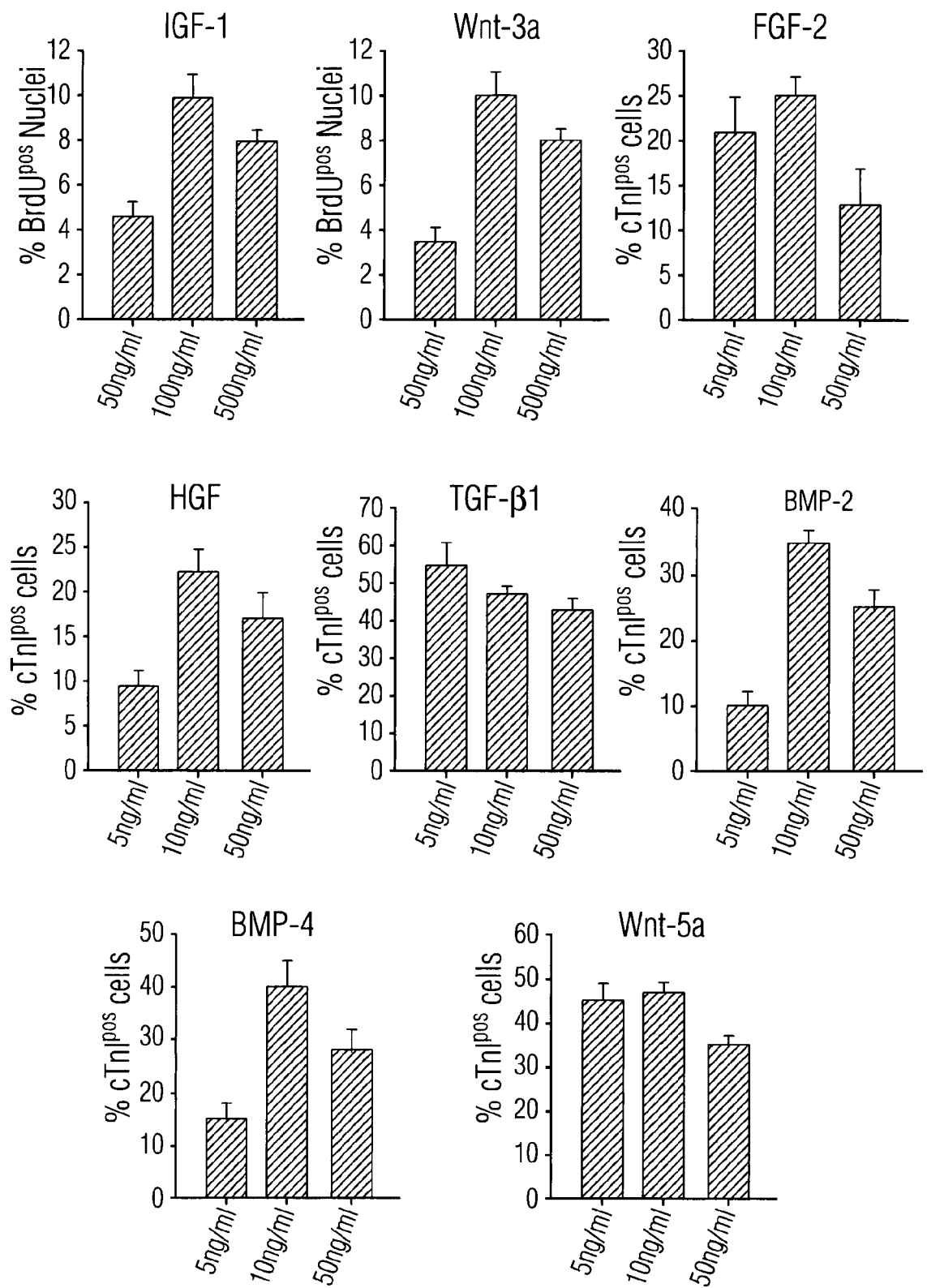

FIG. 13. Dose-response curves for the different growth factors on eCSC proliferation and cardiomyocyte specification.

FIGS. 14(A-L) eCSC Activation and Myogenic Differentiation Following Diffuse Myocardial Damage. (a-c) c-kit$^{pos}$eCSCs in myocardium (a), FACS cell cycle analysis (b) and percentage of activated c-kit$^{pos}$BrdU$^{pos}$eCSCs (c) in CTRL and after ISO. *p<0.01 vs. CTRL. (d-e) Confocal microscopy (d) and quantification of c-kit$^{pos}$/Nkx2.5$^{pos}$ progenitors (e; arrows) and myogenic precursor (arrowhead), 3 days after ISO. Bar=20 μm. *P<0.01 vs. CTRL. (f-i) Confocal microscopy (f,g) and quantification (h-i) of small newly-formed (BrdU), mitotic and proliferating (Ki67) CMs, 28 days after ISO. 50 mg kg$^{-1}$ of BrdU was injected (i.p.) twice daily. Bar=50 μm (f), 20 μm (g). *p<0.05 vs. CTRL. (j) Confocal microscopy of a small BrdU$^{pos}$ CM (arrow) with gap junction formation (Cnx43, white; arrowheads) between neighboring CMs, 28 days after ISO. Bar=20 μm. (k) Rod-shaped BrdU$^{pos}$ ventricular CMs, isolated 28 days after ISO (n=4). Bar=50 μm. (l) BrdU$^{pos}$ CM diameter. All data are Mean±SD. See also FIG. 21.

FIGS. 15(A-I) Myocyte Regeneration after Diffuse Myocardial Damage. (a) Schematic of pulse-chase genetic labeling of CM renewal. (b) Representative immunostaining with antibodies against GFP and β-galactosidase (both brown-DAB staining) in the sub-endocardial, apical layer of CTRL and 28 days after ISO. Bar=50 μm. (c) Fraction of $GFP^{pos}$ and $β-gal^{pos}$ CMs in CTRL and after ISO. $*p<0.05$ vs. CTRL. (d) Confocal microscopy (d) and percentage (e) of newly formed $β-gal^{pos}/BrdU^{pos}$ CMs, 28 days after ISO. Bar=20 μm. $*p<0.05$ vs. CTRL. (f) Immunocytochemistry identifies a small $BrdU^{pos}/YFP^{neg}$, mononucleated rod-shaped CM, isolated from pulse-labelled MerCreMer:RYP mice, 28 days after ISO (g) Flow cytometric analysis of GFP within the $c-kit^{pos}/CD45^{neg}$ eCSC compartment, following $BM^{GFP}$ transplantation and 28 days after ISO. n=5. (h) Confocal microscopy of newly formed $BrdU^{pos}/GFP^{neg}$ CMs. (i) CM regeneration after $BM^{GFP}$ transplantation. All data are Mean±SD. See also FIG. 22.

FIG. 16(A-J). Myocyte replenishment by $c-kit^{pos}$ eCSCs following diffuse myocardial damage. (a) Schematic of pulse-chase genetic labeling approach of resident $c-kit^{pos}$eCSCs and their progeny in situ. (b-c) Flow cytometric analysis show c-kit/cre Lentivirus labelling of eCSCs and CMs in vivo. (d) Representative confocal microscopy of apical YFP-labelled $c-kit^{pos}$eCSCs (d) (c-kit/YFP, green/white arrowheads; $c-kit^{pos}$ eCSCs not transfected, green arrowheads). Bar=20 μm. (e) Percentage of $BrdU^{pos}$ CMs, and those that were $YFP^{pos}$ in the LV and apex 28 days after ISO. $*p<0.05$ vs. CTRL or LV. (f) Representative confocal microscopy of apical $c-kit^{pos}$eCSC-derived $YFP^{pos}BrdU^{pos}$ CMs 28 days after ISO. Bar=20 μm. (g-h) Representative immunocytochemistry of $BrdU^{pos}/YFP^{pos}$ and $BrdU^{pos}/YFP^{neg}$ isolated CMs (g) and flow cytometric analysis of $YFP/cTnI^{pos}$ CMs (h), isolated from lenti c-kit/cre mice 28 days after ISO or saline (CTRL). n=3. (i) Heat map showing two-way hierarchical cluster of the expression of 3774 genes that underwent a log fold change ≥1 or ≤−1 (p value <0.005). See also National Center for Biotechnology Information, Gene Expression Omnibus ("GEO") Series GSE49318; Ellison et al. 2013 Cell 154(4):827-42. Enriched Gene Ontology (GO) terms for the genes of each cluster are shown to the right. (j) Heat map showing expression pattern of CM and cell cycle specific genes in $c-kit^{pos}$eCSCs, $YFP^{pos}$ CMs and adult terminally differentiated CMs. n=3 for each. See also FIG. 24-25; see National Center for Biotechnology Information, Gene Expression Omnibus ("GEO") Series GSE49318; Ellison et al. 2013 Cell 154(4):827-42).

FIG. 17(A-K) $c-kit^{pos}$CSCs exhibit selective homing to ISO-damaged myocardium and differentiate into new CMs. (a) Immunocytochemistry of clonal $c-kit^{pos}CSCs^{GFP}$. Bar=50 μm. (b) Quantification of tail vein injected $c-kit^{neg}$-$MDCCs^{GFP}$ and $c-kit^{pos}CSCs^{GFP}$ in the subendocardial layer after ISO. $*P<0.001$ vs. CTRL and $c-kit^{neg}$ $MDCCs^{GFP}$. (c-f) Confocal microscopy representative images of $GFP^{pos}$ $c-kit^{neg}MDCCs$ (c) and $c-kit^{pos}CSC^{GFP}$ in the myocardium of CTRL (d), and at 1 (e) and 6 (f) days after ISO and tail vein injection. Bar=30 μm (g-h) Confocal microscopy of a $Ki67^{pos}$ (g; arrow) $CSC^{GFP}$ (arrowheads) and a $CSC^{GFP}$-derived CM, 28 days after ISO and tail vein injection. Bar=20 μm. (i) Immunohistochemistry with antibody against SDF-1 (green; inset shows CM specific expression) in the ISO-injured myocardium. Bar=20 μm (j-k) Quantification of $CXCR4^{KO}c-kit^{pos}CSCs^{GFP}$ (j) and $c-kit^{pos}CSC^{GFP}$ in rats treated with a SDF-1 neutralizing antibody (SDF-1Ab) (k). $*p<0.05$ vs. CTRL. $^\#P<0.05$ vs. ISO 1 day. All data are Mean±SD. See also Tables 2-4 and FIG. 25.

FIG. 18(A-D). Ablation of $c-kit^{pos}$ eCSCs blocks myocyte regeneration. (a-b) Quantification of $c-kit^{pos}$eCSCs and $Ki67^{pos}$ new CM formation after ISO+5-Fluorouracil (5-FU) treatment. $*P<0.01$ vs. CTRL and 5-FU. (c) Confocal microscopy representative immunostaining of c-kit and Ki67 on ISO+5-FU treated LV sections, compared to 3 and 28 days after ISO. Bar=30 μm. (d) Echocardiographic LV function measurements following ISO+5-FU administration, compared to ISO+Saline. $*P<0.05$ vs. CTRL and 5-FU. All data are Mean±SD. See also FIG. 26.

FIG. 19(A-h). Restoration of the eCSC pool through exogenous $c-kit^{pos}$ eCSC transplantation normalizes myocardial tissue composition and function. (a) Brief schematic of in vivo rat study design. (b-c) Echocardiography and hemodynamic measurements after tail vein injection of saline, cFibro, $CSCs^{GFP}$ or $CSCs^{GFP/TK}$ in ISO+5-FU treated rats and after administration of GCV to $CSCs^{GFP/TK}$ animals. $*p<0.05$ vs. CTRL. (d) Quantification of $c-kit^{pos}$eCSC and $GFP^{pos}$CMs. $*p<0.05$ vs. CTRL; $^§$ $p<0.05$ vs. groups at 2 m; $^\#p<0.05$ vs. groups at 3 m; (e) Representative confocal microscopy of $c-kit^{pos}$ (white) $CSCs^{GFP}$ (green) in the myocardium of rats with ISO+5FU cardiomyopathy rescued by $CSC^{GFP}$ injection. (f) Flow cytometric analysis of $c-kit^{pos}CSCs^{GFP}$ isolated 2 months after tail vein injection. (g-h) Confocal microscopy of $c-kit^{pos}CSCs^{GFP}$-derived CMs in situ and following isolation, at 3 months after tail vein injection. Bar=20 μm. All data are Mean±SD. See also FIGS. 27-28 and Table 5.

FIG. 20(A-P). Re-isolated $CSCs^{GFP}$ retain tissue-specific stem cell properties. (a-d) $CSC^{GFP}$ isolated from cell chimeric hearts produce single cell-derived clones (a-c) and cardiospheres (d), with similar efficiently to the clonal parental $CSC^{GFP}$. Bar=100 μm (e-f) qRT-PCR transcript profile (e), and profile over passage number (f), of re-isolated $CSC^{GFP}$ (g-j) Immunocytochemistry identifies re-isolated $CSC^{GFP}$ cardiospheres (g), which differentiated into CMs (h; cTnI), smooth muscle (i; SMA) and endothelial (j; vWF) cells, in vitro. Bar=50 μm (k-l) LV function measurements (k) and quantification of new $GFP^{pos}$ CMs (l), following injection of re-isolated clonal $CSC^{GFP}$ into the infarcted rat heart (k, $*P<0.05$ vs. Sham, $†P<0.05$ vs. Saline) (l, $*P<0.05$ vs. Distant). (m-p) Confocal microscopy of new $GFP^{pos}$ CMs (cTnI; m and n), arteries (SMPA; o) and capillaries (vWF; p) in the border/infarct area. Bar=100 μm (m) Bar=20 μm (n-p). All data are Mean±SD. See also FIG. 29.

FIGS. 21(A-K). (A) Hemodynamic measurements (LVEDP=LV end diastolic pressure, LVDevP=LV developed pressure) after 5 mg $kg^{-1}$ dose of ISO. $*P<0.05$ vs. CTRL. Data are Mean±SD of n=7/group. (B) Representative image of $c-kit^{pos}$ eCSCs (green) in the ISO-damaged myocardium (α-sarcomeric actin, red). Nuclei stained with DAPI (blue). Bar=20 μm. (C) Fraction of $c-kit^{pos}/Ki67^{pos}$ eCSCs. $*P<0.01$ vs. CTRL. (D) Representative image of $c-kit^{pos}GATA4^{pos}$ (green/white nuclei dots) cells in the 3 day ISO-injured myocardium. Bar=20 μm. (E) Fraction of $c-kit^{pos}GATA4^{pos}$ cardiac progenitor cells following ISO-induced myocardial damage. $*P<0.01$ vs. CTRL. Data are Mean±SD of n=7/group. (F-H) qRT-PCR data of transcripts (normalized to GAPDH) for GATA-4, Nkx2.5, β-MHC, α-MHC, cTnI and Cn43 in $c-kit^{pos}$eCSCs isolated from CTRL and ISO-injured hearts;$*p<0.05$ vs. CTRL, GATA-4 and Nkx2.5 mRNA levels in day 10 embryonic rat heart and β-MHC, α-MHC, cTnI and Cn43 mRNA levels in adult rat ventricular cardiomyocytes (ARVMs) are shown as positive controls (checked bars) for the expression levels of these genes. (I-J) Flow cytometric analysis of $c-kit^{pos}CD45^{neg}$ eCSCs that express Gata-4 and α-sarcomeric actin (αSA), 3 days after ISO (I), compared to CTRL (J). Data are representative of n=4/group. (K) A small BrdU$^{pos}$ (green) cardiomyocyte (α-sarcomeric actin; red) in the ISO-injured heart at 14 days. Nuclei are stained by DAPI in blue. Bar=20 µm. See also FIG. 14.

FIG. 22(A-J). (A) Representative hematoxylin and eosin (H&E) cross sections of the apical LV wall at 2× and 10× magnifications for CTRL, 3 and 28 days after 200 mg kg$^{-1}$ (s.c) ISO in the mouse heart. At 3 days after ISO there is significant focal, diffuse necrosis with high infiltration of mononuclear cells. This is no longer evident at 28 days after ISO, showing structural recovery of the tissue, which looks similar to CTRL myocardium. (B-C) Number of c-kit$^{pos}$Lin$^{neg}$ and c-kit$^{pos}$Nkx2.5$^{pos}$ progenitors after ISO in the mouse heart. *P<0.05 vs. CTRL. Data are Mean±SD of n=5/group. (D-E) Number of BrdU$^{pos}$ and Ki67$^{pos}$ myocytes after ISO-injury in the mouse heart. *P<0.05 vs. CTRL, 1 day and 3 days. Data are Mean±SD of n=5/group. (F) Hemodynamic measurements (LVEDP=LV end diastolic pressure, LVDevP=LV developed pressure) after 200 mg kg$^{-1}$ dose of ISO in the mouse. *P<0.05 vs. CTRL and 28 days. Data are Mean±SD of n=5/group. (G) hsTnT plasmatic levels 1 day after 200 mg kg$^{-1}$ (s.c) ISO in the mouse. P<0.05 vs. CTRL. Data are Mean±SD of n=5/group. (H-J) Necrotic and apoptotic myocyte death in β-Gal$^{pos}$ vs. GFP$^{pos}$ myocytes in recombined (tamoxifen induced) double transgenic merCremer/ZEG mice, 1 day after ISO. *p<0.05 vs. CTRL. Data are Mean±SD of n=4/group. See also FIG. 15.

FIG. 23 (A-G) (A) c-kit/cre Lentivirus labelling of eCSCs in vitro. c-kit$^{pos}$CD45$^{neg}$eCSCs were isolated from RYP mice (cytospin preparation, c-kit staining, red fluorescence) and transfected in vitro with lenti c-kit/cre or Lenti empty. Flow cytometric analysis shows highly efficient cre/lox recombination with (E)YFP expression in Lenti c-kit/cre transfected eCSCs. Data are representative of n=4/group. (B) c-kit/cre Lentivirus labelling of eCSCs in vivo. Flow cytometric analysis of (E)YFP positive cells in myocyte-depleted c-kit$^{neg}$ cardiac small cells (c-kit$^{neg}$MDCCs), total un-fractioned, Lin$^{neg}$ Bone Marrow Cells and Peripheral Blood Cells freshly isolated from CTRL RYP mice, 14 days after polymer-based myocardial delivery plus direct intramyocardial injection of Lenti-c-kit/cre, or after polymer-based myocardial delivery plus direct intramyocardial injection of Lenti-c-kit/cre at 28 days after ISO (that is 42 days after initial lenti injection)*. Data are representative of n=4-5/group. (C) Isolated Lenti c-kit/cre in vivo recombined c-kit$^{pos}$ CD45$^{neg}$eCSCs. 14 days after polymer-based myocardial delivery plus direct intramyocardial injection of Lenti-c-kit/Cre in RYP mice, YFP$^{pos}$c-kit$^{pos}$ CD45$^{neg}$eCSCs were separated by FACS and compared to c-kit$^{pos}$CD45$^{neg}$eCSCs isolated from wild type C57BL/6 mice. The cre-lox recombined YFP$^{pos}$ CSCs and wild type eCSCs expressed similar levels of known cardiac stem/progenitor markers, like c-kit, Sca-1 and CD105, while were negative for known hematopoietic markers, like CD45 and CD34. Data are representative of n=4/group. (D) qRT-PCR revealed similar levels of known cardiac stem/progenitor transcripts in cre-lox recombined YFP$^{pos}$CSCs and wild type eCSCs. Data are Mean±SD of n=3/group. (E-F) The cre-lox recombined YFP$^{pos}$eCSCs were indistinguishable from wild type eCSCs for their clonogenic capacity and cardiosphere (CS) formation. Data are Mean±SD of n=4/group. (G) Accordingly, YFP$^{pos}$eCSCs (similar to wild type eCSCs) were multipotent in vitro, being able to differentiate into myocytes (α-Sarcomeric Actin, Red fluorescence), smooth muscle cells (smooth muscle actin SMA, green fluorescence) and endothelial cells (von Willebrand Factor-vWF, white-Cy5 fluorescence). Nuclei are stained by DAPI in blue. Data are representative of n=4-5/group. See also FIG. 16. *Note that indistinguishable data were obtained analysing total un-fractioned, Lin$^{neg}$ Bone Marrow Cells and Peripheral Blood Cells freshly isolated from CTRL RYP mice after polymer-based myocardial delivery plus direct intramyocardial injection of Lenti-c-kit/cre at 28 days after saline (that is 42 days after initial lenti injection).

FIG. 24 (A) Representative flow cytometric analysis showing the co-localization of c-kit and GFP in c-kit$^{pos}$/CD45$^{neg}$ MACS-sorted eCSCs from CTRL (left) and ISO 28 d (right) Tg$^{c-kit/GFP}$ mice. Data are representative of n=3/group. (B) Representative flow cytometric analysis showing the co-localization of c-kit and GFP in FACS-sorted GFP$^{pos}$ cardiac small (myocyte-depleted) cells from CTRL (left) and ISO 28 d (right) Tg$^{c-kit/GFP}$ mice. Data are representative of n=3/group. These two experiments show that the c-kit/GFP transgene is confined to c-kit$^{pos}$ cells in the control as well as injured hearts. (C-D) Representative confocal microscopy image for c-kit$^{pos}$GFP$^{pos}$ co-localization in LV cardiac sections from CTRL (C) and ISO 28 d (D) Tg$^{c-kit/GFP}$ mice. Note the absence of any GFP labelling of cardiomyocytes. Bar=20 µm. (E) Representative confocal microscopy image of a newly-formed BrdU$^{pos}$ cardiomyocyte in ISO 28 d Tg$^{c-kit/GFP}$ mice. No c-kit/GFP signal was detected in any myocytes (BrdU$^{pos}$ and BrdU$^{neg}$). Bar=10 µm. (F) Representative confocal microscopy image of isolated rod-shaped cardiomyocytes (red; α-sarcomeric actin) showing the absence of GFP expression, and a BrdU$^{pos}$ small new cardiomyocyte in ISO 28 d Tg$^{c-kit/GFP}$ mice. Bar=20 µm. (G) Bar graph showing cumulative percentage of GFP$^{pos}$ and GFP$^{neg}$ BrdU$^{pos}$ myocytes in CTRL and ISO 28 d Tg$^{c-kit/GFP}$ mice. Data are representative of n=4/group. *p<0.05 vs. CTRL 28 d. (H) Flow cytometric analysis showing no GFP myocytes isolated from CTRL and ISO 28 d Tg$^{c-kit/GFP}$ mice. Data are representative of n=4/group. Negative and positive controls for GFP myocytes are shown in the bottom panels. (I) ISO (10 nM) administration in vitro was unable to activate c-kit/GFP transcription adult myocytes isolated from Tg$^{c-kit/GFP}$ mice and cultured for 48 hrs. However, ISO correctly re-activated the fetal myocyte gene program as shown by increased ANP expression. Data are representative of n=3/group. *p<0.05 vs. Tg$^{c-kit/GFP}$; #p<0.05 vs. Base. (J) Flow cytometric analysis showing pre- and post-sorting YFP expression in cardiomyocytes (CMs) isolated from Lenti-c-kit/cre-injected RYP mice at 28 days after ISO. Data are representative of n=3/group. (K) Histogram showing FACS sorted YFP positive CMs were >99% positive for αSA. Data are representative of n=3/group. (L) Linear regression analysis between the log 2 transformed and normalized intensities of YFP$^{pos}$CMs and c-kit$^{pos}$eCSCs, CMs and c-kit$^{pos}$eCSCs, YFP$^{pos}$CMs and CMs, and the linear regression analysis between the fold change values (log 2 scale) of CMs and YFP$^{pos}$CMs. See also FIG. 16.

FIG. 25(A-G). (A) Representative confocal microscopy images of CSCs$^{GFP}$ (green) in the extra-cardiac tissues (liver, lung, slow skeletal soleus muscle and spleen) at 1 day after tail vein injection in CTRL animals and 1, 6 and 28 days after tail vein injection in ISO-treated rats. –ve CTRL denotes staining for 2° Ab FITC and omission of 1° Ab for GFP on 1 day after ISO and tail vein injection samples. Bar=100 µm. (B-C) Flow cytometric analysis quantifying the number of exogenous c-kit$^{pos}$ CSC$^{GFP}$-derived myocytes (GFP$^{pos}$) within the isolated cardiomyocyte preparation, 28 days after ISO and tail vein cell injection. No GFP$^{pos}$ cardiomyocytes were found in the hearts where c-kit$^{neg}$MDCCs$^{GFP}$ were tail vein injected (B). On the contrary, GFP$^{pos}$ cardiomyocytes (2.5±1) were identified in the ISO-treated hearts where c-kit$^{pos}$CSC$^{GFP}$ were injected (C). The flow cytometry data is in agreement with the immunohistochemistry data presented in FIG. 4. Data are representative of n=3/group. (D) CSC-derived newly-generated myocytes 28 days after ISO damage and tail vein injection of c-kit$^{pos}$CSCs transfected with a lentivirus vector carrying the GFP under the cardiac troponin I (cTnI) promoter (Gallo P, Grimaldi S, Latronico M V, Bonci D, Pagliuca A, Ausoni S et al. *A lentiviral vector with a short troponin-I promoter for tracking cardiomyocyte differentiation of human embryonic stem cells. Gene Ther* 2008; 15(3): 161-70). Bar=10 μm. Data are representative of n=4 treated rats. (E) Representative western blot of SDF-1 expression in isolated cardiomyocytes from CTRL rat hearts and 1, 3, 6 and 12 hours after ISO injection. (F) Representative western blot of SDF-1 expression in isolated cardiomyocytes from CTRL rat hearts and 1, 6, 14 and 28 days after ISO injection. Data are representative of n=5/group. (G) Representative western blot showing CXCR4 expression in c-kit$^{pos}$ CSCs$^{GFP}$ and its efficient knock-down by the specific Lentiviral-shRNA. Data are representative of n=4/group. See FIG. 17.

FIG. 26(A-G). (A) Representative H&E and caspase 3 immunostaining of ISO+5-FU treated (after 4×5 cycles of 5-FU) rat LV sections, compared to 3 and 28 days after ISO. Positive Caspase 3 staining is identified by DAB+metal enhancer in black. Bar=50 μm. (B) Bone marrow cell distribution analysed by CD45 expression and side scatter revealing similar bone marrow blood cell lineage fractions in CTRL and 5-FU-treated rats (after 4×5 cycles of 5-FU). (C) Cardiac remodelling and function in ISO+5-FU cardiomyopathy; (C & D) 5-FU administration after ISO injury resulted in progressive drop-out of cardiomyocytes by apoptosis over 28 days. *P<0.01 vs. CTRL and 5-FU. †P<0.05 vs. ISO at the same time point. w/wo 5-FU denotes with/without 5-FU. (E & F) ISO+5-FU treated rats showed increased LV weight due to significant maladaptive hypertrophy of the spared myocytes over 28 days. *P<0.01 vs. CTRL and 5-FU. †P<0.05 vs. ISO at the same time point. (G) Following 5-FU administration, the recovery of LV function of the ISO-treated animals, at 7 through to 28 days, was no longer apparent. *P<0.05 vs. CTRL and 5-FU. Data are Mean±SD of n=5 for saline vehicle (CTRL), n=5 for 5-FU, n=6 at 1, 7, 14 days after ISO, n=10 at 28 days after ISO, n=6 at 7 and 14 days after ISO+5-FU and n=4 at 28 days after ISO+5-FU. See FIG. 18.

FIG. 27(A-I). (A) Cardiac cellular remodelling (apoptosis and hypertrophy) of the myocyte cell compartment at 56 days (2 months) after saline or cell treatments in vivo in rats with ISO+5-FU cardiomyopathy. *P<0.05 vs. CTRL and CSCs$^{GFP}$ and CSCs$^{GFP/TK}$. Data are n=5 for saline vehicle (CTRL), n=5 for ISO+5-FU+Saline, n=5 for ISO+5-FU+cFibro, n=6 for ISO+5-FU+CSCs$^{GFP}$ and n=5 for ISO+5-FU+CSCs$^{GFP/TK}$. (B) Flow cytometric analysis of cell chimerism at 56 days after tail vein injection of saline, CSC$^{GFP}$ and CSC$^{GFP/TK}$, isolated from ISO+5-FU treated rats. Data are n=3 for each group. (C) Cardiac cellular remodelling (apoptosis and hypertrophy) of the myocyte compartment at 84 days (3 months) after Saline or GCV treatment of CSCs$^{GFP}$ or CSCs$^{GFP/TK}$ treated rats with ISO+5-FU cardiomyopathy. *P<0.05 vs. all. Data are n=5 for saline vehicle (CTRL), n=6 for ISO+5-FU+CSCs$^{GFP}$+Saline, n=7 for ISO+5-FU+CSCs$^{GFP}$+GCV (Ganciclovir), n=5 for ISO+5-FU+CSCs$^{GFP/TK}$+Saline and n=6 for ISO+5-FU+CSCs$^{GFP/TK}$+GCV. (D) Treatment with ganciclovir (GCV, $10^{-5}$ M) leads to growth arrest of Lenti-GFP/TK-transfected CSCs (CSCs$^{GFP/TK}$) in vitro, when compared to normal un-transfected CSCs. *p<0.01 vs. all. Note: GFP-transfected CSCs (CSCs$^{GFP}$) have indistinguishable growth kinetics when compared to normal CSCs (data not shown). (E) Serial confocal sectioning shows a GFP$^{pos}$ myocyte (right panel; arrow) that is derived from a male tail vein injected CSC$^{GFP}$, with X (red; left panel) and Y (green; left panel) chromosomes (left panel; arrow). Male CSC$^{GFP}$, which were injected into female rat recipients with ISO+5FU cardiomyopathy, can also been seen (arrowheads). A Female, with two X chromosomes, GFP negative myocyte nuclei can also be seen (star). (F-G) Representative flow cytometric analysis showing the transfection efficiency in c-kit$^{pos}$eCSCs isolated from MerCreMer mice of Ad-Empty (F) or of an adenovirus carrying the red fluorescent protein (Ad-RFP) (G). (H-I) Representative flow cytometric analysis showing no isolated myocytes expressed RFP or YFP in the ISO+5-FU-+Saline group (H), while 7.9±2.2 RFP$^{pos}$ myocytes were evident in the LV of ISO+5-FU+CSC$^{RFP}$ mice, at 56 days (I). None of these newly generated RFP$^{pos}$ cardiomyocytes expressed YFP, ruling out cell fusion as a prevalent phenomenon for the observed new myocyte formation by the transplanted cells. Data are representative of n=4/group. See also FIG. 19.

FIGS. 28(A-F). (A) Representative z-stack confocal series scans of isolated newly-generated CSC$^{GFP}$-derived GFP$^{pos}$ (green) myocytes (red; α-sarcomeric actin) and pre-existing GFP negative myocytes at 84 days after ISO+5-FU cardiomyopathy with CSC$^{GFP}$ tail vein injection. (B-C) Flow cytometric analysis showing quantification of the number of c-kit$^{pos}$ CSC$^{GFP}$-derived rat myocytes (GFP$^{pos}$), in hearts with ISO+5-FU cardiomyopathy injected with saline (ISO+5-FU+Saline) (B) or CSC$^{GFP}$ (ISO+5-FU+CSC$^{GFP}$) (C) at 84 days (n=3). (D) Average diameter of CSC$^{GFP}$-derived GFP$^{pos}$ and pre-existing GFP negative myocytes at 84 days (3 months) in rats with ISO+5-FU-induced cardiomyopathy rescued by CSC$^{GFP}$ injection. At this time point, the CSC-derived GFP$^{pos}$ cardiomyocytes were the same size as pre-existing cardiomyocytes, indicating that maturation of newly-generated myocytes is completed by two months. (E) Heatmap and qRT-PCR analysis showing CSC$^{GFP}$-derived GFP$^{pos}$ cardiomyocytes express similar mRNA transcript levels of a set of cardiac transcription factors and contractile genes, when compared to GFP$^{neg}$ adult cardiomyocytes. CSCs$^{GFP}$ do not express mRNA transcripts for cardiac contractile genes. *p<0.05 vs. GFP$^{neg}$ CMs; #p<0.05 vs. CSCs$^{GFP}$. Data are n=3/group. (F) Ganciclovir (GCV, $10^{-5}$ M) does not cause any relevant effect on adult rat ventricular myocyte (ARVM) apoptosis nor directly or indirectly when co-cultured (at a 1:10 ratio) with CSC$^{GFP/TK}$ in vitro. The latter dispels any significant bystander effects of CSC$^{GFP/TK}$ suicide by GCV on adult cardiomyocytes in vitro. Apoptosis was measured by TdT labelling as well as by cleaved Casapase-3 detection. *P<0.05 vs. 3 d. Data are n=3/group. See also FIG. 19.

Figure 29A:
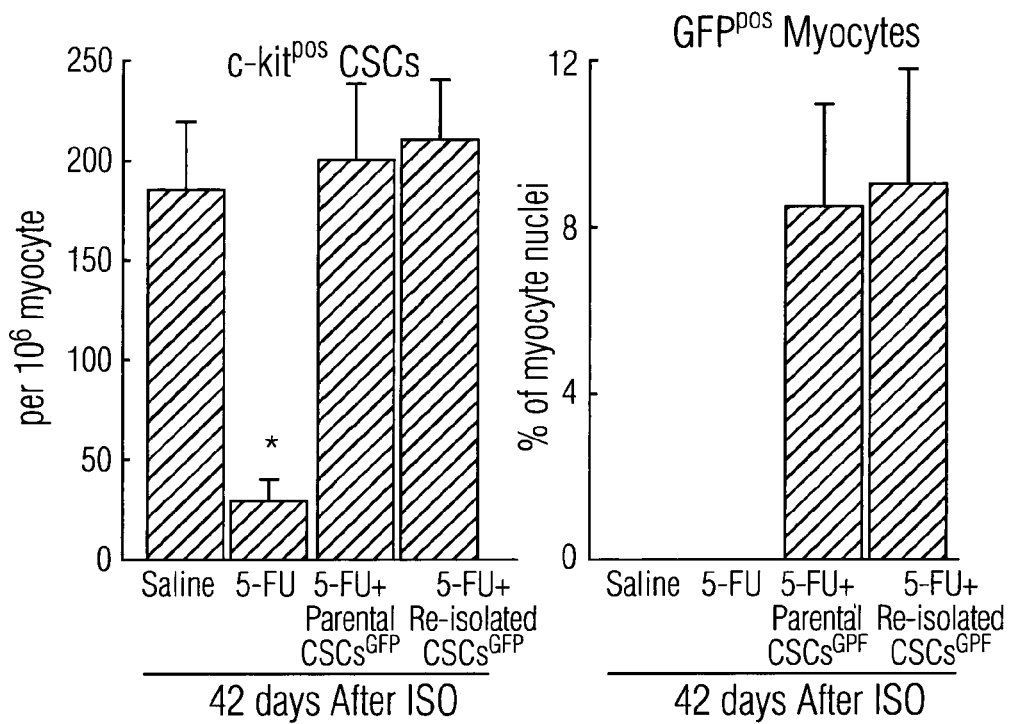
Figure 29B:
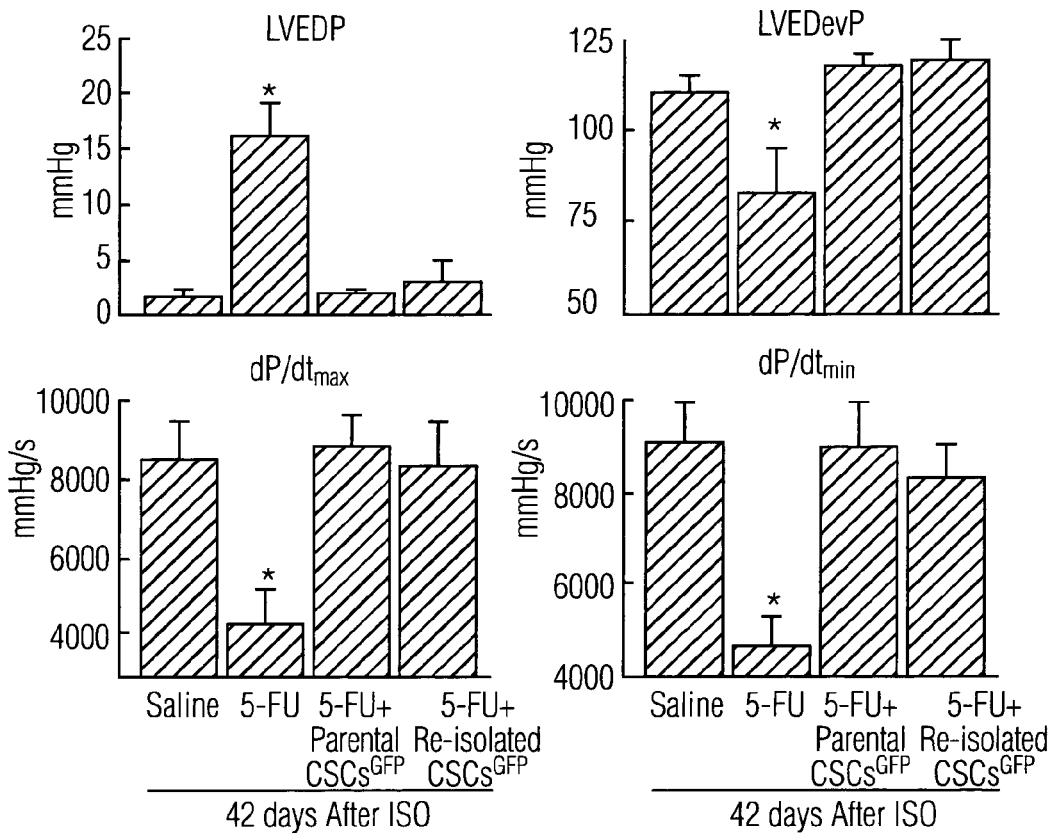
Figure 30A:
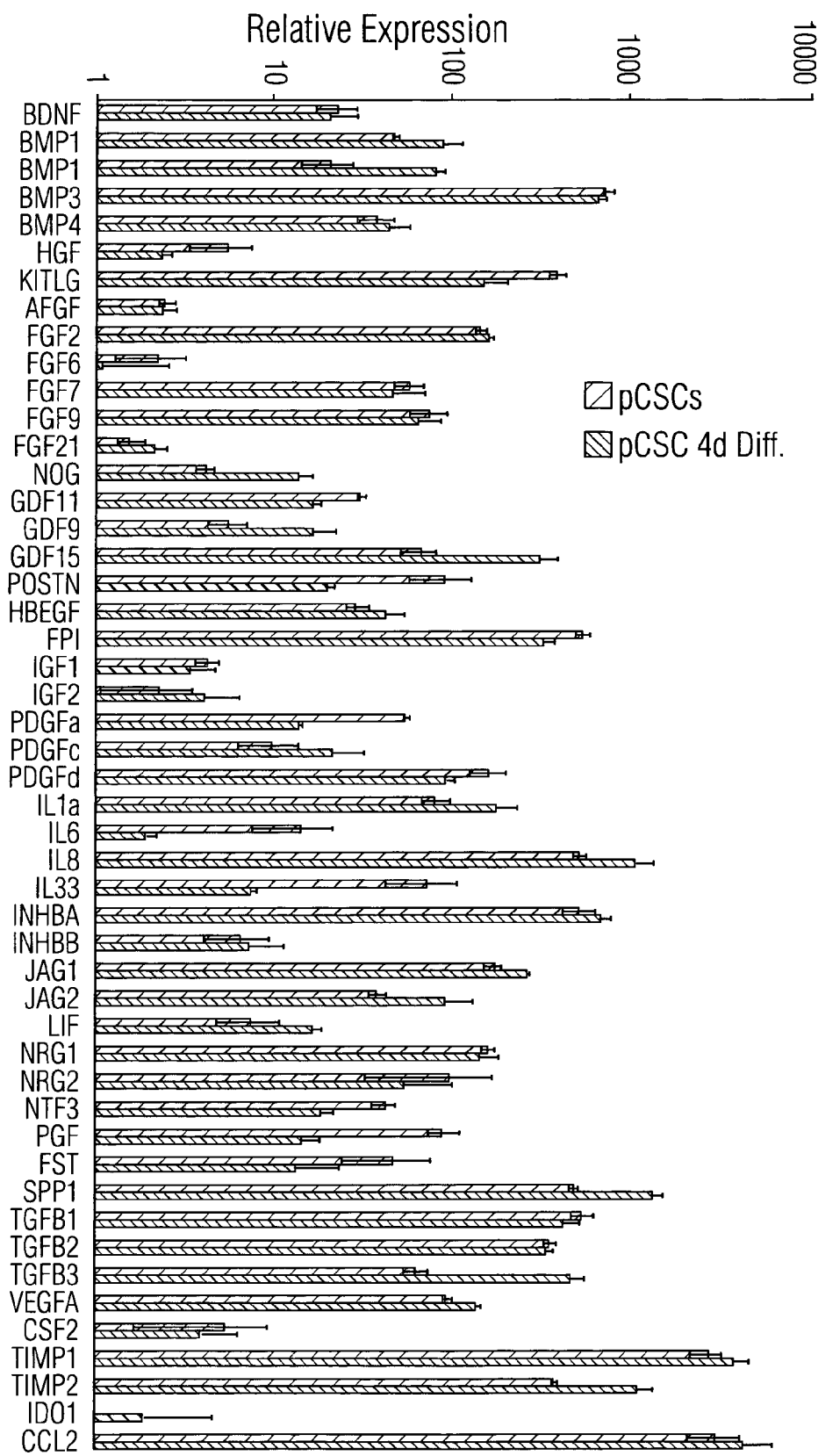
Figure 30B:
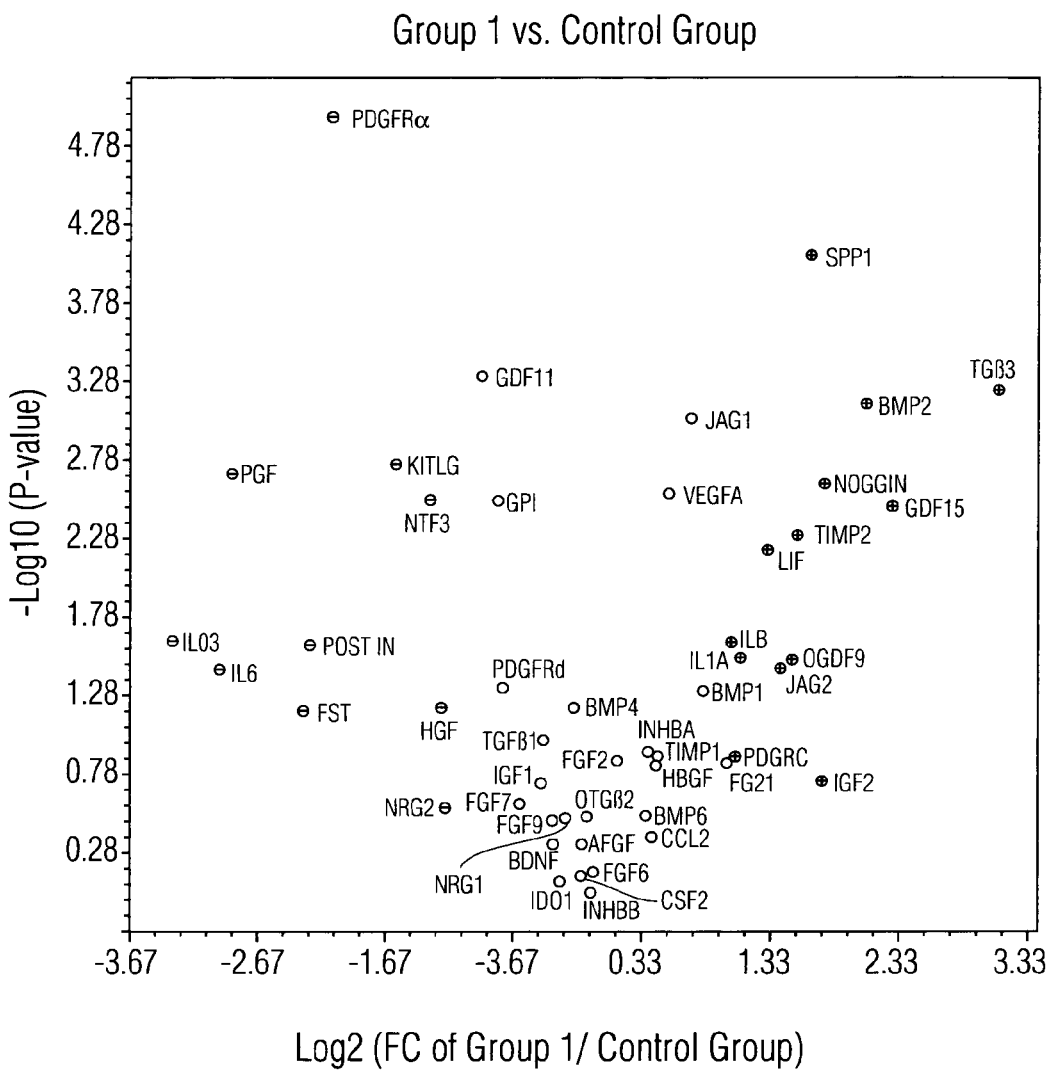
Figure 30D:
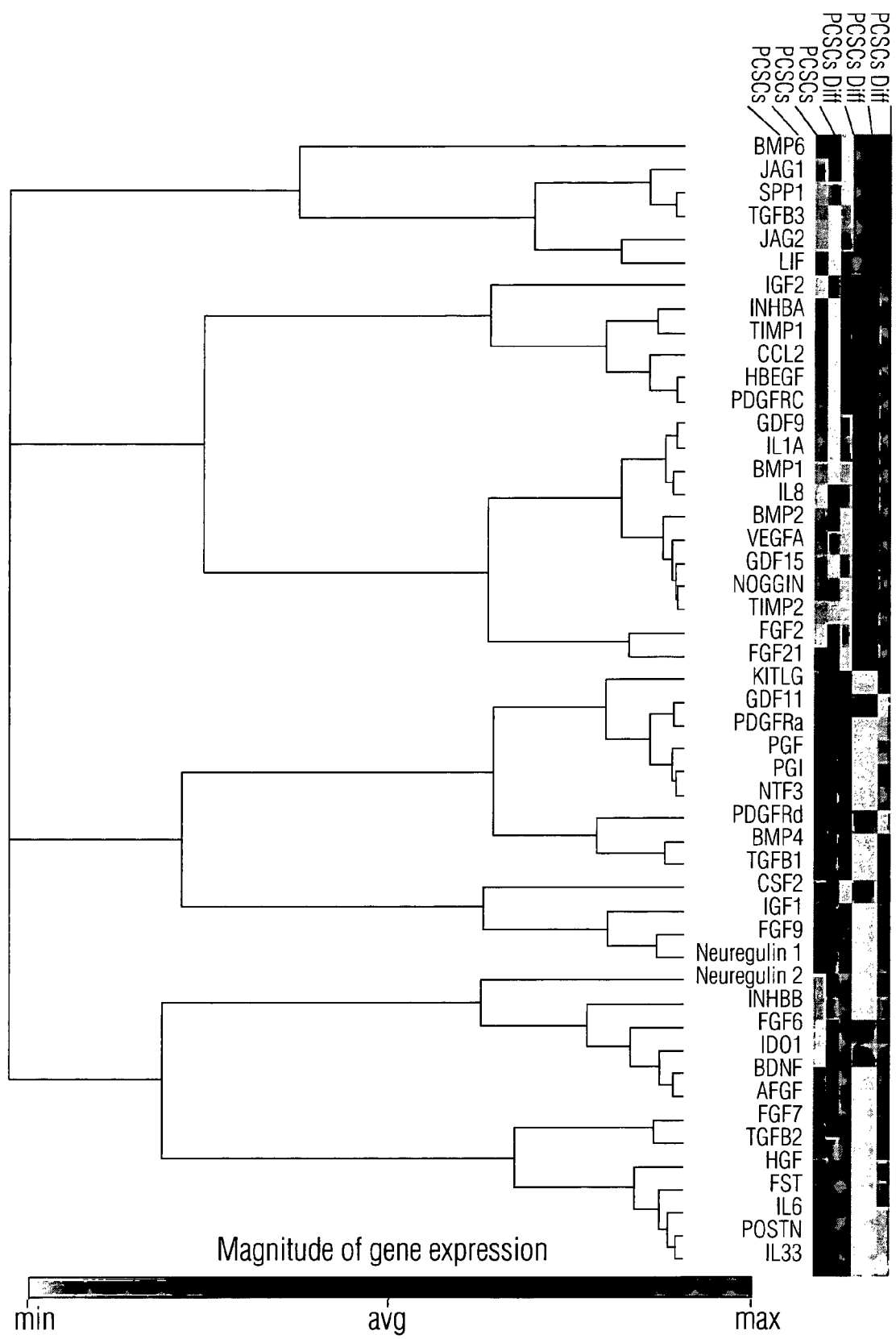
Figure 31A:
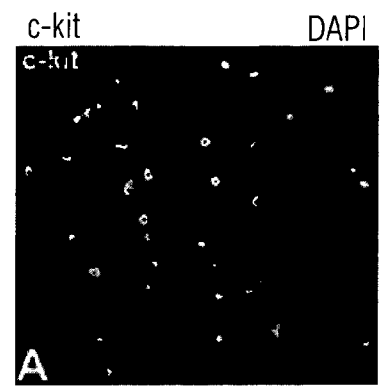
Figure 31B:
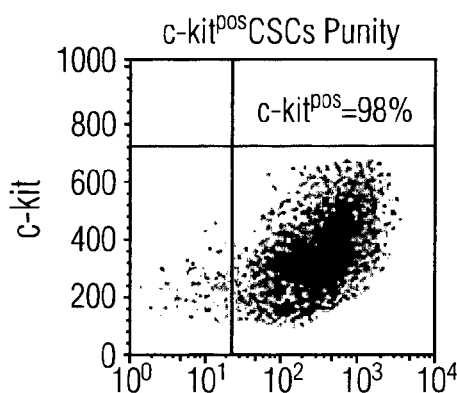
Figure 31C:
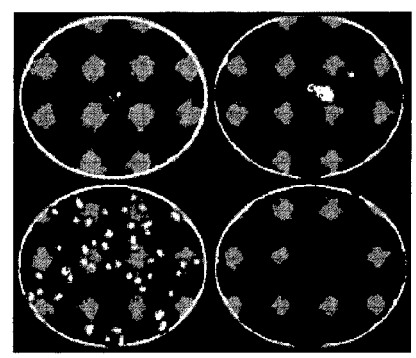
Figure 31D:
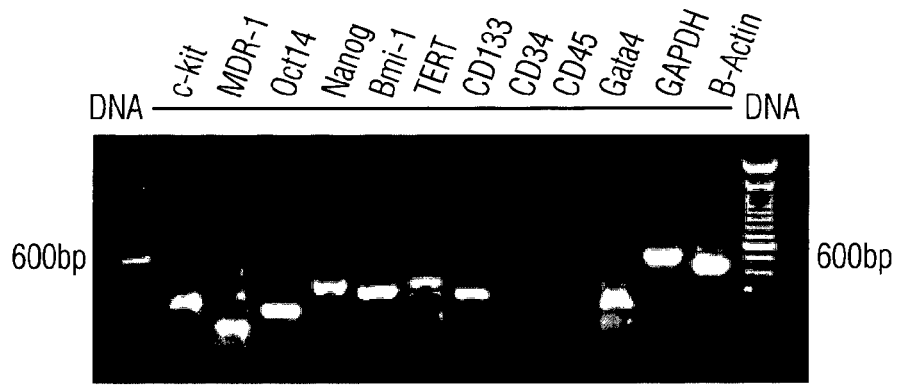
Figure 31E:
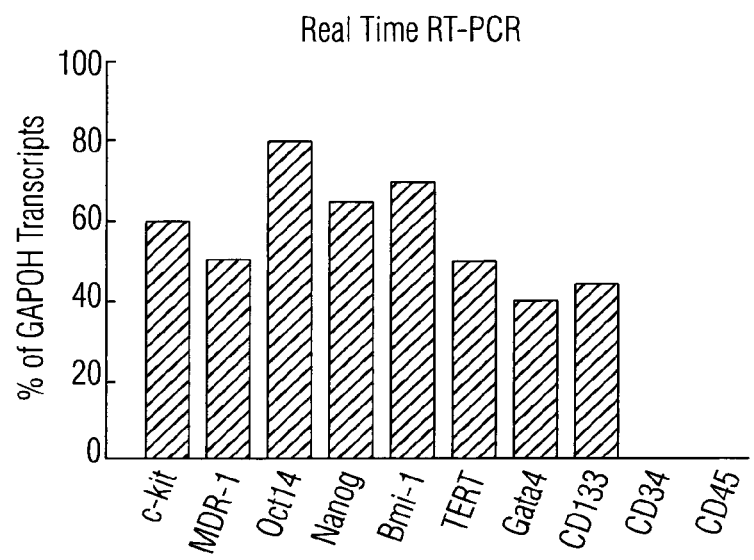
Figure 31F:
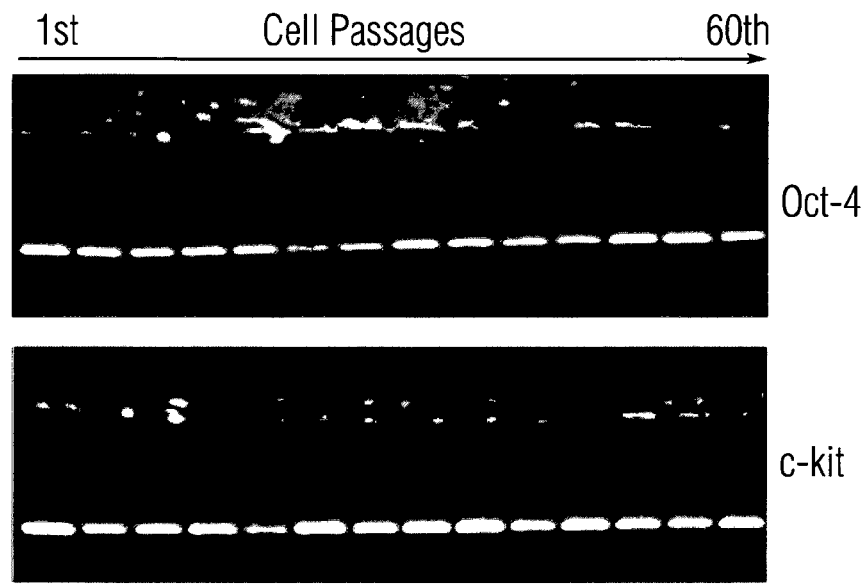
Figure 31G:
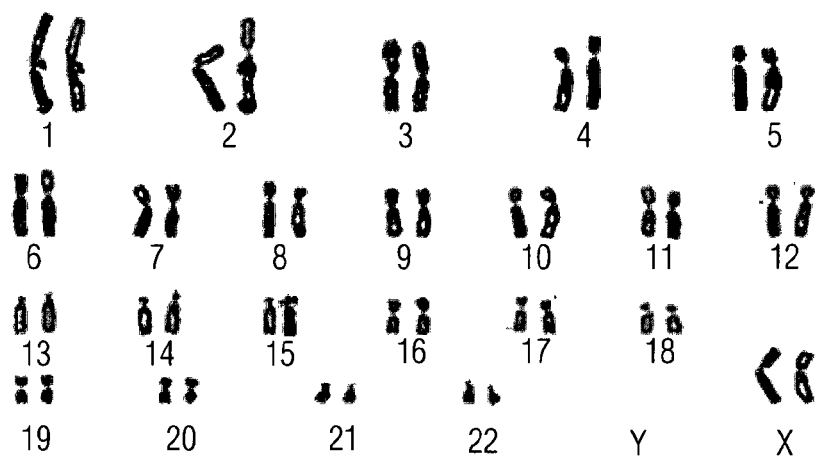
Figure 31H:
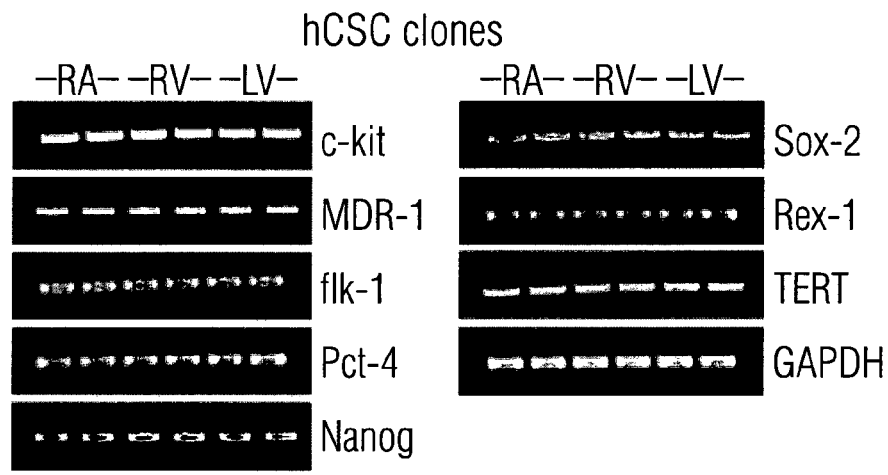
Figure 31I:
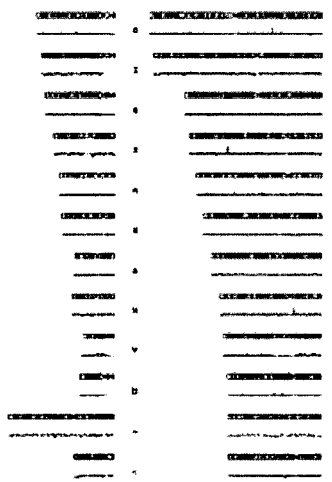

FIGS. 29(A-B). (A-B) Re-isolated and re-transplanted CSC$^{GFP}$ restore c-kit$^{pos}$eCSC number and contribute to new cardiomyocytes (G) and restore cardiac function (H) in ISO+5-FU hearts after tail vein injection, indistinguishably from parental CSCs$^{GFP}$. *p<0.05 vs. all. Data are n=5/group. See also FIG. 20.

FIGS. 30A-D. Human CSC secretome data summary The modulation in the expression of the secretome of the human stem-progenitor cells during the process of differentiation is listed. (A) qRT-PCR secretome array relative expression profile of undifferentiated pCSC compared to pCSC subjected to 4 days of differentiation, n=3. (B-C) Genes that were differentially regulated by at least two folds were selected by a t test, p<0.01 and illustrated in a volcano plot. Genes that are to the right of the plot were significantly unpregulated. Those in the middle of the plot represents genes whose expression levels did not significantly change while those on the left indicate genes that were significantly downregulated, n=3. (D) Hierarchical clustering of differentially regulated pCSC transcripts. The clustergram represents the resulting qRT-PCT expression profile from an array of 80 genes of which 49 genes were found to be expressed. The data set is notably divided into four distinct clusters with more than half of the genes downregulated as pCSCs differentiated while a similar proportion were upregulated. The intensity of the color represents the magnitude of gene expression for the measured average difference in values. The tree on the left of the clustergram indicates the pairwise similarity relationships between the clustered expression patterns.

FIGS. 31A-I. Isolation, expansion and characterization of the human cardiac c-kit CSCs. (A-E) Stability of multipotency gene expression in the human cardiac c-kit CSCs upon extensive passage. (F) cell passages, Oct-4 and c-kit expression. (G) Karyotype human CSC clone. (H) Stemness gene profile of clonogenic hCSC clones. (I) Genetic stability of human eCSCs after 68 passages.

Figure 32A:
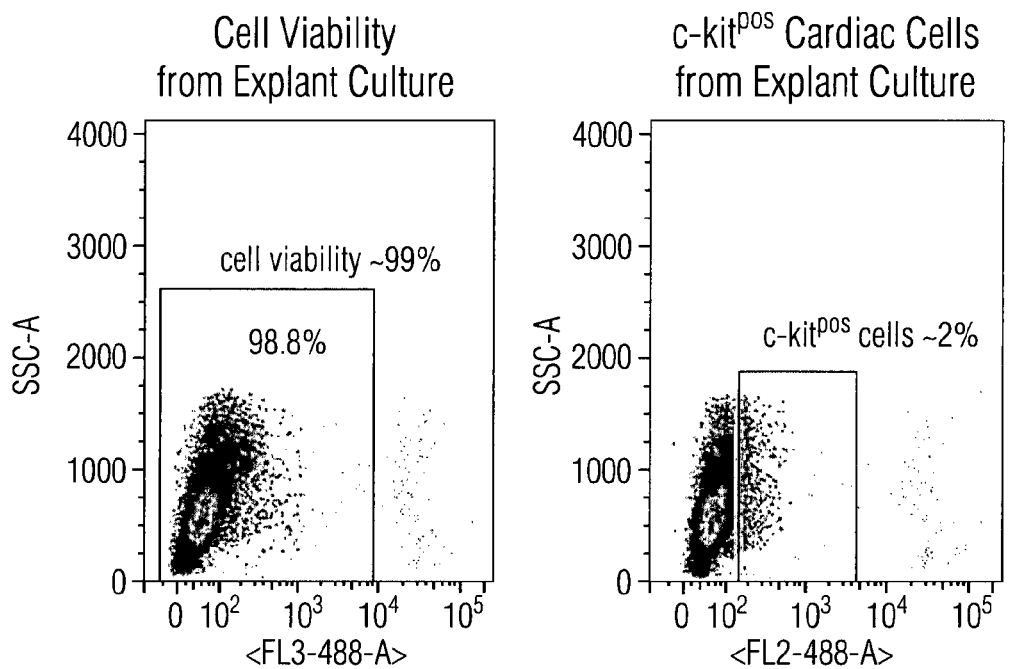
Figure 32B:

FIGS. 32A-B. (A) Expanded c-kit CSCs from human cardiac explants before sorting. (B) Expanded c-kit CSCs from human cardiac explants after sorting.

FIGS. 33A-C. Allogeneic cardiac stem-progenitor cells are well tolerated and have an anti-inflammatory and immunomodulating role. (A). Injection of cells to pigs over time. (B-C). IgM pCSC humoral response over time.

FIGS. 34A-C. Allogeneic cardiac stem-progenitor cells are well tolerated and have an anti-inflammatory and immunomodulating role. (A). Injection of cells to pigs over time. (B-C). IgG pCSC humoral response over time.

Figure 35A:
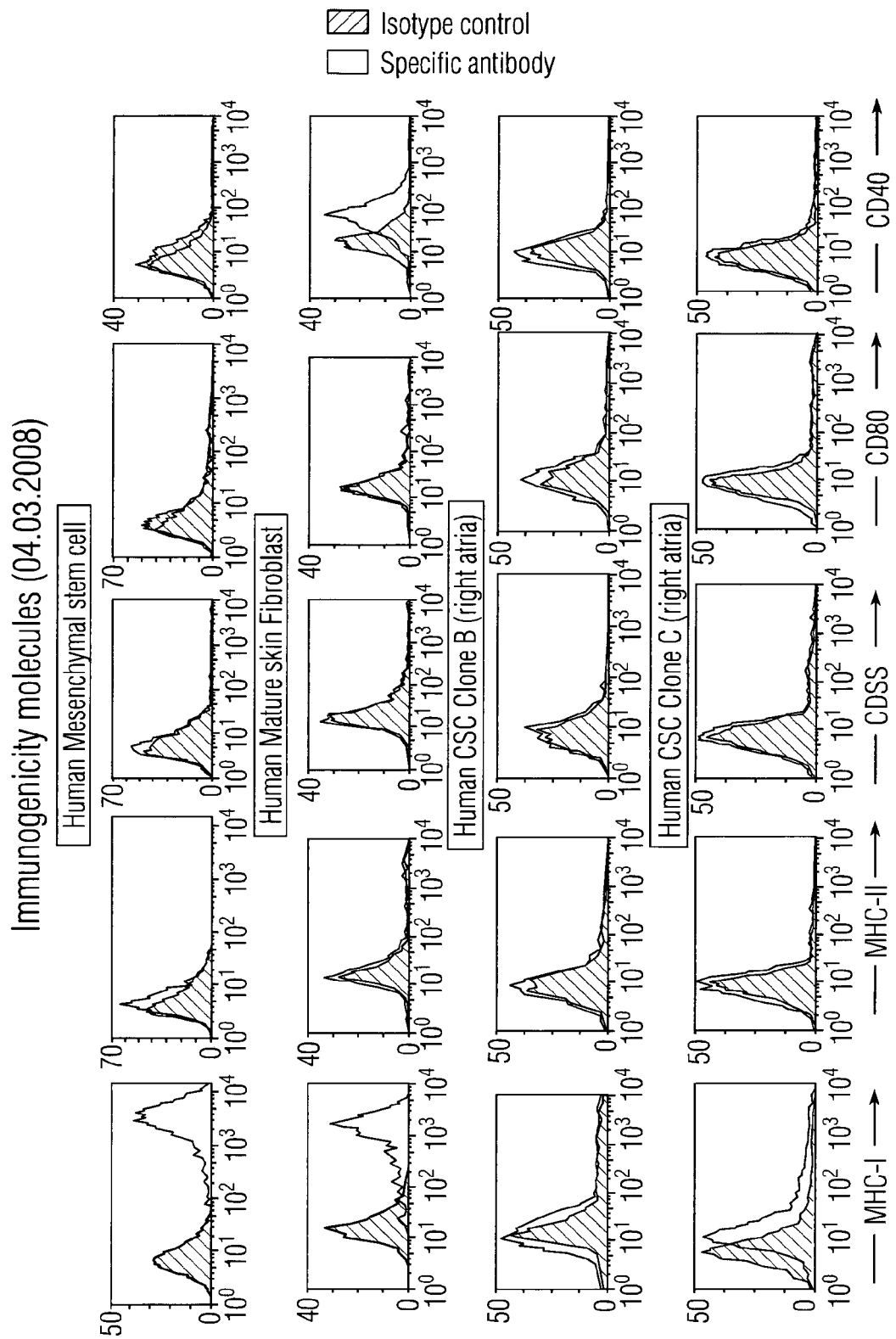
Figures 36A, 36B, 36C:
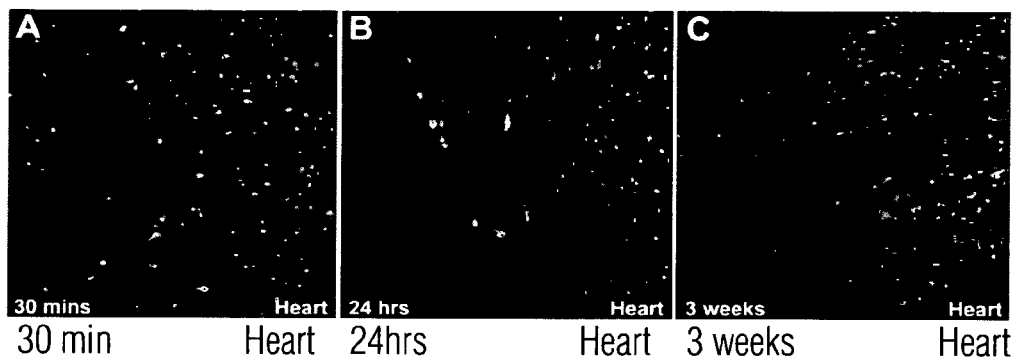
Figure 36D:
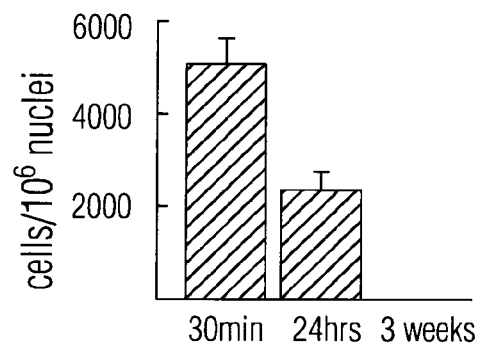
Figures 36E, 36F:
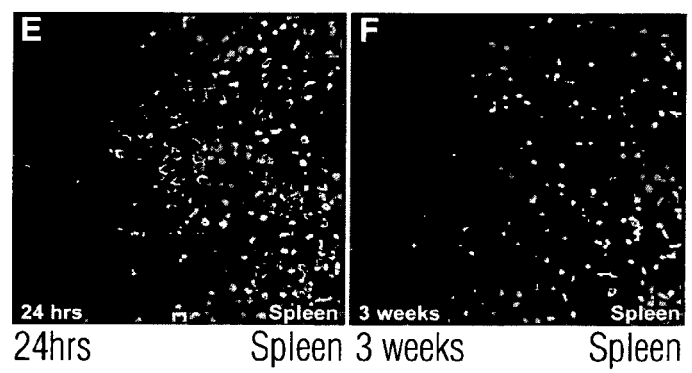
Figure 37A:
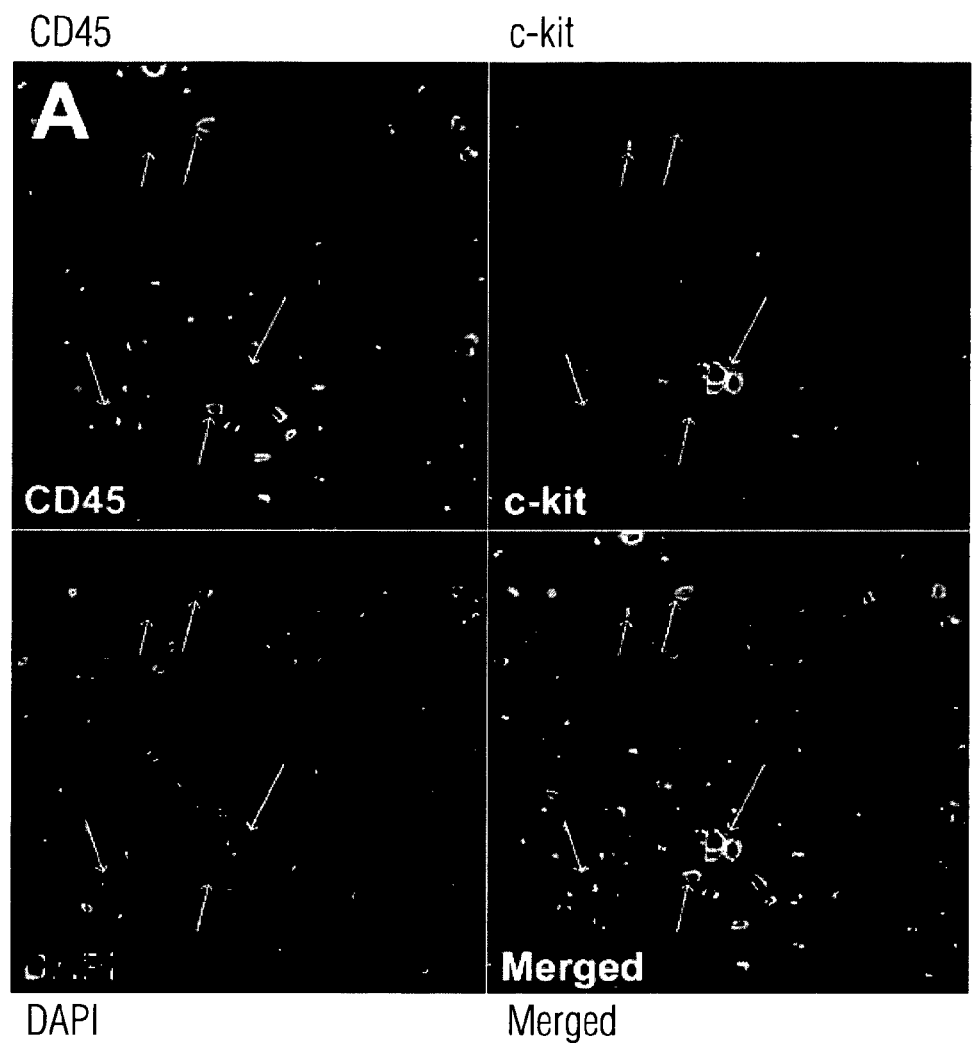
Figure 37B:
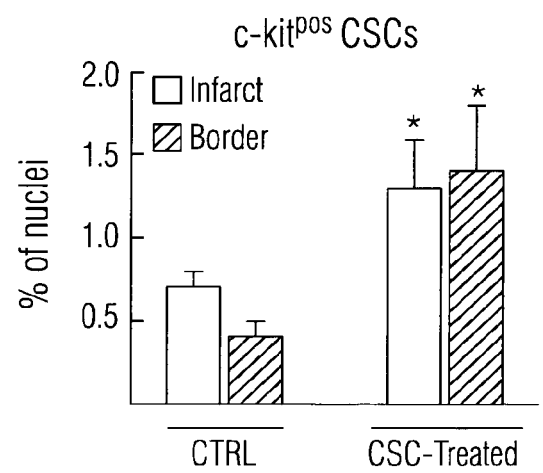
Figures 37C, 37D:
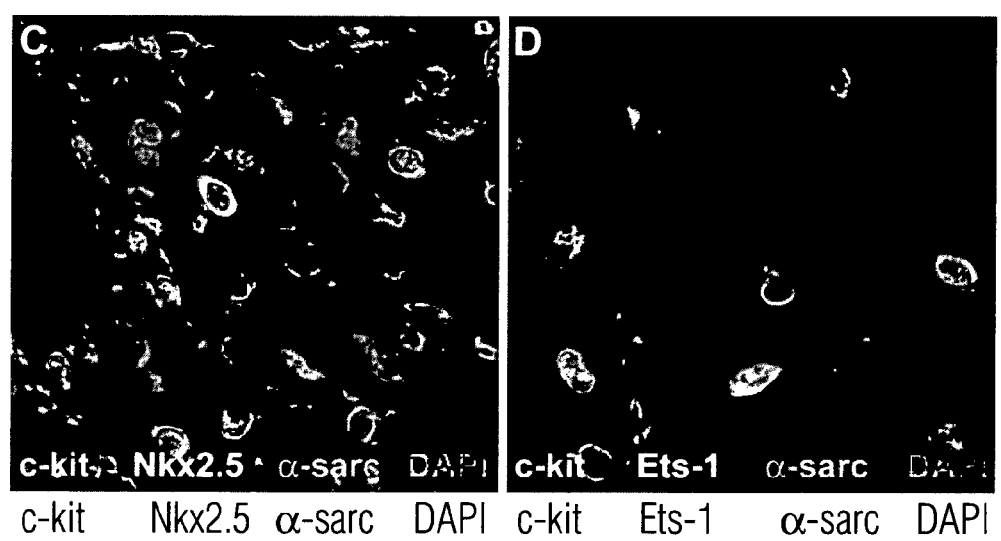
Figure 38A:
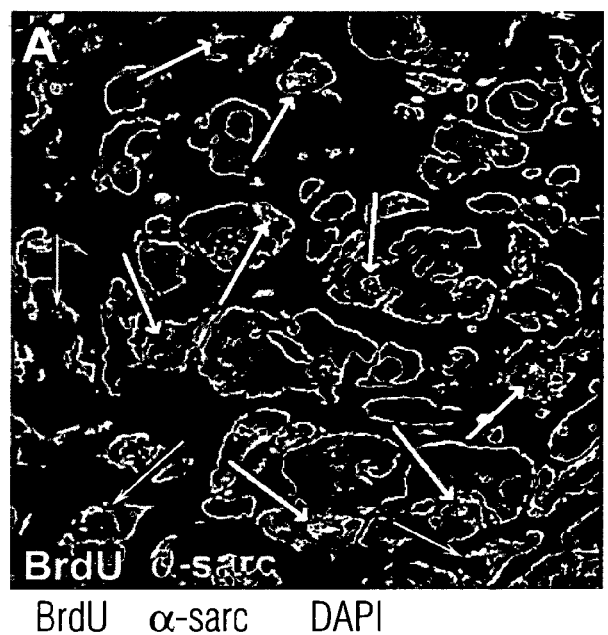
Figure 38B:
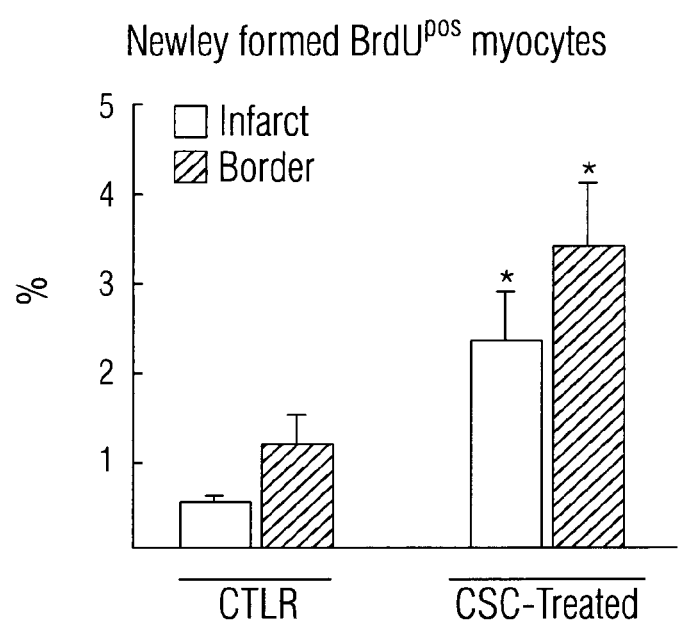
Figure 38C:
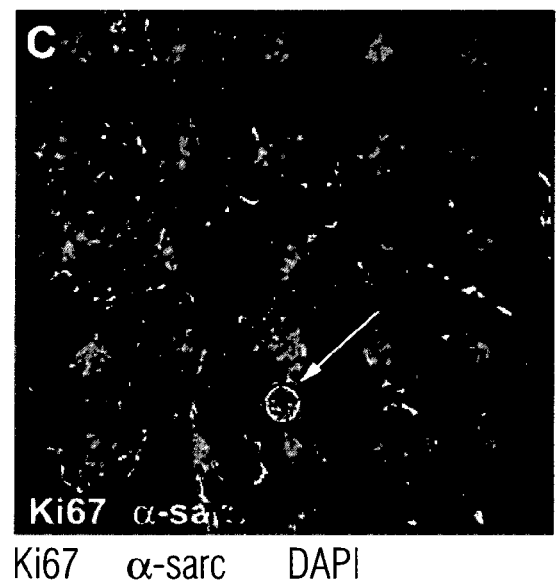
Figure 38D:
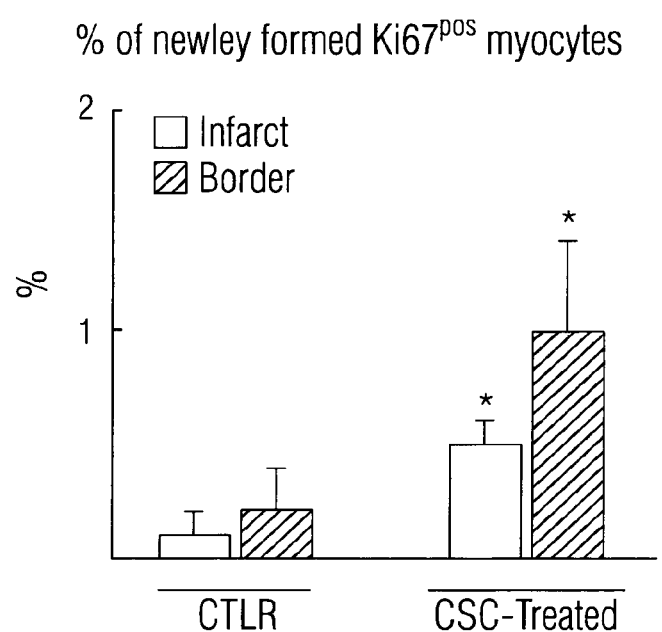
Figure 38E:
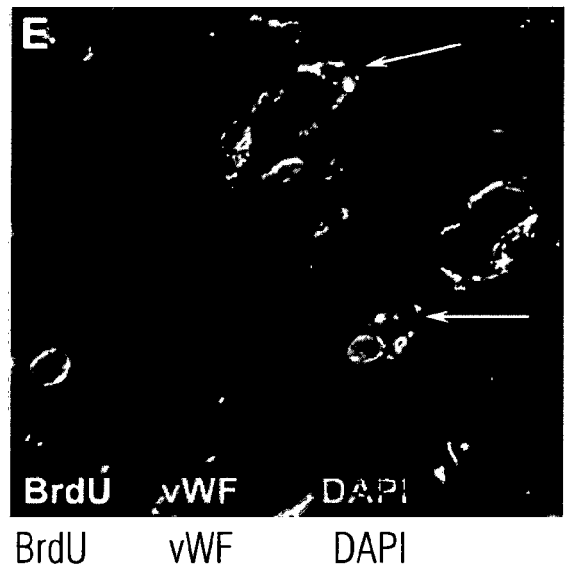
Figure 38F:
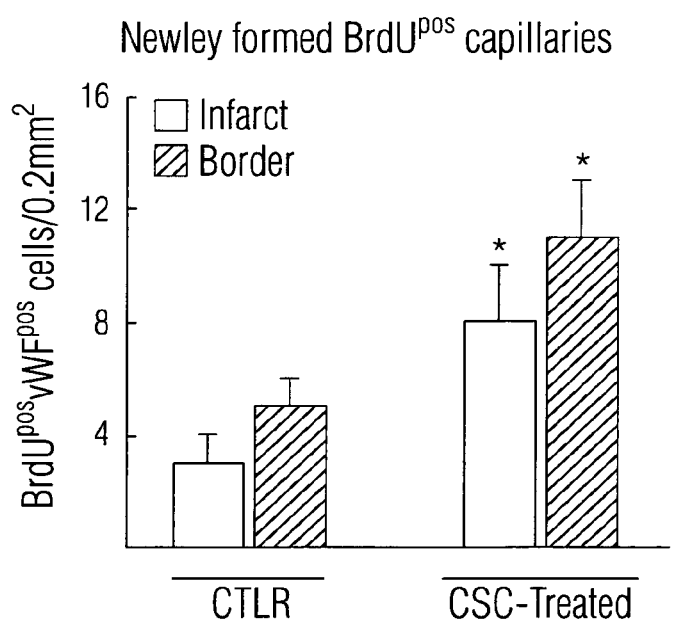
Figure 39A:
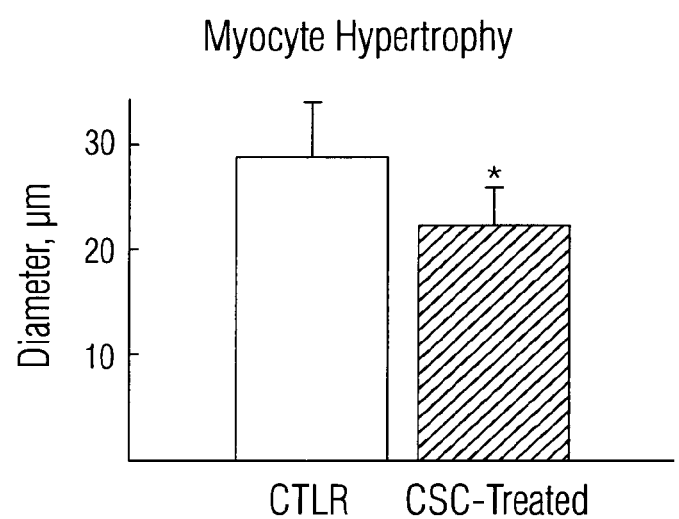
Figure 39B:
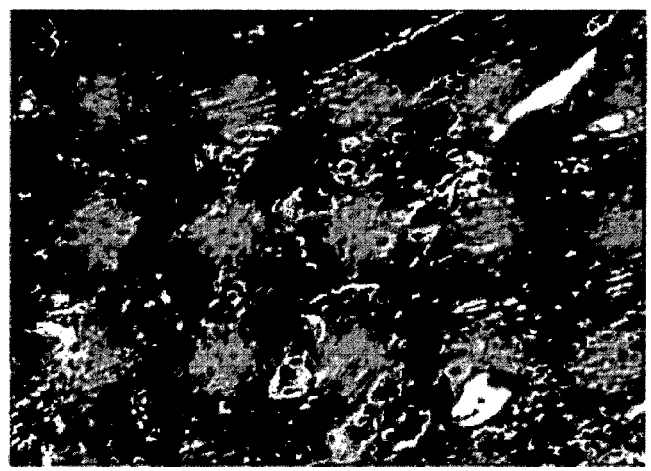
Figure 39C:
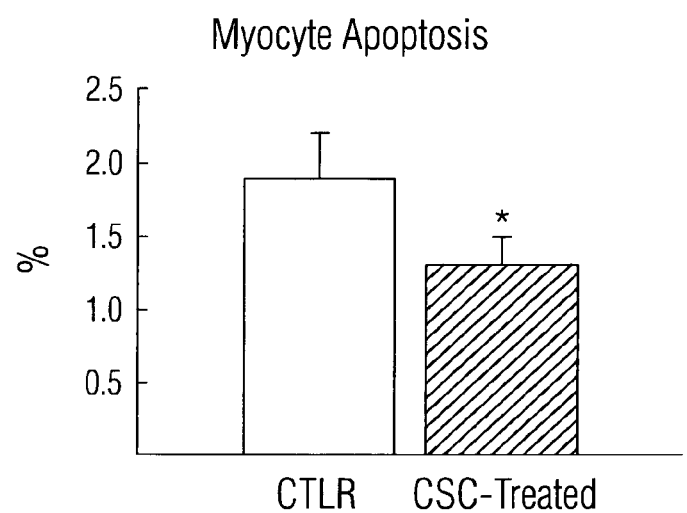
Figure 39D:
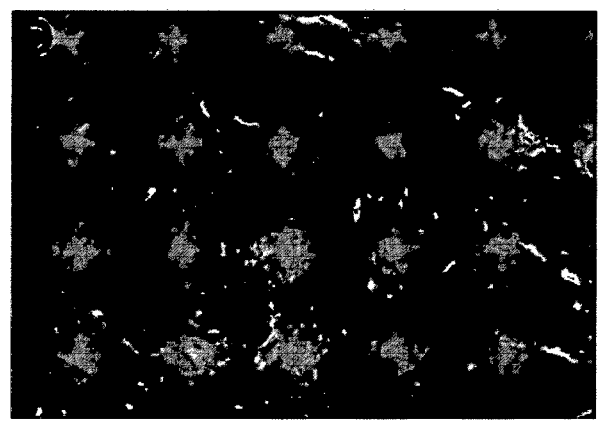
Figure 39E:
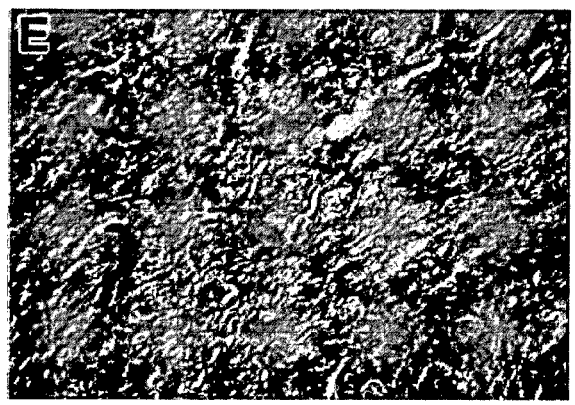
Figure 39F:
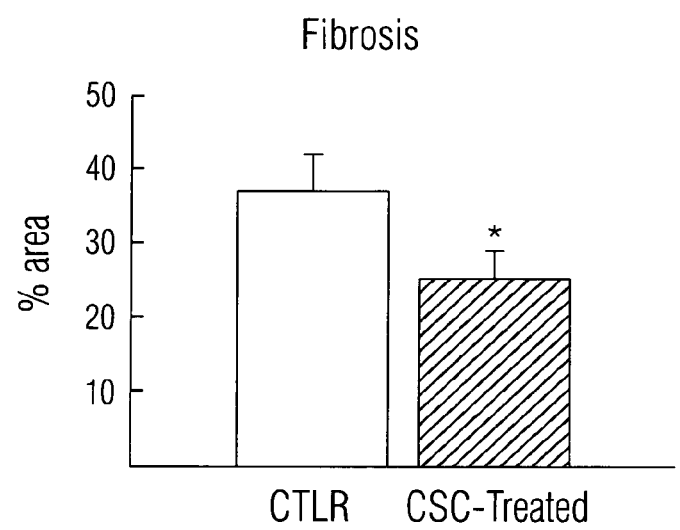

FIG. 35A. Immunogenicity molecules in human mature skin fibroblast, human CSC clone B (right atria) and human CSC clone C (right atria).

FIGS. 36A-F. EGFP+/c-kit+ heterolous HLA non-matched porcine CSCs nest in the damaged pig myocardium at 30 mins through to 1 day after MI. (A-C) representative images of EGFP$^{pos}$ CSCs in the infarcted porcine heart at 30 mins (A) 24 hours (B) 3 weeks (C) after intracoronary injection. (D). The number of EGFP$^{pos}$ CSCs in the infarcted porcine heart at 30 mins, 24 hours and 3 weeks after intracoronary injection of $1\times10^8$ EGFP$^{pos}$ CSCs. (E-F). Representative images of EGFP$^{pos}$ CSCs in the spleen. No EGFP$^{pos}$ CSCs were found at 3 weeks in the heart (C and D) or other tissues (F). Nuclei are stained by DAPI.

FIGS. 37A-D. Activation of endogenous CSCs following intracoronary injection of c-kit+ heterologous HLA non-matched porcine CSCs, after MI in pigs. (A) Representative image of CD45 negative, c-kit positive endogenous CSCs in the 3 week infarcted region of the CSC-treated porcine myocardium. Nuclei are stained by DAPI. (B) The percent number of endogenous CD45 negative, c-kit positive CSCs significantly increased following EGFP+/c-kit+ heterologous HLA non-matched CSC treatment. *P<0.05 vs. CTRL. (C&D) Representative images of endogenous progenitor cells differentiating into the myocyte. (C-Nkx2.5, c-kit, α-sarcomeric actin) and capillary (D-Ets-1, c-kit, α-sarcomeric actin) lineages. Nuclei are stain by DAPI.

FIGS. 38A-F. Increased new cardiomyocyte and capillary formation after c-kit+ heterologous non-matched porcine treatment. A & B The percent number of newly formed BrdU$^{pos}$ myocytes (A-sarcomeric actin) significantly increased following CSC treatment. *P<0.01 vs. CTRL. E & F. The fraction of newly formed BrdU$^{pos}$ capillaries significantly increased following CSC treatment. *P<0.01 vs. CTRL. Nuclei are stained by DAPI.

FIGS. 39A-F. Through paracrine mechanisms, c-kit+ heterologous HLA non-matched CSC treatment preserves myocardial wall structure and attenuates remodelling. (A) CSC treatment led to significantly decreased myocyte hypertrophy in the border region. *P<0.05 vs. CTRL. (B) Representative H&E staining showing a band of hypertrophic myocytes in the border region of CTRL pig myocardium. (C) CSC treatment significantly decreased percent number of apoptotic (caspase 3 positive) myocytes in the border region. *P<0.05 vs. CTRL. (D & E) Representative images of Sirius red staining to identify fibrotic tissue and muscle in the infarct region of CTRL (D) and CSC-treated (E) pig hearts. (F) CSC-treated pig hearts had a decreased percentage area fraction of fibrosis in the infarct zone. *P<0.05 vs. CTRL.

FIG. 40A-F. Human cardiac tissue explants and isolation of the c-kit positive stem-progenitor cells.

Figure 41:
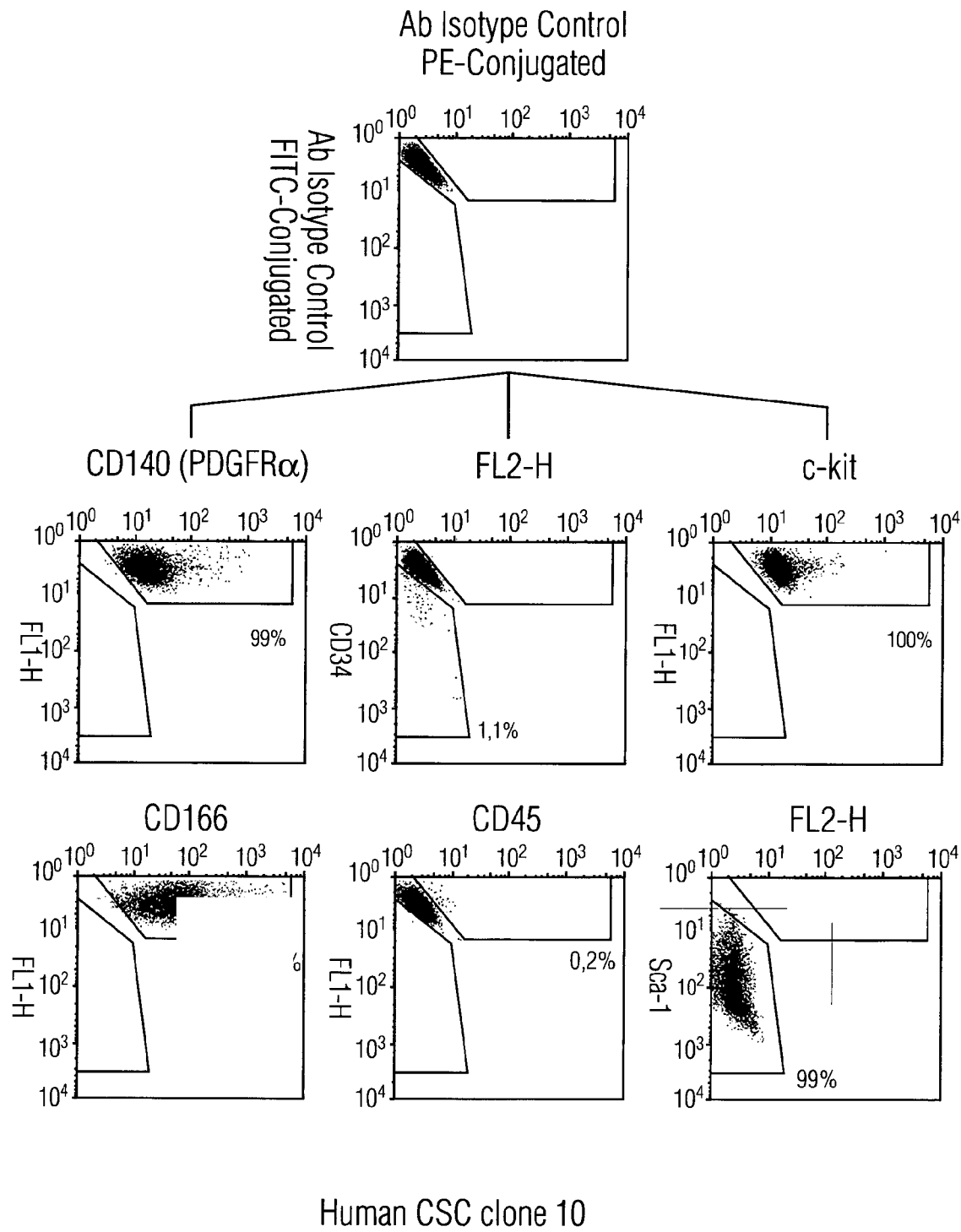
Figures 42A, 42B:
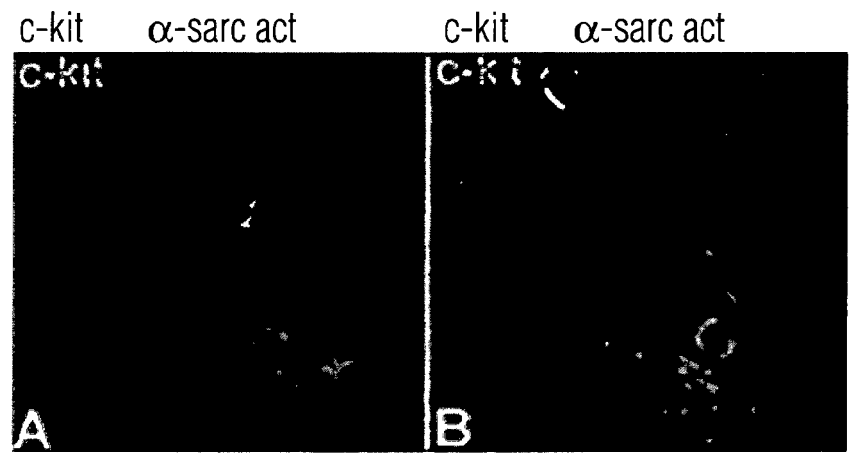
Figure 42C:
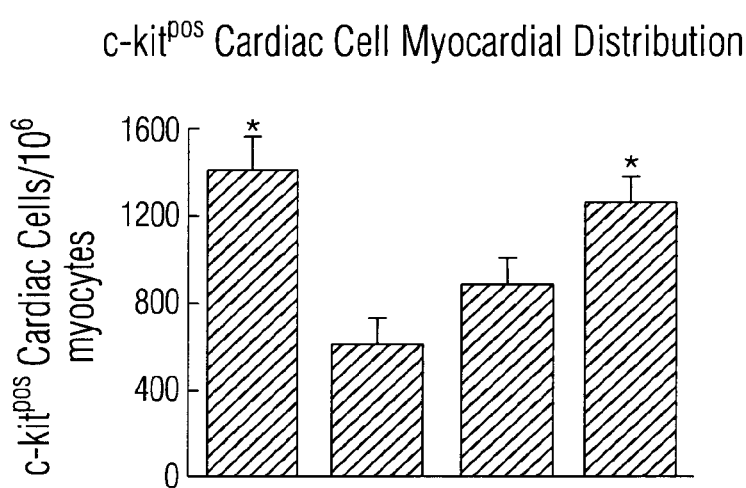
Figure 42D:
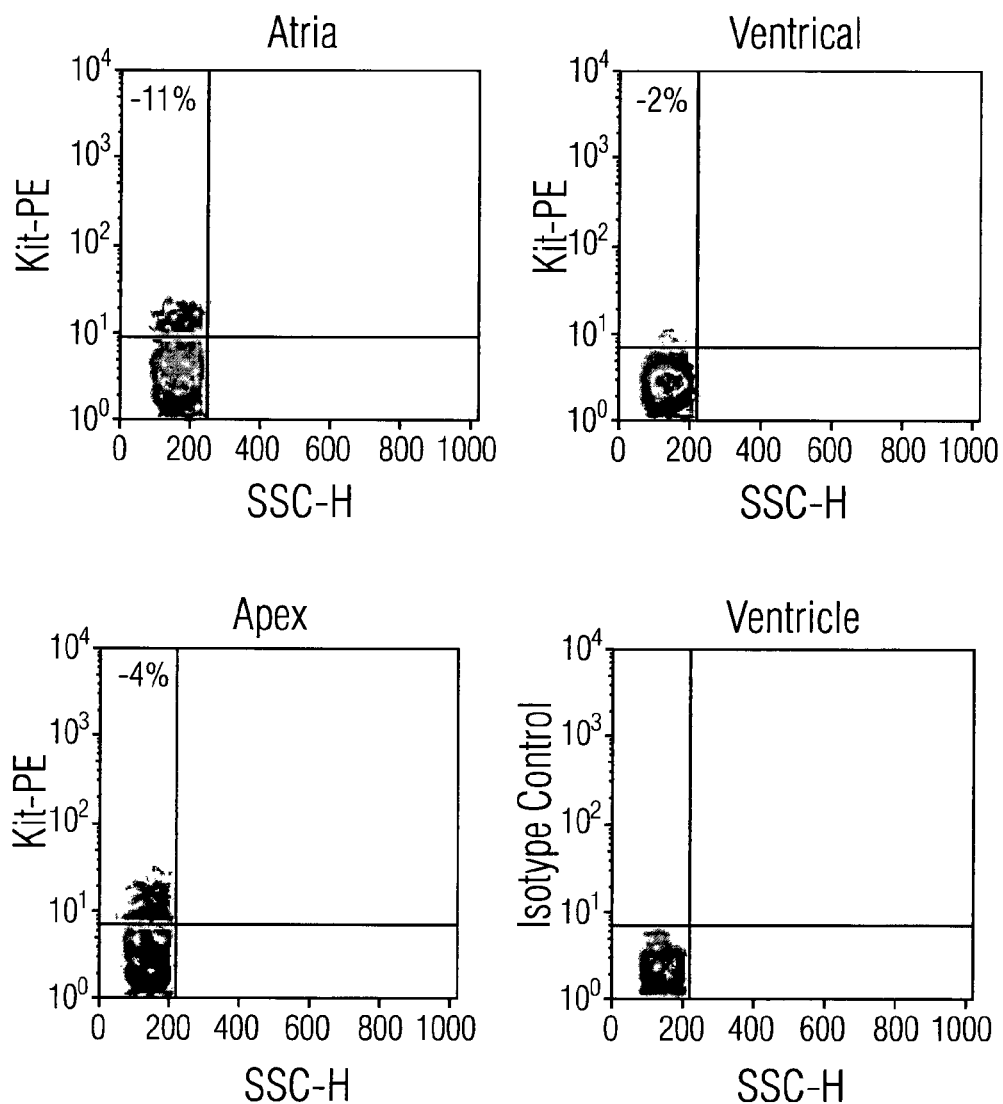
Figure 42E:
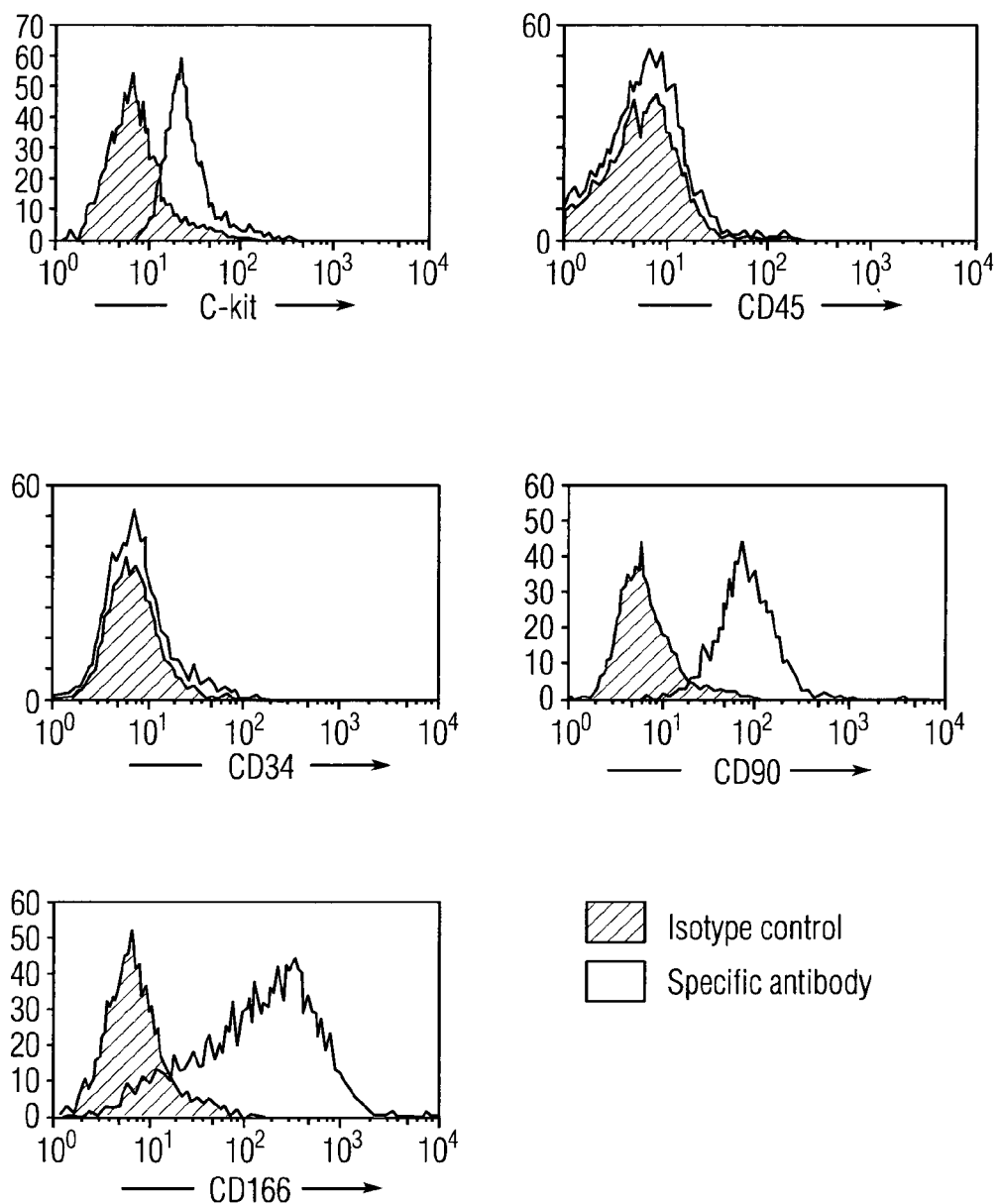
Figures 43A, 43B:
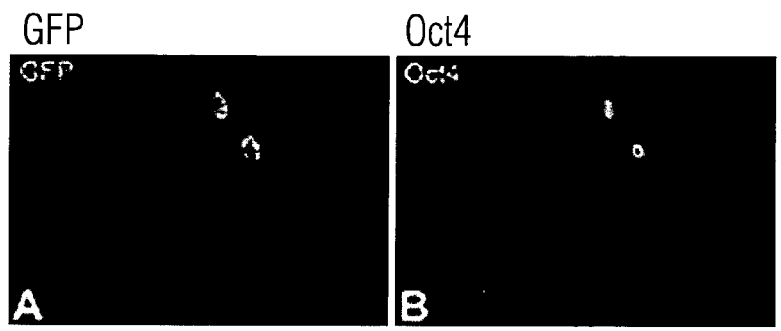
Figures 43C, 43D:
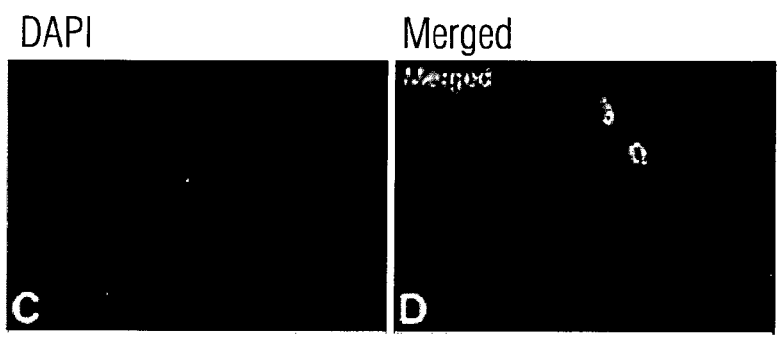
Figures 43E, 43F:
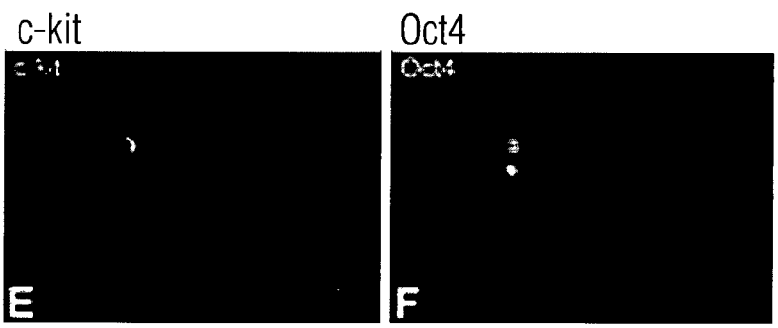
Figures 43G, 43H:
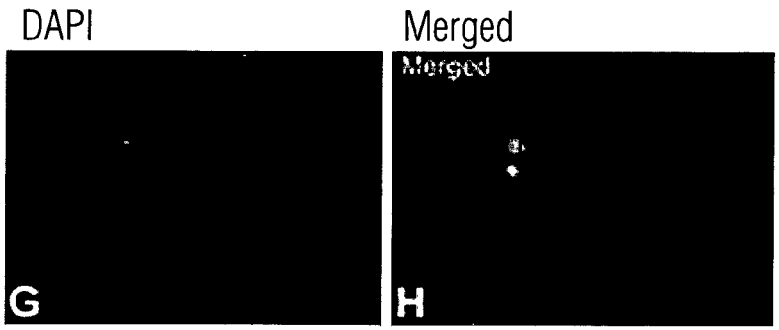

FIG. 41. Human CSC clone has a high cloning efficiency with very high uniform expression of the diagnostic markers.

FIGS. 42A-E. Porcine c-kit positive stem-progenitor cells and their characterization.

FIGS. 43A-H. In situ Oct4 cells in mouse and human. A-D correspond to section of myocardium from a mouse transgenic for GFP driven by the promoter of Oct4. (E-H) correspond to sections of normal human myocardium stained for c-kit and GFP.

5. DETAILED DESCRIPTION

The present disclosure is based, in part, on the discovery that within the adult myocardium, c-kit$^{pos}$eCSCs contain both primitive and more committed progenitors are isolated as negative for the hematopoietic marker, CD45 and the mast cell marker, Tryptase. Freshly isolated c-kit$^{pos}$ eCSCs express at differential levels, CD90, PDGFrα, CXCR4, Nestin, CD146, CD166 and Flk-1, yet do not express Wilms Tumor-1 (Wt1). At clonal level from single cell derivation, c-kit$^{pos}$ eCSCs express the known pluripotency genes, Oct-4, Klf-4, Nanog and Sox-2. When grown in defined media these single cell derived eCSCs can differentiate into a variety of specific cell types corresponding to the derivatives of the three embryonic germ layers. The Wnt/β-Catenin pathway is required for c-kit$^{pos}$eCSC expansion, while through its antagonism c-kit$^{pos}$ eCSCs turn on the expression multiple cardiomyogenic genes. Furthermore, TGF-β1/Smad2 pathway activation drives c-kit$^{pos}$eCSC cardiomyogenic differentiation. These growth factors are expressed by the adult myocardium in response to injury. A stage-specific TGF-β-Family/Wnt-Inhibitor composition comprising growth factors and small molecules modulate in vitro myogenic specification and maturation of c-kit$^{pos}$ eCSCs. Nadal-Ginard 2014 "Endogenous c-kit$^{pos}$ cardiac stem-progenitor cells have a broad developmental plasticity and depend on known embryonic signalling pathways for cardiomyogenic specification" (Submitted).

The exposure of eCSCs to the composition as described herein results in a regulatable means of controlling the differentiation of eCSCs into specific cell types, such as cardiomyocytes, endothelial and smooth muscle vascular cells. In particular, the exposure of eCSCs to the composition described herein results in the regulatable differentiation and expansion of specific populations of cardiac muscle cells. Such regulation of differentiation is accomplished without significant loss of yield due to cell death or differentiation to undesired cell types or cell lineages; in other words, the composition do not cause apoptosis or necrosis of one or more cell populations.

Thus, disclosed herein are methods of modulating eCSCs differentiation, specifically c-kit$^{pos}$eCSCs that are negative for the hematopoietic marker, CD45 and the mast cell marker, Tryptase. Also provided herein are modulation of isolated c-kit$^{pos}$ eCSCs to express at different levels, CD90, PDGFrα, CXCR4, Nestin, CD146, CD166 and Flk-1 and do not express Wilms Tumor-1 (Wt1). Also provided herein are modulation of clonal population of c-kit$^{pos}$ eCSCs from single cell derivation, that expresses the pluripotency genes, Oct-4, Klf-4, Nanog and Sox-2.

In particular, the present invention provides methods that employ small organic molecules that regulating the activity of Wnt, β-catenin or TGF-β. Examples of the small molecules that may be used in connection with the methods, include, but are not limited to, Wnt-3a, Dkk-1, β-catenin$^{shrna}$ or a combination thereof. In certain embodiments, the small molecule is BMP-2, BMP-4, TGF-β1, Smad2$^{shrna}$ or a combination thereof. In certain embodiments, the small molecule is IGF-1, Wnt3a, FGF-2, HGF or a combination thereof. In certain embodiments, the small molecule is BMP-2, BMP-4, TGF-β1, Wnt5a or a combination thereof.

Provided herein are methods for the control or regulation of eCSCs in vivo by the administration of both eCSCs and a composition described herein to a patient in need thereof. In certain embodiments, the methods comprise administration of eCSCs and a composition described herein into the coronary arterial tree, directly into the myocardium or into a peripheral vein of a patient in need thereof.

Provide here in is a protocol for the isolation, expansion and characterization of human cardiac stem-progenitor cells from a myocardial biopsy either obtained through a biopsy catheter or by direct sampling during cardiac surgery or from a cadaver.

5.1. Cardiac Stem-Progenitor Cells and Cell Populations

Cardiac stem-progenitor cells are cells, obtainable from a heart or part thereof, that adhere to a tissue culture substrate and have the capacity to differentiate into various cell types. In certain embodiments, the heart is mammalian, including human or pig. Provided herein are populations of cardiac stem-progenitor cells, or populations of cells comprising cardiac stem-progenitor cells. The cardiac stem-progenitor cells, and populations of cells comprising the cardiac stem-progenitor cells, can be identified and selected by the morphological, marker, and culture characteristic discussed in Nadal-Ginard 2013 Cell 154: 827-842 and below.

5.1.1. Physical and Morphological Characteristics

The eCSCs as described herein, when cultured in primary cultures or in cell culture, adhere to the tissue culture substrate, e.g., tissue culture container surface (e.g., tissue culture plastic). eCSCs in culture from species ranging from mouse to human assume a similar morphology which makes them indistinguishable under the light microscope. They are generally bi-refringent fusiform morphology with a volume inferior to a sphere 15 μm in diameter. The eCSCs have a paucity of cytoplasm with few mitochondria which is limited to a noeeow ring around the nucleus

5.1.2. Cell Surface, Molecular and Genetic Markers

Cardiac stem-progenitor cells and populations of cardiac stem-progenitor cells, express a plurality of markers that can be used to identify and/or isolate the stem-progenitor cells, or populations of cells that comprise the stem-progenitor cells. The cardiac stem-progenitor cells, and cardiac stem-progenitor cell populations include stem-progenitor cells and stem-progenitor cell-containing cell populations obtained directly from the heart, or any part thereof (e.g., muscle and non-muscle). Cardiac stem-progenitor cell populations also includes populations of (that is, two or more) cardiac stem-progenitor cells in culture, and a population in a container, e.g., a bag or a vial.

The cardiac stem-progenitor cells generally express the markers c-kit$^{pos}$ and are negative for the hematopoietic marker, CD45 and the mast cell marker, Tryptase. Also freshly isolated c-kit$^{pos}$ eCSCs express at different levels, CD90, PDGFrα, CXCR4, Nestin, CD146, CD166 and Flk-1 and do not express Wilms Tumor-1 (Wt1). Clonal population of c-kit$^{pos}$ eCSCs from single cell derivation expresses the pluripotency genes, Oct-4, Klf-4, Nanog and Sox-2. These markers can be used to identify cardiac stem-progenitor cells, and to distinguish cardiac stem-progenitor cells from other stem cell types.

Thus, in certain embodiments, provided herein is an isolated eCSC that is c-kit$^{pos}$ and are negative for the hematopoietic marker, CD45 and the mast cell marker, Tryptase. In certain embodiments, the eCSCs express CD90, PDGFrα, CXCR4, Nestin, CD146, CD166 and Flk-1 and do not express Wilms Tumor-1 (Wt1). In certain embodiments, provided herein is a clonal population of c-kit$^{pos}$ eCSCs derived from single cell (a clone) expresses the pluripotency genes, Oct-4, Klf-4, Nanog and Sox-2.

In another embodiment, provided herein is a method of selecting a eCSCs from a plurality of stem cells, comprising selecting a eCSC that is c-kit$^{pos}$ and are negative for the hematopoietic marker, CD45 and the mast cell marker, Tryptase. In certain embodiments, the method comprises selecting a eCSC express CD90, PDGFrα, CXCR4, Nestin, CD146, CD166 and Flk-1 and do not express Wilms Tumor-1 (Wt1). In certain embodiments, the method comprises selecting a clonal population of c-kit$^{pos}$ eCSCs from single cell derivation expresses the pluripotency genes, Oct-4, Klf-4, Nanog and Sox-2.

In another embodiment, provided herein is an isolated population of cells comprising, e.g., that is enriched for, c-kit$^{pos}$ and CD45$^{neg}$ and Tryptase$^{neg}$. In a specific embodiment, said population is a population of eCSCs. In various embodiments, at least about 10%, at least about 20%, at least about 30%, at least about 40%, at least about 50%, or at least about 60% of said cells are c-kit$^{pos}$ and CD45$^{neg}$ and Tryptase$^{neg}$ eCSCs. Preferably, at least about 70% of said cells are c-kit$^{pos}$ and CD45$^{neg}$ and Tryptase$^{neg}$ eCSCs. More preferably, at least about 90%, 95%, or 99% of said cells are c-kit$^{pos}$ and CD45$^{neg}$ and Tryptase$^{neg}$ eCSCs.

In another embodiment, provided herein is an isolated population of cells, e.g., that is enriched with the following properties, c-kit$^{pos}$ CD166$^{pos}$ and CD45$^{neg}$ and Tryptase$^{neg}$ In a specific embodiment, said population is a population of eCSCs. In various embodiments, at least about 10%, at least about 20%, at least about 30%, at least about 40%, at least about 50%, or at least about 60% of said cells are c-kit$^{pos}$ CD166$^{pos}$ and CD45$^{neg}$ and Tryptase$^{neg}$ eCSCs. Preferably, at least about 70% of said cells are c-kit$^{pos}$ CD166$^{pos}$ and CD45$^{neg}$ and Tryptase$^{neg}$ eCSCs. More preferably, at least about 90%, 95%, or 99% of said cells are c-kit$^{pos}$ CD166$^{pos}$ and CD45$^{neg}$ and Tryptase$^{neg}$ eCSCs.

Provided herein are eCSCs, or populations of eCSCs, wherein the eCSCs or population of eCSCs has been passaged at least 1, 2, 3, 4, 5, 6, 7, 8, 9, 10, 12, 14, 16, 18, or 20 times, or more, or expanded for 1, 2, 3, 4, 5, 6, 7, 8, 9, 10, 12, 14, 16, 18, 20, 22, 24, 26, 28, 30, 32, 34, 36, 38 or 40 population doublings, or more.

In a specific embodiment, the karyotype of the cells, or at least about 95% or about 99% of the cells in said population, is normal. That is, it has the diploid number of chromosomes and their banding pattern characteristic of the species from which the cells were obtained.

In certain embodiments, to obtain a pure population of cardiac stem cells (c-kit+/CD45−), including human cardiac stem cells, after the dissociation of the cardiac tissue either by coronary retroperfusion with a protease solution (rat and mouse) or by digestion of small fragments of tissue with a protease solution (human, pig, rat and mouse) and separation of the small cell fraction from the myocytes, undigested tissue and debris by gradient centrifugation, the c-kit positive population is isolated through negative and positive sorting using Miltenyi column immunobeads to first remove the CD 45 positive cells (comprising all the mast cells) and subsequently obtaining the remaining c-kit positive fraction which comprises the cardiac stem-progenitor cell population. This population can be further characterized by testing for the presence or absence of the positive and negative markers, respectively, listed in 0056.

The following methods are used.
Negative Sorting: Miltenyi Biotec: CD45 MicroBead kit MS (cat. #130-045-801)
Positive Sorting: Miltenyi Biotec: CD117 MicroBead kit MS (cat. #130-091-332)
Check purification with Miltenyi antibody Anti-CD117 (A3C6E2) (cat. #130-091-734)
Plate purified c-kit$^+$/CD45$^-$ cells in culture in 35 mm dishes pre-coated with CELLstart™ (Invitrogen) or porcine gelatin (Sigma).
Plate isolated cardiac c-kit+/CD45− cells in the following medium:

| | | |
|---|---|---|
| F12K/DMEM | (Gibco 31330) | 500 ml |
| FBS (ESCq) | (Gibco 10439-024) | 10% |
| hEPO | (Sigma E5627) | 0.005 u/ml |
| EGF | (Peprotech 100-15) | 20 ng/ml |
| bFGF | (Invitrogen PHG0021) | 10 ng/ml |
| hLIF | (Millipore LIF1010) | 500 µl |
| β-mercaptoethanol | (Sigma M7522) | 1.6 µl |
| 1x NE A.A. | (Sigma 100x) | 5 ml |
| Glutathione 0.2 mM | (Invitrogen) | 5 ml |
| P/S | (Invitrogen 15140122) | 5 ml |
| Gentamicin | (Gibco 15710) | 1 ul/ml stock (only till passage 4) |
| Fungizone | (Gibco 15290-026) | 1 ul/ml stock (only till passage 4) |

Bulk culture and cloned c-kitposCD45neg human cardiac cells express the mesenchymal marker, CD90 (40 to 60%) and the adhesion molecule/cardiac progenitor marker, CD166 (70 to 99%). They are practically negative for CD45 (0%) and CD34 (<5%). When analyzed at the single cell level by immunofluorescence for the expression of known cardiac progenitor markers, hCSCs show positivity for Telomerase, Gata-4, and Nkx2.5 (See FIG. 41). The above markers are the ones used for the isolation and identification of the c-kit+ CSCs. In addition by gene ship analysis they are also positive and negative, respectively for the following markers:

POSITIVE: Surface Markers: c-kit (≥90%) (CD117): CXCR4 (CD184); SSEA3/4 (≥80%) only in human CSCs; SSEA1 in human <65%, in murine CSCs (<80%); TRA-1-60(R)++; CD90++; CD133; PDGFR-α (CD140a); CD166++; VEGFR-2 or KDR (Flk-1 or VEGFR-2) (also known as CD309)++; ABCG2++; MDR1++.
Transcription factors: GATA-4+++; Oct4++; KLf4++; Nanog++; Sox2++; Bmi-1++; Tert (telomerase)++; Mesp1+; NKX2.5+; MEF2C+; TBX5+; TBX18+; Cripto+; Hand1+; Hand2+.
NEGATIVE: Surface Markers: CD11b; CD13; CD14; CD29; CD31; CD33; CD34; CD36; CD38; CD40; CD44; CD45; CD49f; CD56; CD62; CD71; CD73; CD106; CD146; CD234 (E-cadherin); CD326 (EpCAM), Tryptase. Transcription factors: WT1; c-myc; Islet-1

The modulation in the expression of the secretome of the human stem-progenitor cells during the process of differentiation is listed in Figure ??? entitled "Human CSC secretome data summary".

5.1.3 Growth in Culture

The growth of the eCSCs described herein, as for any mammalian cell, depends in part upon the particular medium selected for growth. Under optimum conditions, eCSCs typically double in number in 18-22 hours. During culture, the eCSCs adhere to a substrate in culture, e.g. the surface of a tissue culture container (e.g., tissue culture dish plastic, fibronectin-coated plastic, and the like) and form a monolayer. Populations of isolated eCSCs, when cultured under appropriate conditions in bacteriological plastic dishes, form cardiospheres. Cardiospheres grow in suspension (not attached to the culture vessel) and consist of cluster of CSCs ranging from a few hundreds to several million. These cardiospheres are distinguished from those produced by others by the fact that they consist of a pure population of CSCs without contamination with other cell types, such as connective tissue cells, vascular cells, etc. When these cardiospheres are placed in a tissue culture dish with the proper medium described herein, they attach to the dish, spread and differentiate into cardiomyocytes, endothelial, smooth muscle vascular cells and fibroblasts.

5.2 Methods of Obtaining eCSCs

5.2.1 Stem-Progenitor Cell Collection Composition

The present invention further provides methods of collecting and isolating eCSCs. Generally, eCSCs are obtained from a mammalian heart using a physiologically-acceptable solution, e.g., a stem-progenitor cell collection composition. In certain embodiments, the mammal ranging from mouse to human. In an embodiment, the mammal is a pig.

The stem-progenitor cell collection composition can comprise any physiologically-acceptable solution suitable for the collection and/or culture of stem-progenitor cells, for example, a saline solution (e.g., phosphate-buffered saline, Kreb's solution, modified Kreb's solution, Eagle's solution, 0.9% NaCl. etc.), a culture medium (e.g., DMEM, H.DMEM, etc.), and the like.

The stem-progenitor cell collection composition can comprise one or more components that tend to preserve eCSCs, that is, prevent the eCSCs from dying, or delay the death of the eCSCs, reduce the number of eCSCs in a population of cells that die, or the like, from the time of collection to the time of culturing. Such components can be, e.g., an apoptosis inhibitor (e.g., a caspase inhibitor or JNK inhibitor); a vasodilator (e.g., magnesium sulfate, an antihypertensive drug, atrial natriuretic peptide (ANP), adrenocorticotropin, corticotropin-releasing hormone, sodium nitroprusside, hydralazine, adenosine triphosphate, adenosine, indomethacin or magnesium sulfate, a phosphodiesterase inhibitor, etc.); a necrosis inhibitor (e.g., 2-(1H-Indol-3-yl)-3-pentylamino-maleimide, pyrrolidine dithiocarbamate, or clonazepam); a TNF-.alpha. inhibitor; and/or an oxygen-carrying perfluorocarbon (e.g., perfluorooctyl bromide, perfluorodecyl bromide, etc.); an anticoagulant (e.g. heparin).

The stem-progenitor cell collection composition can comprise one or more tissue-degrading enzymes, e.g., a metalloprotease, a serine protease, a neutral protease, an RNase, or a DNase, or the like. Such enzymes include, but are not limited to, collagenases (e.g., collagenase I, II, III or IV, a collagenase from *Clostridium histolyticum*, etc.); dispase, thermolysin, elastase, trypsin, LIBERASE, hyaluronidase, and the like.

The stem-progenitor cell collection composition can comprise a bacteriocidally or bacteriostatically effective amount of an antibiotic. In certain non-limiting embodiments, the antibiotic is a macrolide (e.g., tobramycin), a cephalosporin (e.g., cephalexin, cephradine, cefuroxime, cefprozil, cefaclor, cefixime or cefadroxil), a clarithromycin, an erythromycin, a penicillin (e.g., penicillin V) or a quinolone (e.g., ofloxacin, ciprofloxacin or norfloxacin), a tetracycline, a streptomycin, etc. In a particular embodiment, the antibiotic is active against Gram(+) and/or Gram(−) bacteria, e.g., *Pseudomonas aeruginosa, Staphylococcus aureus*, and the like.

The stem-progenitor cell collection composition can also comprise one or more of the following compounds: adenosine (about 1 mM to about 50 mM); D-glucose (about 20 mM to about 100 mM); magnesium ions (about 1 mM to about 50 mM); a macromolecule of molecular weight greater than 20,000 daltons, in one embodiment, present in an amount sufficient to maintain endothelial integrity and cellular viability (e.g., a synthetic or naturally occurring colloid, a polysaccharide such as dextran or a polyethylene glycol present at about 25 g/l to about 100 g/l, or about 40 g/l to about 60 g/l); an antioxidant (e.g., butylated hydroxyanisole, butylated hydroxytoluene, glutathione, vitamin C or vitamin E present at about 25 µM to about 100 µM); a reducing agent (e.g., N-acetylcysteine present at about 0.1 mM to about 5 mM); an agent that prevents calcium entry into cells (e.g., verapamil present at about 2 .mu.M to about 25 .mu.M); nitroglycerin (e.g., about 0.05 g/L to about 0.2 g/L); an anticoagulant, in one embodiment, present in an amount sufficient to help prevent clotting of residual blood (e.g., heparin or hirudin present at a concentration of about 1000 units/l to about 100,000 units/l); or an amiloride containing compound (e.g., amiloride, ethyl isopropyl amiloride, hexamethylene amiloride, dimethyl amiloride or isobutyl amiloride present at about 1.0 µM to about 5 µM).

5.2.2 Collection and Handling of Heart Tissues

The heart, prior to stem-progenitor cell collection, can be stored under sterile conditions and at either room temperature or at a temperature of 5 to 25° C. The heart may be stored for a period of for a period of four to twenty-four hours, up to forty-eight hours, or longer than forty eight hours, prior to perfusing the heart to remove any residual blood. The heart is preferably stored in an anticoagulant solution at a temperature of 5 to 25°. Suitable anticoagulant solutions are well known in the art. For example, a solution of heparin or warfarin sodium can be used. In a preferred embodiment, the anticoagulant solution comprises a solution of heparin (e.g., 1% w/w in 1:1000 solution). The heart is preferably stored for no more than 12 hours before stem-progenitor cells are collected. In certain embodiments, the heart or heart tissue are processed as soon as possible after the death of the donor. The mammalian heart or a part thereof, once collected and prepared generally as above, can be treated in any art-known manner, e.g., can be perfused or disrupted, e.g., digested with one or more tissue-disrupting enzymes, to obtain stem-progenitor cells. Alternatively, the heart tissue after collection can be stored deep frozen for later processing. For that the heart tissue has to be extensively minced to small pieces of 2-3 mm$^3$ in phosphate buffered solution or DMEM under sterile conditions. After the mincing is complete the processed tissue can be stored in DMEM and 20% fetal bovine calf serum and 5 to 10% dimethyl sulfoxide (DMSO), placed at −20° C. for 12-24 hours so that the anti-freeze solution can penetrate the tissue particles, followed by indefinite storage at −70° C. or in liquid nitrogen.

5.2.3 Physical Disruption and Enzymatic Digestion of Heart Tissue

Enzymatic Digestion Protocol:

Collect samples from fresh available heart chamber. Example: From atrium pieces, weight 0.084-0.200 gr, ~1 to 10×10$^6$ cells are obtained. The sample is washed 2-3 times in ~3 ml of cold PBS with antibiotics and transfer into a 10 cm bacteriological dish with ~2-3 ml of DMEM without serum. The tissue is cut in small pieces in 15 ml of Collagenase Type 2 (Worthington LS004177) (1 mg/ml in MEM/no serum) and incubate in a stirring conical Erlenmeyer glass flask for 5' 37° C. The supernatant is collected and spun down (300 g for 5 min). The small cell pellet is re-suspended into a 15 ml tube with 10 ml of DMEM with 10% FCS and kept on ice. Repeat the latter step ~9 times with the rest of the tissue (until all tissue is digested) and collect supernatant after each step. Strain all collected SN cells once through a 40 µm filter, collect flow-through into 50 ml tubes. Spin at 300 g for 7 min to recover the cells, remove the supernatant and resuspend the cell pellets in 1 ml of incubation medium (see Myltenyi protocol), count cells and proceed to MACS sorting according to Miltenyi protocols (MACS sorting protocol below).

Human cardiac stem cells have been isolated from human cardiac samples (or biopsies) from every cardiac chamber using two main protocols, Enzymatic Digestion or Cardiac tissue culture protocol, which are summarized below.

Cardiac Tissue Culture Protocol:

Collect samples from fresh available heart chamber. Wash the sample 2-3 times in ~3 ml of cold PBS with antibiotics and transfer into a 10 cm bacteriological dish with ~2-3 ml of DMEM without serum. Cut the samples in small pieces. Plate small pieces on gelatin-coated 100 mm Petri dishes with 6 ml medium detailed below. For the first week, every 48 h remove 4 ml of media and add 4 ml fresh media; afterwards change media every 48 h. By 2-3 weeks there is significant cell outgrowth surrounding the cultured little tissue fragments. When cells reach confluent growth around the tissue, detach first the tissues from the plate (the tissue fragments can be re-plated as above and start a new cycle of cell isolation from the start) and then using trypsin to detach cells. Spin at 300 g for 7 min to recover the cells, remove the supernatant and resuspend the cell pellets in 1 ml of incubation medium (see Myltenyi protocol), count cells and proceed to MACS sorting according to Miltenyi protocols (MACS sorting protocol below). (See FIGS. 40A-F and FIGS. 32A-B).

In one embodiment, stem-progenitor cells are collected from a mammalian heart by physical disruption of a part or of all the organ. For example, the heart, or a portion thereof, may be, e.g., crushed, sheared, minced, diced, chopped, macerated or the like. The tissue can then be cultured to obtain a population of stem-progenitor cells. Typically, the heart tissue is disrupted using, e.g., in, a stem-progenitor cell collection composition which contains a buffered solution with a protease (e.g. collagenase) or a mixture of proteases.

In another specific embodiment, stem-progenitor cells are collected by physical disruption of heart tissue, wherein the physical disruption includes enzymatic digestion, which can be accomplished by use of one or more tissue-digesting enzymes. The heart, or a portion thereof, may also be physically disrupted and digested with one or more enzymes, and the resulting material then immersed in, or mixed into, a stem-progenitor cell collection composition.

In another specific embodiment, the whole heart is retroperfused by canulation of the aortic stump and pumping under pressure the tissue digestive solution (e.g. collagenase) at 37° C. with a minimum of 5 times the weight of the heart of digestive solution (1 g heart=5 ml solution). After perfusion the myocardial tissue is easily disrupted mechanically by shaking, teasing and repeated pipetting into individual cells and small clumps of cells.

5.2.5 Isolation, Sorting, and Characterization of Cardiac Stem-Progenitor Cells Isolation of stem-progenitor cells from the heart of larger mammalian species such as the pig, bovine and human where retrograde perfusion might be impractical because of the large volumes needed or because only a sample of the myocardium is available a reproducible methods of isolation involves the seeding of the minced heart tissue in tissue culture dishes, particles placed ~0.5 cm apart from each other in stem-progenitor growth medium. In 48-72 hours the tissue particles attach to the bottom of the dish and cells start to migrate out of the tissue forming a halo around the tissue particle. Two weeks later the tissue particles are removed with a steril forceps and the migrated cells removed from the dish by trypsinization and prepared for either FACS sorting to select the c-kit$^{pos}$ CD166$^{pos}$ and CD45$^{neg}$ and Tryptase$^{neg}$ eCSCs. Alternatively, the CSCs can be purified from the cell mixture by magnetic immunosorting using the columns and procedures recommended by the provider of the immune-magnetic kits (Miltenyi) to isolate the c-kit$^{pos}$ CD45$^{neg}$ and Tryptase$^{neg}$ eCSCs.

Stem-progenitor cells from mammalian heart, such as obtained by enyzmatic digestion, can initially be purified from (i.e., be isolated from) other cells by Ficoll gradient centrifugation. Such centrifugation can follow any standard protocol for centrifugation speed, etc. In one embodiment, for example, cells collected from the heart are recovered by centrifugation at 5000×g for 15 minutes at room temperature, which separates cells from, e.g., contaminating debris. In another embodiment, the processed heart is concentrated to about 200 ml, gently layered over Ficoll, and centrifuged at about 1100×g for 20 minutes at 22° C., and the low-density interface layer of cells is collected for further processing.

Cell pellets can be resuspended in fresh stem-progenitor cell collection composition, or a medium suitable for stem-progenitor cell maintenance, e.g., IMDM serum-free medium containing 2 U/ml heparin and 2 mM EDTA (GibcoBRL, NY).

As used herein, "isolating" cardiac stem-progenitor cells means to remove at least 20%, 30%, 40%, 50%, 60%, 70%, 80%, 90%, 95% or 99% of the cells with which the stem-progenitor cells are normally associated in the intact mammalian heart. A stem-progenitor cell from an organ is "isolated" when it is present in a population of cells that comprises fewer than 5% of the cells with which the stem-progenitor cell is normally associated in the intact organ.

Cardiac cells obtained by digestion can, for example, be further, or initially, isolated by differential trypsinization using, e.g., a solution of 0.05% trypsin with 0.2% EDTA (Sigma, St. Louis Mo.). The detached cardiac stem-progenitor cells can be harvested following trypsinization and trypsin neutralization, using, e.g., Trypsin Neutralizing Solution (TNS, Cambrex). In one embodiment of isolation of adherent cells, aliquots of, for example, about 5-10×10$^6$ cells are placed in each of several T-75 flasks, preferably fibronectin-, gelatin- or laminin-coated T75 flasks. In such an embodiment, the cells can be cultured with commercially available Stem-progenitor Cell Growth Medium, and placed in a tissue culture incubator (37° C., 5% CO$_2$). After 10 to 15 days, non-adherent cells are removed from the flasks by washing with PBS. The PBS is then replaced by new media. Flasks are preferably examined daily for the presence of various adherent cell types and in particular, for identification and expansion of clusters of stem-progenitor cells.

The number and type of cells collected from a mammalian heart can be monitored, for example, by measuring changes in morphology and cell surface markers using standard cell detection techniques such as flow cytometry, cell sorting, immunocytochemistry (e.g., staining with tissue specific or cell-marker specific antibodies) fluorescence activated cell sorting (FACS), magnetic activated cell sorting (MACS), by examination of the morphology of cells using light or confocal microscopy, and/or by measuring changes in gene expression using techniques well known in the art, such as PCR and gene expression profiling. These techniques can be used, too, to identify cells that are positive for one or more particular markers. For example, using antibodies or by RT-PCR as known in the art. In an embodiment, about 45,000 stem-progenitor cells are isolated from one gram of human myocardial tissue.

Cardiac cells, particularly cells that have been isolated by Ficoll separation, differential adherence, or a combination of both, may be sorted using a fluorescence activated cell sorter (FACS). Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In one sorting scheme, stem-progenitor cells from heart are sorted on the basis of expression of the markers as described herein. This can be accomplished in connection with procedures to select stem-progenitor cells on the basis of their low adherence properties in culture. For example, an adherence selection stem-progenitor cell can be accomplished before or after sorting on the basis of marker expression. While most of the isolated cardiac cells generated by the digestion procedures described herein will adhere to the cell culture plate in the first 24 hours, the stem-progenitor cells require 36-72 hours to adhere to the plate. A reliable enrichment protocol is to place the cell mixture with the proper medium in the culture plates and pass the supernatant (containing the non-attached cells) to a new plate every 6-8 hours for the first 36 hours of culture. This will deplete the mixture of connective tissue, vascular cells and myocytes while enriching the supernatant with the stem-progenitor cells.

With respect to antibody-mediated detection and sorting of cardiac stem-progenitor cells, any antibody, specific for a particular marker, can be used, in combination with any fluorophore or other label suitable for the detection and sorting of cells (e.g., fluorescence-activated cell sorting). Antibody/fluorophore combinations to specific markers include, but are not limited to, fluorescein isothiocyanate (FITC) conjugated monoclonal antibodies.

Cardiac stem-progenitor cells can be labeled with an antibody to a single marker and detected and/sorted. Cardiac stem-progenitor cells can also be simultaneously labeled with multiple antibodies to different markers tagged with the same or different fluorophores.

In another embodiment, magnetic beads can be used to separate cells. The cells may be sorted using a magnetic activated cell sorting (MACS) technique, a method for separating particles based on their ability to bind magnetic beads (0.5-100 .mu.m diameter). A variety of useful modifications can be performed on the magnetic microspheres, including covalent addition of antibody that specifically recognizes a particular cell surface molecule or hapten. The beads are then mixed with the cells to allow binding. Cells are then passed through a magnetic field to separate out cells having the specific cell surface marker. In one embodiment, these cells can then isolated and re-mixed with magnetic beads coupled to an antibody against additional cell surface markers. The cells are again passed through a magnetic field, isolating cells that bound both the antibodies. Such cells can then be diluted into separate dishes, such as microtiter dishes for clonal isolation.

Cardiac stem-progenitor cells can also be characterized and/or sorted based on cell morphology and growth characteristics. For example, cardiac stem-progenitor cells can be characterized as having, and/or selected on the basis of, e.g., their appearance in culture. Cardiac stem-progenitor cells can also be characterized as having, and/or be selected, on the basis of their ability to form cardiospheres. Said cardiospheres are cell aggregates formed when the cardiac stem-progenitor cells are grown in bacteriological dishes (those are plastic dishes whose surface is not negatively charged and which does not allow the attachment of animal cells) ranging from a few hundreds to a few million cells. The property to form this type of aggregates is a characteristic of stem-progenitor cells from solid tissues. As such it is shared with the neural stem-progenitor (neurospheres), epithelium, liver, etc.

In another embodiment, cardiac stem-progenitor cells can be identified and characterized by a colony forming unit assay.

Cardiac stem-progenitor cells can be assessed for viability, proliferation potential, and longevity using standard techniques known in the art, such as trypan blue exclusion assay, fluorescein diacetate uptake assay, propidium iodide uptake assay (to assess viability); and thymidine uptake assay, MTT cell proliferation assay (to assess proliferation). Longevity may be determined by methods well known in the art, such as by determining the maximum number of population doubling in an extended culture.

Cardiac stem-progenitor cells can also be separated from other cardiac cells using other techniques known in the art, e.g., selective growth of desired cells (positive selection), selective destruction of unwanted cells (negative selection); separation based upon differential cell agglutinability in the mixed population as, for example, with soybean agglutinin; freeze-thaw procedures; filtration; conventional and zonal centrifugation; centrifugal elutriation (counter-streaming centrifugation); unit gravity separation; countercurrent distribution; electrophoresis; and the like.

The tables below show the results of representative isolations of cardiac stem-progenitor cells from the mouse, rat, pig and human. These results have been used to calculate the total number of stem-progenitor cells in the whole heart of each of these species, as well as the distribution of cardiac c-kit$^{pos}$ cells between mast cells (c-kit$^{pos}$CD45$^{pos}$Tyr$^{pos}$) and stem-progenitor cells (c-kit$^{pos}$CD166$^{pos}$CD45$^{neg}$Tryp$^{neg}$).

| % in the small cell population | UNSORTED CARDIAC SMALL CELLS | | | | SORTED FOR C-KIT | | PIG AVERAGE (ATRIA AND LV) |
|---|---|---|---|---|---|---|---|
| | MOUSE | RAT | PIG ATRIA | PIG LV | PIG ATRIA | PIG LV | |
| C-KIT+, CD45+ (mast cells) | 10 | 14 | 10 | ~5.25 | ~8 | ~6 | |
| C-KIT+, CD45− (eCSCs) | 3 | 4 | 1 | 3.5 | ~2 | ~4 | |
| total | 13 | 18 | 11 | ~8.75 | ~10 | ~10 | |
| Distribution of c-kit+ cells | | | | | | | |
| C-KIT+, CD45+ (mast cells) | 76.92 | 77.78 | 90.91 | 60 | 80 | 60 | 73.58 |
| C-KIT+, CD45− (eCSCs) | 23.07 | 22.22 | 9.09 | 40 | 20 | 40 | 26.41 |

CSC numbers in normal hearts of mouse, rat and human:

| | RAT | MOUSE | RAT/MOUSE | MOUSE/RAT | HUMAN | HUMAN/MOUSE |
|---|---|---|---|---|---|---|
| Heart weight (mg) | 900 | 150 | 6 | 0.166666667 | 315,000 | 2100 |
| Cardiomyocyte number | 40,000,000 | 8,000,000 | 5 | 0.2 | $1.1 \times 10^{10}$ | 2795 |
| Cardiomyocytes/mg | 44,444 | 53,333 | 0.8 | 1.2 | 35,500 | 0.80 |
| C number recovered the whole organ | 150,000 | 30,000 | 5 | 0.2 | $1.4 \times 10^7$ | 315 |
| eCSCs/mg | 165 | 200 | 0.8 | 1.2 | 45 | 0.225 |
| CSCs/1000 C-myocytes | 3.75 | 3.75 | 1 | 1 | 3.634615385 | 0.969230769 |

5.3 Culture Cardiac Stem-Progenitor Cells

5.3.1 Culture Media

Isolated cardiac stem-progenitor cells, or cardiac stem-progenitor cell population, or cells or cardiac tissue from which cardiac stem-progenitor cells grow out, can be used to initiate, or seed, cell cultures. Cells are generally transferred to sterile tissue culture vessels either uncoated or coated with extracellular matrix or ligands such as laminin, collagen (e.g., native or denatured), gelatin, fibronectin, ornithine, vitronectin, and extracellular membrane protein (e.g., MATRIGEL® (BD Discovery Labware, Bedford, Mass.)).

Cardiac stem-progenitor cells can be cultured in any medium, and under any conditions, recognized in the art as acceptable for the culture of stem-progenitor cells. Preferably, the culture medium comprises serum, preferably fetal bovine calf serum.

The culture medium can be supplemented with one or more components including, for example, serum (e.g., fetal bovine serum (FBS), preferably about 2-15% (v/v); equine (horse) serum (ES); human serum (HS)); beta-mercaptoethanol (BME), preferably about 0.001% (v/v); platelet extract, one or more growth factors and one or more antibiotic and/or antimycotic agents to control microbial contamination, such as, for example, penicillin G, streptomycin sulfate, amphotericin B, gentamicin, and nystatin, either alone or in combination.

Cardiac stem-progenitor cells can be cultured in standard tissue culture conditions, e.g., in tissue culture dishes or multiwell plates. One or more small molecules as disclosed herein may be contacted with a cardiac stem-progenitor cell, or population of cardiac stem-progenitor cells, at a concentration of, for example, between about 1 µM to about 10 µM.

5.3.2 Expansion and Proliferation of Cardiac Stem-Progenitor Cells

Once an isolated cardiac stem-progenitor cell, or isolated population of stem-progenitor cells (e.g., a stem-progenitor cell or population of stem-progenitor cells separated from at least 50% of the cardiac cells with which the stem-progenitor cell or population of stem-progenitor cells is normally associated in vivo), the stem-progenitor cell or population of stem-progenitor cells can be proliferated and expanded in vitro. For example, a population of cardiac stem-progenitor cells can be cultured in tissue culture containers, e.g., dishes, flasks, multiwell plates, bioreactors or the like, for a sufficient time for the stem-progenitor cells to proliferate to 70-90% confluence, that is, until the stem-progenitor cells and their progeny occupy 70-90% of the culturing surface area of the tissue culture container.

Cardiac stem-progenitor cells can be seeded in culture vessels at a density that allows cell growth. For example, the cells may be seeded at low density (e.g., about 1,000 to about 5,000 cells/cm$^2$) to high density (e.g., about 50,000 or more cells/cm$^2$). In a preferred embodiment, the cells are cultured at about 0 to about 5 percent by volume $CO_2$ in air. In some preferred embodiments, the cells are cultured at about 2 to about 25 percent $O_2$ in air, preferably about 3 to about 20 percent $O_2$ in air. The cells preferably are cultured at about 25° C. to about 40° C., preferably 37° C. The cells are preferably cultured in an incubator. The culture medium can be static or agitated, for example, using a bioreactor. Cardiac stem-progenitor cells preferably are grown under low oxidative stress (e.g., 3% $O_2$ with addition of glutathione, ascorbic acid, catalase, tocopherol, N-acetylcysteine, or the like).

Once 70%-90% confluence is obtained, the cells may be passaged. For example, the cells can be enzymatically treated, e.g., trypsinized, using techniques well-known in the art, to separate them from the tissue culture surface. After removing the cells by pipetting and counting the cells, about 20,000-100,000 stem cells, preferably about 50,000 stem cells, are passaged to a new culture container containing fresh culture medium (if the container is a T-75 flask the ideal number of cells seeded is ~500,000 per flask). Typically, the new medium is the same type of medium from which the stem cells were removed. In certain embodiments, populations of cardiac stem cells have been passaged at least 1, 2, 3, 4, 5, 6, 7, 8, 9, 10, 12, 14, 16, 18, or 20 times, or more.

5.3.3 Cardiac Stem-Progenitor Cell Populations

Provided herein are populations of cardiac stem-progenitor cells. Cardiac stem-progenitor cell population can be isolated directly from one or more hearts; that is, the cardiac stem-progenitor cell population can be a population of cardiac cells comprising cardiac stem-progenitor cells obtained from, or contained within, perfusate, or obtained from, or contained within, disrupted heart tissue, e.g., heart tissue digestate (that is, the collection of cells obtained by enzymatic digestion of a heart or part thereof). Isolated cardiac stem-progenitor cells of the invention can also be cultured and expanded to produce cardiac stem-progenitor cell populations. Populations of cardiac cells comprising cardiac stem-progenitor cells can also be cultured and expanded to produce cardiac stem-progenitor cell populations.

Cardiac stem-progenitor cell populations of the invention comprise cardiac stem-progenitor cells, for example, cardiac stem-progenitor cells as described herein. In various embodiments, at least 10%, 20%, 30%, 40%, 50%, 60%, 70%, 80%, 90%, 95%, 99% or 99.9% of the cells in an isolated cardiac stem-progenitor cell population are cardiac stem-progenitor cells. That is, a cardiac stem-progenitor cell population can comprise, e.g., as much as 0.1%, 1%, 5%, 10%, 20%, 30%, 40%, 50%, 60%, 70%, 80%, 90% non-stem-progenitor cells.

The invention provides methods of producing isolated cardiac stem-progenitor cell population by, e.g., selecting cardiac stem-progenitor cells, whether derived from enzymatic digestion or perfusion, that express particular markers and/or particular culture or morphological characteristics. In one embodiment, for example, provided herein is a method of producing a cell population comprising selecting cardiac cells that (a) adhere to a substrate, and (b) express specific markers; and isolating said cells from other cells to form a cell population. Such cell populations can be used to treat any of the diseases or conditions listed hereinbelow. Such cell populations can also be used to assess populations of cardiac stem-progenitor cells, e.g., as part of a quality control method.

In the above embodiments, the substrate can be any surface on which culture and/or selection of cells, e.g., cardiac stem-progenitor cells, can be accomplished. Typically, the substrate is plastic, e.g., tissue culture dish or multiwell plate plastic. Tissue culture plastic can be coated with a biomolecule, e.g., gelatine, laminin or fibronectin.

Cells, e.g., cardiac stem-progenitor cells, can be selected for a cardiac stem-progenitor cell population by any means known in the art of cell selection. For example, cells can be selected using an antibody or antibodies to one or more cell surface markers, for example, in flow cytometry or FACS. Selection can be accomplished using antibodies in conjunction with magnetic beads. Antibodies that are specific for certain stem-progenitor cell-related markers are known in the art.

The isolated cardiac stem-progenitor cell population can comprise cardiac cells that are not stem-progenitor cells, or cells that are not cardiac cells.

Isolated cardiac stem-progenitor cell populations can be combined with one or more populations of non-stem-progenitor cells or non-cardiac cells. For example, an isolated population of cardiac stem-progenitor cells can be combined with blood (e.g., cardiac blood or umbilical cord blood), blood-derived stem cells (e.g., stem cells derived from cardiac blood or umbilical cord blood), umbilical cord stem cells, populations of blood-derived nucleated cells, bone marrow-derived mesenchymal cells, bone-derived stem cell populations, crude bone marrow, adult (somatic) stem cells, populations of stem cells contained within tissue, cultured stem cells, populations of fully-differentiated cells (e.g., chondrocytes, fibroblasts, amniotic cells, osteoblasts, muscle cells, cardiac cells, etc.) and the like. Cells in an isolated cardiac stem cell population can be combined with a plurality of cells of another type in ratios of about 100,000,000:1, 50,000,000:1, 20,000,000:1, 10,000,000:1, 5,000,000:1, 2,000,000:1, 1,000,000:1, 500,000:1, 200,000:1, 100,000:1, 50,000:1, 20,000:1, 10,000:1, 5,000:1, 2,000:1, 1,000:1, 500:1, 200:1, 100:1, 50:1, 20:1, 10:1, 5:1, 2:1, 1:1; 1:2; 1:5; 1:10; 1:100; 1:200; 1:500; 1:1,000; 1:2,000; 1:5,000; 1:10,000; 1:20,000; 1:50,000; 1:100,000; 1:500,000; 1:1,000,000; 1:2,000,000; 1:5,000,000; 1:10,000,000; 1:20,000,000; 1:50,000,000; or about 1:100,000,000, comparing numbers of total nucleated cells in each population. Cells in an isolated cardiac stem-progenitor cell population can be combined with a plurality of cells of a plurality of cell types, as well.

Isolated cardiac stem-progenitor cell populations can be combined with one or more growth factors which can affect their growth, differentiation and/or survival properties or those of the recipient tissues in the case of their transplantation to the donor or to a recipient with the same genetic makeup as the donor (autologous or syngeneic transplantation) or to a recipient or recipients of the same species but with a different genetic makeup from the donor (allogeneic transplantation).

Cells in an isolated cardiac stem cell population can be combined with a plurality of growth factors such us (the factors listed in the publication WO2009/136283A3).

5.4 Production of a Cardiac Stem-Progenitor Cell Bank

Stem-progenitor cells from hearts can be cultured in a number of different ways to produce a set of lots, e.g., a set of individually-administrable doses, of cardiac stem-progenitor cells. Such lots can, for example, be obtained from stem-progenitor cells from cardiac perfusate or from enzyme-digested cardiac tissue. Sets of lots of cardiac stem-progenitor cells, obtained from a single or from a plurality of hearts, can be arranged in a bank of cardiac stem-progenitor cells for, e.g., long-term storage. Generally, adherent stem-progenitor cells are obtained from an initial culture of cardiac material to form a seed culture, which is expanded under controlled conditions to form populations of cells from approximately equivalent numbers of doublings. Lots are preferably derived from the tissue of a single heart, but can be derived from the tissue of a plurality of hearts.

In one embodiment, stem-progenitor cell lots are obtained as follows. Cardiac tissue is first disrupted, e.g., by mincing, digested with a suitable enzyme, e.g., collagenase. The cardiac tissue preferably comprises tissues from a single heart, but can comprise more than one heart. The digested tissue is cultured, e.g., for about 1-3 weeks, preferably about 2 weeks. After removal of non-adherent dead cells, high-density colonies that form are collected, e.g., by trypsinization. These cells are collected and resuspended in a convenient volume of culture medium, and defined as Passage 0 cells.

Passage 0 cells are then used to seed expansion cultures. Expansion cultures can be any arrangement of separate cell culture apparatuses, e.g., a Cell Factory by NUNC™. Cells in the Passage 0 culture can be subdivided to any degree so as to seed expansion cultures with, e.g., $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $1\times10^4$, $2\times10^4$, $3\times10^4$, $4\times10^4$, $5\times10^4$, $6\times10^4$, $7\times10^4$, $8\times10^4$, $9\times10^4$, or $10\times10^4$ stem-progenitor cells. Preferably, from about $2\times10^4$ to about $3\times10^4$. Passage 0 cells are used to seed each expansion culture. The number of expansion cultures can depend upon the number of Passage 0 cells, and may be greater or fewer in number depending upon the particular heart(s) from which the stem-progenitor cells are obtained.

Expansion cultures are grown until the density of cells in culture reaches a certain value, e.g., about $1\times10^5$ cells/cm². Cells can either be collected and cryopreserved at this point, or passaged into new expansion cultures as described above. Cells can be passaged, e.g., 2, 3, 4, 5, 6, 7, 8, 9, 10, 11, 12, 13, 14, 15, 16, 17, 18, 19 or 20 times prior to use. A record of the cumulative number of population doublings is preferably maintained during expansion culture(s). The cells from a Passage 0 culture can be expanded for 2, 3, 4, 5, 6, 7, 8, 9, 10, 12, 14, 16, 18, 20, 22, 24, 26, 28, 30, 32, 34, 36, 38 or 40 doublings, or up to 60 doublings. Preferably, however, the number of population doublings, prior to dividing the population of cells into individual doses, is between about 15 and about 30, preferably about 20 doublings. The cells can be culture continuously throughout the expansion process, or can be frozen at one or more points during expansion.

Cells to be used for individual doses can be frozen, e.g., cryopreserved for later use. Individual doses can comprise, e.g., about 1 million to about 100 million cells per ml, and can comprise between about $10^6$ and about $10^9$ cells in total.

In a specific embodiment, of the method, Passage 0 cells are cultured for a first number of doublings, e.g., approximately 4 doublings, then frozen in a first cell bank. Cells from the first cell bank are frozen and used to seed a second cell bank, the cells of which are expanded for a second number of doublings, e.g., about another eight doublings. Cells at this stage are collected and frozen and used to seed new expansion cultures that are allowed to proceed for a third number of doublings, e.g., about eight additional doublings, bringing the cumulative number of cell doublings to about 20. Cells at the intermediate points in passaging can be frozen in units of about 100,000 to about 10 million cells per ml, preferably about 1 million cells per ml for use in subsequent expansion culture. Cells at about 20 doublings can be frozen in individual doses of between about 1 million to about 100 million cells per ml for administration or use in making a stem-progenitor cell-containing composition.

In one embodiment, therefore, the invention provides a method of making a cardiac stem-progenitor cell bank, comprising: expanding primary culture cardiac stem-progenitor cells from a human heart for a first plurality of population doublings; cryopreserving said cardiac stem cells to form a Master Cell Bank; expanding a plurality of cardiac stem cells from the Master Cell Bank for a second plurality of population doublings; cryopreserving said cardiac stem cells to form a Working Cell Bank; expanding a plurality of cardiac stem cells from the Working Cell Bank for a third plurality of population doublings; and cryopreserving said cardiac stem cells in individual doses, wherein said individual doses collectively compose a cardiac stem cell bank. In a specific embodiment, the total number of population doublings is about 20. In another specific embodiment, said first plurality of population doublings is about four population doublings; said second plurality of population doublings is about eight population doublings; and said third plurality of population doublings is about eight population doublings. In another specific embodiment, said primary culture cardiac stem cells comprise cardiac stem cells from cardiac perfusate. In another specific embodiment, said primary culture cardiac stem cells comprise cardiac stem cells from digested cardiac tissue. In another specific embodiment, said primary culture cardiac stem cells comprise cardiac stem cells from cardiac perfusate and from digested cardiac tissue. In another specific embodiment, all of said cardiac stem cells in said cardiac stem cell primary culture are from the same heart. In another specific embodiment, said primary culture comprise a single stem-progenitor cell which is expanded to form a clone and said clone is further expanded to form the master and working cell banks. Therefore, all the resulting vials of the composition are descendent from a single cell and, therefore are similar in their genetic and epigenetic makeup. In another specific embodiment, the method further comprises the step of selecting c-kit positive cardiac stem cells from said plurality of said cardiac stem cells from said Working Cell Bank to form individual doses. In another specific embodiment, said individual doses comprise from about $10^4$ to about $10^5$ cardiac stem cells. In another specific embodiment, said individual doses comprise from about $10^5$ to about $10^6$ cardiac stem cells. In another specific embodiment, said individual doses comprise from about $10^6$ to about $10^7$ cardiac stem cells. In another specific embodiment, said individual doses comprise from about $10^7$ to about $10^8$ cardiac stem cells.

In a preferred embodiment, the donor from which the heart is obtained is tested for at least one pathogen. If the donor tests positive for a tested pathogen, the entire lot from the heart is discarded. Such testing can be performed at any time during production of cardiac stem cell lots, including before or after establishment of Passage 0 cells, or during expansion culture. Pathogens for which the presence is tested can include, without limitation, hepatitis A, hepatitis B, hepatitis C, hepatitis D, hepatitis E, human immunodeficiency virus (types I and II), cytomegalovirus, herpesvirus, and the like. If intended for human use, the different lots of the composition will be tested according to the regulations of the US FDA and the European Medicine Agency.

5.5 Differentiation of Cardiac Stem-Progenitor Cells

Provided herein are methods of modulating human stem-progenitor cell differentiation. In certain embodiments, the methods encompass the regulation of stem or progenitor cell differentiation in vitro, comprising incubating the stem cells with the compound in vitro, followed by direct transplantation of the differentiated cells to a subject. In other embodiments, the methods encompass the regulation of stem or progenitor cell differentiation in vivo, comprising delivering the compounds to a subject that is the recipient of unconditioned stem cells, followed by direct administration of the compound to the subject.

The embryonic-like stem cells obtained by the methods described herein may be induced to differentiate along specific cell lineages, including, but not limited to a neurogenic, hepatic, or osteogenic lineage.

In certain embodiments, stem-progenitor cells obtained according to the methods provided herein are induced to differentiate for use in transplantation and ex vivo treatment protocols. In certain embodiments, stem-progenitor cells obtained by the methods disclosed herein are induced to differentiate into a particular cell type and genetically engineered to provide a therapeutic gene product. In a specific embodiment, stem-progenitor cells obtained by the methods described herein are incubated with a compound, such as a small organic molecule or a polypeptide, in vitro, that induces it to differentiate, followed by direct transplantation of the differentiated cells to a subject. In a specific embodiment, stem-progenitor cells obtained by the methods described herein are incubated with a compound or combination of compounds that inhibit differentiation and stimulate the proliferation of the stem-progenitor cells, increasing the number of the stem-progenitor cells. In certain embodiments, the compounds that are used to control or regulate differentiation of stem-progenitor cells are not polypeptides, peptides, proteins, hormones, cytokines, oligonucleotides or nucleic acids. In certain embodiments, the compounds that are used to control or regulate growth and/or differentiation of stem-progenitor cells are administered together with the cells at the time of their transplantation.

In particular, the methods encompass the regulation of the differentiation of stem-progenitor cell populations, into specific tissue lineages. For example, the methods may be employed to regulate the differentiation of a stem-progenitor cell into myogenic lineage cells by promoting specific musculoskeletal regeneration and repair and repopulation of specific muscular tissues, such as myocardium and skeletal muscle. The methods of the invention may be employed to regulate differentiation of a stem-progenitor cell into cell of cardiac, vascular, osteogenic, neurogenic or hepatogenic lineage.

5.5.1 Induction of Differentiation into Myocardial Cell Lineages

Once cells established in culture, these can be used for the stem-progenitor cardiosphere formation assay: ~40,000 eCSCs are grown in suspension in 5 ml of LIF deprived CSC growth medium in a 10 cm bacteriological dish (to minimise CSC surface adherence). Cells are fed with 2 ml of LIF deprived eCSC growth medium every 2-3 days. Counts of number of CSC spheres per plate are carried out and expressed as number per CSCs plated.

For Cardiomyogenic beating assay, cloned c-kit$^{pos}$ CD45$^{neg}$ CSCs are treated with 100 nM Oxytocin for 72 hours and transferred to bacteriological dishes for the generation of CSC spheres. CSC spheres are transferred to laminin (1 µg/ml) coated dishes or chamber slides (for later immunostaining) with cardiomyogenic differentiation medium, with addition of factors at specified time points, for up to 14 days. The number of beating eCSC spheres is counted for each dish and expressed as a percentage relative to the total number of eCSC spheres/clusters counted. The cardiomyogenic differentiation of eCSCs in vitro requires up to 20 days (~3 days to grow eCSC spheres, 3 days oxytocin pre-treatment; 14 days of differentiation in defined stage-specific medium).

We induce specification of c-kit$^{pos}$ CD45$^{neg}$ eCSCs into functional, contracting cardiomyocytes in vitro. Oxytocin and specific growth factors governing embryonic cardiogenesis, given in a stage/sequence-specific manner, produced contractile cardiomyocytes derived from cloned c-kit$^{pos}$ CD45$^{neg}$ eCSCs. This eCSC sphere-beating assay is similar to the protocol used to assess cardiomyocyte differentiation in embryoid bodies[12]. Cloned c-kit$^{pos}$ CD45$^{neg}$ eCSCs were treated with 100 nM Oxytocin for 72 hours before they were transferred to bacteriological dishes for the generation of eCSC spheres. Spheres grown in suspension were picked and plated in laminin-coated chamber slides or dishes. Through trial and error we identified and demonstrated that supplementation of BMP-2, BMP-4, TGF-β1 and Dkk-1 for 4 days increased the number of cardiac troponin I expressing cells to ~40%. However, with removal of TGF-β1, BMP2, and BMP4 at day 4, and supplementing the medium with Dkk-1 for the remaining 10 days, the cardiomyocyte differentiation increased to ~70% cTnI positive cells. These cells exhibited abundant, well-organized sarcomere structures and functional synchronized rhythmic beating, which was stable and maintained for the duration of the culture. These cardiomyocytes behaved like a syncytium connected through Cnx43-containing gap junctions. A similar beating phenotype was exhibited by isolated cells when the sphere was disaggregated and cells individually plated. qRT-PCR of differentiated eCSC spheres at 14 days of culture in the cardiomyogenic cocktail showed a progressive decrease in transcripts for stemness and concomitant up-regulation of cardiomyocyte specific transcription factors and sarcomeric proteins genes.

To monitor and quantify the results of the myocardiogenic differentiation assay is better to use the chamber slide culture and cell fixation protocol: 2- or 4-well chamber slides are coated with laminin dissolved in DMEM (to a final concentration of 1 µg/ml) for 1-2 hours and rinsed in PBS immediately prior to use. CSC spheres (2 to 4 spheres per well) are plated in LIF deprived eCSC growth medium for 7 days for multipotency assay or up to 14 days in cardiomyogenic differentiation medium for beating assay. Medium is refreshed every 3 days. When end-point of experiment is reached, cells are rinsed once with PBS and fixed by applying 4% formaldehyde in PBS for 20 minutes on ice. Formaldehyde is aspirated, and slides are now prepared for immunocytochemistry procedure.

Immunocytochemistry is achieved by: slides are washed three times in 0.1% Tween in PBS for 5 minutes on orbital shaker. Non-specific binding sites on cells blocked with 10% donkey serum at room temperature (all secondary antibodies used are raised in donkey). Incubate overnight with primary antibody in humidified chamber, diluted in 0.1% Tween in PBS at 4° C. Slides washed three times in 0.1% Tween in PBS for 5 minutes each on orbital shaker. Incubate with secondary antibody in light-shielded, humidified chamber for 1 hour at 37° C. Slides washed three times in 0.1% Tween in PBS for 5 minutes each on orbital shaker (shielded from light). Incubate with 4',6-diamidino-2-phenylindole (DAPI; 1 ng/ml in PBS) for 14 minutes at room temperature (shielded from light). Slides washed three times in PBS for 5 minutes each on orbital shaker. Slides mounted in Vectashield (for chamber slides, chamber wells must be removed immediately prior to this step). Proceed to confocal microscopy imaging.

5.5.2 Induction of Differentiation into Osteocytic Cells

Osteogenic differentiation of cardiac stem-progenitor cells can be accomplished, for example, by placing cardiac stem-progenitor cells in cell culture conditions that induce differentiation into osteocytes. A preferred osteocytic medium comprises DMEM, followed by Osteogenic Induction Medium (Cambrex) containing 0.1 .mu.M dexamethasone, 0.05 mM ascorbic acid-2-phosphate, 10 mM beta glycerophosphate. In another embodiment, cardiac stem-progenitor cells are cultured in medium (e.g., DMEM-low glucose) containing about $10^7$ to about $10^9$ M dexamethasone, about 10-50 µM ascorbate phosphate salt (e.g., ascorbate-2-phosphate) and about 10 nM to about 10 mM. β-glycerophosphate. Osteogenic medium can also include serum, one or more antibiotic/antimycotic agents, transforming growth factor-beta (e.g., TGF-β1) and/or bone morphogenic protein (e.g., BMP-2, BMP-4, or a combination thereof).

Differentiation can be assayed using a calcium-specific stain, e.g., von Kossa staining, and RT/PCR detection of, e.g., alkaline phosphatase, osteocalcin, bone sialoprotein and/or osteopontin gene expression. A cardiac stem-progenitor cell is considered to have differentiated into an osteocytic cell when the cell displays one or more of these characteristics.

5.5.3 Induction of Differentiation into Neuronal or Neurogenic Cells

Neuronal differentiation of cardiac stem-progenitor cells can be accomplished, for example, by placing cardiac stem-progenitor cells in cell culture conditions that induce differentiation into neurons. In an example method, a neurogenic medium comprises DMEM/20% FBS and 1 mM beta-mercaptoethanol; such medium can be replaced after culture for about 24 hours with medium consisting of DMEM and 1-10 mM betamercaptoethanol. In another embodiment, cells are contacted with DMEM/2% DMSO/200 µM butylated hydroxyanisole. In a specific embodiment, the differentiation medium comprises serum-free DMEMIF-12, butylated hydroxyanisole, potassium chloride, insulin, forskolin, valproic acid, and hydrocortisone. In another embodiment, neuronal differentiation is accomplished by plating cardiac stem-progenitor cells on laminin-coated plates in Neurobasal-A medium (Invitrogen, Carlsbad Calif.) containing B27 supplement and L-glutamine, optionally supplemented with bFGF and/or EGF. Cardiac stem-progenitor cells can also be induced to neural differentiation by co-culture with neural cells, or culture in neuron-conditioned medium.

Neuronal differentiation can be assessed, e.g., by detection of neuron-like morphology (e.g., bipolar cells comprising extended processes) detection of the expression of e.g., nerve growth factor receptor and neurofilament heavy chain genes by RT-PCR; or detection of electrical activity, e.g., by patch-clamp. A cardiac stem-progenitor cell is considered to have differentiated into a neuronal cell when the cell displays one or more of these characteristics.

5.6 Preservation of Cardiac Stem-Progenitor Cells

Cardiac stem-progenitor cells can be preserved, that is, placed under conditions that allow for long-term storage, or conditions that inhibit cell death by, e.g., apoptosis or necrosis.

Cardiac stem-progenitor cells can be preserved using, e.g., a composition comprising an apoptosis inhibitor, necrosis inhibitor and/or an oxygen-carrying perfluorocarbon. In one embodiment, provided herein is a method of preserving a population of stem-progenitor cells comprising contacting said population of stem-progenitor cells with a stem-progenitor cell collection composition comprising an inhibitor of apoptosis and an oxygen-carrying perfluorocarbon, wherein said inhibitor of apoptosis is present in an amount and for a time sufficient to reduce or prevent apoptosis in the population of stem-progenitor cells, as compared to a population of stem-progenitor cells not contacted with the inhibitor of apoptosis. In a specific embodiment, said inhibitor of apoptosis is a caspase inhibitor. In another specific embodiment, said inhibitor of apoptosis is a JNK inhibitor. In a more specific embodiment, said JNK inhibitor does not modulate differentiation or proliferation of said stem-progenitor cells. In another embodiment, said stem-progenitor cell collection composition comprises said inhibitor of apoptosis and said oxygen-carrying perfluorocarbon in separate phases. In another embodiment, said stem-progenitor cell collection composition comprises said inhibitor of apoptosis and said oxygen-carrying perfluorocarbon in an emulsion. In another embodiment, the stem-progenitor cell collection composition additionally comprises an emulsifier, e.g., lecithin. In another embodiment, said apoptosis inhibitor and said perfluorocarbon are between about 0° C. and about 25° C. at the time of contacting the stem-progenitor cells. In another more specific embodiment, said apoptosis inhibitor and said perfluorocarbon are between about 2° C. and 10° C., or between about 2° C. and about 5° C., at the time of contacting the stem-progenitor cells. In another more specific embodiment, said contacting is performed during transport of said population of stem-progenitor cells. In another more specific embodiment, said contacting is performed during freezing and thawing of said population of stem-progenitor cells.

In another embodiment, the invention provides a method of preserving a population of cardiac stem-progenitor cells comprising contacting said population of stem-progenitor cells with an inhibitor of apoptosis and an organ-preserving compound, wherein said inhibitor of apoptosis is present in an amount and for a time sufficient to reduce or prevent apoptosis in the population of stem-progenitor cells, as compared to a population of stem-progenitor cells not contacted with the inhibitor of apoptosis. In another embodiment, said organ-preserving compound is hydroxyethyl starch, lactobionic acid, raffinose, or a combination thereof. In another embodiment, the stem-progenitor cell collection composition additionally comprises an oxygen-carrying perfluorocarbon, either in two phases or as an emulsion.

In another embodiment of the method, cardiac stem-progenitor cells are contacted with a stem-progenitor cell collection composition comprising an apoptosis inhibitor and oxygen-carrying perfluorocarbon, organ-preserving compound, or combination thereof, during perfusion. In another embodiment, said stem-progenitor cells are contacted during a process of tissue disruption, e.g., enzymatic digestion. In another embodiment, cardiac stem-progenitor cells are contacted with said stem-progenitor cell collection compound after collection by perfusion, or after collection by tissue disruption, e.g., enzymatic digestion.

Typically, during cardiac cell collection, enrichment and isolation, it is preferable to minimize or eliminate cell stress due to hypoxia and mechanical stress. In another embodiment of the method, therefore, a stem-progenitor cell, or population of stem-progenitor cells, is exposed to a hypoxic condition during collection, enrichment or isolation for less than six hours during said preservation, wherein a hypoxic condition is a concentration of oxygen that is less than 3% oxygen concentration. In a more specific embodiment, said population of stem-progenitor cells is exposed to said hypoxic condition for less than two hours during said preservation. In another more specific embodiment, said population of stem-progenitor cells is exposed to said hypoxic condition for less than one hour, or less than thirty minutes, or is not exposed to a hypoxic condition, during collection, enrichment or isolation. In another specific embodiment, said population is not subjected to oxygen damage by exposure to atmospheric air (20% $O_2$ concentration). In another specific embodiment, said population of stem-progenitor cells is not exposed to shear stress during collection, enrichment or isolation.

The cardiac stem-progenitor cells of the invention can be cryopreserved, e.g., in cryopreservation medium in small containers, e.g., ampoules. Suitable cryopreservation medium includes, but is not limited to, culture medium including, e.g., growth medium, or cell freezing medium, for example commercially available cell freezing medium, e.g., C2695, C2639 or C6039 (Sigma). Cryopreservation medium preferably comprises DMSO (dimethylsulfoxide), at a concentration of, e.g., about 10% (v/v). Cryopreservation medium may comprise additional agents, for example, methylcellulose and/or glycerol. In a preferred embodiment the stem-progenitor cells are cryopreserved in stem-progenitor cell culture medium, 20% BFS and 5% DMSO. Cardiac stem-progenitor cells are preferably cooled at about 1° C./min during cryopreservation. A preferred cryopreservation temperature is about −80° C. to about −180° C., preferably about −125° C. to about −140° C. Once the ampoules have reached about −20° C., cryopreserved cells can be transferred to liquid nitrogen until thawed for use. In some embodiments, for example, they are transferred to a liquid nitrogen storage area. Cryopreservation can also be done using a controlled-rate freezer. Cryopreserved cells preferably are thawed at a temperature of about 25° C. to about 40° C., preferably to a temperature of about 37° C.

5.7 Uses of Cardiac Stem-Progenitor Cells

5.7.1 Cardiac Stem-Progenitor Cell Populations

Cardiac stem-progenitor cell populations can be used to treat any disease, disorder or condition that is amenable to treatment by administration of a population of stem-progenitor cells. As used herein, "treat" encompasses the cure of, remediation of, improvement of, lessening of the severity of, or reduction in the time course of, a disease, disorder or condition, or any parameter or symptom thereof.

Cardiac stem-progenitor cells, and populations of cardiac stem-progenitor cells, can be induced to differentiate into a particular cell type, either ex vivo or in vivo, in preparation for administration to an individual in need of stem-progenitor cells, or cells differentiated from stem-progenitor cells. For example, cardiac stem-progenitor cells can be injected into a damaged organ, and for organ neogenesis and repair of injury in vivo. Such injury may be due to such conditions and disorders including, but not limited to, myocardial infarction, seizure disorder, multiple sclerosis, stroke, hypotension, cardiac arrest, ischemia, inflammation, age-related loss of cognitive function, radiation damage, cerebral palsy, neurodegenerative disease, Alzheimer's disease, Parkinson's disease, Leigh disease, AIDS dementia, memory loss, amyotrophic lateral sclerosis, muscular dystrophy, brain or spinal cord trauma, autoimmune disease (e.g. lupus, Chron's disease, etc) or heart-lung bypass.

Isolated populations of cardiac stem-progenitor cells can be used, in specific embodiments, in autologous or heterologous replacement therapy to treat specific diseases or conditions. Isolated populations of cardiac stem-progenitor cells, alone or in combination with stem-progenitor or progenitor cell populations, may be used alone, or as autologous or heterologous transgene carriers in gene therapy, to correct inborn errors.

In other embodiments, isolated populations of cardiac stem-progenitor cells may be used in autologous or heterologous tissue regeneration or replacement therapies or protocols, including, but not limited to, reconstruction of damaged or diseased organs or tissues.

The cardiac stem-progenitor cells of the invention, alone or in combination with other stem-progenitor cell or progenitor cell populations, can be used in the manufacture of a tissue or organ in vivo. The methods encompass using cells obtained from the heart, e.g., stem-progenitor cells or progenitor cells, to seed a matrix and to be cultured under the appropriate conditions to allow the cells to differentiate and populate the matrix. The tissues and organs obtained by the present methods can be used for a variety of purposes, including research and therapeutic purposes.

In a preferred embodiment of the invention, cardiac stem-progenitor cells and cardiac stem-progenitor cell populations may be used for autologous and allogenic transplants.

In another preferred embodiment of the invention, cardiac stem-progenitor cells and cardiac stem-progenitor cell populations may be used for autologous and allogenic transplants in combination with one or more of the growth factors and cytokines listed herein.

Cardiac stem-progenitor cells, either alone or in combination with one or more other stem-progenitor cell populations, can be used in therapeutic transplantation protocols, e.g., to augment or replace stem-progenitor or progenitor cells of the liver, nervous system-progenitor, muscular system-progenitor, or bone. Additionally, cardiac stem-progenitor cells may be used instead of specific classes of progenitor cells (e.g., chondrocytes, hepatocytes, hematopoietic cells, pancreatic parenchymal cells, neuroblasts, muscle progenitor cells, etc.) in therapeutic or research protocols in which progenitor cells would typically be used.

The cardiac stem-progenitor cells of the invention can be used to repair damage to tissues and organs resulting from, e.g., trauma, metabolic disorders, genetic disorder or disease. The trauma can be, e.g., trauma from surgery, e.g., heart surgery. In such an embodiment, a patient can be administered cardiac stem-progenitor cells, alone or combined with other stem-progenitor or progenitor cell populations, or in combination of growth factors and/or cytokines to regenerate or restore tissues or organs which have been damaged as a consequence of disease.

In a specific embodiment, provided herein is a method of replacing a defective endogenous stem-progenitor cells of a subject (e.g. genetic mutations including but not limited to genes such as those encoding the sarcomeric proteins which result in defective cardiac muscle, damage to the endogenous cardiac stem-progenitor cojort by cardiotoxic drugs commonly used as anti-neoplastic therapies such as Herceptin, Doxorubicin or other tyrosine kinase receptor inhibitors and other anthracycline drugs) with normal or genetically corrected cardiac stem-progenitor cells autologous, HLA matched that express c-Kit and CD166 but do not express CD45 and Tryptase, by administering a therapeutically effective amount of said cells through the peripheral circulation so that they spontaneously home and nest to the damaged myocardium of the recipient.

In a specific embodiment, provided herein is a method of treating a subject in need of repairing damaged cardiac tissue comprising administering intravenously, intra-coronary or directly into the myocardium a therapeutically effective amount of cardiac stem-progenitor cells that express c-Kit and CD166 but do not express CD45 and Tryptase.

In a specific embodiment, provided herein is a method of treating a subject in need of repairing damaged cardiac tissue comprising administering intravenously, intra-coronary or directly into the myocardium a therapeutically effective amount of cardiac stem-progenitor cells that express c-Kit and CD166 but do not express CD45 and Tryptase together with one or a combination of growth factors.

In a specific embodiment, provided herein is a method of treating a subject in need of repairing damaged central nervous system, liver, skeletal muscle tissue, bone or any other solid tissue into which the cardiac stem progenitor cells are able to differentiate into. Such method comprises administering intravenously, intra-arterial or directly into the damaged tissue of a therapeutically effective amount of cardiac stem-progenitor cells that express c-Kit and CD166 but do not express CD45 and Tryptase together with one or more growth factors.

In a specific embodiment, provided herein is a method of treating a subject with a deficit of cardiac stem-progenitor cells, independently of the ethiology of this deficit, by administering through the peripheral circulation, a therapeutically effective amount of autologous, HLA matched or allogeneic cardiac stem-progenitor cells that express c-Kit and CD166 but do not express CD45 and Tryptase.

5.7.2 Compositions Comprising Cardiac Stem-Progenitor Cells

The present disclosure provides compositions comprising cardiac stem-progenitor cells, or biomolecules therefrom.

The cardiac stem-progenitor cells can be combined with any physiologically-acceptable or medically-acceptable compound, composition or device for use in, e.g., research or therapeutics.

5.7.2.1 Cryopreserved Cardiac Stem-Progenitor Cells

The cardiac stem-progenitor cell populations can be preserved, for example, cryopreserved for later use. Methods for cryopreservation of cells, such as stem-progenitor cells, are well known in the art. Cardiac stem-progenitor cell populations can be prepared in a form that is easily administrable to an individual. For example, the invention provides a cardiac stem-progenitor cell population that is contained within a container that is suitable for medical use. Such a container can be, for example, a sterile plastic bag, flask, jar, or other container from which the cardiac stem-progenitor cell population can be easily dispensed. For example, the container can be a small blood bag or other plastic, or a vial which allows hermetic and sterile seal medically-acceptable and suitable for the intravenous administration of a liquid to a recipient. The container is preferably one that allows for cryopreservation of the combined stem-progenitor cell population.

The cryopreserved cardiac stem-progenitor cell population can comprise cardiac stem-progenitor cells derived from a single donor, or from multiple donors. The cardiac stem-progenitor cell population can be completely HLA-matched to an intended recipient (autologous or HLA matched transplantation) mismatched in one, several or all the HLA genes (allogeneic transplantation).

Thus, in one embodiment, the invention provides a composition comprising a cardiac stem-progenitor cell population in a container. In a specific embodiment, the stem-progenitor cell population is cryopreserved. In another specific embodiment, the container is a bag, flask, or jar. In more specific embodiment, said bag is a sterile plastic bag. In a more specific embodiment, said bag is suitable for, allows or facilitates intravenous administration of said cardiac stem-progenitor cell population. The bag can comprise multiple lumens or compartments that are interconnected to allow mixing of the cardiac stem-progenitor cells and one or more other solutions, e.g., a drug, prior to, or during, administration. In another specific embodiment, the composition comprises one or more compounds that facilitate cryopreservation of the combined stem-progenitor cell population. In another specific embodiment, said cardiac stem-progenitor cell population is contained within a physiologically-acceptable aqueous solution. In a more specific embodiment, said physiologically-acceptable aqueous solution is a 0.9% NaCl solution. In another specific embodiment, said cardiac stem-progenitor cell population is suspended in the recipient blood serum. In another specific embodiment, said cardiac stem-progenitor cell population is suspended in commercially available serum of the same species. In another specific embodiment, said cardiac stem-progenitor cell population comprises cardiac cells that are HLA-matched to a recipient of said stem-progenitor cell population. In another specific embodiment, said cardiac stem-progenitor cells are derived from a plurality of donors.

5.7.2.2 Pharmaceutical Compositions

Populations of cardiac stem-progenitor cells, or populations of cells comprising cardiac stem-progenitor cells, can be formulated into pharmaceutical compositions for use in vivo. Such pharmaceutical compositions comprise a population of cardiac stem-progenitor cells, or a population of cells comprising cardiac stem-progenitor cells, in a pharmaceutically-acceptable carrier, e.g., a saline solution or other accepted physiologically-acceptable solution for in vivo administration. Pharmaceutical compositions of the invention can comprise any of the cardiac stem-progenitor cell populations, or cardiac stem-progenitor cell types, described herein. The pharmaceutical compositions of the invention can further comprise cardiac stem-progenitor cells obtained from a single individual or heart, or from a plurality of individuals or heart.

The pharmaceutical compositions of the invention can comprise any number of cardiac stem-progenitor cells. For example, a single unit dose of cardiac stem-progenitor cells can comprise, in various embodiments, about, at least, or no more than $1 \times 10^5$, $5 \times 10^5$, $1 \times 10^6$, $5 \times 10^6$, $1 \times 10^7$, $5 \times 10^7$, $1 \times 10^8$, $5 \times 10^9$, $1 \times 10^9$, $5 \times 10^9$, $1 \times 10^{10}$, $5 \times 10^{10}$, $1 \times 10^{11}$ or more cardiac stem-progenitor cells.

The pharmaceutical compositions comprise populations of cells that comprise 50% viable cells or more (that is, at least 50% of the cells in the population are functional or living). Preferably, at least 60% of the cells in the population are viable. More preferably, at least 70%, 80%, 90%, 95%, or 99% of the cells in the population in the pharmaceutical composition are viable.

The pharmaceutical compositions can comprise one or more compounds that, e.g., facilitate engraftment (e.g., anti-T-cell receptor antibodies, an immunosuppressant, or the like); stabilizers such as albumin, dextran 40, gelatin, hydroxyethyl starch, and the like and growth factors and cytokines which will enhance the survival, engraftment, replication and/or differentiation of the stem-progenitor cells transplanted.

When formulated as an injectable solution, in one embodiment, the pharmaceutical composition comprises about 1.25% HSA and about 2.5% dextran. In another embodiment the stem-progenitor cells are suspended in serum of the recipient of the same species. Other injectable formulations, suitable for the administration of cellular products, may be used.

The pharmaceutical composition can be formulated for intra-venous, intra-arterial, including intra-coronary administration or by direct injection into the target tissue by means of the appropriate injection systems known to those familiar with cell therapy.

The pharmaceutical composition can be specifically formulated for the treatment of acute or chronic myocardial infarction and heart failure with intracoronary administration, intramyocardial injection through the endocardium using the NOGA™ system or directly through the epicardium during open heart surgery or through the thoracic wall by needle injection.

5.7.2.3 Cardiac Stem-Progenitor Cell Conditioned Media

The cardiac stem-progenitor cells can be used to produce conditioned medium, that is, medium comprising one or more biomolecules secreted or excreted by the stem-progenitor cells. In various embodiments, the conditioned medium comprises medium in which cardiac stem-progenitor cells have grown for at least 1, 2, 3, 4, 5, 6, 7, 8, 9, 10, 11, 12, 13, 14 or more days. In other embodiments, the conditioned medium comprises medium in which cardiac stem-progenitor cells have grown to at least 30%, 40%, 50%, 60%, 70%, 80%, 90% confluence, or up to 100% confluence. Such conditioned medium can be used to support the culture of a separate population of cardiac stem-progenitor cells, or stem-progenitor cells of another kind. In another embodiment, the conditioned medium comprises medium in which cardiac stem-progenitor cells have been differentiated into an adult cell type. In another embodiment, the conditioned medium of the invention comprises medium in which cardiac stem-progenitor cells and non-cardiac stem-progenitor cells have been cultured.

5.7.2.4 Matrices Comprising Cardiac Stem-Progenitor Cells

Provided herein are matrices, hydrogels, scaffolds, and the like that comprise a cardiac stem-progenitor cell, or a population of cardiac stem-progenitor cells.

Cardiac stem-progenitor cells can be seeded onto a natural matrix, e.g., a cardiac biomaterial. Such biomaterial can be dissected directly from a mammalian heart; fixed or heat-treated, substantially dry (i.e., <20% $H_2O$) biomaterial, and the like.

Cardiac stem-progenitor cells can be suspended in a hydrogel solution suitable for, e.g., injection. Suitable hydrogels for such compositions include self-assembling peptides, such as RAD16. In one embodiment, a hydrogel solution comprising the cells can be allowed to harden, for instance in a mold, to form a matrix having cells dispersed therein for implantation. Cardiac stem-progenitor cells in such a matrix can also be cultured so that the cells are mitotically expanded prior to implantation. The hydrogel is, e.g., an organic polymer (natural or synthetic) that is cross-linked via covalent, ionic, or hydrogen bonds to create a three-dimensional open-lattice structure that entraps water molecules to form a gel. Hydrogel-forming materials include polysaccharides such as alginate and salts thereof, peptides, polyphosphazines, and polyacrylates, which are crosslinked ionically, or block polymers such as polyethylene oxide-polypropylene glycol block copolymers which are crosslinked by temperature or pH, respectively. In some embodiments, the hydrogel or matrix of the invention is biodegradable.

In some embodiments, the polymers are at least partially soluble in aqueous solutions, such as water, buffered salt solutions, or aqueous alcohol solutions, that have charged side groups, or a monovalent ionic salt thereof. Examples of polymers having acidic side groups that can be reacted with cations are poly(phosphazenes), poly(acrylic acids), poly(methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

The cardiac stem-progenitor cells or co-cultures thereof can be seeded onto a three-dimensional framework or scaffold and implanted in vivo. Such a framework can be implanted in combination with any one or more growth factors, cells, drugs or other components that stimulate tissue formation or otherwise enhance or improve the practice of the present disclosure.

Examples of scaffolds that can be used include nonwoven mats, porous foams, or self assembling peptides. Nonwoven mats can be formed using fibers comprised of a synthetic absorbable copolymer of glycolic and lactic acids (e.g., PGA/PLA) (VICRYL, Ethicon, Inc., Somerville, N.J.). Foams, composed of, e.g., poly(.epsilon.-caprolactone)/poly(glycolic acid) (PCL/PGA) copolymer, formed by processes such as freeze-drying, or lyophilization, can also be used as scaffolds.

Cardiac stem-progenitor cells can also be seeded onto, or contacted with, a physiologically-acceptable ceramic material including, but not limited to, mono-, di-, tri-, alpha-tri-, beta-tri-, and tetra-calcium phosphate, hydroxyapatite, fluoroapatites, calcium sulfates, calcium fluorides, calcium oxides, calcium carbonates, magnesium calcium phosphates, biologically active glasses such as BIOGLASS®, and mixtures thereof. Porous biocompatible ceramic materials currently commercially available include SURGIBONE® (CanMedica Corp., Canada), ENDOBON® (Merck Biomaterial France, France), CEROS® (Mathys, AG, Bettlach, Switzerland), and mineralized collagen bone grafting products such as HEALOS™ (DePuy, Inc., Raynham, Mass.) and VITOSS®, RHAKOSS™, and CORTOSS® (Orthovita, Malvern, Pa.). The framework can be a mixture, blend or composite of natural and/or synthetic materials.

In another embodiment, cardiac stem-progenitor cells can be seeded onto, or contacted with, a felt, which can be, e.g., composed of a multifilament yarn made from a bioabsorbable material such as PGA, PLA, PCL copolymers or blends, or hyaluronic acid.

The cardiac stem-progenitor cells can, in another embodiment, be seeded onto foam scaffolds that may be composite structures. Such foam scaffolds can be molded into a useful shape, such as that of a portion of a specific structure in the body to be repaired, replaced or augmented. In some embodiments, the framework is treated, e.g., with 0.1M acetic acid followed by incubation in polylysine, PBS, and/or collagen, prior to inoculation of the cells of the invention in order to enhance cell attachment. External surfaces of a matrix may be modified to improve the attachment or growth of cells and differentiation of tissue, such as by plasma-coating the matrix, or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate, etc.), a cellular matrix, and/or other materials such as, but not limited to, gelatin, alginates, agar, agarose, and plant gums, and the like.

In some embodiments, the scaffold comprises, or is treated with, materials that render it non-thrombogenic. These treatments and materials may also promote and sustain endothelial growth, migration, and extracellular matrix deposition. Examples of these materials and treatments include but are not limited to natural materials such as basement membrane proteins such as laminin and Type IV collagen, synthetic materials such as EPTFE, and segmented polyurethaneurea silicones, such as PURSPAN™ (The Polymer Technology Group, Inc., Berkeley, Calif.). The scaffold can also comprise anti-thrombotic agents such as heparin; the scaffolds can also be treated to alter the surface charge (e.g., coating with plasma) prior to seeding with cardiac stem-progenitor cells.

In some of the embodiments the cells are seaded onto or into the polymer/scaffold matrix together with one or several of the factors and cytokines listed herein.

5.7.3 Immortalized Cardiac Stem-Progenitor Cell Lines

Mammalian stem-progenitor cardiac cells can be conditionally immortalized by transfection with any suitable vector containing a growth-promoting gene, that is, a gene encoding a protein that, under appropriate conditions, promotes growth of the transfected cell, such that the production and/or activity of the growth-promoting protein is regulatable by an external factor. In a preferred embodiment the growth-promoting gene is an oncogene such as, but not limited to, v-myc, N-myc, c-myc, p53, SV40 large T antigen, polyoma large T antigen, E1a adenovirus or E7 protein of human papillomavirus.

In another embodiment, the stem-progenitor cardiac cells become spontaneously immortalized through the cell culture selection process while maintaining a normal phenotype, karyotype and genotype.

External regulation of the growth-promoting protein can be achieved by placing the growth-promoting gene or other factor to be overproduced by the cells under the control of an externally-regulatable promoter, e.g., a promoter the activity of which can be controlled by, for example, modifying the temperature of the transfected cells or the composition of the medium in contact with the cells. in one embodiment, a tetracycline (tet)-controlled gene expression system can be employed (see Gossen et al., Proc. Natl. Acad. Sci. USA 89:5547-5551, 1992; Hoshimaru et al., Proc. Natl. Acad. Sci. USA 93:1518-1523, 1996). In the absence of tet, a tet-controlled transactivator (tTA) within this vector strongly activates transcription from ph.sub.CMV*-1, a minimal promoter from human cytomegalovirus fused to tet operator sequences. tTA is a fusion protein of the repressor (tetR) of the transposon-10-derived tet resistance operon of *Escherichia coli* and the acidic domain of VP16 of herpes simplex virus. Low, non-toxic concentrations of tet (e.g., 0.01-1.0 .mu.g/mL) almost completely abolish transactivation by tTA.

In another embodiment, the gene to be expressed by the stem-progenitor cells either to produce a growth factor or a robust marker which allows the identification of the cell's progeny, is linked to an inducible estrogen receptor which is normally inactive in mammals, including the human, but becomes activated following the administration of an estrogen analogue, tamoxifen. In another embodiment, the regulated gene is the viral thymidine kinase gene which in the absence of its specific substrate is inactive and innocuous but becomes toxic upon the administration of the antiviral drug Gancyclovir which selectively kills all the cells bearing the transgene.

In one embodiment, the vector further contains a gene encoding a selectable marker, e.g., a protein that confers drug resistance. The bacterial neomycin resistance gene ($neo^R$) is one such marker that may be employed within the present invention. Cells carrying $neo^R$ may be selected by means known to those of ordinary skill in the art, such as the addition of, e.g., 100-200 µg/mL G418 to the growth medium.

Transfection can be achieved by any of a variety of means known to those of ordinary skill in the art including, but not limited to, retroviral infection. In general, a cell culture may be transfected by incubation with a mixture of conditioned medium collected from the producer cell line for the vector and DMEM/F12 containing N2 supplements. For example, a cardiac cell culture prepared as described above may be infected after, e.g., five days in vitro by incubation for about 20 hours in one volume of conditioned medium and two volumes of DMEM/F12 containing N2 supplements. Transfected cells carrying a selectable marker may then be selected as described above.

In an embodiment, the transgenes can also be obtained by infecting the cells with lenti-virus constructs which can infect cycling and non-cycling cells at very high efficiency and do not integrate into the host's genome, therefore, diminishing the risk of producing unwanted mutations.

In another embodiment, the cells can be modified by homologous recombination by introducing the transgene downstream of a gene locus which is expressed in all or more cells of interest and does not become silenced by epigenetic modifications. For the human cardiac stem-progenitor cells the genomic insertions of the gene of interest is targeted into a constitutively expressed loci such as the AAVS1 locus using Zinc Finger Nucleases (ZFN) (e.g. Sigma Aldrich's zinc-finger-nuclease-technology).

Following transfection, cultures are passaged onto a surface that permits proliferation, e.g., allows at least 30% of the cells to double in a 24 hour period. Preferably, the substrate is a polyornithine/laminin substrate, consisting of tissue culture plastic coated with polyornithine (10 µg/mL) and/or laminin (10 µg/mL), a polylysine/laminin substrate or a surface treated with fibronectin. Cultures are then fed every 3-4 days with growth medium, which may or may not be supplemented with one or more proliferation-enhancing factors. Proliferation-enhancing factors may be added to the growth medium when cultures are less than 50% confluent.

The conditionally-immortalized cardiac stem-progenitor cell lines can be passaged using standard techniques, such as by trypsinization, when 80-95% confluent. Up to approximately the twentieth passage, it is, in some embodiments, beneficial to maintain selection (by, for example, the addition of G418 for cells containing a neomycin resistance gene). Cells may also be frozen in liquid nitrogen for long-term storage.

Clonal cell lines can be isolated from a conditionally-immortalized human cardiac stem-progenitor cell line prepared as described above. In general, such clonal cell lines may be isolated using standard techniques, such as by limit dilution or using cloning rings, and expanded. Clonal cell lines may generally be fed and passaged as described above.

Conditionally-immortalized human cardiac stem-progenitor cell lines, which may, but need not, be clonal, may generally be induced to differentiate by suppressing the production and/or activity of the growth-promoting protein under culture conditions that facilitate differentiation. For example, if the gene encoding the growth-promoting protein is under the control of an externally-regulatable promoter, the conditions, e.g., temperature or composition of medium, may be modified to suppress transcription of the growth-promoting gene. For the tetracycline-controlled gene expression system discussed above, differentiation can be achieved by the addition of tetracycline to suppress transcription of the growth-promoting gene. In general, 1 µg/mL tetracycline for 4-5 days is sufficient to initiate differentiation. To promote further differentiation, additional agents may be included in the growth medium. For the estrogen regulated gene, the addition of tamoxifen induces the expression of the protein of interest. For the selective killing of the cells after transplantation without harming the host cells, the administration of glancyclovier may be used.

5.7.4 Assays

The cardiac stem-progenitor cells can be used in assays to determine the influence of culture conditions, environmental factors, molecules (e.g., biomolecules, small inorganic molecules. etc.) and the like on stem-progenitor cell proliferation, expansion, and/or differentiation, compared to cardiac stem-progenitor cells not exposed to such conditions.

In a preferred embodiment, the cardiac stem-progenitor cells of the present invention are assayed for changes in proliferation, expansion or differentiation upon contact with a molecule. In one embodiment, for example, provided herein is a method of identifying a compound that modulates the proliferation of a plurality of cardiac stem-progenitor cells, comprising contacting said plurality of stem-progenitor cells with said compound under conditions that allow proliferation, wherein if said compound causes a detectable change in proliferation of said plurality of stem-progenitor cells compared to a plurality of stem-progenitor cells not contacted with said compound, said compound is identified as a compound that modulates proliferation of cardiac stem-progenitor cells. In a specific embodiment, said compound is identified as an inhibitor of proliferation. In another specific embodiment, said compound is identified as an enhancer of proliferation.

In another embodiment, provided herein is a method of identifying a compound that modulates the expansion of a plurality of cardiac stem-progenitor cells, comprising contacting said plurality of stem-progenitor cells with said compound under conditions that allow expansion, wherein if said compound causes a detectable change in expansion of said plurality of stem-progenitor cells compared to a plurality of stem-progenitor cells not contacted with said compound, said compound is identified as a compound that modulates expansion of cardiac stem-progenitor cells. In a specific embodiment, said compound is identified as an inhibitor of expansion. In another specific embodiment, said compound is identified as an enhancer of expansion.

In another embodiment, provided herein is a method of identifying a compound that modulates the differentiation of a cardiac stem-progenitor cell, comprising contacting said stem-progenitor cells with said compound under conditions that allow differentiation, wherein if said compound causes a detectable change in differentiation of said stem-progenitor cells compared to a stem-progenitor cell not contacted with said compound, said compound is identified as a compound that modulates proliferation of cardiac stem-progenitor cells. In a specific embodiment, said compound is identified as an inhibitor of differentiation. In another specific embodiment, said compound is identified as an enhancer of differentiation.

In another embodiment, provided herein is a method to test in vitro the potential cardiac side effects of different drugs prior to development in animal and/or clinical testing. Any drug that affect the viability, growth and differentiation properties of the human cardiac stem-progenitor cells has a high probability to produce cardiac side-effects upon medium and long term use: e.g. Many anti-oncogenic drugs of the last generation such as the anthracyclines (e.g. Doxorubicine) and those acting against the tyrosine kinase (Trk) receptor family on the survival and biological characteristics of endogenous cardiac stem cells. These drugs are known to induce cardiotoxicity, with the agents affecting a variety of different subtypes of tyrosine kinase receptor (Chen et al., 2008, Circ. 118:84-95). The ERBB2 Trk inhibitor trastuzumab (Herceptin) affects the properties of cardiac-derived stem cells, reducing their ability to differentiate and their regenerative properties.

6 EXAMPLES

Figure 1C:
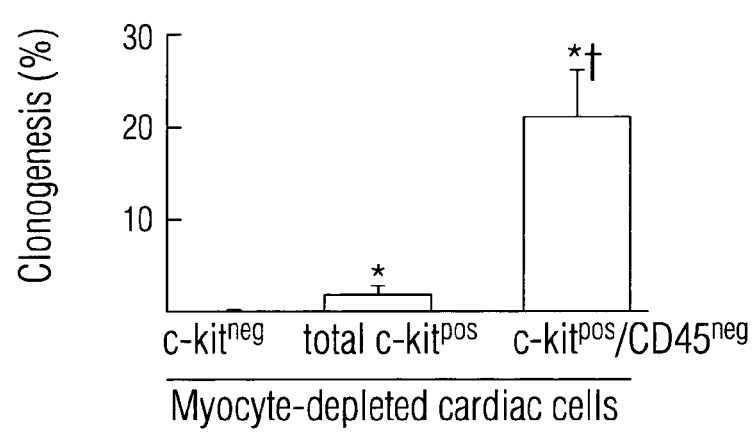

6.1 Adult c-kit$^{pos}$ CD45$^{neg}$ CSCs Express Pluripotency Markers and Fulfil the Criteria of Bona Fide Tissue Specific Stem-Progenitor Cells In Vitro Roughly half of the total resident c-kit$^{pos}$ cardiac cells express CD45 and the cardiac mast cell marker, tryptase (FIG. 9A-F), representing cardiac mast cells (10). Once depleted of CD45, the c-kit$^{pos}$CD45$^{neg}$ eCSCs are indeed also tryptase negative, a classical mast cell marker (FIG. 9A-F). Thus, a highly enriched population of c-kit$^{pos}$ CD45$^{neg}$ eCSCs (>98%) were isolated from adult male rat hearts through sequential immunomagnetic bead negative (for CD45) and positive (for c-kit) sorting (FIG. 1A). Freshly isolated c-kit$^{pos}$CD45$^{pos}$ CSCs are practically negative for CD34 (~1%) and CD31 (<0.5%). Concurrently, when isolated from the adult mouse heart, c-kit$^{pos}$CD45$^{neg}$ CSCs are also positive for Sca-1 (60±5%), Abcg2 (70±4%) and CD105 (56±5%). Remarkably, some of freshly isolated mouse, rat and human c-kit$^{pos}$CD45$^{pos}$ CSCs expressed the four genes known to be required for the induction of the pluripotent phenotype (11): Oct4 (3±1%), Nanog (11±4%), Klf4 (7±3%) and Sox-2 (6±2%). Also, c-kit$^{pos}$ CD45$^{neg}$ eCSCs expressed Tert (47±4%) and Bmi-1 (51±4%), regulatory genes of stem cell proliferation and self-renewal (7) but also cardiac specific transcription factors such as Gata-4 (53±11%) and Nkx2.5 (19±4%). The clonal efficiency of mouse, rat and human c-kit$^{pos}$ CD45$^{neg}$ eCSCs at passage 4 was 21±5% (FIG. 1B-C) In contrast, the clonal expansion of c-kit$^{neg}$ as well as total c-kit$^{pos}$ (including the CD45$^{pos}$ cardiac mast cell fraction) cardiac cells was negligible (FIG. 1C).

Figure 1D:
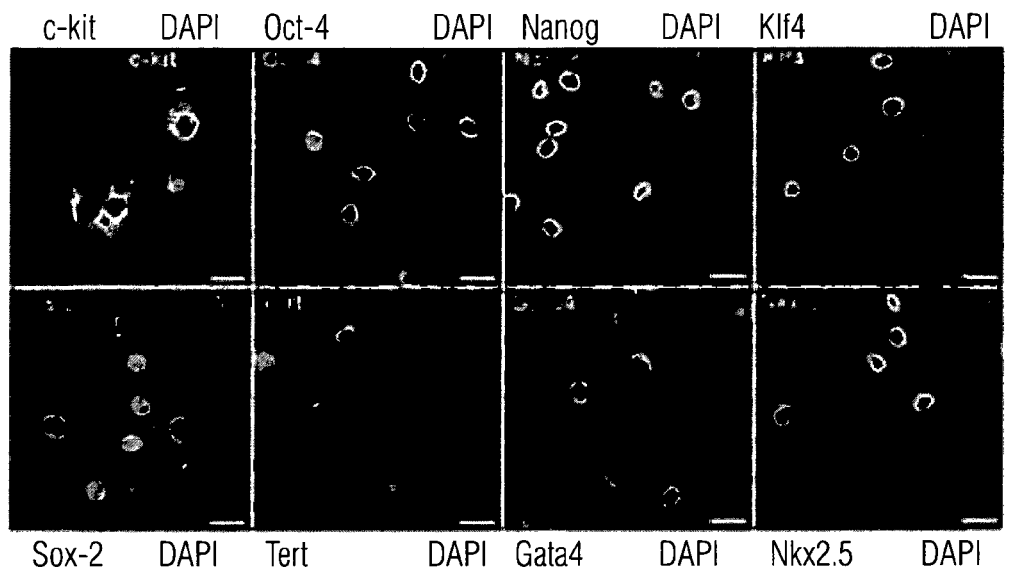
Figure 1E:
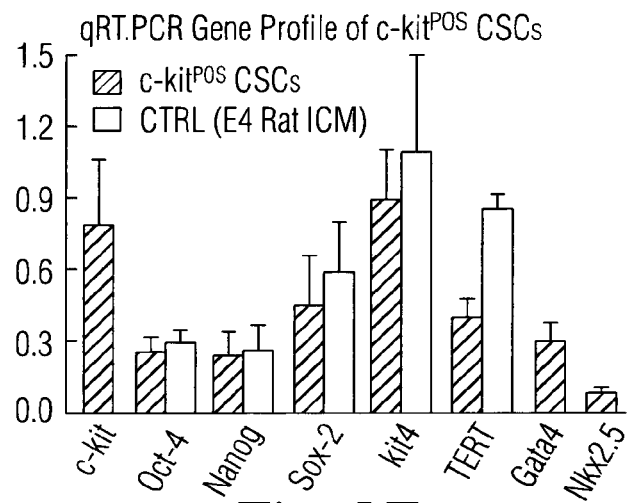
Figure 1F:
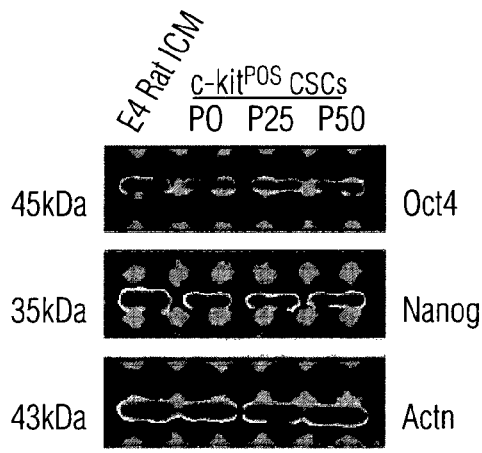
Figure 10A:
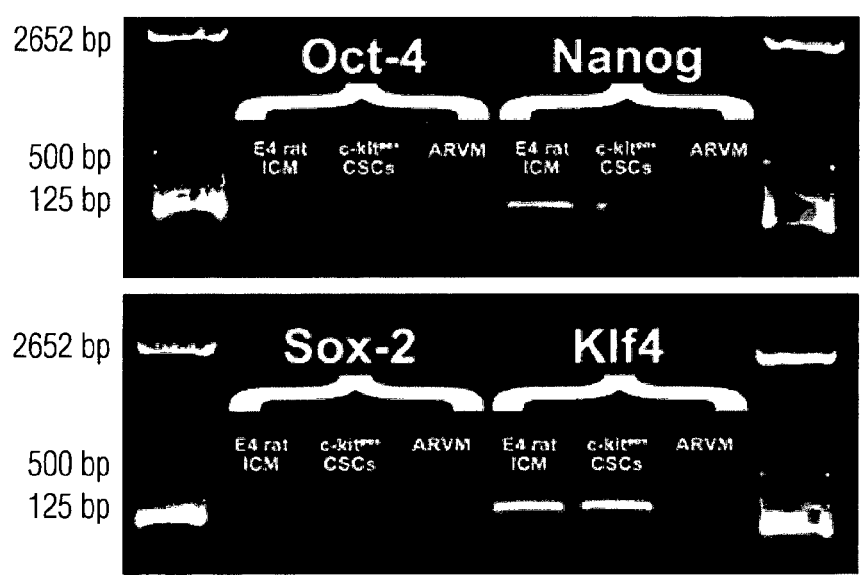

Because the c-kit$^{pos}$ CD45$^{neg}$ cell population isolated from the adult mouse, rat and human heart is heterogenous in nature, comprising putative more primitive cells and also more committed precursors, a clonal analysis was performed. Thus, the 10 fastest growing c-kit$^{pos}$CD45$^{neg}$ eCSC clones from a clonal seeding of 288 cells were further expanded and analyzed for expression, at the mRNA and protein level, of markers of stemness and cardiac-lineage progenitor/precursor markers using immunocytochemistry and qRT-PCR (FIG. 1D-E). 8 out of 10 clones expressed most multipotency genes expressed by embryonic stem cells both at the mRNA and protein levels (FIG. 1E-F). In particular, cells of a typical c-kit$^{pos}$ CD45$^{neg}$ cell clone (C5) analyzed by immunocytochemistry expressed c-kit (94±5%), Oct3/4 (71±8%), Nanog (66±6%), Klf-4 (56±8%), Sox-2 (38±11%), Tert (78±13%) and Bmi-1 (80±9%). Importantly, the mRNA level of the four multipotency factors is similar to those of the inner cell mass cells of day 4 rat blastocysts (FIGS. 1E and 10A-B). Oct-4 cDNA sequencing and western blot ascertained that these sequences represent expression of the functional genes and are not the product of a pseudogene (FIGS. 1F and 10A-B). Furthermore, a sub-population of the c-kit$^{pos}$CD45$^{neg}$ clones expressed Gata-4 (73±11%) and Nkx2.5 (44±8%) (FIG. 1D). The increase in both the frequency and the level of expression of the multipotency genes in the cloned cells is due to the significantly higher clonal efficiency of the cells expressing the multipotency genes, as compared to the cells from the same isolate which are also CD45$^{neg}$Tryptase$^{neg}$c-kit$^{pos}$ but negative for the expression of the multipotency genes (data not shown).

Figure 2A:
Figure 2B:
Figure 2C:
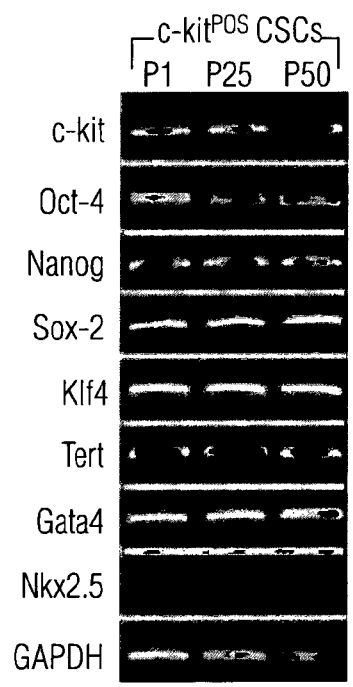
Figure 2D:
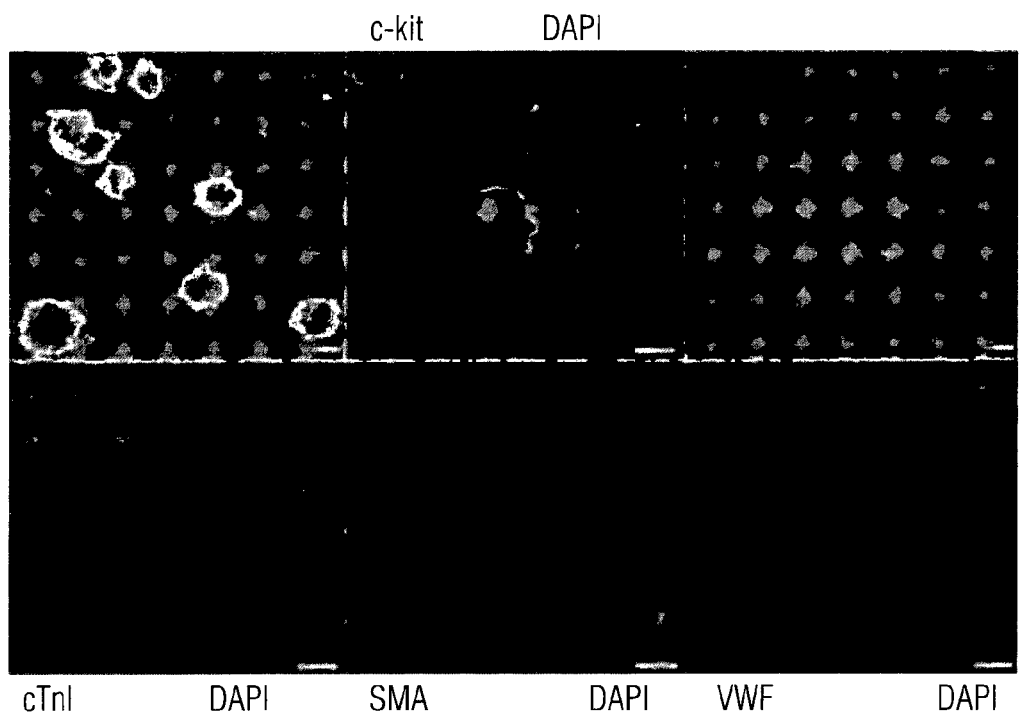

6.2 Adult c-kit$^{pos}$ CD45$^{neg}$ CSCs have a Stable Phenotype and Genotype To determine the phenotypic and genetic stability of the c-kit$^{pos}$ eCSCs, a typical clone (C5) was selected for further analysis. Flow cytometry and immuno-phenotyping revealed that C5 was positive at differential levels for CD90, PDGFrα, CXCR4, CD146, CD166, Nestin, and Flk-1, yet negative for Wt1 (FIGS. 2A-B). C5 had an ~18 hour doubling time, has been propagated so far for more than 120 passages and serially sub-cloned every 10 passages, maintaining a stable phenotype and without signs of growth arrest, senescence or down regulation of the pluripotency and cardiac gene expression (FIG. 2C). Throughout their culture, these c-kit$^{pos}$ eCSC sub-clones have maintained a normal karyotype without detectable chromosomal alterations (FIG. 11). Cloned c-kit$^{pos}$ eCSCs plated in modified cardiosphere formation medium (mCSFM) (10, 12), grow in suspension and generate cardiospheres (FIG. 2D). Cardiosphere derived eCSCs gave rise to secondary and tertiary cardiospheres, without evidence of cell death or growth arrest. Cardiospheres placed in laminin-coated plastic dishes with LIF-deprived growth medium, attached and spread out, acquiring a flat morphology (FIG. 2D). Seven to ten days after plating, these peripheral flat cells spontaneously differentiated and expressed proteins specific for myocyte (cTnI, 39±8%), endothelial (vWF, 31±5%) and smooth muscle cell (SMA, 34±7%) lineages (FIG. 2D).

6.3 c-kit$^{pos}$ eCSCs Differentiate In Vitro into Cell Types Characteristic of Tissues Derived from Each of the Three Germ Layers As of today, many varied phenotypes of putative cardiac progenitor/stem cells have been identified in the adult mammalian myocardium according to the expression or lack of specific markers used for their isolation (5,7) and these putatively different regenerative cells brings into question whether they are all actually different or rather the intermediate at different physiological states of the same, yet undefined, cell population. The presence of the main pluripotency genes, Oct-4, Nanog, Klf-4 and Sox-2, in a subpopulation of eCSCs and their selective growth advantage in vitro, as shown by their enrichment by cloning the mixed population, raises the question of whether these cells indeed have a broader differentiation potential than just for mesodermal germ layer, being so a more immature eCSC than the ones previously identified (12).

In order to test for true multipotency and distinguish it from a mixture of cells with different developmental potential and/or fate, it is imperative to perform the analysis using the progeny of a single cell. For this reason we have tested whether eCSCs from clone C5 are able to differentiate into cell types derivative from the endoderm and ectoderm germ layers.

Figure 3A:
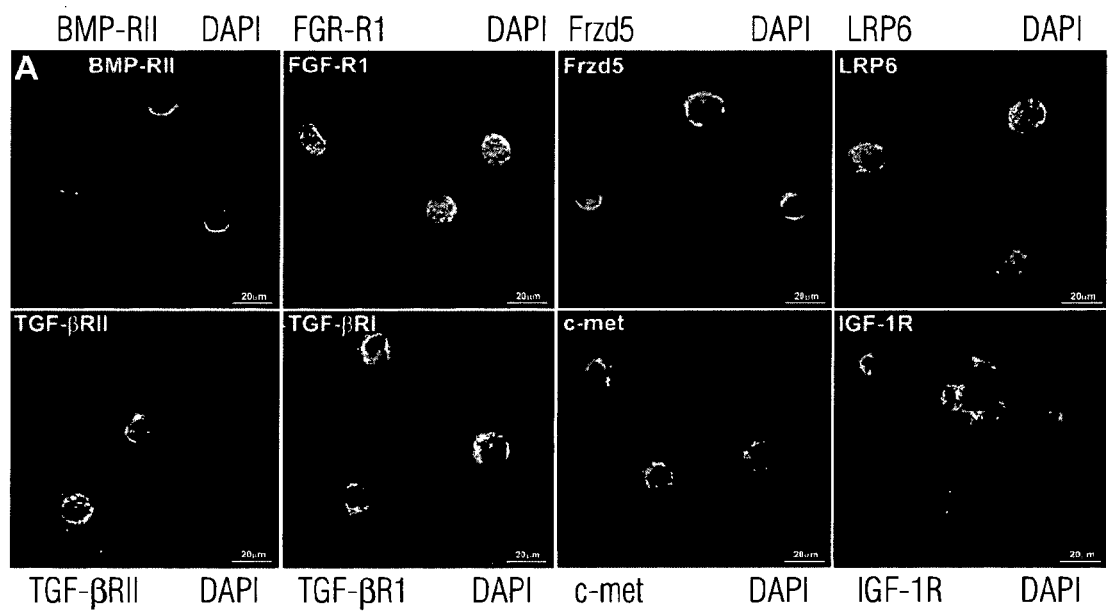

First, we exposed C5 eCSCs to a modified osteogenic medium for 14 days (13). The c-kit$^{pos}$ eCSCs significantly increased the transcription of the osteogenic lineage marker, osteocalcin and became positive to osteocalcin immunostaining (FIG. 3A). Furthermore, Alizarin Red staining detected calcium deposits (FIG. 3A).

Figure 3B:
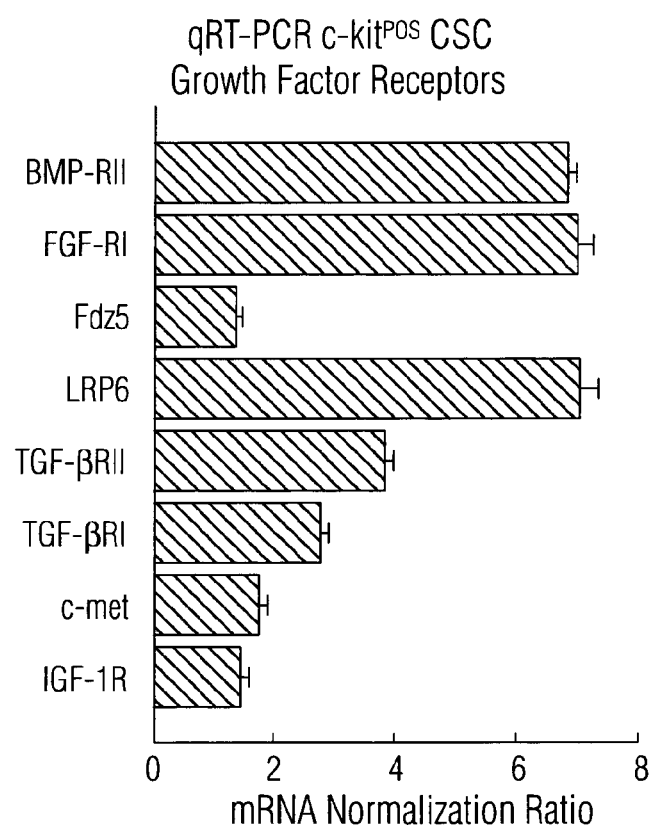

In order to verify if c-kit$^{pos}$ eCSCs were able to generate endodermal derivatives we cultivated the eCSCs using a protocol known to induce hepatic differentiation of ES and iPS cells (14). Differentiated cells assumed a globular shape with an eccentric nucleus, progressively decreasing their anchorage to the substrate. These cells increased their transcription and stained positive for cytokeratins 18 and 19, albumin and HNFα1 (FIG. 3B). They also expressed high levels of albumin (~79% positivity), determined by flow cytometry. Finally, they acquired some hepatocytic function such as the ability to store glycogen, as demonstrated by PAS staining (FIG. 3B).

Figure 3C:
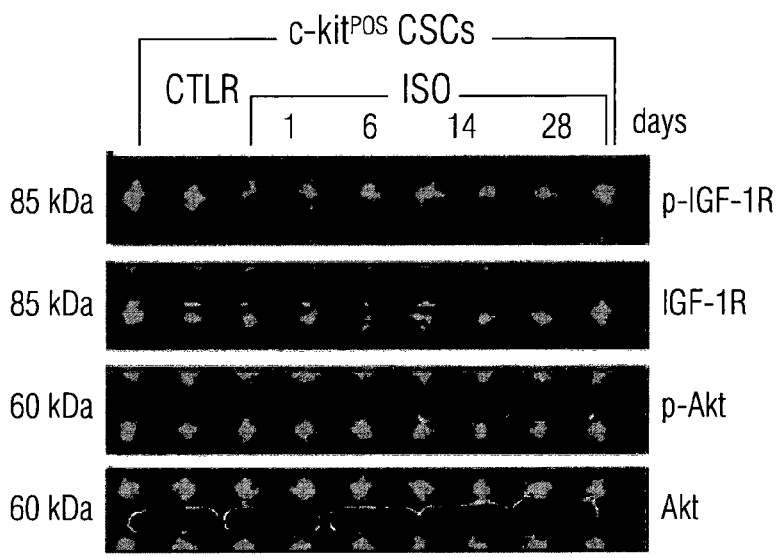
Figure 3D:
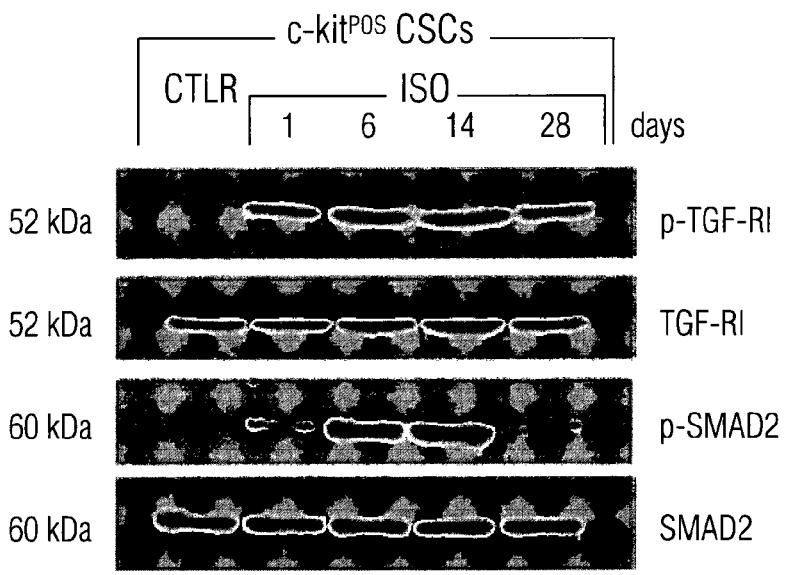
Figure 3E:
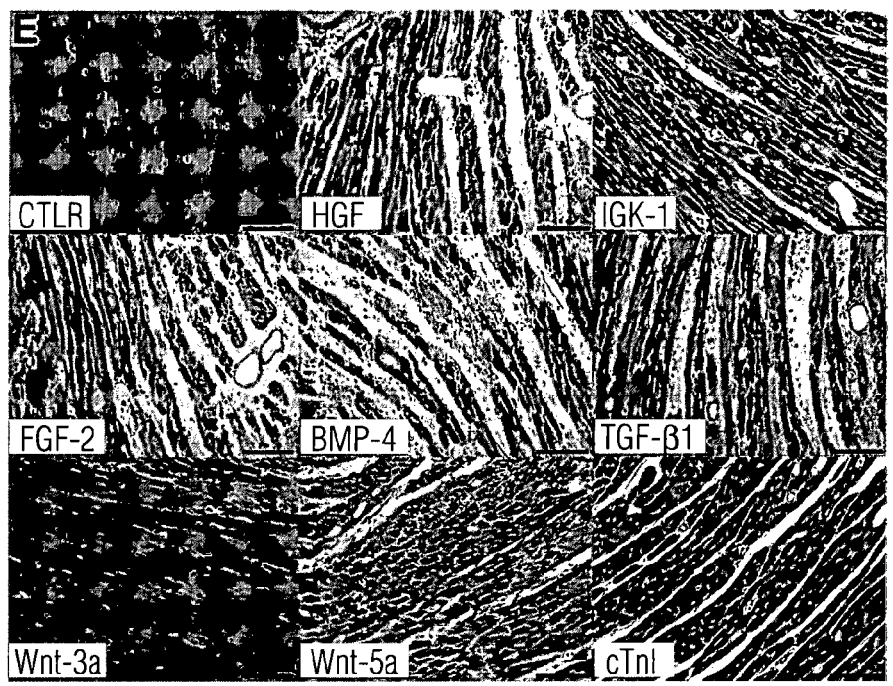
Figure 3F:
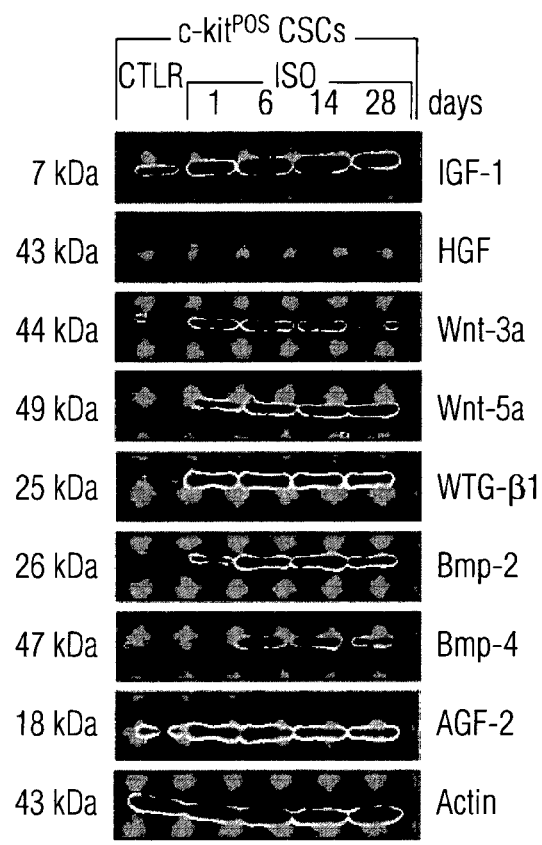
Figure 4A:
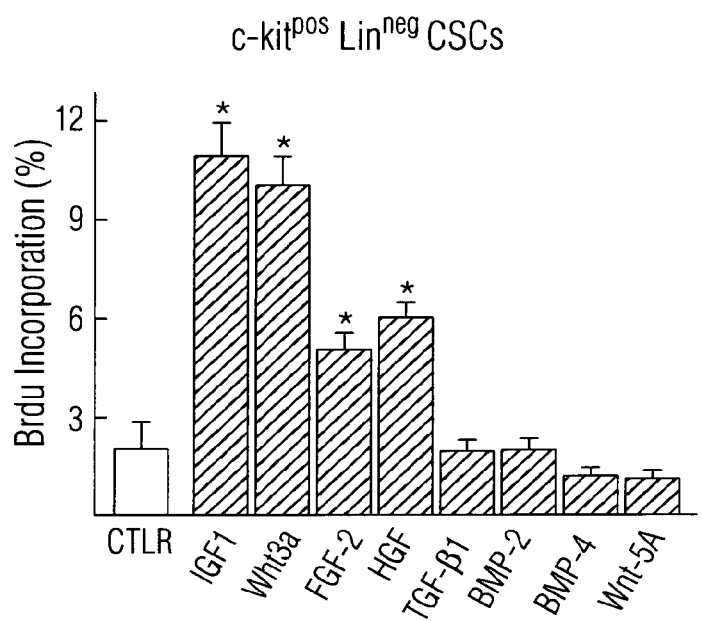
Figure 4B:
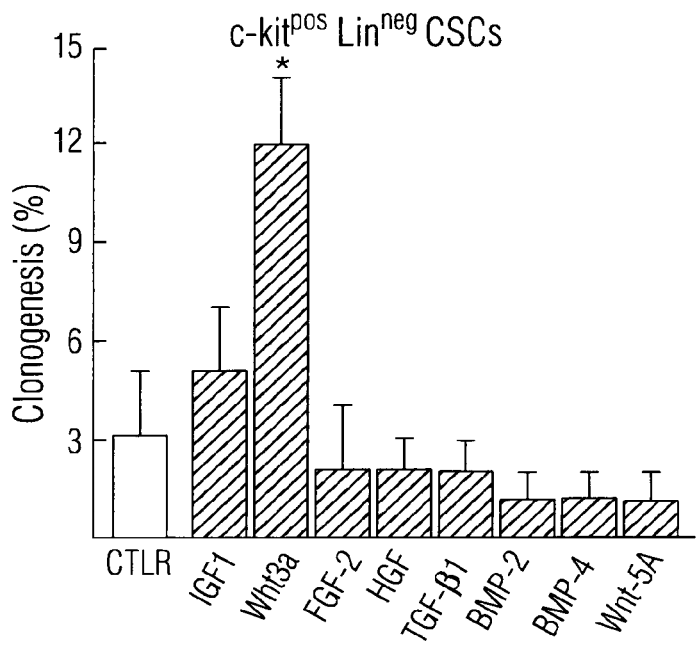
Figure 4C:
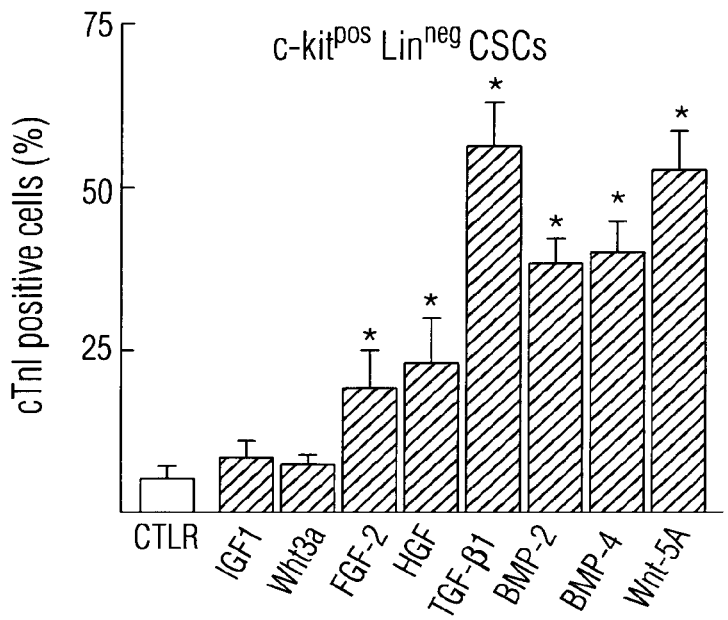
Figure 4D:
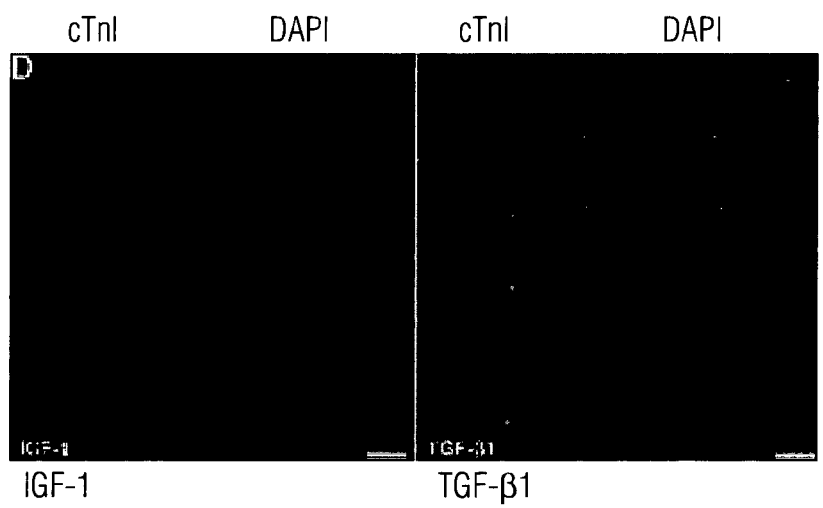
Figure 4E:
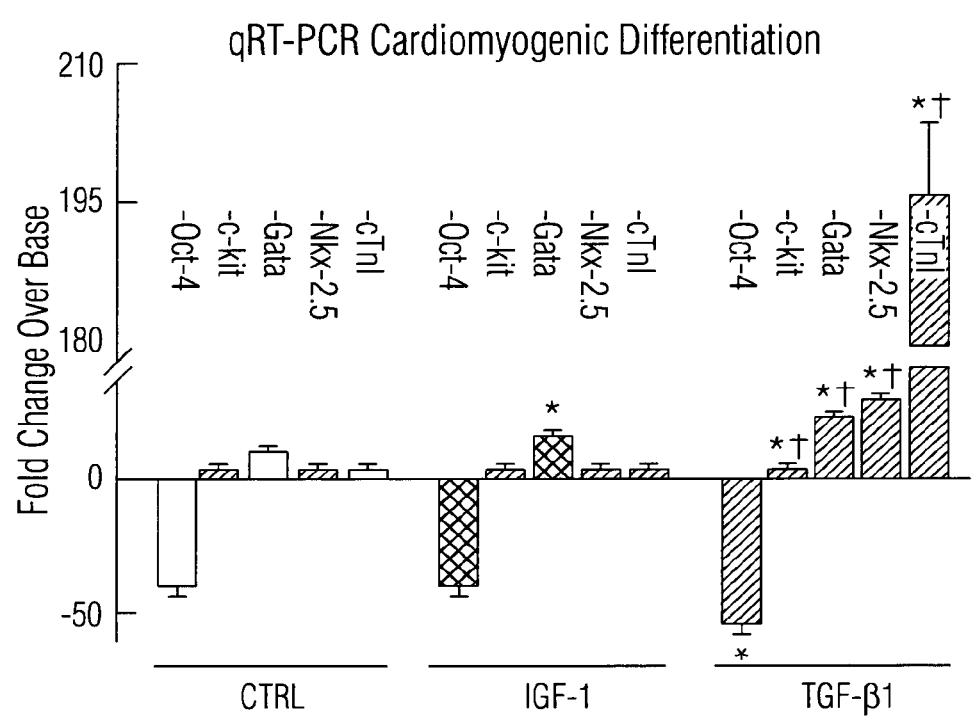
Figure 5A:
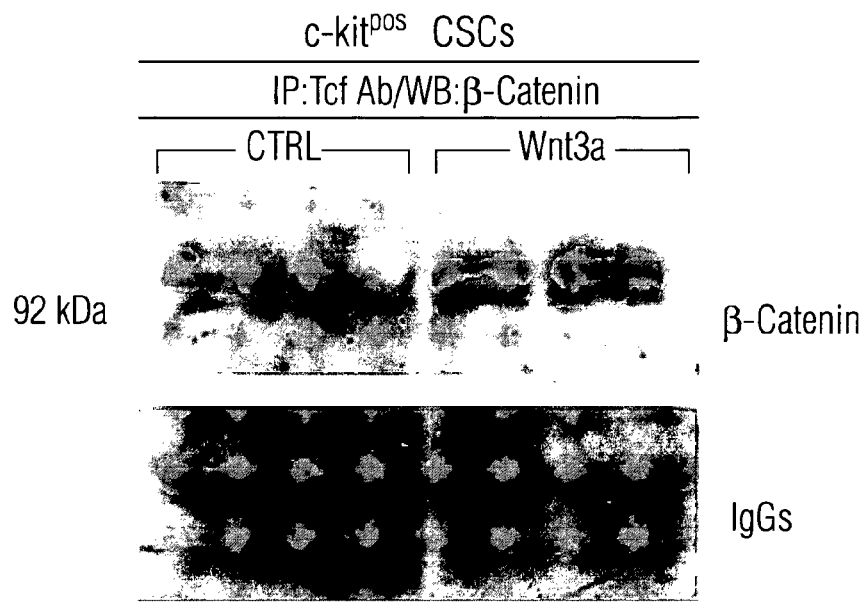
Figure 5B:
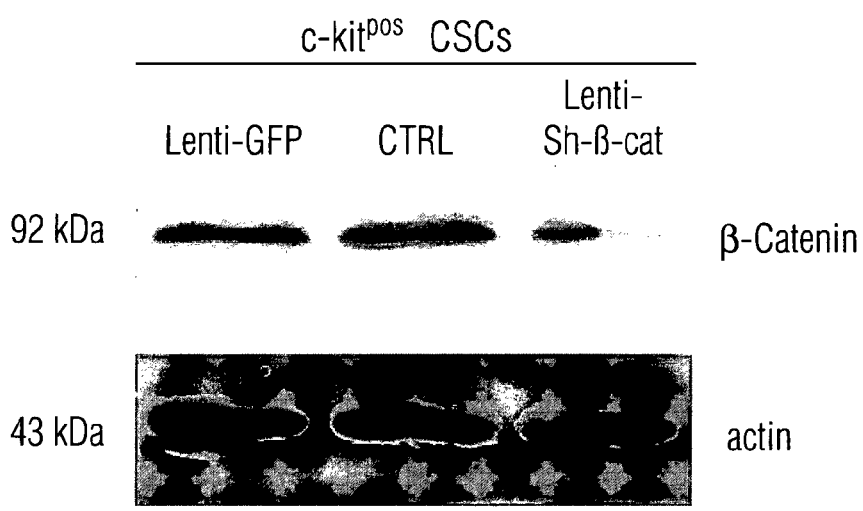
Figure 5C:
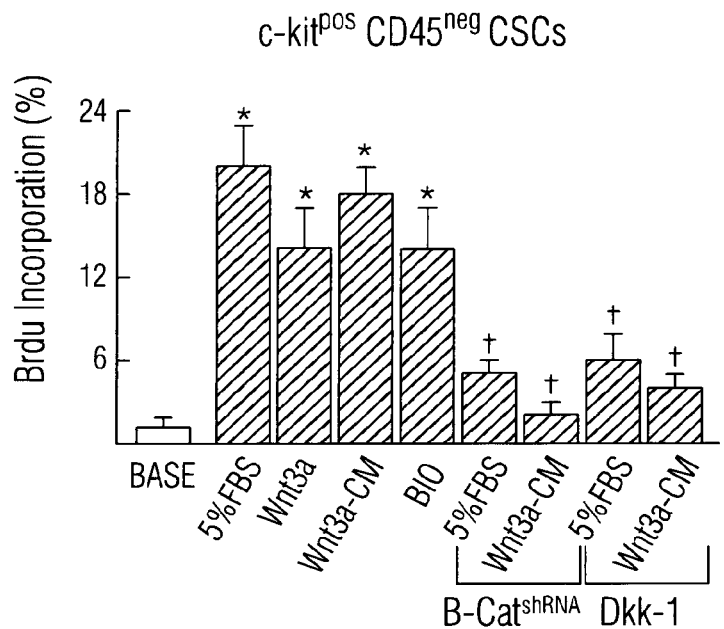
Figure 5D:
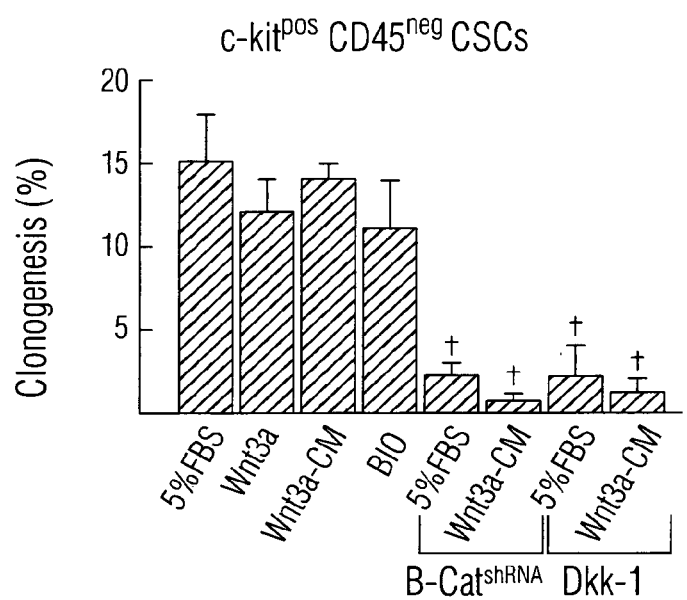
Figure 5E:
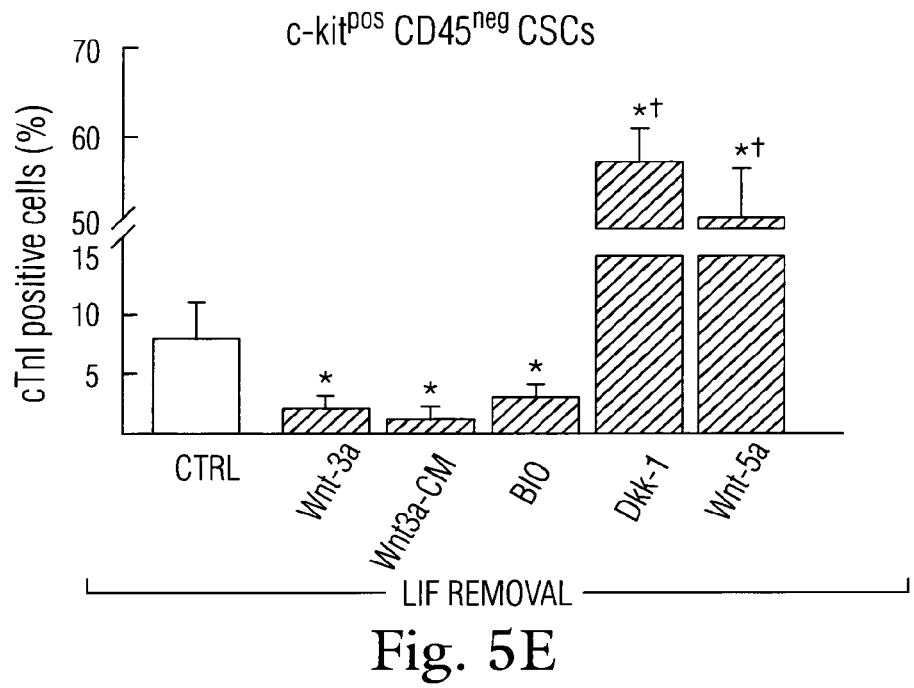
Figure 5F:
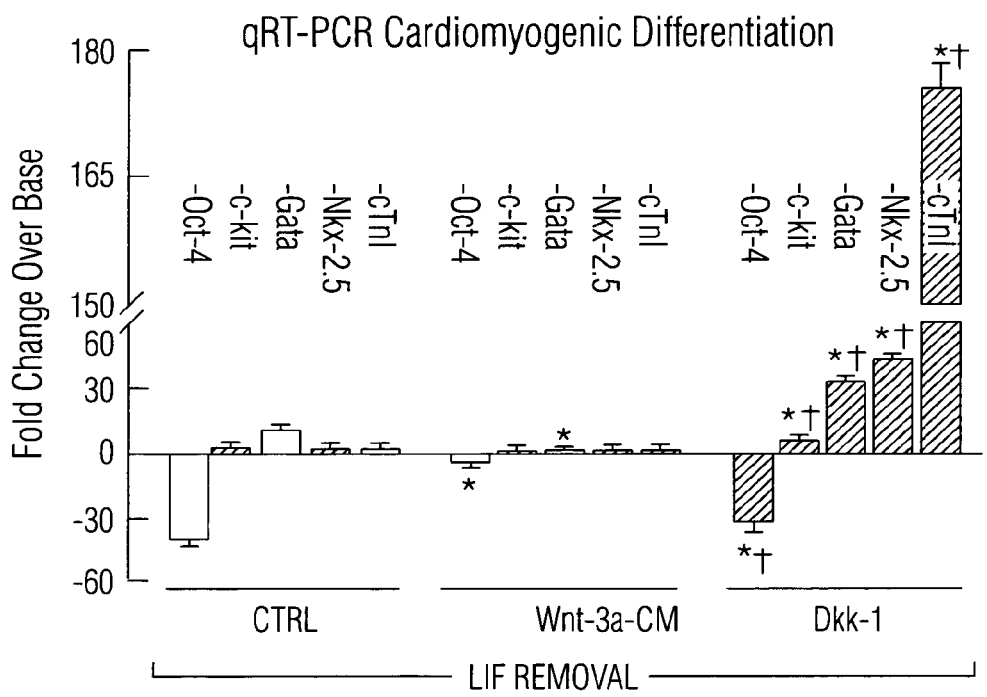
Figure 6A:
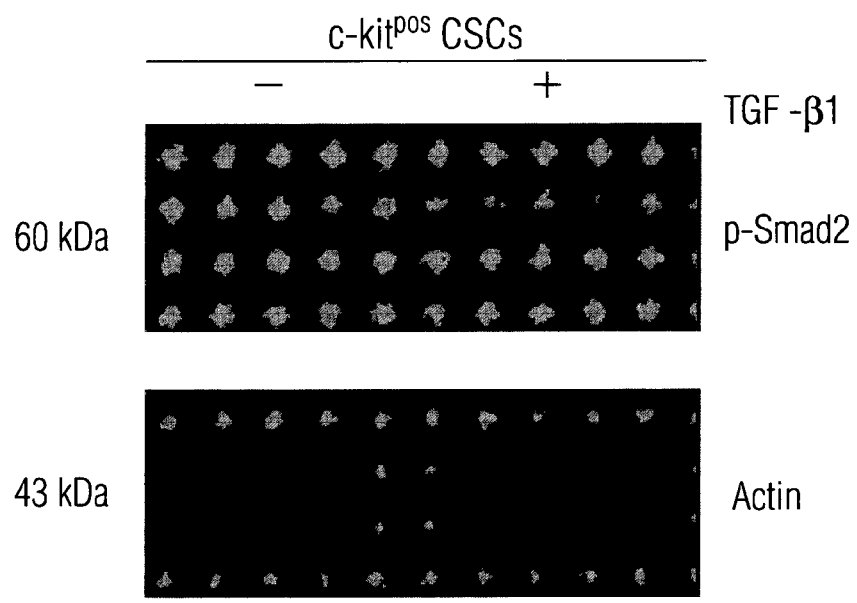
Figure 6B:
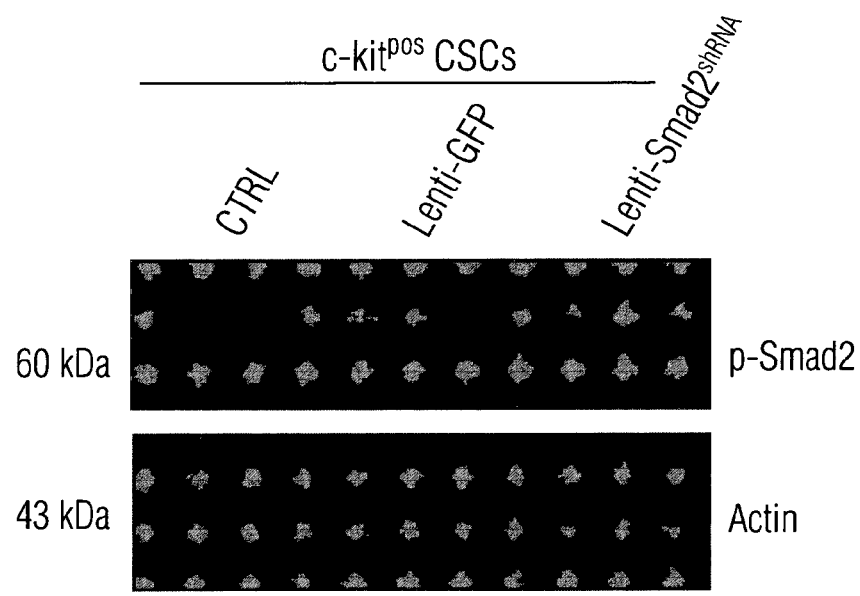
Figure 6C:
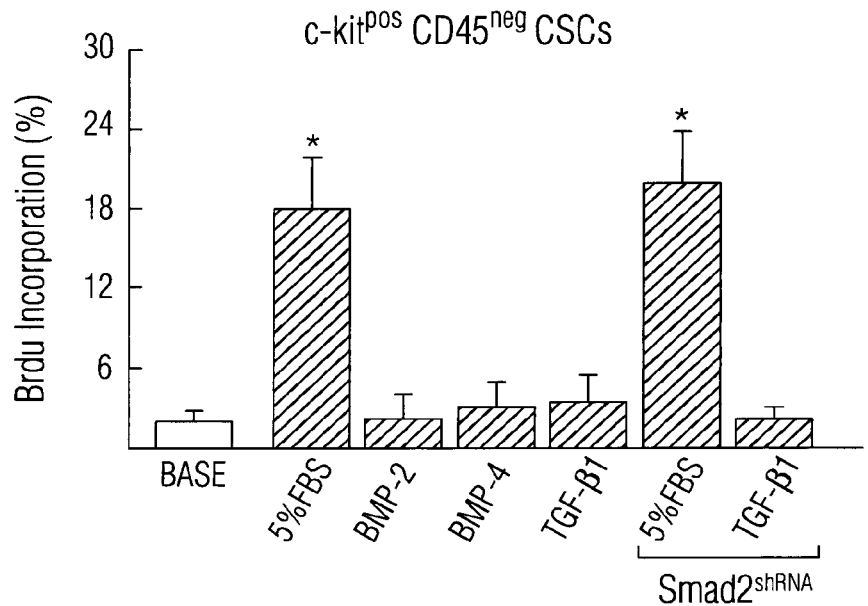
Figure 6D:
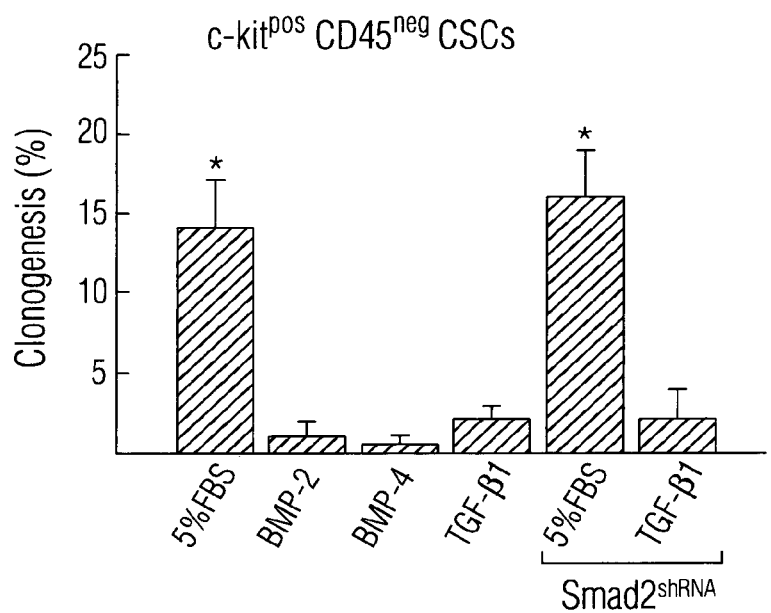
Figure 6E:
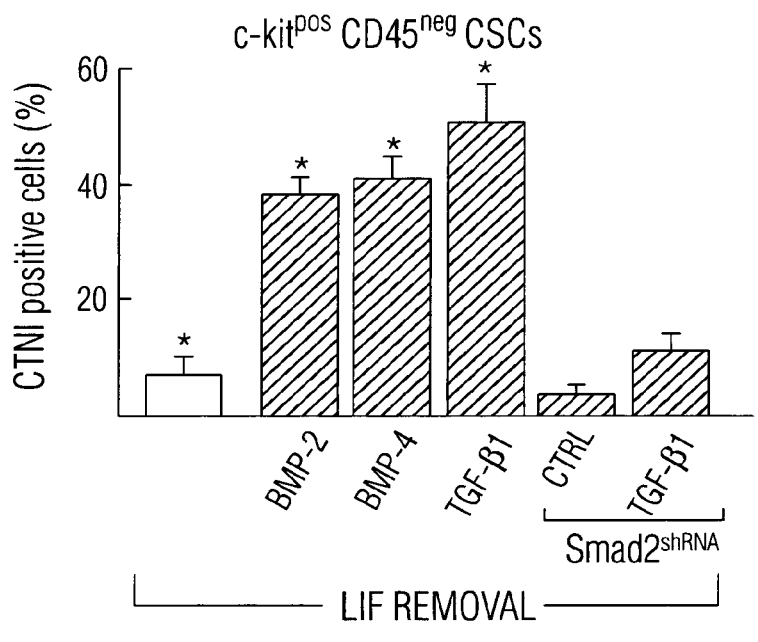
Figure 6F:
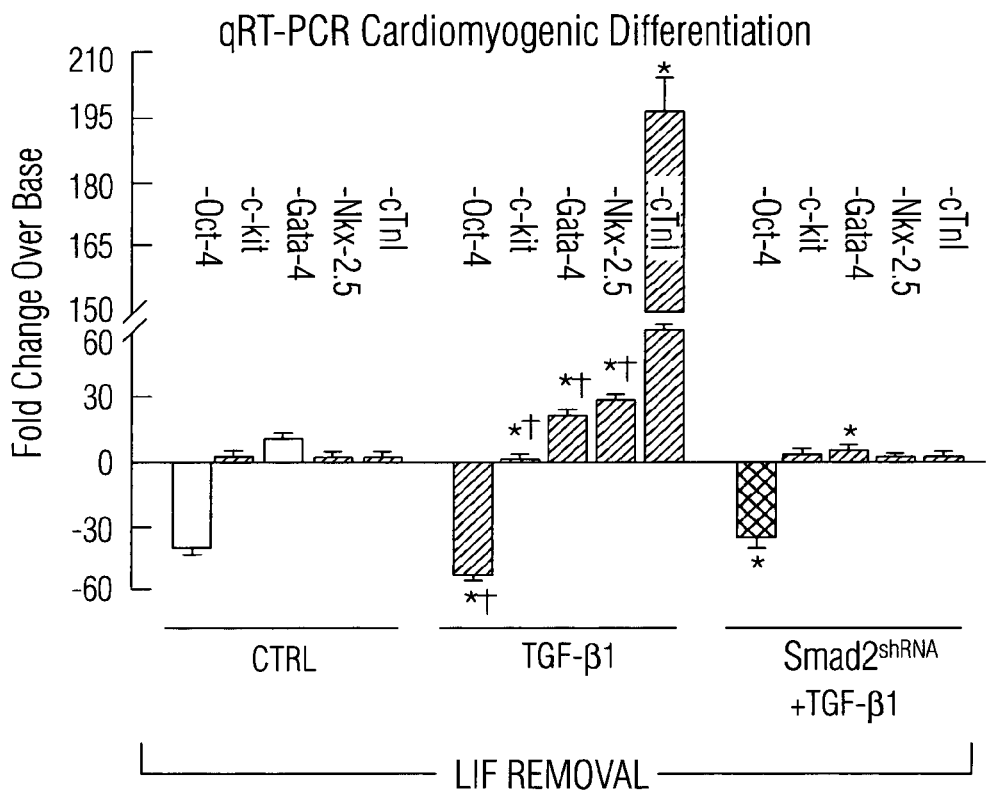

It has been previously shown that cardiac side population cells that express the neural progenitor marker, Nestin, can be induced to differentiate into the ectoderm layer, producing neurons and glial cells (15). We then purified for a population of Nestin$^{pos}$ progenitor cells from clonal-derived c-kit$^{pos}$ eCSCs. When placed into differentiation medium supplemented with Retinoic Acid or LIF for 7 days, we found up-regulation of GFAP, MATH2/NeuroD6, a neuron specific transcription factor (FIG. 3C), β-3 tubulin arrayed in filaments and bundles (FIG. 3C), neuron-specific enolase (FIG. 3C), acetylcholintransferase (FIG. 3C), doublecortin (DCX), and S-100β (FIG. 3C). Furthermore, after RA differentiation, cells had characteristics of neuronal dendrites, indicating a morphological change that resembled neurons (FIG. 3C).

These data show that clonal c-kit$^{pos}$eCSCs amplified by single cell deposition express pluripotency genes and can give rise to cells of the 3 germ layers, demonstrating that c-kit$^{pos}$ eCSCs contain a more immature cell that has a broad degree of developmental plasticity.

Figure 12A:
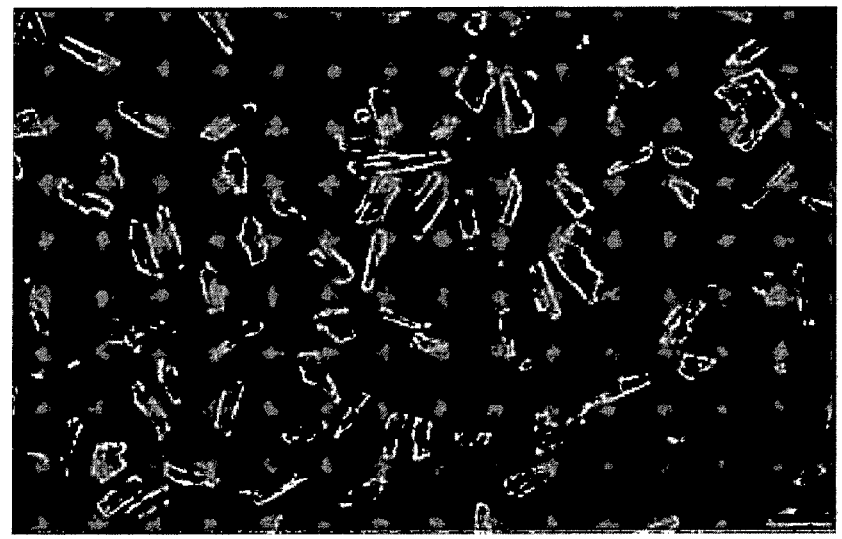
Figure 12B:
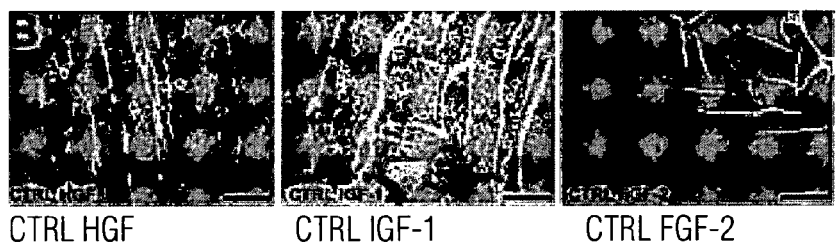
Figure 12B:
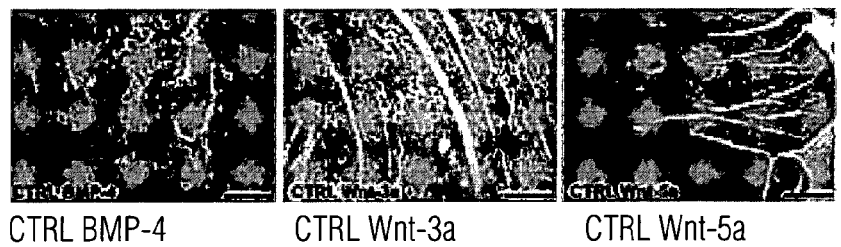
Figure 12C:
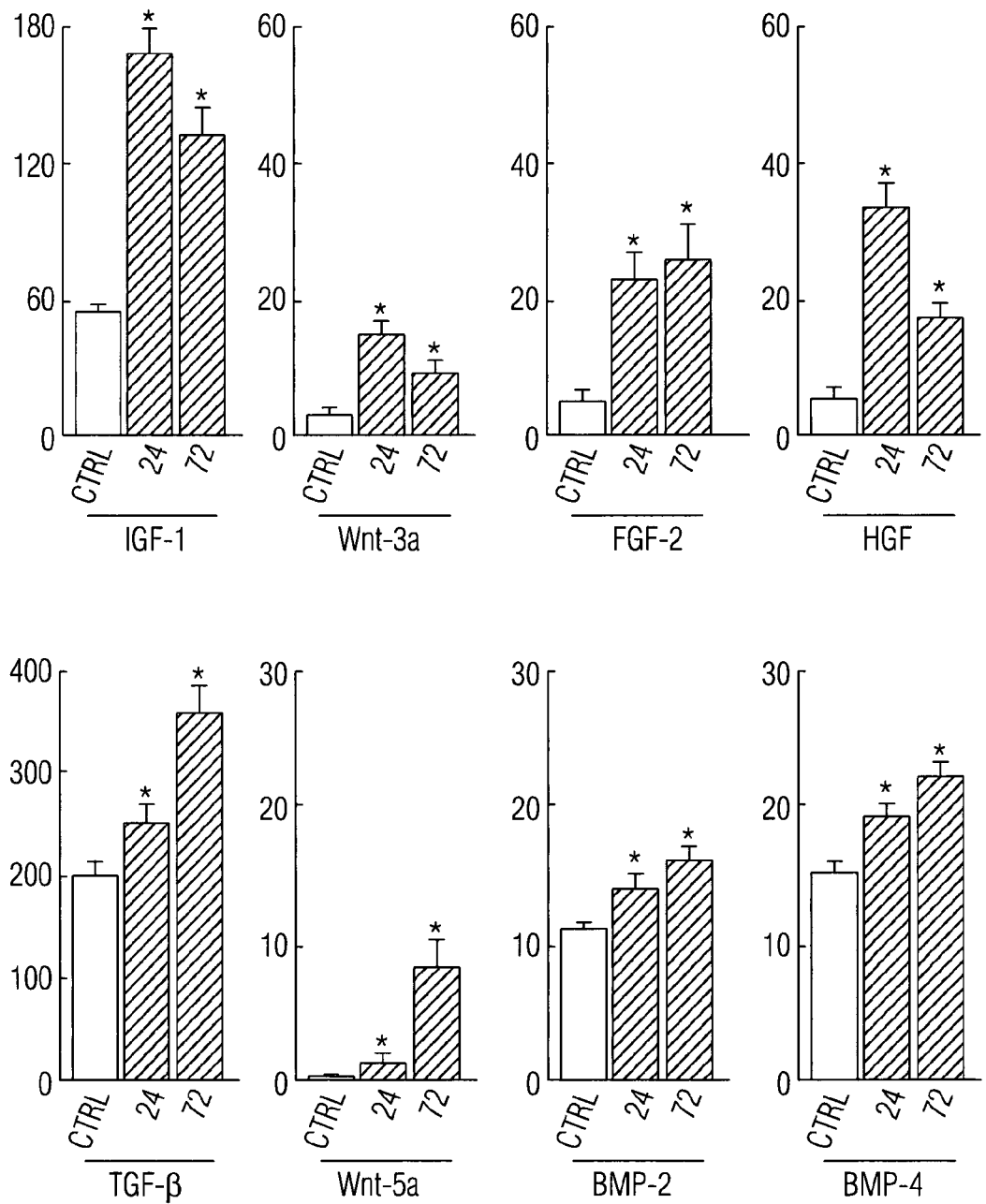

6.4 The Adult Myocardium Express Cardiopoietic Growth Factors Affecting c-kit$^{pos}$ CD45$^{neg}$ eCSC Fate In Vivo and In Vitro Adult c-kit$^{pos}$eCSCs are scattered throughout the myocardium with higher density within the atria and the ventricular apex (10). When the apical myocardium is severely injured by catecholamine overdrives, induced through Isoproterenol bolus injection, c-kit$^{pos}$eCSCs are rapidly activated and respond to damage by increasing their number (16) and differentiate into cardiomyocyte lineage (Unpublished data). The same growth response by these cells is detectable in the ischemic myocardium (17) as well as in hearts with pathologic or physiological overload (18,19). During embryonic life, a progressive process of cell specification or commitment, precisely regulated in space and time, determine cardiac muscle cell creation from cardiac progenitor cells (20). In the latter phenomenon, "cell-autonomous" decisions (intrinsic to a cell) are accompanied by "cell-non-autonomous" events, which entail extracellular cardiomyogenic instructive molecules known as morphogens or cardiopoietic growth factors (cGFs) (8,9). Interestingly, following diffuse myocardial damage by ISO injection there is significantly increased expression of several known cardiopoietic growth factors (FIG. 4 and FIG. 12A-D). Specifically, pure populations of adult cardiomyocytes (FIG. 12A-D) isolated at different times after ISO injury had significant increased expression of IGF-1, Wnt3a, FGF-2, HGF, TGFβ-1, Wnt5a, BMP-2 and BMP-4, BMP-10, Neuroregulin and Periostin when compared to CTRL (FIG. 12C). TGF-β1 was the most highly up-regulated and, like BMP-2, BMP-4, and FGF-2, showed increasing mRNA levels after injury, which peaked at 72 hours after ISO. Also, highly up-regulated were IGF-1 and HGF that peaked at 24 hrs after damage (FIG. 4). Histochemical analyses of apical left ventricle (LV) cross-sections of ISO-damaged and CTRL hearts, show that induction of these cardiopoietic growth factors (cGFs) was mainly confined to the spared cardiomyocytes which survived within the sub-endocardial layer (FIG. 4). The mRNA levels for different cGFs and their detection by immunohistochemistry correlated with the levels of the corresponding protein (FIG. 4).

Furthermore, we detected a rapid increase in the expression of all these cGFs in the cardiac fibroblasts of ISO-treated hearts after ISO but these returned to normal at 6 days, when compared to CTRL (FIG. 12A-D). Interestingly, cGFs are rapidly and progressively up-regulated. Their increased expression is already evident at 3-6 hours after ISO (FIG. 4), a time when the number and activation of the c-kit$^{pos}$eCSC are still at baseline and similar to the saline-treated CTRL (FIG. 4). Thus, cGF up-regulation precedes eCSC activation, generating the hypothesis of a cause-effect relationship between these two processes.

c-kit$^{pos}$CD45$^{neg}$ eCSCs express functional receptors for these cardiopoetic factors (cGFs) (FIG. 4). In particular, both TGF-β1 and Wnt receptors are activated and signal to their known downstream effectors in eCSCs isolated from ISO injured hearts (FIG. 4). We thus directly tested in vitro the growth response of freshly isolated c-kit$^{pos}$ CD45$^{neg}$ eCSCs grown in limited serum (1% ESQ-FBS) to individual cGFs. Dose-response curves were performed to determine the optimal concentration for each cGF (FIG. 13A-H). Supplementation with either Wnt3a, IGF-1, FGF-2 or HGF significantly increased c-kit$^{pos}$ eCSC proliferation (FIG. 5) with Wnt3a being the most effective in increasing clonogenicity (FIG. 5). In contrast, supplementation with either Wnt5a, TGF-β1, BMP-4 or BMP-2 did not affect growth or clonogenicity but promoted differentiation of eCSCs into the cardiomyocyte lineage (FIG. 5). Interestingly, the combined use of IGF-1 and Neuroregulin stimulated growth of the CSCs in a more than an additive effect, suggesting a synergy between the two activated downstream pathways. These effects were confirmed by qRT-PCR of cardiomyocyte-specific mRNAs (FIG. 5). Together, these data show that the canonical Wnts and IGF-1 are the most effective in supporting eCSC self-renewal and expansion, while the TGFβ family and the non-canonical Wnts are the strongest inducers of their biochemical differentiation.

6.5 The Effects of Canonical Wnt and TGF-β1/SMAD-2 Pathways on c-kit$^{pos}$ CD45$^{neg}$ eCSC Fate Wnt/β-catenin and TGF-β/SMADs signaling play critical roles in the regulation of embryonic as well as different tissue-specific stem cell fate (21-23). In particular, these two signaling pathways have distinct functions in mammalian cardiogenesis (24-27). Thus, to extend our findings we have tested through gain and loss of function experiments the effects of Wnt/β-catenin and TGF-β/SMADs signaling pathways on c-kit$^{pos}$ eCSC fate in vitro. To promote Wnt/β-catenin pathway, we used soluble Wnt-3a, conditioned medium from a Wnt-3a-secreting cell line or 6-bromoindirubin-3'-oxime (BIO, a specific inhibitor of GSK-3 that stabilizes β-catenin). To disrupt Wnt/ρ-catenin, c-kit$^{pos}$ eCSCs were either treated with Dickkopf-1 (Dkk-1), an inhibitor of canonical Wnts or transfected with a specific short hairpin RNA for β-catenin (β-cat$^{shRNA}$). BrdU incorporation proliferation and clonogenic assays revealed that Wnt-3a, Wnt-3a-conditioned medium and BIO were able to stimulate c-kit$^{pos}$ eCSC expansion, and clonogenicity (FIG. 6). In contrast, inhibiting canonical Wnt signaling with Dkk-1 or β-cat$^{shRNA}$ resulted in a significant decrease of c-kit$^{pos}$ eCSCs proliferation, and clonogenicity (FIG. 6). The positive and negative modulators of Wnt/β-catenin physiologically acted on their known molecular targets by respectively stabilizing or degrading β-catenin and its LEF/TCF-dependent transcriptional activity (FIG. 6). When c-kit$^{pos}$ eCSC were placed in differentiation medium by LIF withdrawal, qRT-PCR revealed that Wnt-3a, Wnt-3a-conditioned medium and BIO significantly reduced the transcription of myogenic lineage markers and the number of myocyte differentiating (cTnI$^{pos}$) cells (FIG. 5). On the other hand, Dkk-1 increased c-kit$^{pos}$ CSC myocyte specification (FIG. 5), even though its effect was not sufficient to produce a fully differentiated phenotype as indicated by the lack of cells which expressed abundant and organised sarcomeric structures (FIG. 5). These data suggest that the canonical Wnt pathway not only promotes but is required for c-kit$^{pos}$ eCSC expansion while its antagonism drives c-kit$^{pos}$ eCSC myogenic specification, however other factors are required to produce a fully differentiated and functional phenotype in vitro.

To evaluate the role of TGF-β/SMAD signaling, BMP-2, BMP-4 and TGF-β1 were added to cultured c-kit$^{pos}$ eCSCs. In loss of function experiments, we disrupted TGF-β1-dependent SMAD signaling by transfecting a plasmid vector expressing a shRNA specific for Smad2 (Smad2$^{shRNA}$) which is highly effective in reducing the corresponding protein levels (FIG. 6). Neither BMP-2, BMP-4, TGF-β1 supplementation nor Smad2 knock-down affected c-kit$^{pos}$ eCSC expansion, or clonogenicity (FIG. 6). However, when c-kit$^{pos}$ eCSCs were placed in differentiation medium, BMP-2, BMP-4, BMP-10 or TGF-β1 significantly induced the transcription of myogenic lineage markers and the number of myocyte cTnI$^{pos}$ differentiating cells (FIG. 6). Accordingly, under differentiation conditions Smad2$^{shRNA}$, reduced eCSC myocyte specification and completely blocked the TGFβ1-dependent positive myogenic effect (FIG. 6). These data show that TGF-β1/Smad2 pathway is dispensable for c-kit$^{pos}$ eCSC expansion while its activation drives c-kit$^{pos}$ eCSC myogenic specification.

6.6 A Stage-Specific TGF-β-Family/Wnt Inhibitor Cocktail Fosters Functional In Vitro Myogenesis of c-kit$^{pos}$ eCSCs Despite the existence of an increasingly large body of experimental evidence documenting a precursor product relationship between the adult CD45$^{neg}$c-kit$^{pos}$ cardiac stem-progenitor cells and differentiated myocytes in vivo and in vitro (10, 12, 17, 18, 19, 28, 29), scepticism still exists about these cells as the source of fully differentiated, functional myocytes (30, 31). The most common caveat raised against these adult cells has been that the differentiated cells they give origin to, although they have biochemical parameters of myocytes, so far all have failed to exhibit spontaneous contractions, the so-called cardinal characteristic of functional cardiac myocytes. To establish a precursor-product relationship between the c-kit$^{pos}$ eCSCs and contractile myocytes, it is necessary not only to show specification of eCSCs into functional, contracting cardiomyocytes but also to identify the molecule(s) responsible for inducing this phenotype. Therefore, we tested whether the growth factors and signalling pathways identified above together with other factors, given in a stage/sequence-specific manner, were capable to produce contractile myocytes derived from cloned c-kit$^{pos}$ CD45$^{neg}$ eCSCs.

Figure 7A:
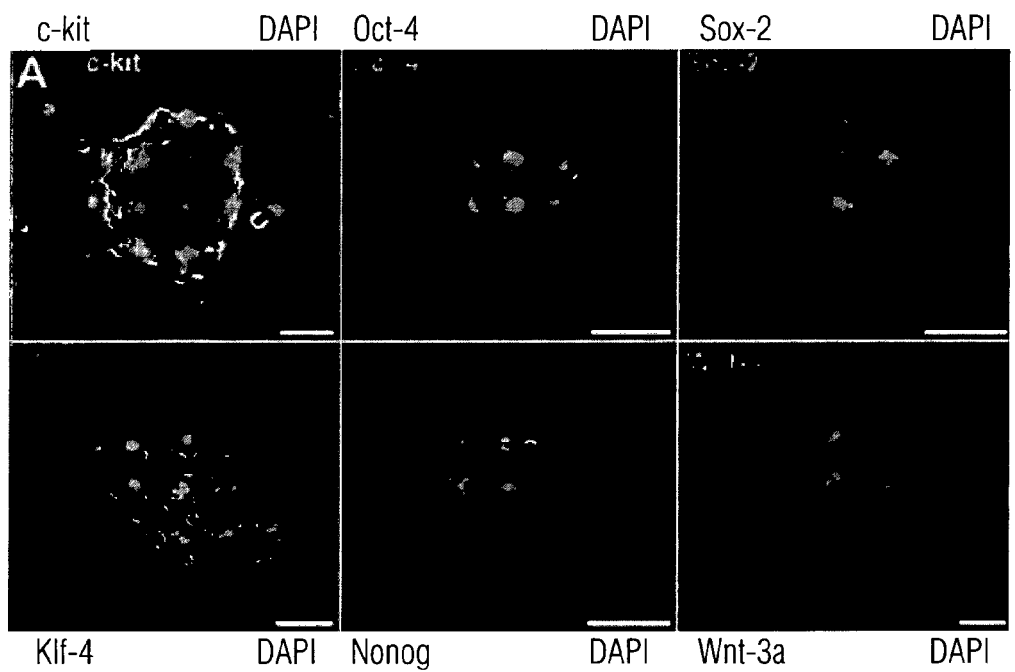
Figure 7B:
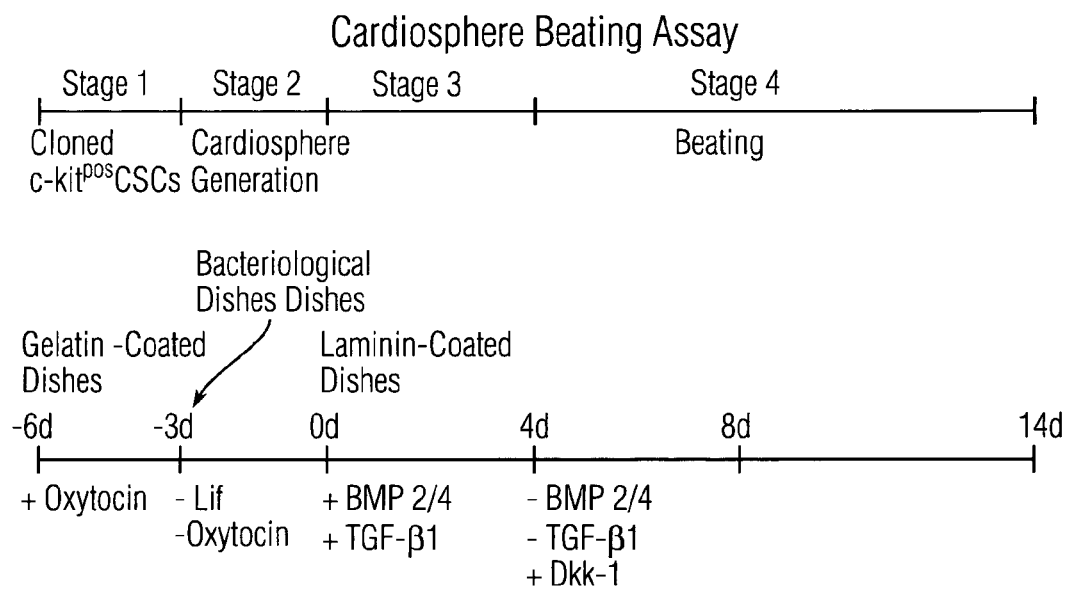
Figure 7C:
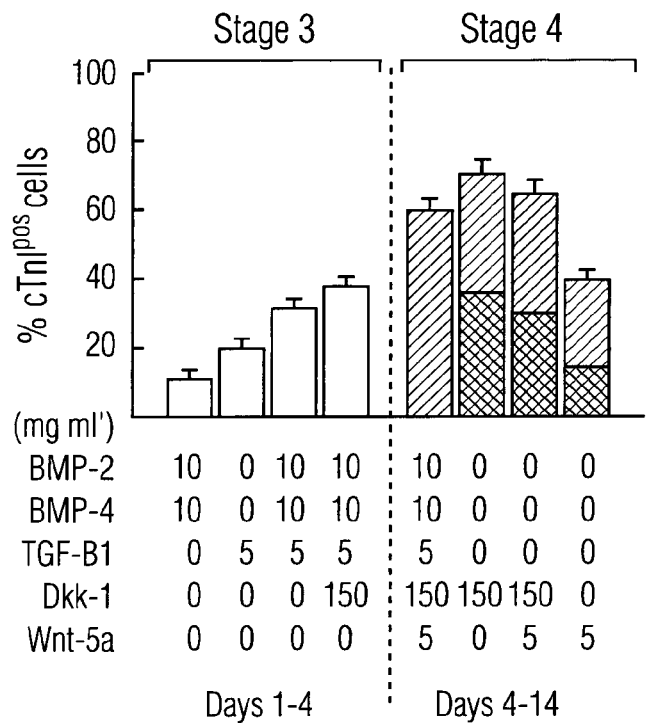
Figure 7D:
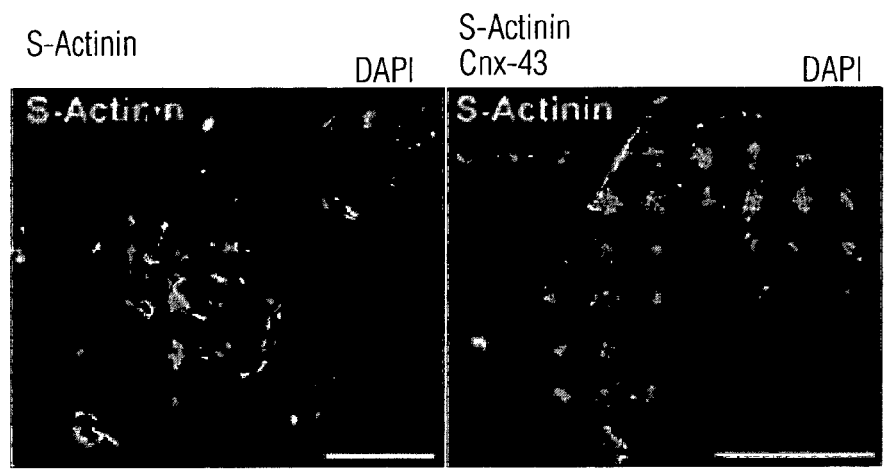
Figure 7E:
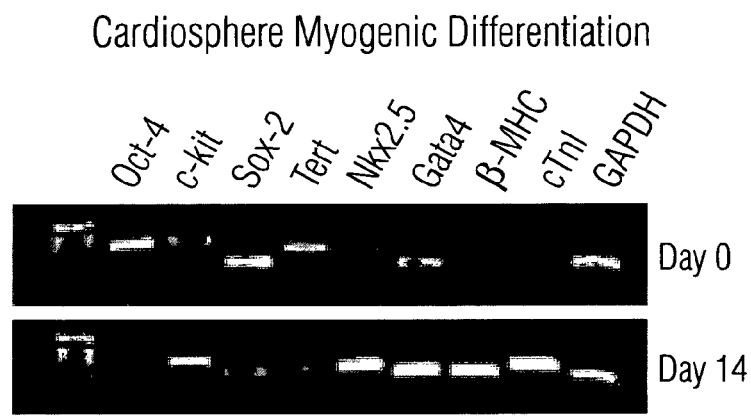
Figure 7F:
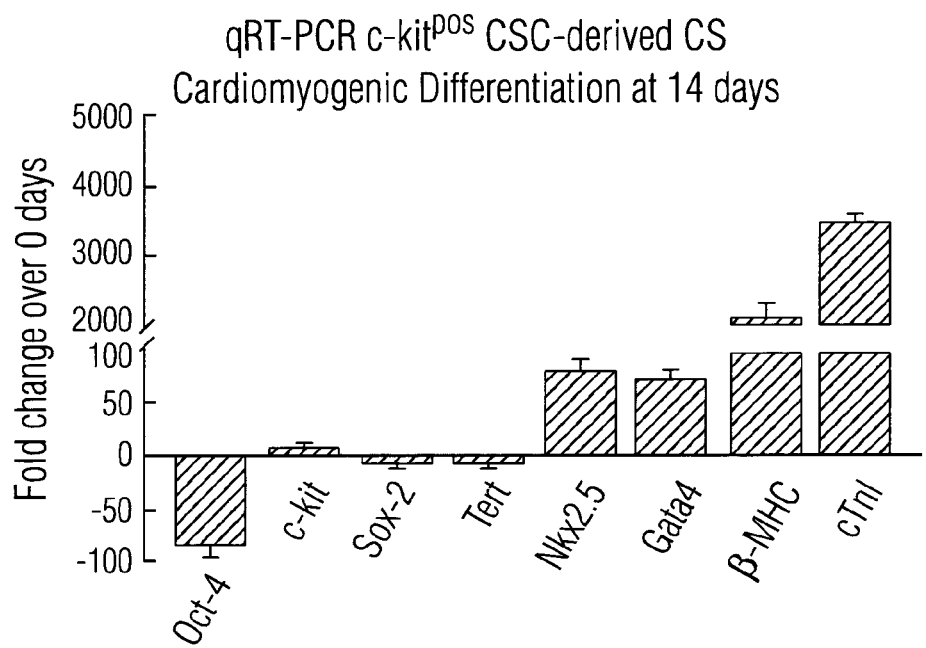
Figure 8A:
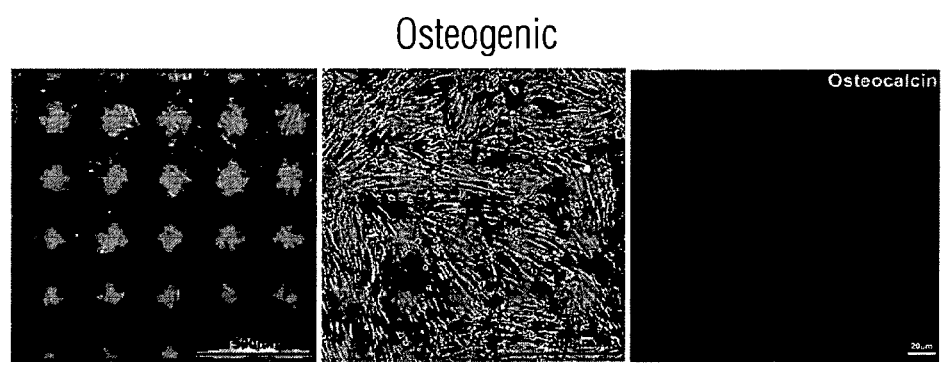
Figure 8A:
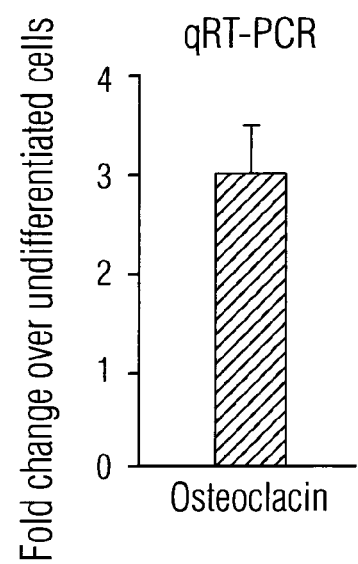
Figure 8B:
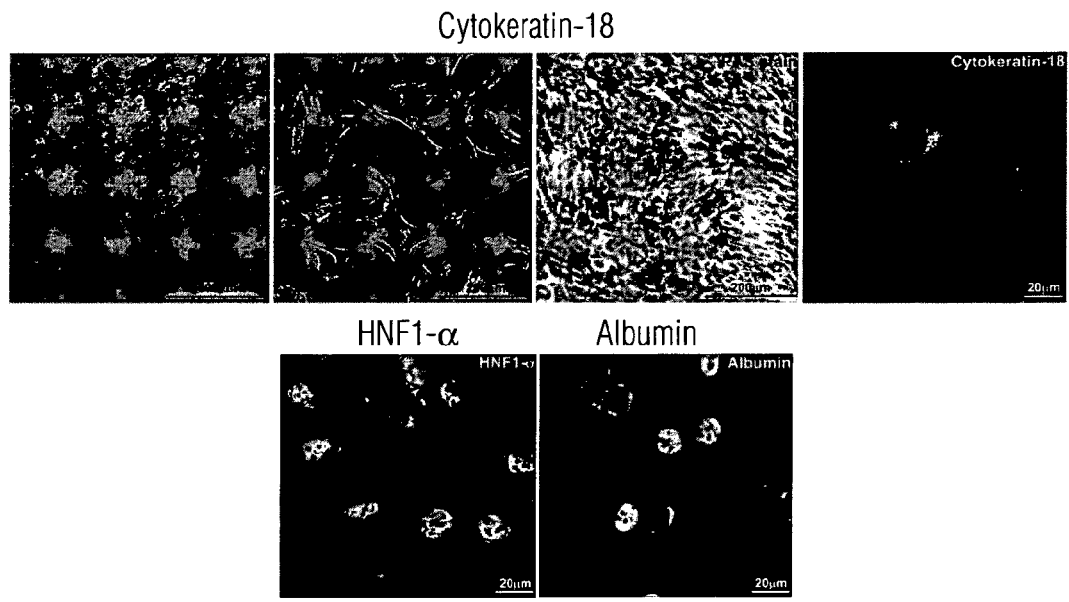
Figure 8B:
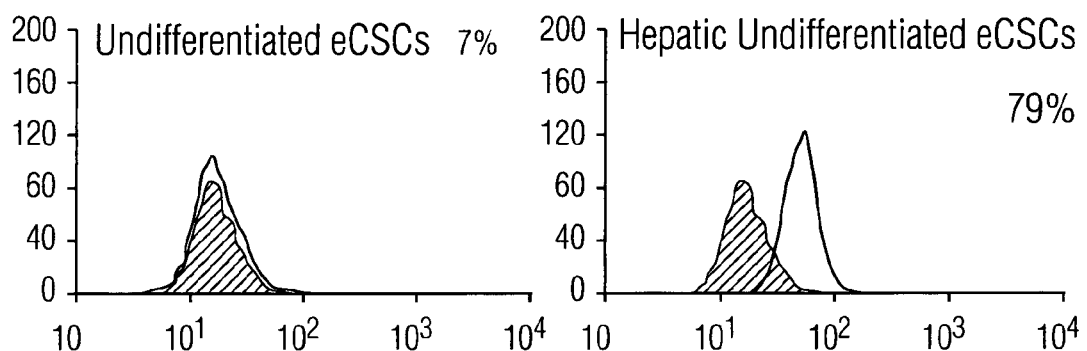
Figure 8B:
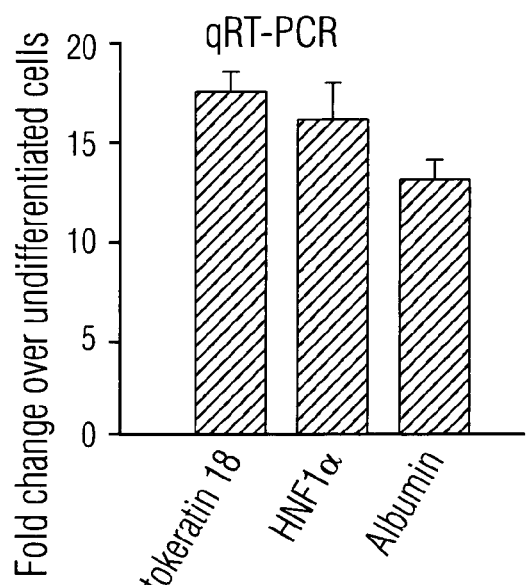
Figure 8C:
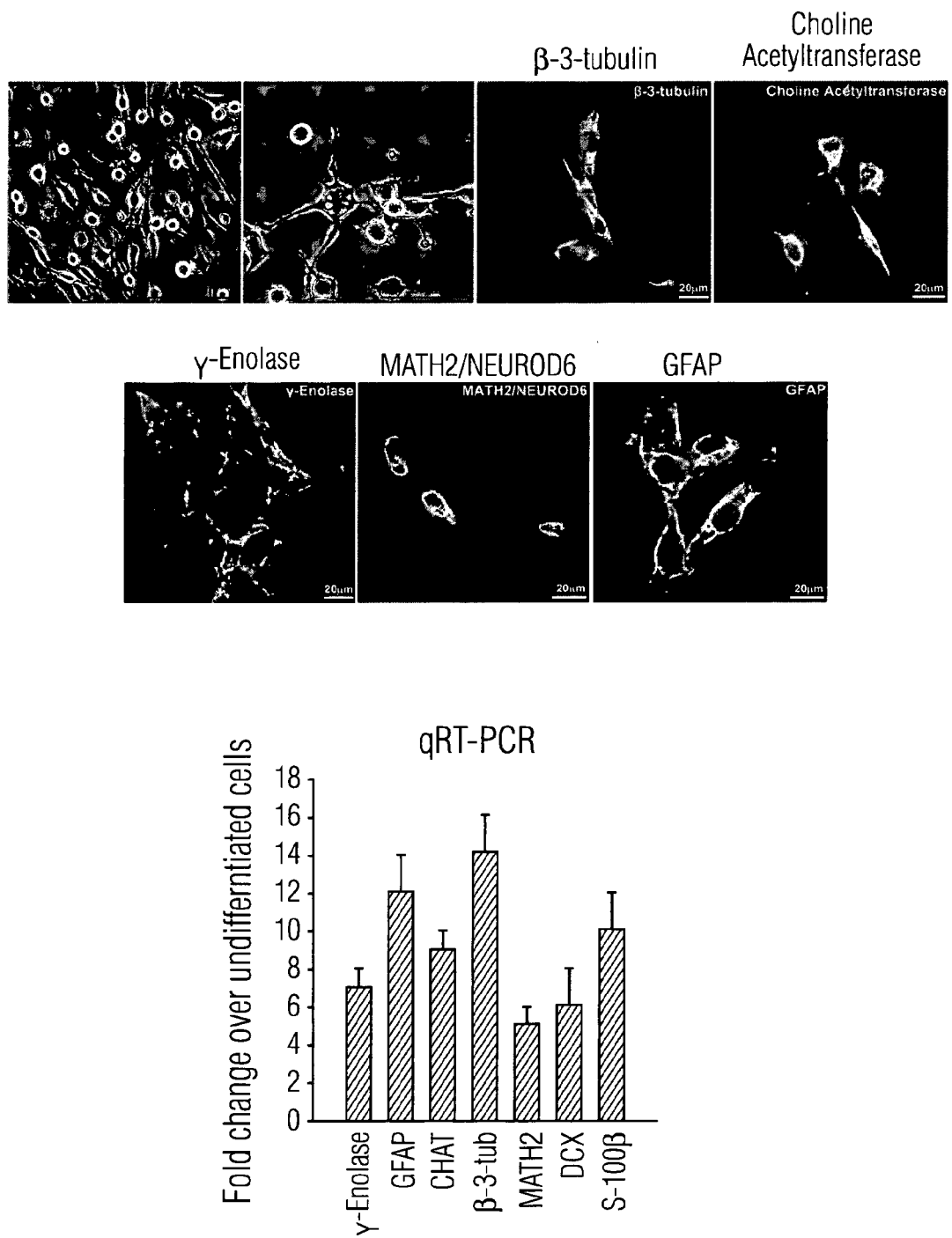
Figure 9A:
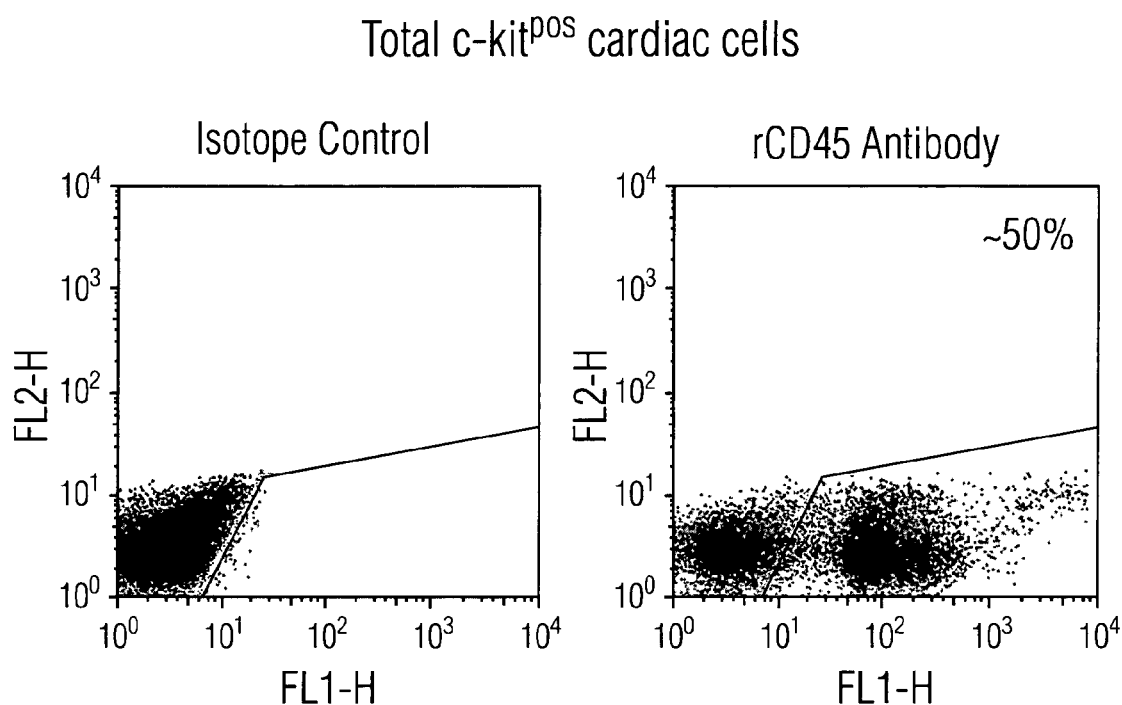
Figure 9B:
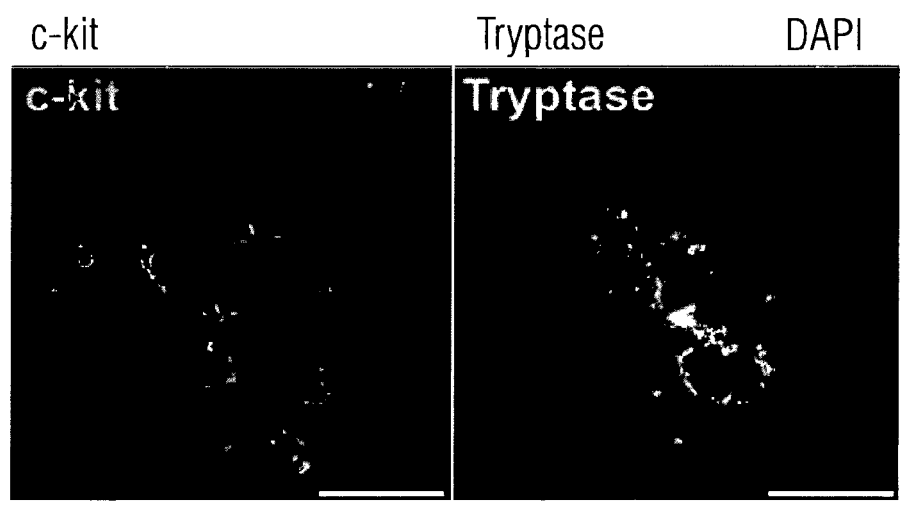
Figure 9C:
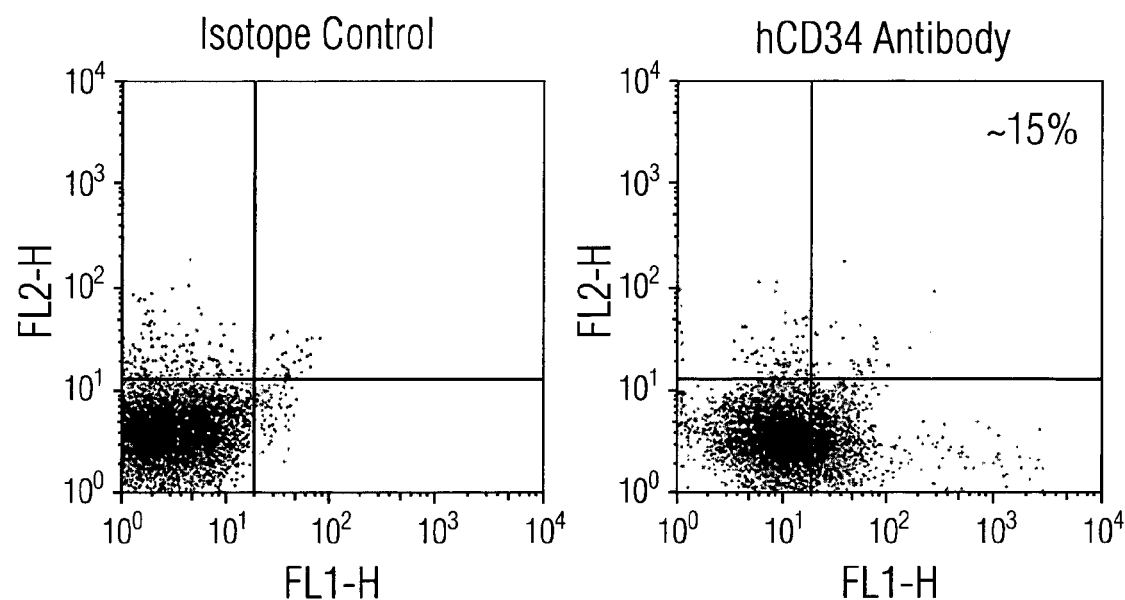
Figure 9D:
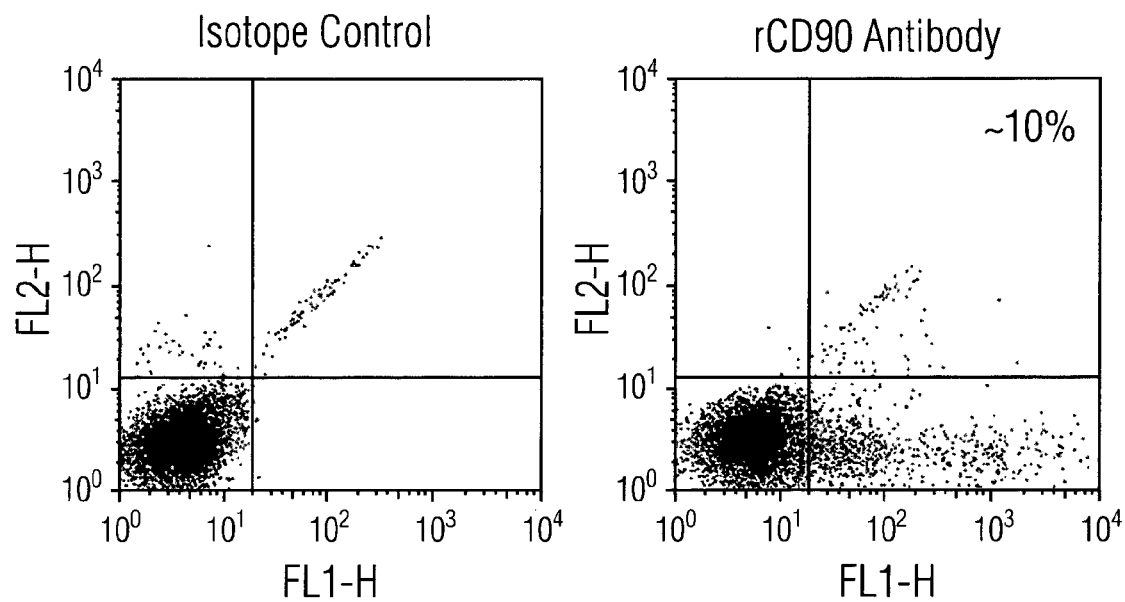
Figure 9E:
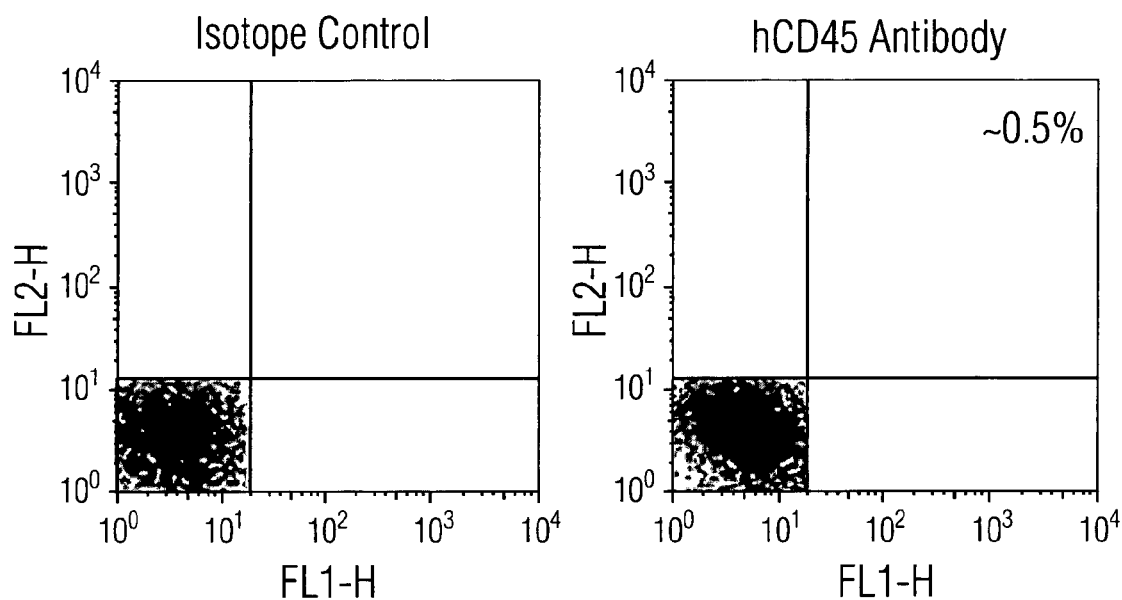
Figure 9F:
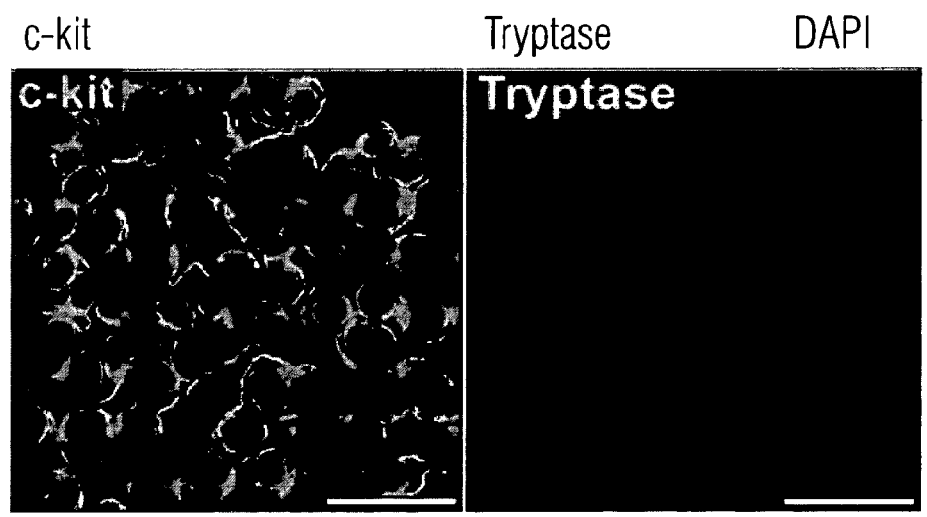
Figure 9G:
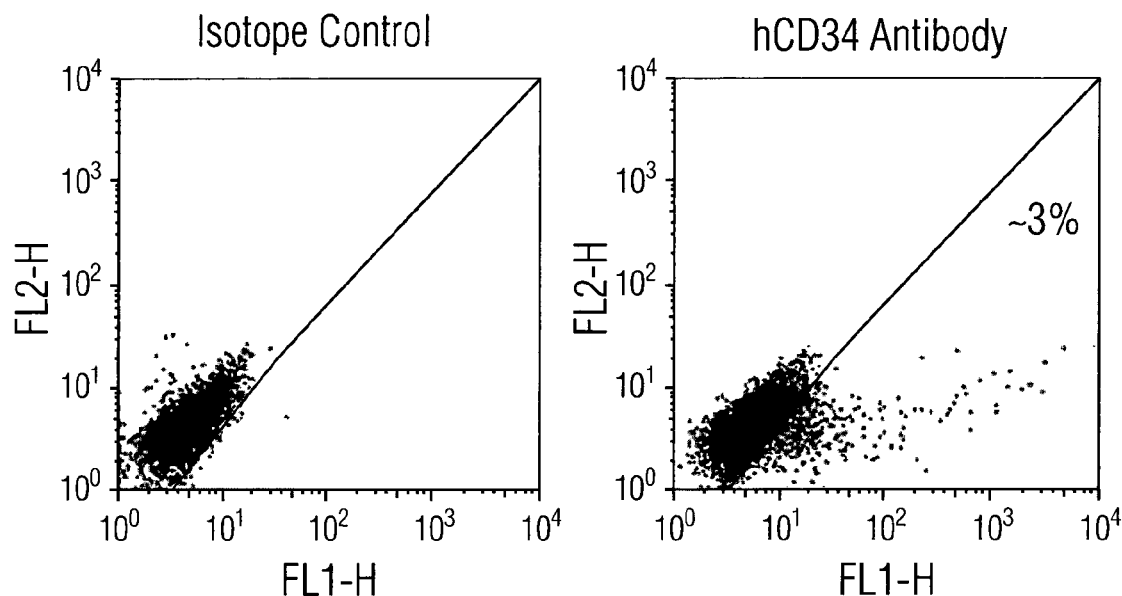
Figure 9H:
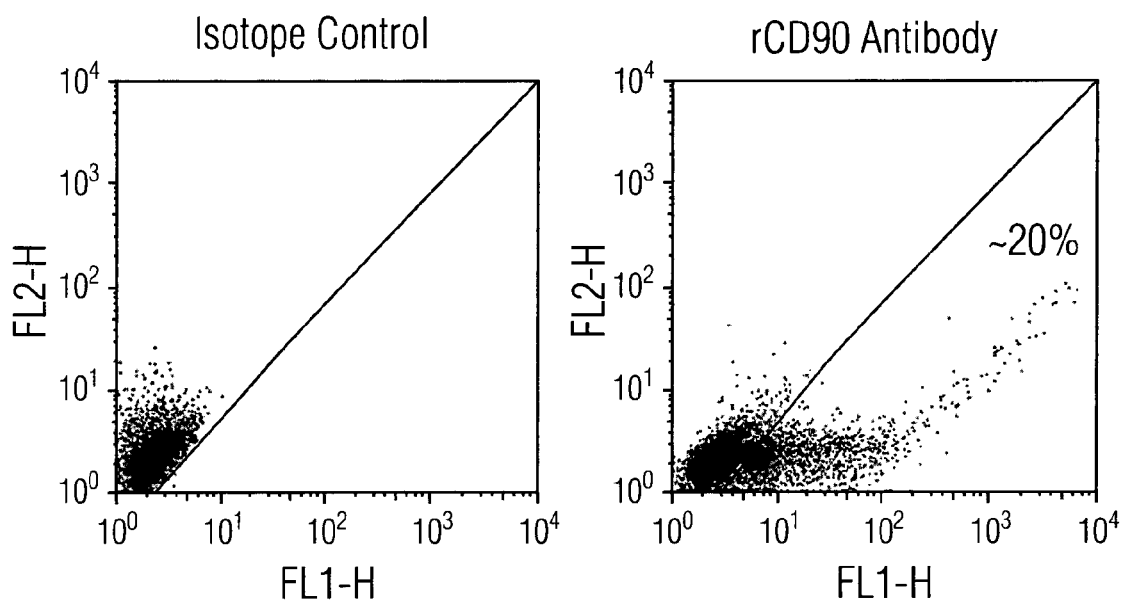

Using eCSC-derived cardiosphere multipotency assay as the in vitro model, we developed a cardiosphere-beating assay, similar to how embryoid bodies are used to assess cardiomyocyte differentiation (26,32). These c-kit$^{pos}$ eCSC-derived cardiospheres at their indifferentiated state expressed stemness markers, such as Oct-4, Sox-2, Nanog, Klf-4 and Wnt3a (FIG. 7A). Oxytocin, has been shown to play a key role in myogenic differentiation of embryonic and adult-derived cardiac stem-progenitor cells, although its mechanism of action is incompletely defined (33,34). Cloned c-kit$^{pos}$ eCSCs plated in flasks were treated with 100 nM Oxytocin for 72 hours before they were transferred to bacteriological dishes for the generation of cardiospheres (FIG. 7B). Cardiospheres grown in suspension, were picked and plated in laminin-coated dishes. Through trial and error progressive steps, we developed and effective myocardiogenic medium and protocol (FIG. 7B). We showed that through the supplementation of BMP-2, BMP-4, TGF-β1 and Dkk-1 for 4 days increased the myogenic differentiation of c-kit$^{pos}$ eCSC cardiospheres, exhibited through increased percent (~40%) of cardiac troponin I expressing cells (FIG. 7C). However, with the removal of TGF-β1, FIG. 7B-C) c-kit$^{pos}$ eCSC cardiospheres BMP2, and BMP4 at day 4, and supplement of Dkk-1 for the remaining 10 days consistently produced high levels of myocyte differentiation (~70% cTnI positive cells; FIG. 7C), with well-organized and abundant sarcomere structures (FIG. 7D), and functional synchronized rhythmic beating, which was maintained for the duration of the culture. These myocytes were also connected through Cnx43-containing gap junctions (FIG. 7D). Similar beating phenotype was exhibited by isolated cells, when the sphere was disaggregated and cells singly plated. qRT-PCR of differentiated cardiospheres at different time points of culture in the cardiomyogenic cocktail, showed a progressive decrease in transcripts for stemness and concomitant up-regulation of cardiomyocyte specific genes (FIG. 7E). These findings unambiguously document a precursor-product relationship and generation of bona fide autonomously beating cardiomyocytes from c-kit$^{pos}$ eCSCs.

The principal findings are that: i) The mixture of c-kit$^{pos}$ eCSCs harbours a cell fraction expressing known pluripotency genes that has robust expansion potential and it is capable of generating cell lineages derivative of the 3 germ layers; ii) Adult myocardium produces in response to injury a variety of known cardiopoietic growth factors acting on resident c-kit$^{pos}$eCSCs with some combinations having a synergistic effect on the proliferation of these cells; iii) Using gain and loss of function in vitro technologies, we defined that among these cardiopoietic factors, the canonical Wnt/β-catenin and the TGF-β/SMAD2 pathways play key roles in determining eCSC fate in vitro; iv) a stage specific cocktail of these morphogens' families with high efficiency drive c-kit$^{pos}$eCSC to myogenic commitment and cardiomyocyte specification.

For a long time the heart has been considered a terminally differentiated organ without any regenerative potential. The latter has been classically based on two lines of evidence: first, the mature cardiomyocytes, the main cell type of the adult heart, are terminally differentiated cells unable to divide under any physiologic or pathologic stimuli and second, the absence of a pool of resident tissue-specific stem cells. This view has been modified by the discovery of resident cardiac stem and progenitor cells throughout the atria and ventricles of the adult mammalian heart (35). However, at minimum, 5-6 apparently different cell types with tissue-specific characteristics of stem and/or progenitor cells have been described in the adult heart so far (5,7). Thus, we have changed from a view of the heart as a static tissue to one of an organ with the highest number of tissue-specific stem and progenitor cell populations. As the latter is improbable to be proved correct, aside from Isl-1$^{pos}$ cardiac progenitor cells (36), it is likely that the different putative adult cardiac stem and progenitor cells reported so far, do not represent different cell types but, instead, different developmental and/or physiological stages of a unique resident adult cardiac stem cell. Under this view, it would be fair to argue the existence of one CSC and would predict the existence of a 'true' stem cell in the adult heart which exhibits more primitive characteristics than all the previously described adult "cardiac stem/progenitor cells". The results of the present study document the high degree of plasticity and differentiation potential of the c-kit$^{pos}$eCSCs. At least in culture and after cloning these cells can respond to different environmental stimuli designed to mimic specific tissues derived from different germ layers and commit them to this particular developmental pathway to the exclusion of the others known to be available to them. Whether this behaviour reflects the intrinsic developmental potential of these cells or, on the contrary, it is artefact resulting from the culture, remains to be determined. Yet, the latter possibility seems unlikely because a similar multipotency is exhibited by the recent isolation of a small population of Oct-4$^{pos}$/c-kit$^{low}$ cells in the myocardium of adult Oct-4/EGFP transgenic mice (See FIGS. 43A-H). Moreover, this multipotency is not due to the development of a recognizable transformed phenotype because their karyotype remains normal (FIG. 2) and they are unable to form teratomas when injected into suitable hosts (unpublished data). These findings suggest that the eCSCs, although developmentally highly plastic, they are not pluripotent since the latter cells identified so far are able to form teratomas when injected into susceptible mice (11). Interestingly, Chong et al. reported similar broad developmental potential of Sca-1/PDGFrα-positive pericardial cells, a subpopulation of which also expresses multipotency genes but could not form teratomas on their own (37). Concurrently, a unique multipotent cell has been described within the adult mesenchymal cell populations and these so-called 'Muse' (multilineage-differentiating stress-enduring) cells exhibit a broad developmental plasticity in vitro and in vivo despite being unable to form teratomas (38). Taken together these results give further emphasis to the question about the origin of and lineage relationships among the different adult tissue stem cells.

The next relevant issue for any adult tissue specific stem/progenitor cells is how these cells regulate through cell autonomous and non-autonomous events their fate decisions. Here we show that the adult myocardium and the cardiac myocytes in particular are able to titrate the levels of known embryonic cardiomyogenic morphogens increasing their levels in response to injury. eCSCs possess the specific receptors for these cardiopoietic factors (cGFs) which are activated as part of the response to myocardial injury. Through a small throughput screening of several of these cGFs we were able to spot few molecules, namely IGF-1 and Wnt-3a, Neuroregulin and Periostin that specifically activate c-kit$^{pos}$eCSC expansion while others, like TGF-β1 and BMP2/4, and BMP-10 specify c-kit$^{pos}$eCSC toward a cardiac muscle lineage. As cardiomyocytes are the main source of these factors in vivo, it is then tempting to speculate that the latter partially explains the higher level of myocyte replenishment from cardiac stem-progenitors within the peri-infarct border on one hand (6, 39) and the absence of spontaneous regeneration of myocardial infarction with net loss of cardiomyocytes in the area of necrosis perfused by the occluded coronary artery on the other hand. However, disentangling the molecular cues underlying eCSC activation will base myocardial regeneration protocols based on specific growth factors without the need for cell transplantation (5). Indeed, we have also shown that other myocyte-secreted cGFs like Neuregulin and Periostin contribute to physiologically determine eCSC fate (19). It is then predicted that a cocktail, yet undefined, of the most powerful cGFs might constitute in the next future an off-the-shelf, readily available, and effective cardiac regenerative therapy.

Finally, we have established a stage-specific cocktail of factors mainly belonging to the Wnt and TGF-β families that commit with high specificity and efficiency c-kit$^{pos}$eCSCs to functionally beating cardiomyocytes. This assay has the value to offer an in vitro system to dissect both at molecular and cellular level all the steps from the adult undifferentiated cardiac stem cell to electro-mechanically coupled differentiated myocytes. The latter could provide an additional tool as model system for human rare cardiac diseases, to screen for novel therapeutic applications and for potential drug cardiotoxicity as currently performed with induced pluripotent stem cells (40).

6.7 Robust eCSC Activation and Myocyte Regeneration Follow Myocardial Damage in the Presence of a Patent Coronary Circulation Animals Diffuse myocardial damage was induced by a single injection (s.c.) of isoproterenol (ISO) to rats (5 mg kg$^{-1}$) or mice (200 mg kg$^{-1}$). To ablate cycling cells including eCSCs after ISO-damage, 5-fluorouracil (5-FU; Sigma) was administered (10 mg kg$^{-1}$) for 4×5 day cycles starting at the 3rd day post ISO-injection. Mer-CreMer mice were kindly provided by Drs. Tammie Bishop and Ludwig Thierfelder (see below). ZEG and RYP mice were purchased at Jackson Laboratory. Ganciclovir (GCV) was administered (i.p.) at the dose of 50 mg kg$^{-1}$ twice daily for 14 days.

Figure 14A:
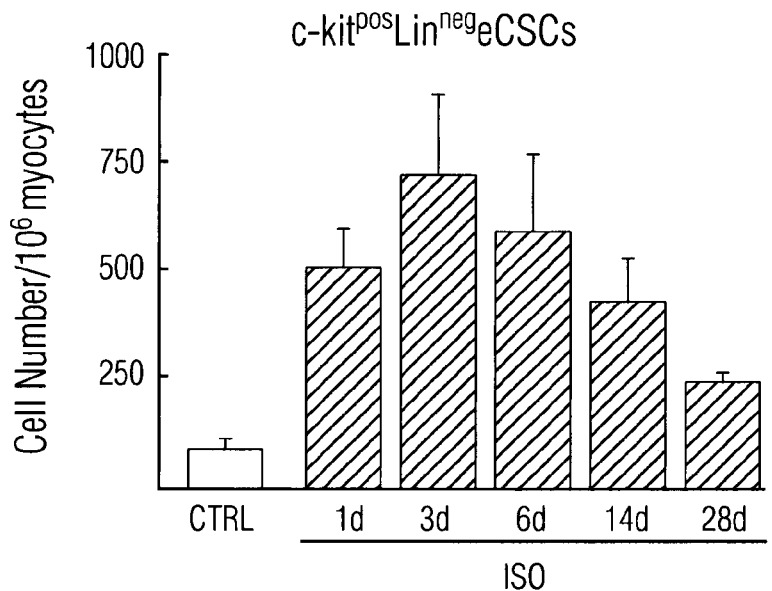
Figure 14B:
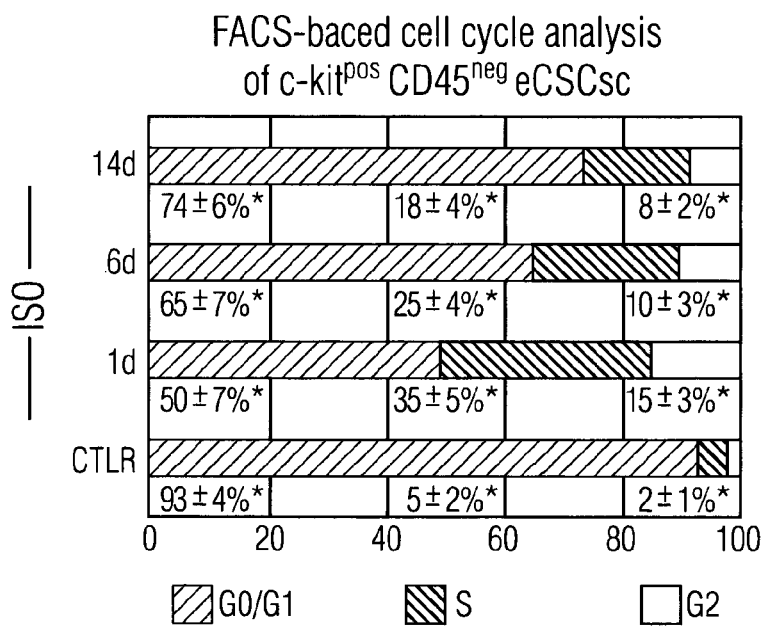
Figure 14C:
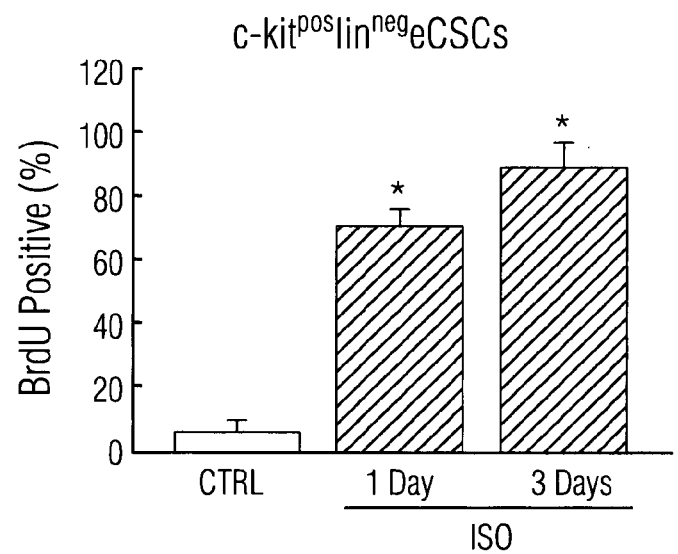

To follow c-kit$^{pos}$eCSC physiological response to cardiac injury, we induced severe diffuse myocardial damage in adult rats with a single high dose of isoproterenol (ISO) (Ellison et al., 2007b). New cell formation was monitored with BrdU labeling in vivo (Waring et al., 2012). In the presence of a patent coronary circulation, ISO produces a Takotsubo-like cardiomyopathy (Akashi et al., 2008) with both diffuse sub-endocardial and apical CM death. This acute insult kills 8-10% of the LV CMs and results in overt acute heart failure (Ellison et al., 2007b). Interestingly, the myocardial damage and heart failure spontaneously reverse anatomically and functionally by 28 days (FIG. 21). While in the normal myocardium (CTRL) most c-kit$^{pos}$eCSCs are quiescent (>90% BrdU$^{neg}$ and Ki67$^{neg}$), after ISO damage a high fraction enters the cell cycle (FIG. 14A-C and FIG. 21). At day 3, ~88% are BrdU$^{pos}$ (FIG. 14C), leading to an ~8-fold increase in eCSC number, which decreases thereafter but remains above CTRL for up to 28 days (FIG. 14A).

Figure 14D:
Figure 14E:
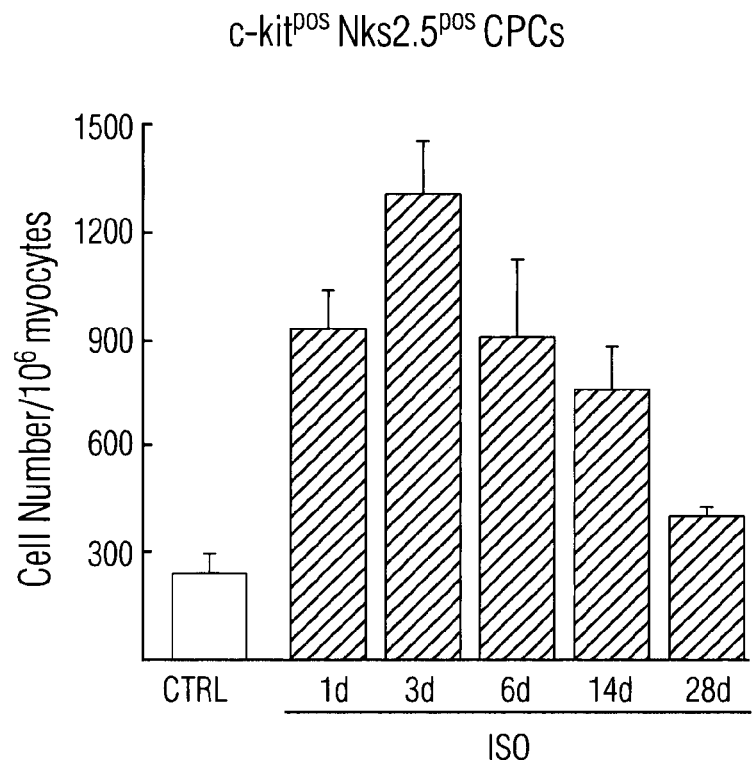
Figure 14F:
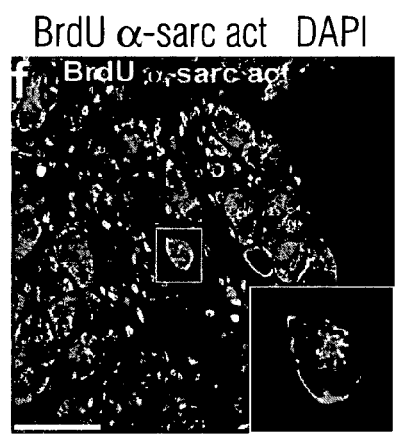
Figure 14G:
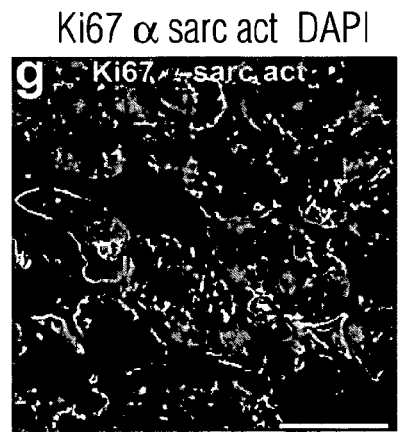
Figure 14H:
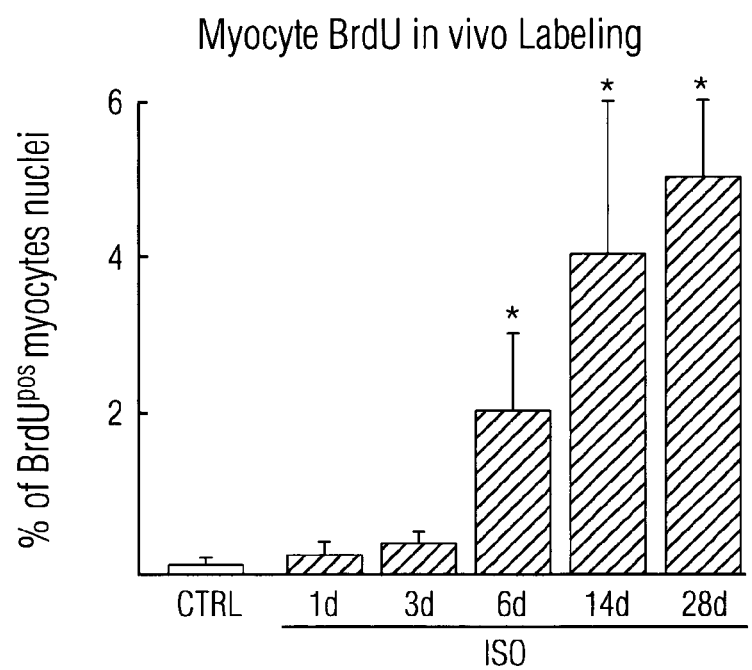
Figure 14I:
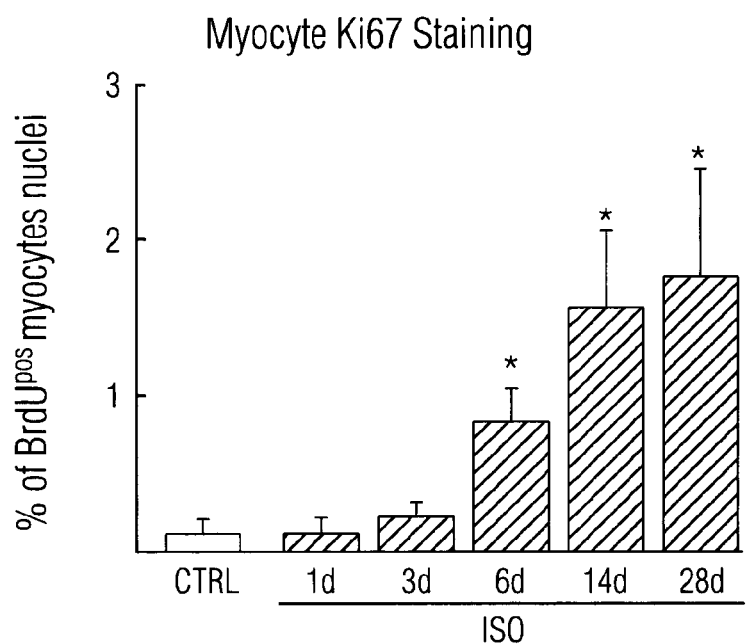

The expansion of the eCSC pool in response to CM loss by ISO damage was followed by their commitment to myocardial cell lineages. Indeed, many of the c-kit$^{pos}$ eCSCs expressed GATA4 (FIG. 21) and Nkx2.5 (FIG. 14D-E), two early transcription factors of the cardiac lineage which, together with Tbx5 and MEF-2C, are essential for the differentiation of mesoderm and reprogramming of fibroblasts into the CM lineage (Takeuchi & Bruneau, 2009; Qian et al., 2012; Song et al., 2012). The number of c-kit$^{pos}$Nkx2.5$^{pos}$GATA4$^{pos}$ cells increased ~4 fold over CTRL by day 3 (FIG. 14E and FIG. 21). This sequential transition from undifferentiated cells to committed progeny is further illustrated by the transcription of sarcomeric and gap junction genes (troponin I, cTnI; connexin 43, Cnx43) and the presence of their corresponding proteins, even though at lower levels than found in the adult spared CMs (FIG. 14D and FIG. 21). These new c-kit$^{pos}$GATA-4$^{pos}$Nkx2.5$^{pos}$ myogenic progenitors express β-MHC, the isoform characteristic of the fetal rat heart (Lomprè et al, 1984). In these new myocytes, there is no expression of the α-MHC gene, characteristic of adult rat CMs and expressed by spared CMs 72 hours after ISO (FIG. 21). For isolation and characterization of eCSC from the adult mouse and rat heart, see Nadal-Ginard 2014 Nature Protocols (submitted).

Figure 14J:
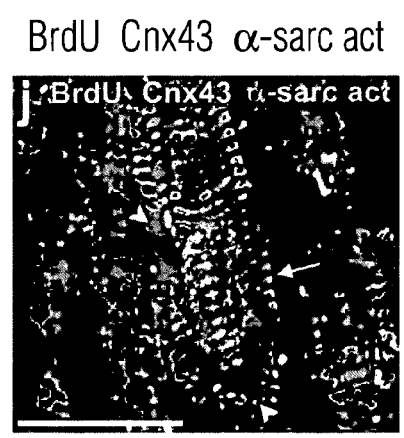
Figure 14K:
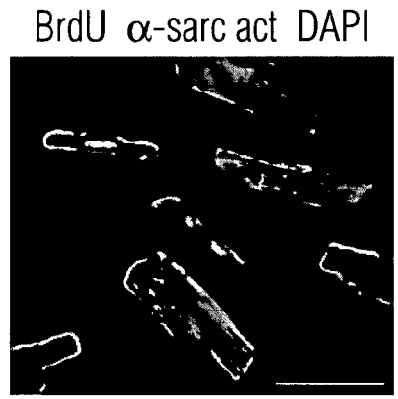
Figure 14L:
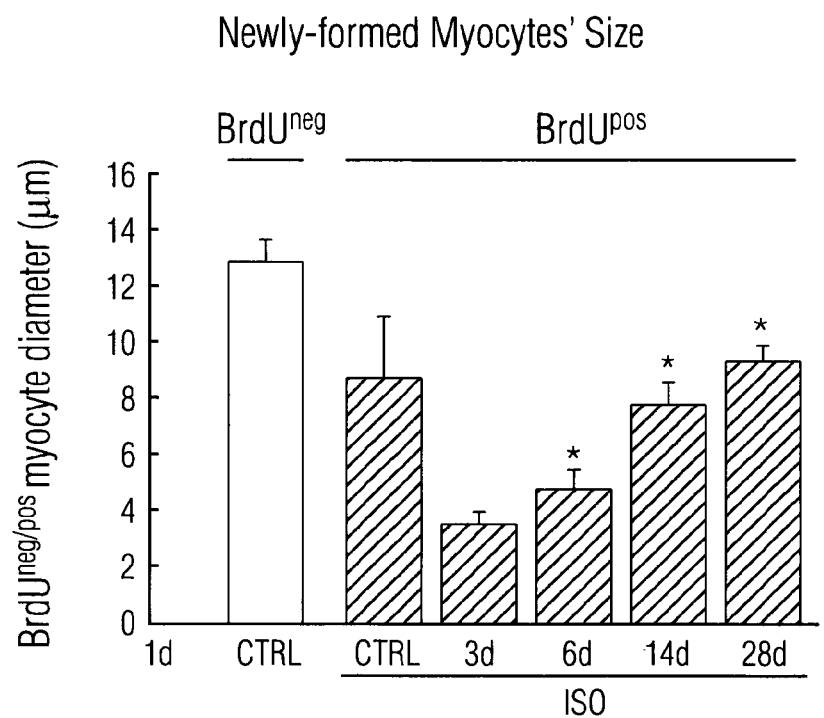

Starting at day 3 post-ISO, very small mononucleated BrdU$^{pos}$Ki67$^{pos}$ CMs, including some in mitosis, were detected (FIG. 14F-L), indicative of immature, proliferative CMs. These new CMs were localized mainly in the LV sub-endocardium and apex, the area most severely damaged by ISO. From 3 to 28 days there was a significant increase in the number (FIG. 14H-I) and size of these CMs which were nearly all mononucleated and smaller than the spared (BrdU$^{neg}$) ones (FIG. 14L). The BrdU$^{pos}$ CMs also expressed Cnx43, suggestive of gap junction formation and integration with the neighboring myocardium (FIG. 14J). Rod-shaped small BrdU$^{pos}$ CMs were also detected as single cells when isolated from ISO-treated hearts (FIG. 14K). Their smaller size indicates that, despite the normal histology and function of the ISO-treated hearts 4 weeks post-injury, the newly regenerated CMs had not yet fully matured.

6.8 Myocyte Regeneration after Diffuse Myocardial Damage is Not the Product of Pre-Existing Myocyte Division or Bone-Marrow Cells BrdU labeling and Ki67 expression by itself cannot establish whether the new CMs are generated by the reported division of pre-existing adult CMs or by the activation and ensuing differentiation of a stem-progenitor cell compartment. To specifically address this issue, we traced the cell lineage of the new CMs. We generated double-transgenic mice (MerCreMer-ZEG) (Hsieh et al., 2007; Loffredo et al., 2011) in which, upon tamoxifen administration, β-galactosidase (β-Gal) is replaced by enhanced green fluorescent protein (GFP) exclusively in cardiac cells which have already activated the Myh6 gene (and, therefore, the transgene carrying the cre recombinase gene) which are either post-mitotic CMs or amplifying cells already committed to the CM lineage (i.e., immature myocytes/myocyte precursors).

Figure 15A:
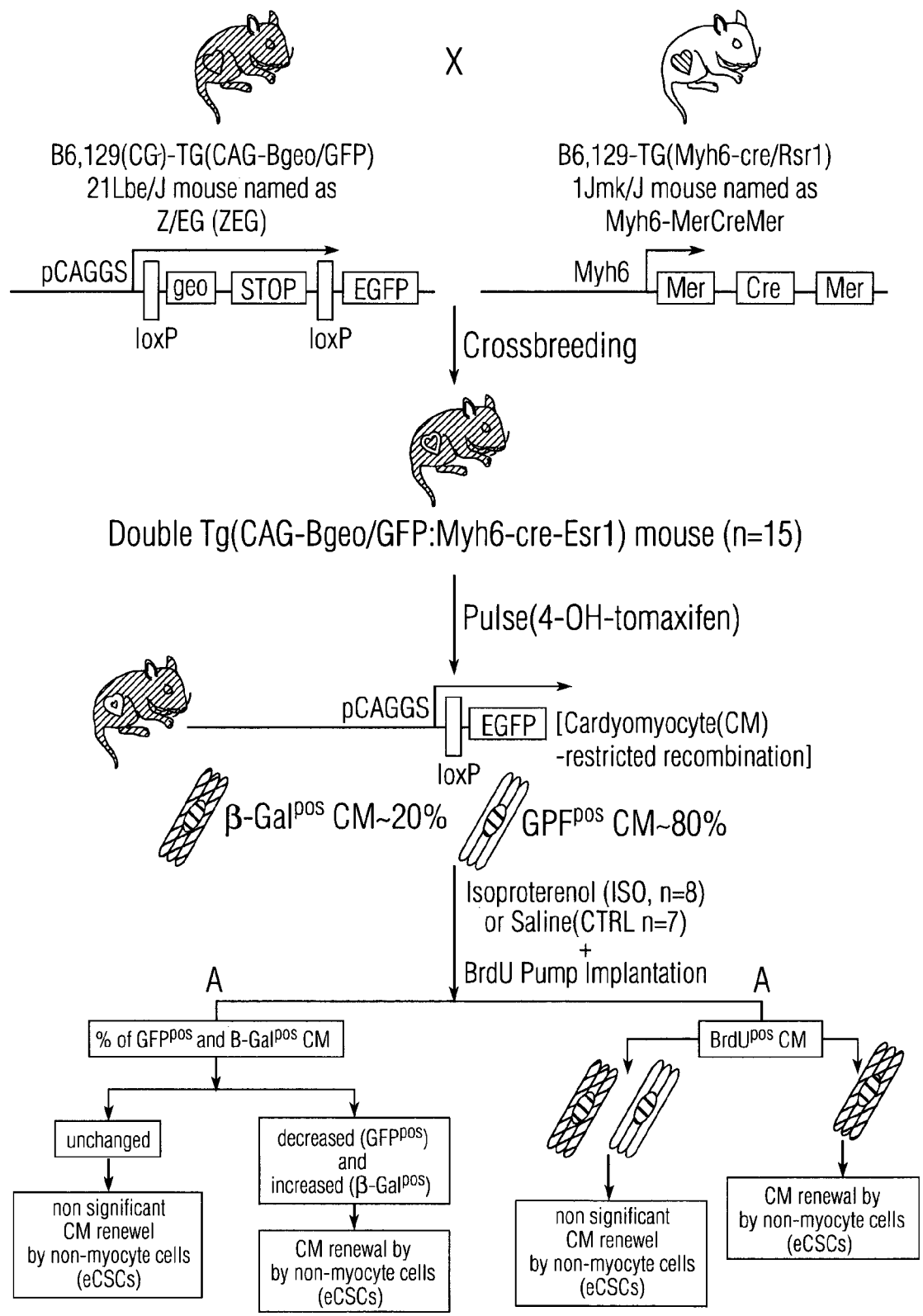
Figure 15B:
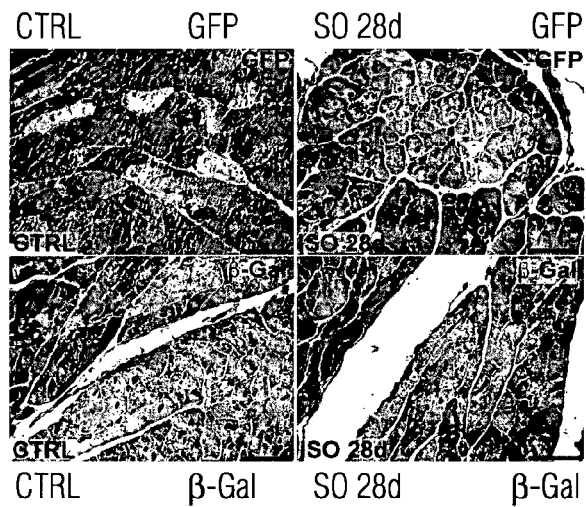
Figure 15C:
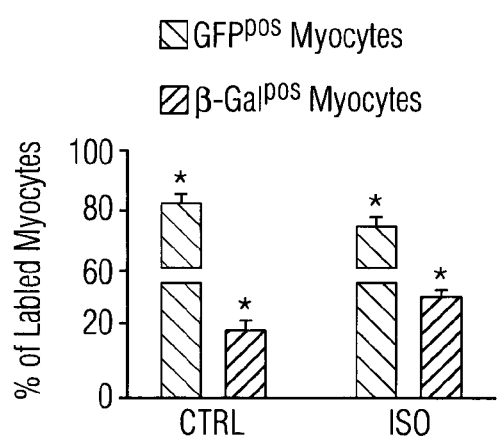

In tamoxifen-naïve MerCreMer-ZEG mice, 99±0.2% of the CMs express β-Gal and are negative for GFP (the leakage of the Myh6-Cre construct in these animals is ~0.2%). Tamoxifen correctly switched β-Gal to GFP in CMs (FIG. 15A-C). This resulted in hearts composed of 83±3% GFP$^{pos}$ and 17±2% β-Gal$^{pos}$ CMs (FIG. 15B-C) as previously reported (Hsieh et al., 2007; Senyo et al. 2013). In this setting, if new CMs (BrdU$^{pos}$) originated from division of pre-existing CMs they should be more GFP$^{pos}$ and the ratio between GFP$^{pos}$ and β-Gal$^{pos}$ CMs should remain unchanged at ~80/20. If instead, the new CMs originate from non-CM cells, they should be β-Gal$^{pos}$ and produce a "dilution" of GFP$^{pos}$ CMs with a decrease of the GFP$^{pos}$/β-Gal$^{pos}$ CM ratio (FIG. 15A).

Figure 15D:
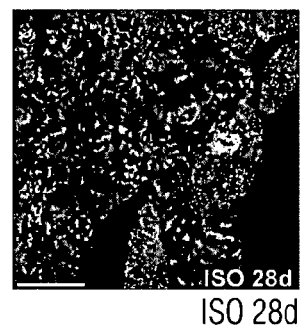
Figure 15E:
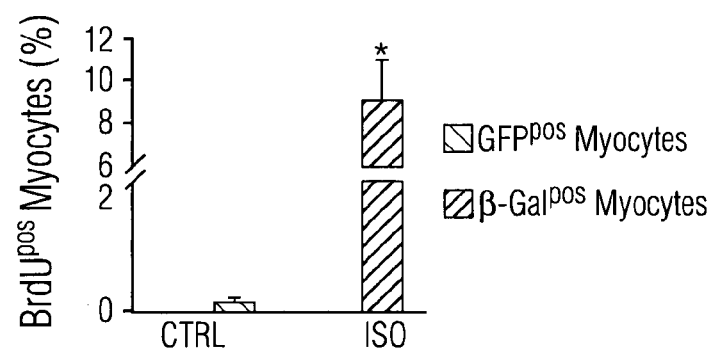

In mice, ISO injection caused the same type of myocardial damage and LV dysfunction shown in rats, resulting in c-kit$^{pos}$eCSC activation, CM regeneration and recovery of cardiac function (FIG. 22). When ISO was administered to CM-recombined MerCreMer/ZEG mice (FIG. 15A) followed by BrdU labeling, 28 days later there was a significant increase in the percentage of β-Gal$^{pos}$ CMs: 18±2.5% in saline-treated vs. 26.5±2% in ISO-injured mice (FIG. 15B-C) accompanied by a decrease of GFP$^{pos}$ CMs in the hearts of ISO-treated (73.5±3.5%) compared to CTRL mice (82±3.5%) (FIG. 15B-C) There was also a concomitant increase of BrdU$^{pos}$ CMs (9±2%) in the ISO-treated hearts and these were β-Gal$^{pos}$ (FIG. 15D-E). These numbers match the CM loss produced by ISO administration (FIG. 22). In contrast, we detected very few newly generated, BrdU$^{pos}$β-Gal$^{pos}$, CMs (0.15±0.05%) in saline-treated CTRL mice (FIG. 15E). This result concurs with Hsieh et al. (2007), but disagrees with the interpretation of Senyo et al. (2013) using the same genetic tools. This discrepancy might be due to the different injury models used. In contrast to coronary ligation, although ISO kills a large number of CMs, because it leaves a patent coronary circulation the eCSCs are spared and provides a more physiologic test for the endogenous reparative potential of the adult heart (Ellison et al., 2007b). Furthermore, during the two-week administration of tamoxifen for Cre induction it would be expected that some eCSCs have committed to the myogenic lineage and activated the Myh6 gene with recombination of the transgene and generation of β-Gal$^{pos}$ CMs, as reported by Dong et al. (2012).

Although cell fusion might allow the expression of both GFP and β-Gal in the same CM, it can be ruled out because the percentage of CMs positive for both markers was negligible (<0.1%) in saline-treated CTRL and ISO-injured mice. The possibility that the decrease in GFP$^{pos}$ and corresponding increase in β-Gal$^{pos}$ CMs after ISO might be due to a higher susceptibility of GFP-labeled CMs to ISO damage was also excluded by the fact that the percentage of necrotic and apoptotic GFP$^{pos}$ and β-Gal$^{pos}$ CMs 1 day after ISO was similar (FIG. 22).

Figure 15F:
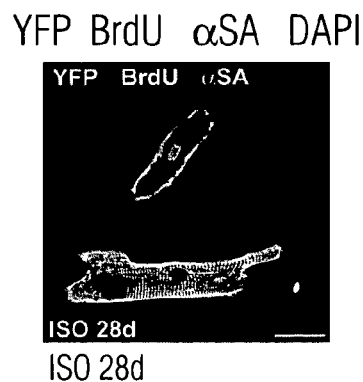

Finally, we dissociated to single cells CMs from the hearts of double transgenic MerCreMer:RYP mice obtained by crossing MerCreMer with R26R-EYFP (RYP) mice (Qian et al., 2012), in which the CMs were labeled with the enhanced yellow fluorescent protein (EYFP) upon tamoxifen injection. In agreement with the data shown on MerCreMer:ZEG mice, tamoxifen-driven induction of YFP marked ~80% of endogenous CMs in the uninjured CTRL heart, which decreased to ~72% in the apex (and sub-endocardium) of injured hearts at 28 days after ISO. Only the YFP$^{neg}$ fraction isolated from the CM-recombined double transgenic mice were BrdU$^{pos}$ (FIG. 15F). Most of these newly generated BrdU$^{pos}$YFP$^{neg}$ CMs were rod-shaped, mono-nucleated and smaller than the pre-existing (mostly binucleated) YFP$^{pos}$- BrdU$^{neg}$ CMs (FIG. 15F).

In conclusion, after diffuse myocardial injury, new CMs are not generated (at least in quantities above background) through the division of pre-existing terminally differentiated CMs as claimed (Senyo et al. 2013), but rather from non-CM cells with the characteristics of a stem-progenitor compartment (Hsieh et al., 2007).

Figure 15G:
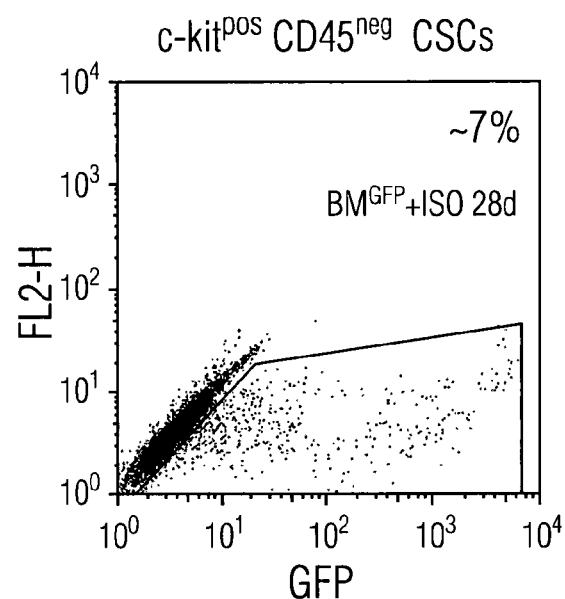
Figure 15H:
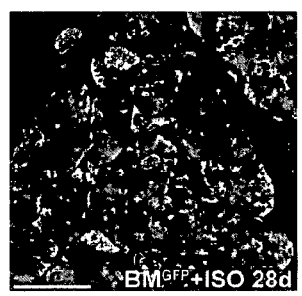
Figure 15I:
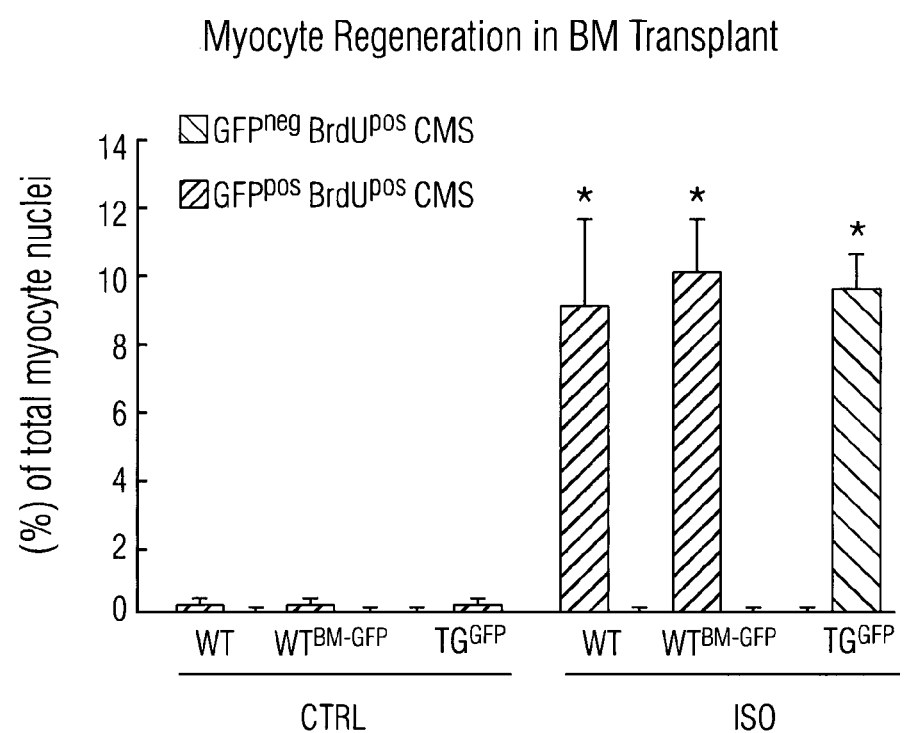

Bone marrow (BM) derived cells have been implicated in cardiac regeneration after myocardial infarction (Orlic et al., 2001; Loffredo et al., 2011). To test this possibility, either saline or ISO was injected to sub-lethally γ-irradiated mice 3 months after successful reconstitution of their bone marrow with BM cells from Tg$^{GFP}$ mice (Sata et al., 2002). In both CTRL and ISO-treated animals, a small fraction (3.5±2 vs. 5±2%, respectively) of c-kit$^{pos}$CD45$^{neg}$ cardiac cells was GFP positive at 28 days (FIG. 15G). However, despite extensive histological analysis and CM isolation, we were unable to find a single BM-derived GFP$^{pos}$BrdU$^{pos}$ or GFP$^{pos}$ CM in either ISO-treated or CTRL hearts (FIG. 15H-I) Therefore, BM-derived cells do not directly contribute in any significant manner to new CM formation in normal or ISO damaged hearts.

Figure 16A:
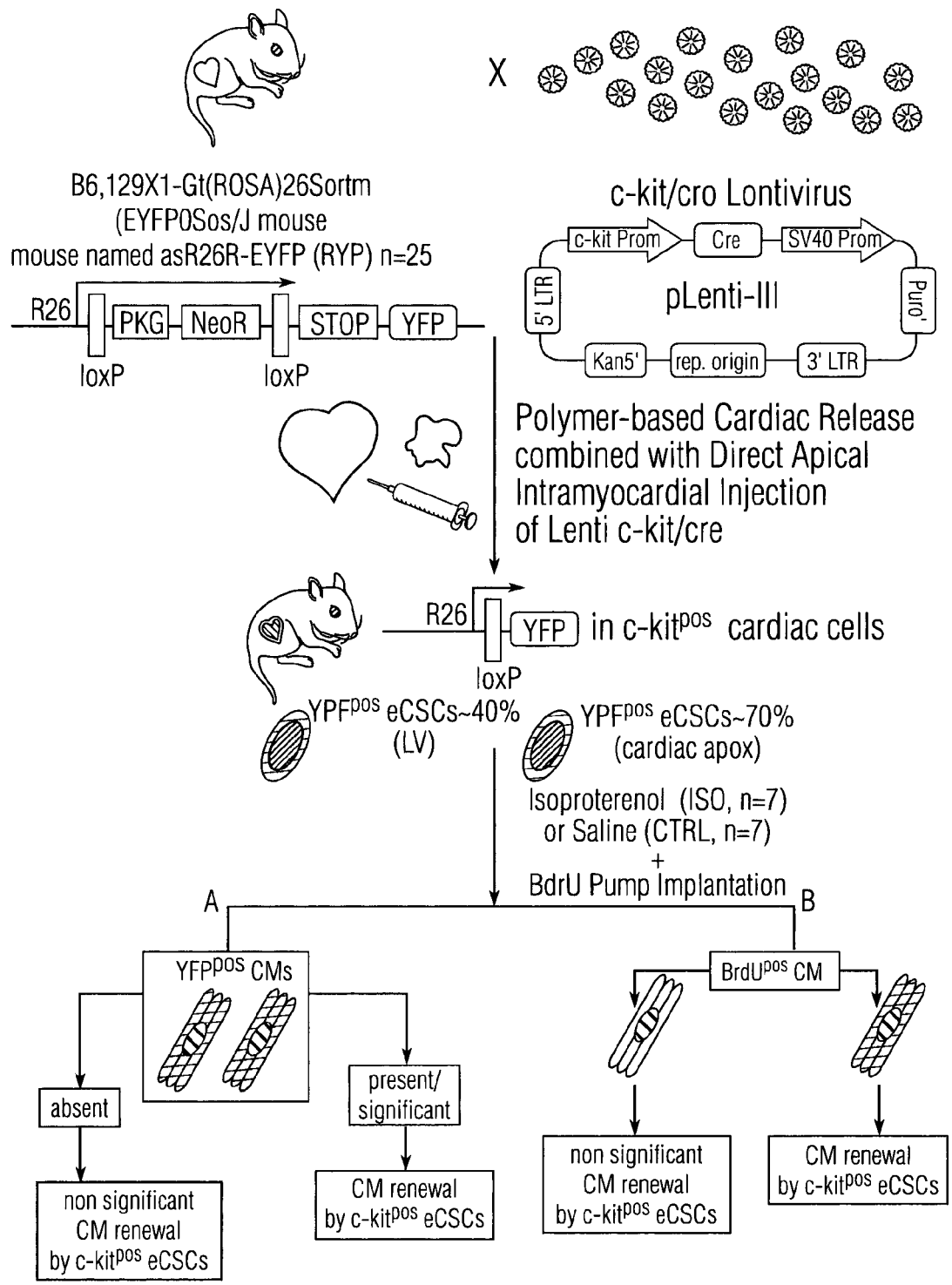
Figure 16B:
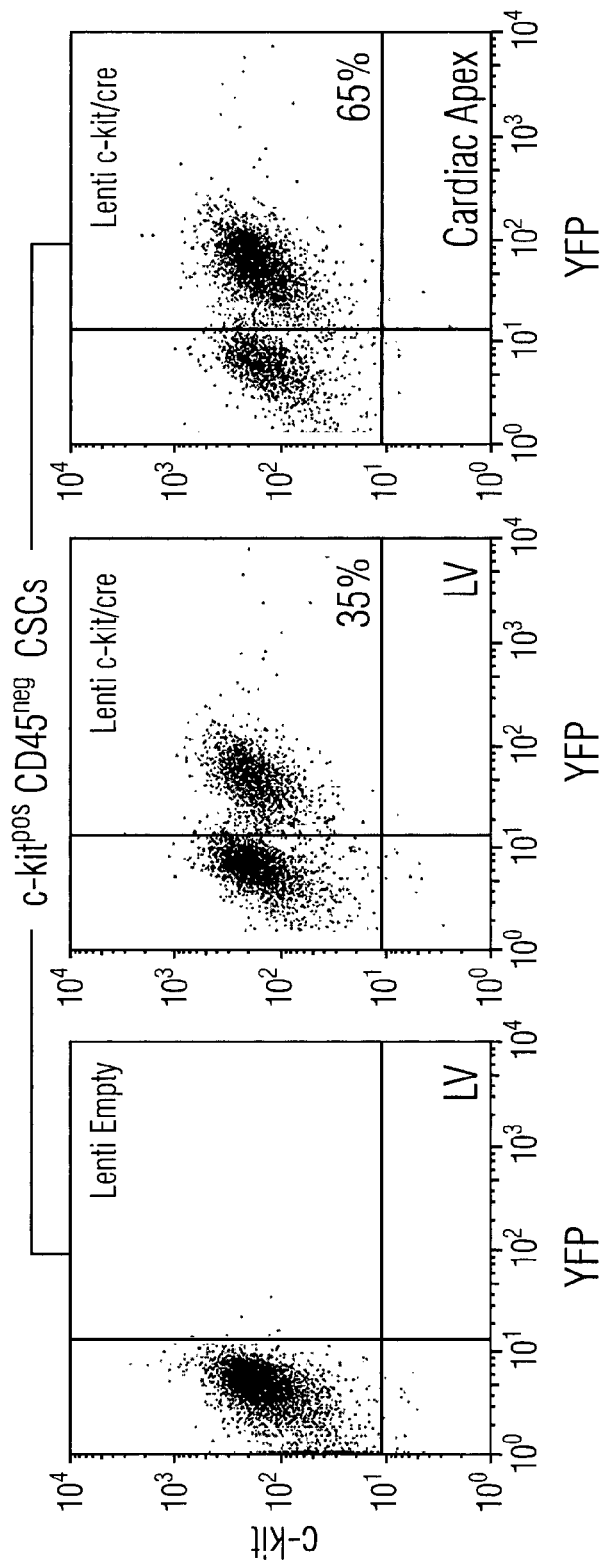
Figure 16C:
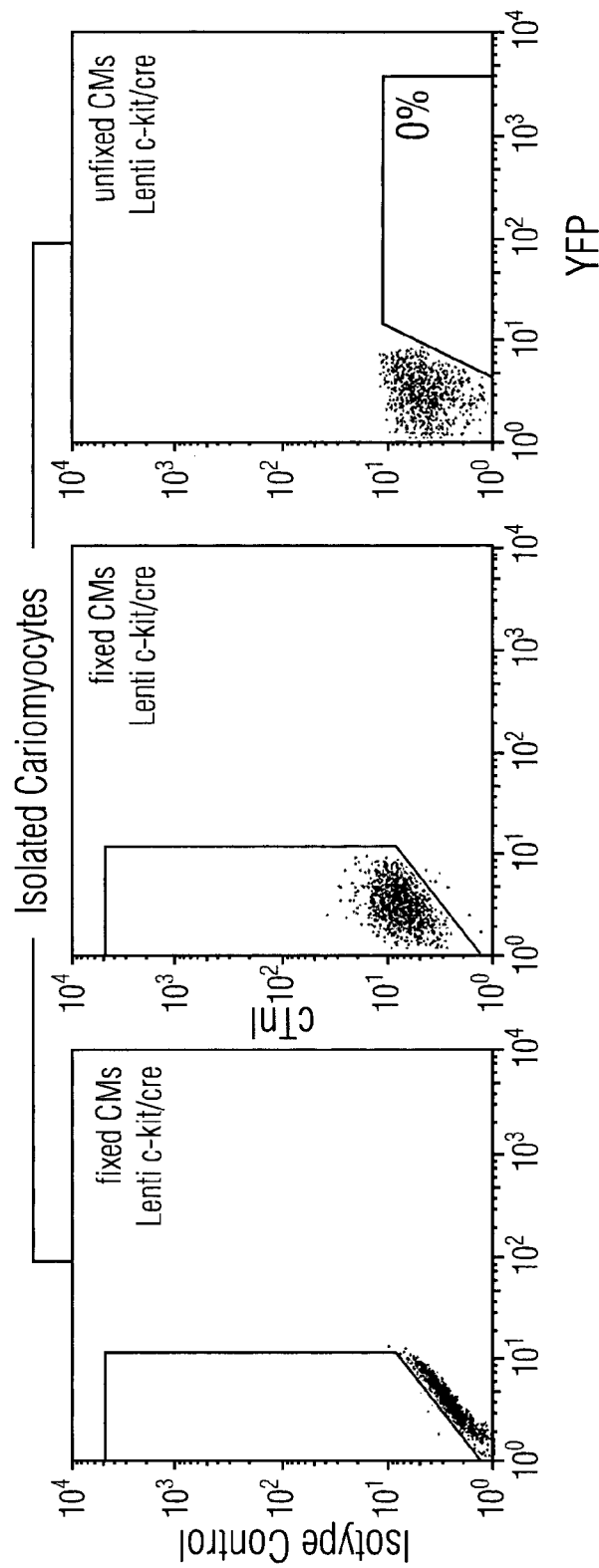
Figure 16D:
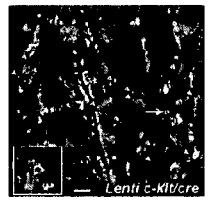

6.9 New Myocytes after Diffuse Myocardial Injury Originate from Resident c-kit$^{pos}$eCSCs To determine whether c-kit$^{pos}$eCSCs replenish the CMs lost by diffuse myocardial damage, we genetically tagged in situ a subset of adult resident c-kit$^{pos}$eCSCs and their myocyte committed progeny (FIG. 16A). We generated a lentivirus carrying Cre-recombinase under the control of the c-kit promoter (Lenti-c-kit/Cre) with a pattern of expression restricted to c-kit$^{pos}$ cells (FIG. 23; Cairns et al., 2003). To confine lentivirus release to the LV myocardium we employed a fibrin-based PEGylated hydrogel for epicardial delivery (Zhang et al., 2006). To increase delivery we also injected the lentivirus directly into the apex, the region with the greatest CM damage after ISO (Ellison et al., 2007b) and the highest concentration of c-kit$^{pos}$ eCSCs (Ellison et al., 2011). This combined strategy was used to selectively release Lenti-c-kit/Cre into the myocardium of RYP reporter mice (FIG. 16A). In these mice the uptake of the c-kit/Cre recombinase lentivirus by any c-kit$^{pos}$ cell deletes the STOP sequence in the transgene and switches on the expression of EYFP. After 2 weeks, peripheral blood cells and BM-derived cells were reproducibly negative for EYFP (FIG. 23). Importantly, 38±5% of total and 65±7% of apex-confined c-kit$^{pos}$eCSCs were EYFP positive (FIG. 16B-D). Lenti-c-kit/Cre injection induced EYFP expression exclusively in cardiac c-kit$^{pos}$ cells, whereas CMs (FIG. 16C) and other c-kit$^{neg}$ myocardial cell types were all negative for EYFP (FIG. 23). When the recombined EYFP$^{pos}$c-kit$^{pos}$CD45$^{neg}$eCSCs were isolated from the hearts of RYP mice at 2 weeks after lentivirus release, they were phenotypically indistinguishable from the un-recombined EYFP$^{neg}$-c-kit$^{pos}$CD45$^{neg}$eCSCs and exhibited the typical properties of resident eCSCs, being clonogenic, self-renewing and multipotent (FIG. 23).

Figure 16E:
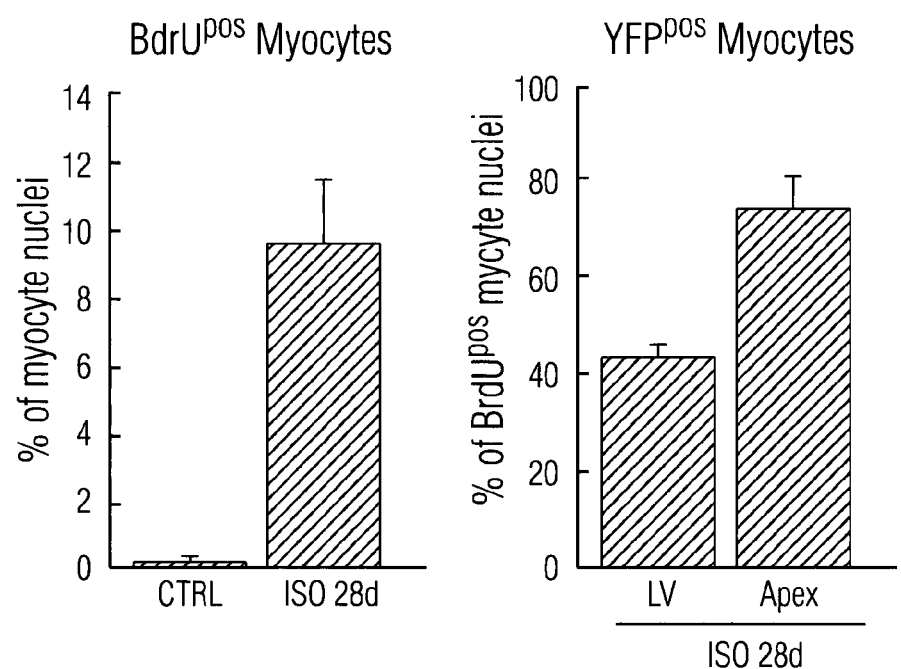
Figure 16F:
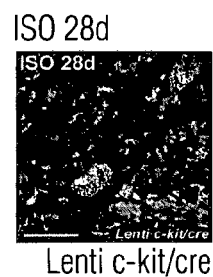
Figure 16G:
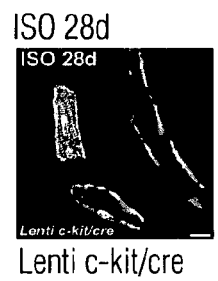
Figure 16H:
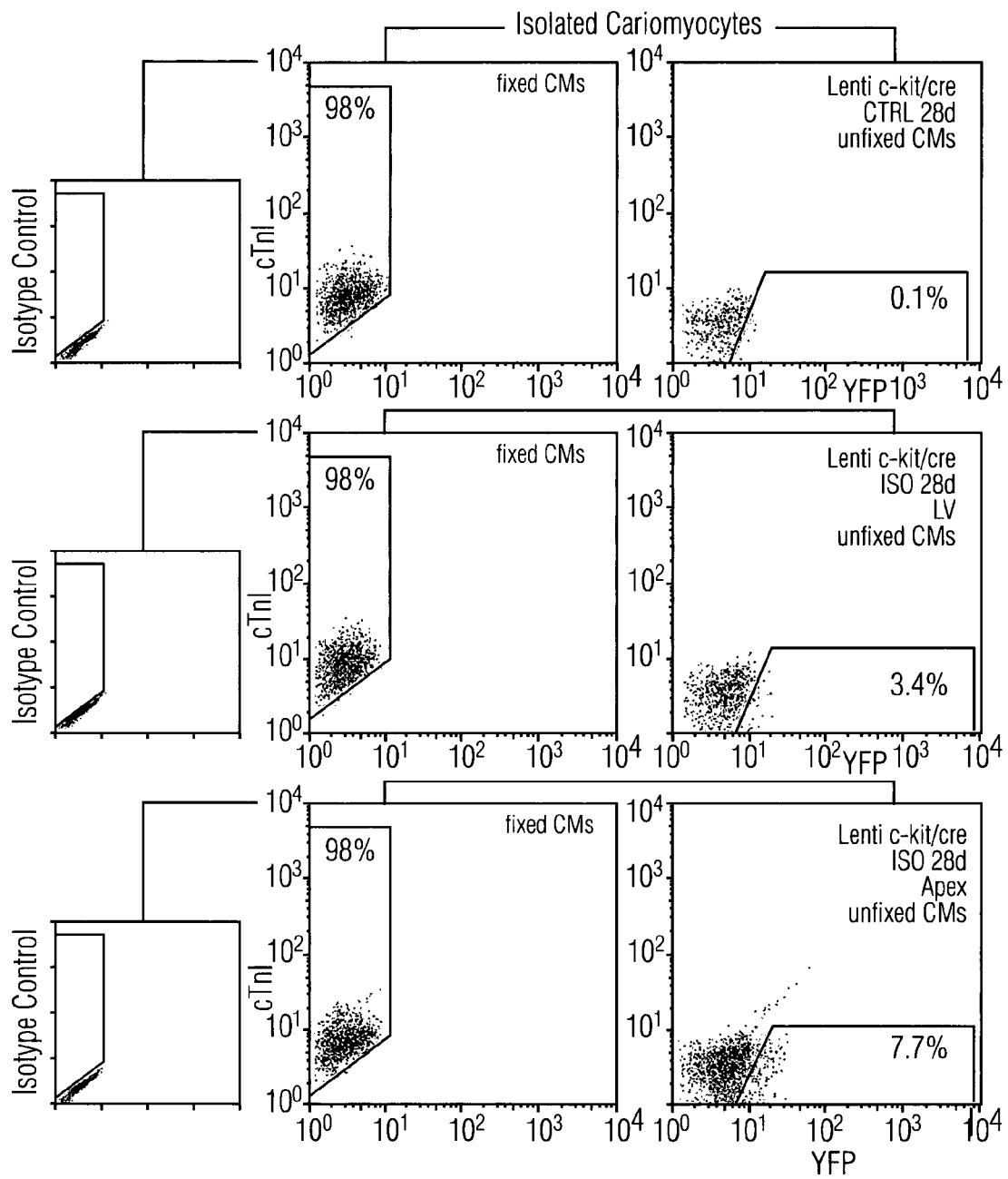

14 days after local release of the Lenti-c-kit/Cre, RYP mice received either ISO or saline (CTRL) injection. 28 days after ISO, we confirmed that there were no recombined EYFP-positive cells in the c-kit$^{pos}$ enriched fraction of the nucleated cells of peripheral blood or within the BM from CTRL and ISO-injured mice. In CTRL mice, after 4 weeks of BrdU in vivo labeling, a total of 0.18±0.07% BrdU$^{pos}$ CMs was detected and only a fraction of those newly generated cells were c-kit$^{pos}$eCSC-derived EYFP$^{pos}$BrdU$^{pos}$ CMs (0.06±0.02%/total CMs) (FIG. 16E). In the ISO-treated hearts a significant fraction of a total 9.5±2% of newly-formed CMs were EYFP positive (43±3% of total BrdU$^{pos}$ CMs, which in the apex reached 74±7%) (FIG. 16E, F), indicating that these newly-generated CMs are the progeny of the c-kit$^{pos}$eCSCs. We confirmed the identity of both YFP$^{pos}$- and YFP$^{neg}$-BrdU$^{pos}$ CMs in isolated CMs 28 days after ISO (FIG. 16G) by FACS. YFP expression was analyzed in unfixed CMs to avoid fluorescent protein leakage, as well as fixative-induced autofluorescence. FACS detected >98% cTnI positive cells in the fixed aliquot of the CM preparation in both CTRL and ISO groups (FIG. 16H). <0.5% of YFP$^{pos}$ cells were detected in the unfixed aliquot of the same CM preparation from CTRL c-kit/Cre recombined RYP mice (FIG. 16H). Thus, it was technically impossible to ascertain by FACS whether they were truly c-kit$^{pos}$ eCSC-derived CMs. More significantly, YFP$^{pos}$ cells were clearly recognized within the unfixed CM preparation from ISO-injured hearts (2.9±0.5% in total LV and 8.3±1% in LV apex) (FIG. 16H). We further verified that the YFP signal truly originated from YFP$^{pos}$ CMs by sorting the total CM preparation and demonstrating that ≥99% were αSA positive after cell fixation (FIG. 23). These results were not due to c-kit re-expression in adult CMs—as suggested previously in cryo-injured hearts (Tallini et al., 2009). The absence of such re-expression in saline- or ISO-treated transgenic mice expressing GFP under the c-kit promoter (FIG. 24) rules out this potential confounding factor.

Figure 16I:
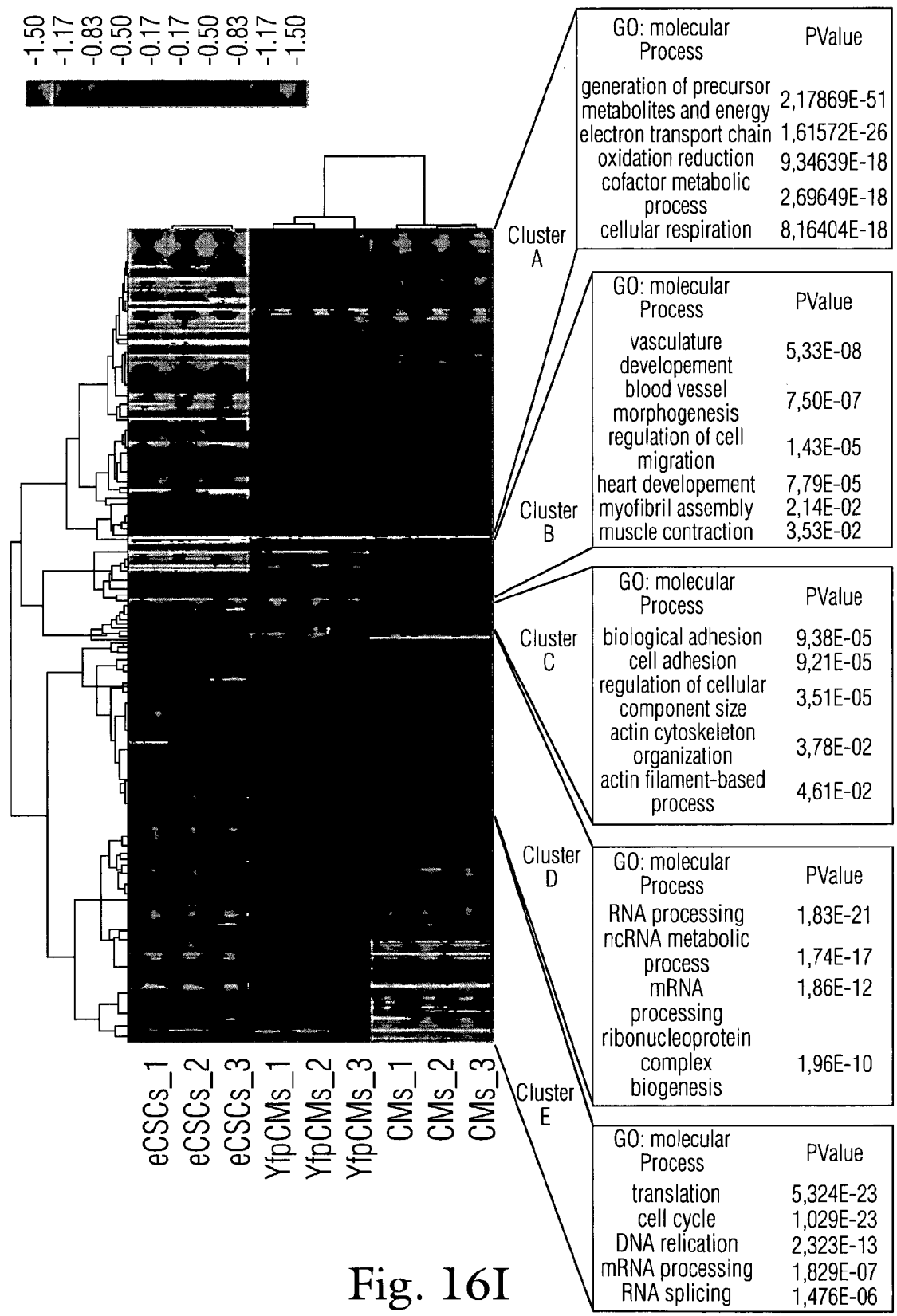

To further test the identity and the degree of differentiation of the newly regenerated eCSC-derived CMs, we obtained global gene expression profiles by microarray of c-kit$^{pos}$ eCSCs, c-kit$^{pos}$ eCSC-derived YFP$^{pos}$ CMs and normal adult CMs. The c-kit$^{pos}$ eCSC-derived YFP$^{pos}$ CMs were obtained by FACS sorting from Lenti-c-kit/cre recombined RYP mice 28 days after ISO injury (FIG. 24). These CMs had a gene expression profile which closely resembled the profile of adult CMs (FIG. 16I, J). Comparison of c-kit$^{pos}$eCSCs vs. c-kit$^{pos}$CSC-derived YFP$^{pos}$ CMs vs. adult mature CMs reveals a clear transcriptome shift going from uncommitted c-kit$^{pos}$CSCs to CM-lineage commitment, followed by immature to mature CMs (FIG. 16I, J and see National Center for Biotechnology Information, Gene Expression Omnibus ("GEO") Series GSE49318; Ellison et al. 2013 Cell 154(4):827-42). The eCSC-derived YFP$^{pos}$ CMs expressed the main CM transcription factors as well as sarcomeric contractile genes but still maintained the expression of cell cycle-related and high metabolic state genes typical of immature (neonatal) not yet terminally differentiated CMs (FIG. 16I, J). Intriguingly, even after having acquired mature sarcomeric structures and a rod-shape (FIG. 16G), eCSC-derived YFP$^{pos}$ CMs show an incomplete switch from retinoblastoma-like 1 (Rb1-1 or p107) to retinoblastoma protein (Rb), which is a requirement for permanent CM withdrawal from the cell cycle (Schneider et al., 1994). These data further demonstrate that resident c-kit$^{pos}$eCSCs generate new CMs in vivo which are still immature four weeks after their birth.

Taken together these in vivo genetic cell-fate mapping experiments show that c-kit$^{pos}$eCSCs have intrinsic cardiac regenerative potential, replacing lost CMs lost after diffuse myocardial injury.

6.10 c-Kit$^{pos}$eCSCs have Strong Tropism for the Damaged Myocardium

To determine whether the ISO-injured myocardium provides a homing milieu for c-kit$^{pos}$eCSCs, $5 \times 10^5$ cells derived from a single eCSC GFP-tagged clone (eCSCs$^{GFP}$) (FIG. 17A) were injected through the tail vein of rats 12 hours after ISO injury. As cell control, ISO-injured rats were injected with $5 \times 10^5$ GFP-tagged c-kit negative sorted CM-depleted cardiac cells (c-kit$^{neg}$MDCCs$^{GFP}$; containing 86±5% cardiac fibroblasts, 13±3% vascular smooth muscle, 1±1% endothelial and <0.001% c-kit$^{pos}$ cardiac cells). To control for the role of injury in the homing, both cell preparations were also administered to uninjured, saline-treated (CTRL) animals.

Figure 17A:
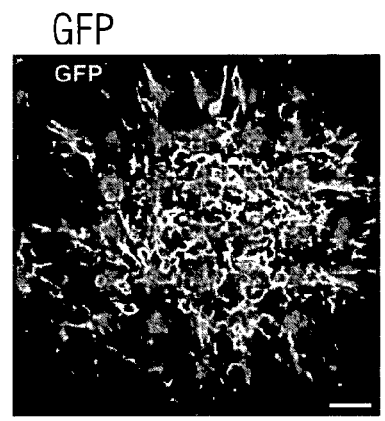
Figure 17B:
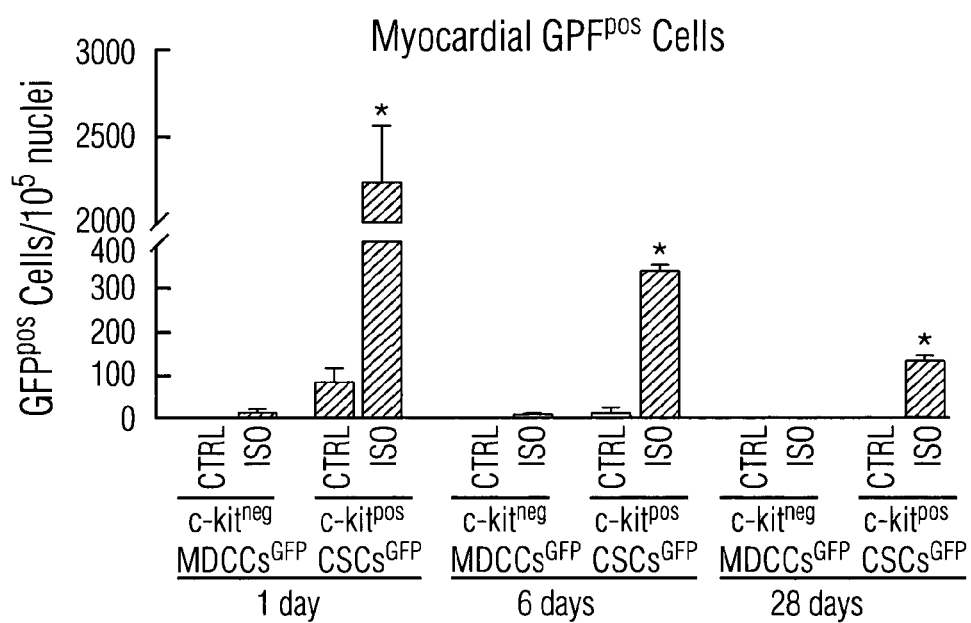
Figure 17C:
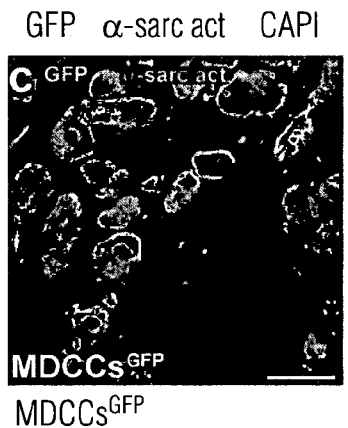
Figure 17D:
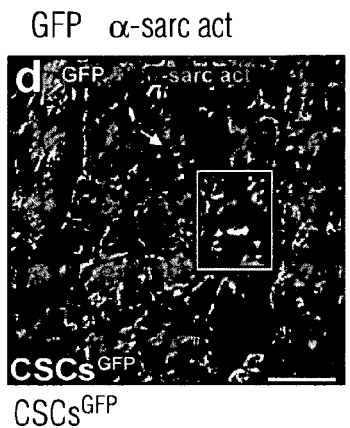
Figure 17E:
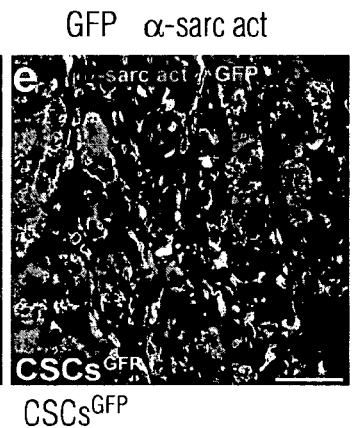
Figure 17F:
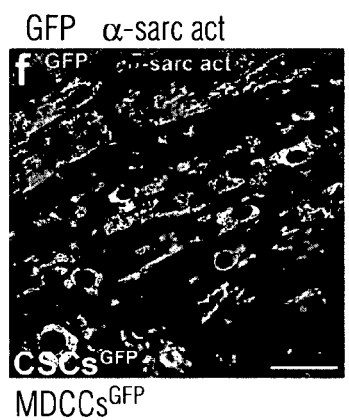
Figure 17G:
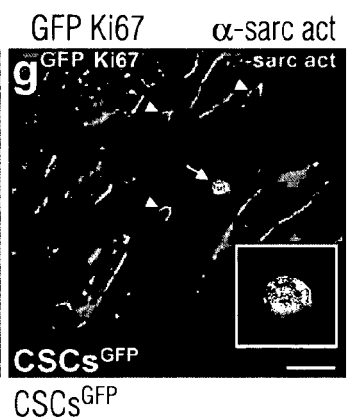
Figure 17H:
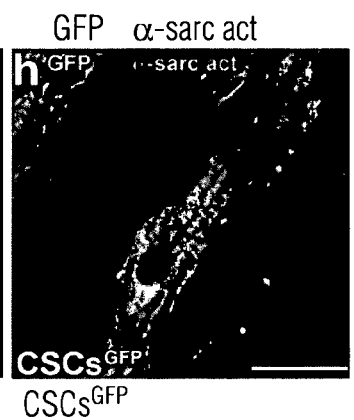
Figure 17I:
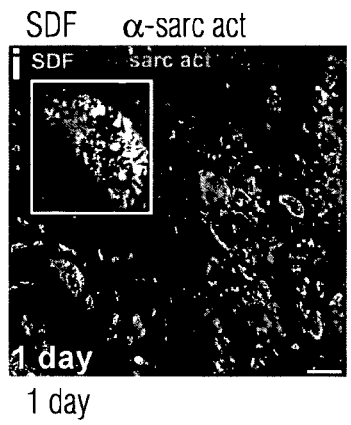

At all-time points the myocardium of CTRL and ISO animals transplanted with c-kit$^{neg}$MDCCs$^{GFP}$ had on average <1 GFP$^{pos}$ cell/$10^5$ nuclei (FIG. 17B-C) In the CTRL hearts transplanted with CSCs$^{GFP}$, there were 81±31 CSCs$^{GFP}$/$10^5$ nuclei at 24 hours after injection (FIG. 17B, D, Table 2). In contrast, in ISO-injured hearts there was very efficient cardiac homing and engrafting of the transplanted CSCs$^{GFP}$, which accounted for most of the injected cells (FIG. 17B, E-F) (Table 2). The high cardiac tropism and engrafting efficiency of the cloned CSCs$^{GFP}$ compared to the extra-cardiac tissues is shown in (Table 2 and FIG. 25). Of the myocardial-homed CSCs$^{GFP}$, 55±5%, 20±4% and 8±3% were Ki67$^{pos}$ at 1, 6 and 28 days post-transplantation, respectively (FIG. 17G). There was also an increase in GFP$^{pos}$ cells expressing α-sarcomeric actin at 6 (25±3%) and 28 (42±3%) days. At 28 days, CSC$^{GFP}$-derived newly-formed GFP$^{pos}$ CMs (4±1%; FIG. 17H) had well developed sarcomeres, were larger and more differentiated (diameter of 10±2 µm), but still smaller than normal adult fully differentiated GFP$^{neg}$ CMs (diameter of 14±1 µm; p<0.01 vs. GFP$^{pos}$ CMs). We further quantified the number of transplanted c-kit$^{pos}$CSC-derived GFP$^{pos}$ CMs by FACS, which was in agreement with the immunohistochemistry data (FIG. 25).

TABLE 2

Quantitative immunohistochemistry of c-kit$^{pos}$CSCs$^{GFP}$ engrafting in cardiac and extra-cardiac tissues (liver, lung, slow skeletal soleus muscle and spleen) at 1 day after tail vein injection in CTRL animals and 1, 6 and 28 days after tail vein injection in ISO-treated rats.

| CSCs$^{GFP}$ | 24 hr CTRL | 24 hr ISO | 6 d ISO | 28 d ISO |
|---|---|---|---|---|
| Heart (ENDO) GFP$^{pos}$cells/$10^5$ nuclei | 17 ± 4 | 974 ± 105# | 83 ± 8# | 26 ± 5# |
| Heart (ENDO) GFP$^{pos}$cells/$10^5$ nuclei | 81 ± 31 | 2231 ± 328# | 322 ± 18# | 113 ± 16# |
| LIVER GFP$^{pos}$cells/$10^5$ nuclei | 0 ± 0 | 0 ± 0 | 0 ± 0 | 0 ± 0 |
| LUNG GFP$^{pos}$cells/$10^5$ nuclei | 2162 ± 269* | 1419 ± 311† | 70 ± 7†‡ | 3 ± 3 |
| SOLEUS MUSCLE GFP$^{pos}$cells/$10^5$ nuclei | 0 ± 0 | 1106 ± 227 | 120 ± 21† | 12 ± 5 |
| SPLEEN GFP$^{pos}$cells/$10^5$ nuclei | 2861 ± 219* | 818 ± 95 | 34 ± 4 | 0 ± 0 |

*vs. heart, liver and soleus muscle
vs. liver, lung, soleus muscle, spleen.
†vs. spleen
‡vs. soleus
Note[1]:
c-kit$^{pos}$CSCs$^{GFP}$ tail vein injected into CTRL rats, were lodged mostly in the spleen and lungs at 24 hours, and not detected in both liver and soleus skeletal muscle (FIG. 25). In contrast, 24 hours after c-kit$^{pos}$CSCs$^{GFP}$ tail-injection following ISO, most CSCs$^{GFP}$ were in the myocardium, although some could be identified in the lungs, soleus skeletal muscle and spleen but not in the liver (FIG. 25). At 6 days post injection, very few CSCs$^{GFP}$ were still found in the extra-cardiac tissues examined and with the exception of the soleus muscle (which is also damaged by ISO) (Burniston et al. 2005). Relative toxicity of cardiotonic agents: some induce more cardiac and skeletal myocyte apoptosis and necrosis in vivo than others. Cardiovasc Toxicol. 5: 355-364). All the transplanted c-kit$^{pos}$CSC$^{GFP}$ cells had disappeared at 28 days (FIG. 25).
Note[2]:
it should be emphasized that the data reported in this table (and in Table 3) are at the best an approximation generated by extrapolating data obtained from counting GFP$^{pos}$ cells out of 1000 nuclei in ten random tissue sections to the whole organ or myocardial region. Thus, these data are relevant when comparing the engraftment of injected cells in the heart vs. the other organs, rather than as absolute values per se.

At 28 days after ISO and CSC$^{GFP}$ tail-vein injection, of the total GFP$^{pos}$ cardiac cells, the majority became CMs (64±4%), but also smooth muscle (10±3%) and endothelial (14±3%) vascular cells and fibroblasts, while few of them stayed as c-kit$^{pos}$CSCs (Table 3).

TABLE 3

Quantitative immunohistochemistry of cardiac cell fate of c-kit$^{pos}$ CSCs$^{GFP}$ engrafting in cardiac tissue at 28 days after tail vein injection in ISO-treated rats.
GFP cell identity in the heart 28 days after ISO

| Cardiac Cell Type | Staining | (%) |
|---|---|---|
| Myocytes | cTnI pos | 64 ± 4 |
| Smooth Muscle Cells | SMA pos | 10 ± 3 |
| Endothelial Cells | vWF pos | 14 ± 3 |
| Fibroblasts | Vimentin pos | 5 ± 2 |
| CSCs | c-kit pos CD45 neg | 3 ± 1 |

To further ascertain that the tail vein-injected cells generated bona fide CMs, c-kit$^{pos}$eCSCs expressing GFP under the control of the cardiac troponin I (cTnI) promoter were tail-injected after ISO as above. At 28 days, a population of CSC-derived cTnI$^{pos}$GFP$^{pos}$ CMs was detected (FIG. 25).

Figure 17J:
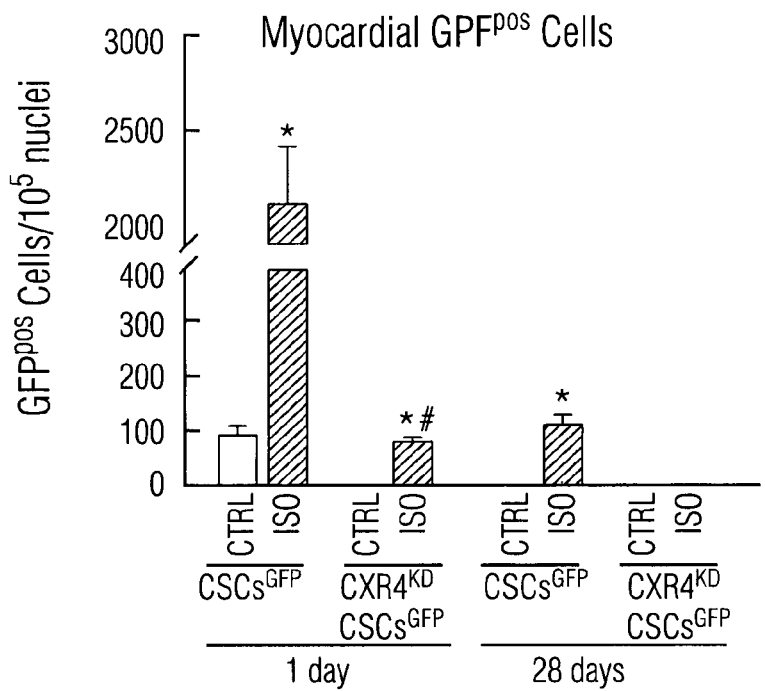
Figure 17K:
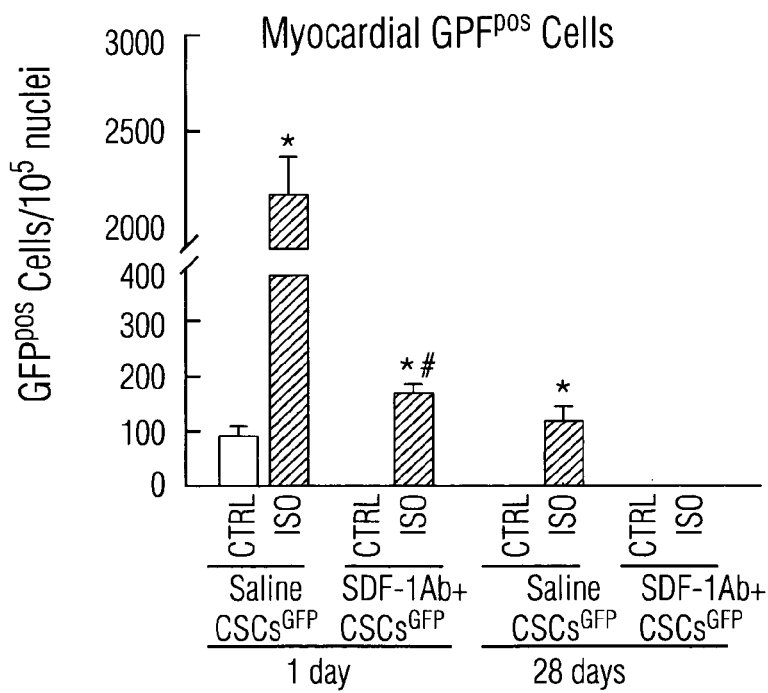
Figure 18A:
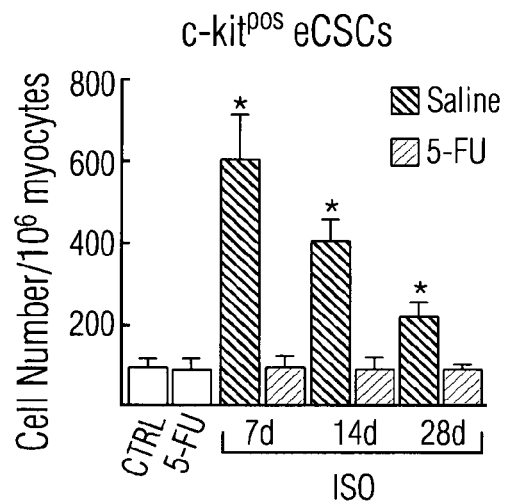
Figure 18B:
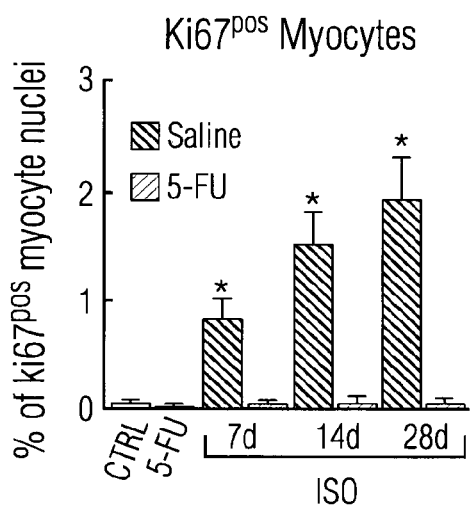
Figure 18C:
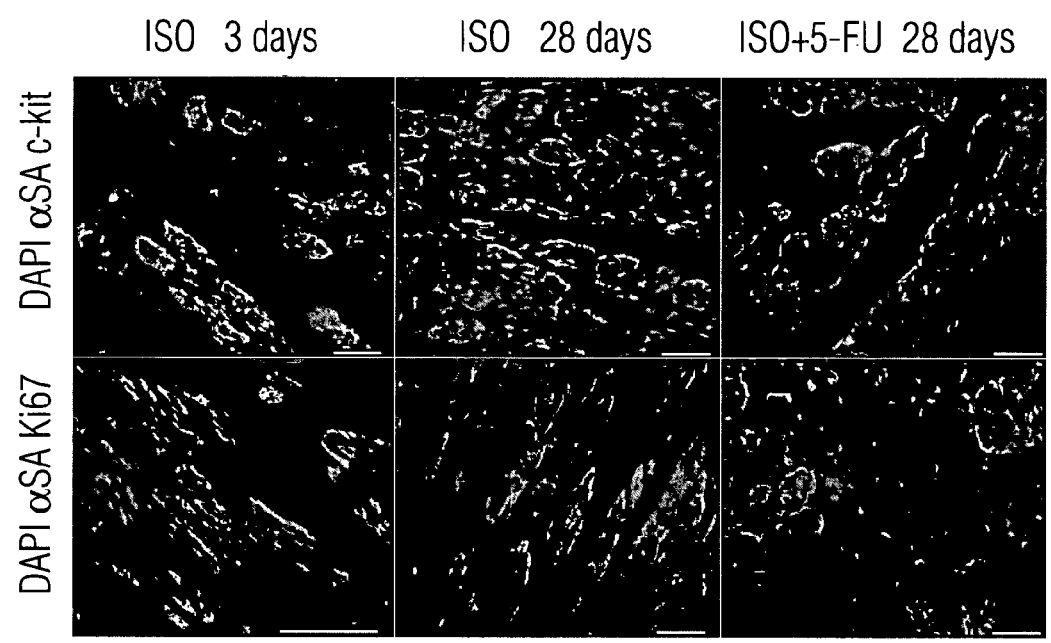
Figure 18D:
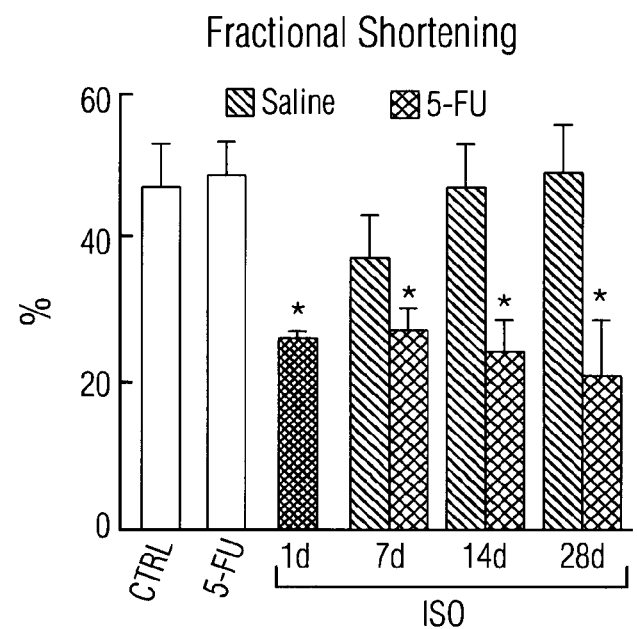
Figure 18D:
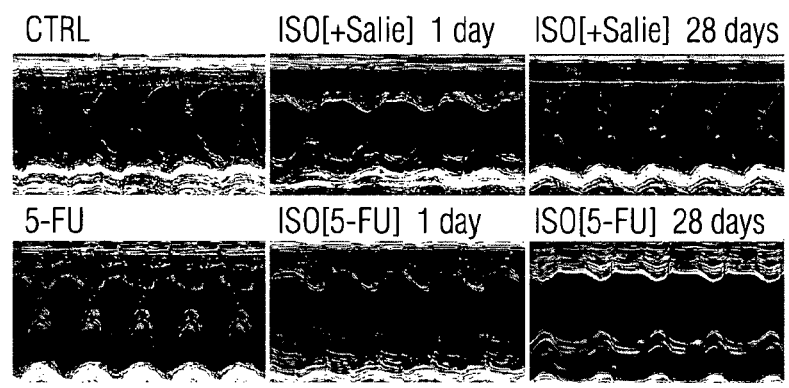

Because the SDF-1-CXCR4 axis is involved in retention and mobilization of stem cells in the adult (Askari et al., 2003), we evaluated whether this receptor-ligand pair homes CSCs$^{GFP}$ to ISO-injured myocardium. SDF-1 is rapidly up-regulated in CMs after ISO-damage (FIG. 17I and FIG. 25). 5×10$^5$-c-kit$^{pos}$eCSCs genetically-modified to knock-down expression of the SDF-1 receptor with a lentiviral vector carrying a CXCR4 shRNA tagged with GFP (CXCR4$^{KD}$CSCs$^{GFP}$; FIG. 25) were tail-vein injected into rats 12 hours after ISO injury. The CXCR4$^{KD}$CSCs$^{GFP}$ did not show any cardiac tropism as most were lodged in the spleen and lungs (FIG. 17J and Table 5). Concurrently, tail-vein injected CSCs$^{GFP}$ also failed to home to the myocardium of ISO-injured rats treated with an anti-SDF-1 neutralizing antibody 20 minutes before and 12 hours after cell injection (FIG. 17K).

TABLE 4

Quantitative immunohistochemistry of CXCR-4$^{KO}$GFP$^{pos}$c-kit$^{pos}$CSCs engrafting in cardiac and extra-cardiac tissues (liver, lung, and spleen) at 1 and 28 days after tail vein injection in CTRL and ISO-treated rats. Data are n = 4/group.

| CXCR4$^{KD}$CSCs$^{GFP}$ | 24 hr CTRL | 24 hr ISO | 28 d CTRL | 28 d ISO |
|---|---|---|---|---|
| Heart (ENDO) GFP$^{pos}$cells/10$^5$ nuclei | 2 ± 6 | 52 ± 12# | 1 ± 2 | 2 ± 2 |
| LIVER GFP$^{pos}$cells/10$^5$ nuclei | 0 ± 0 | 0 ± 0 | 0 ± 0 | 0 ± 0 |
| LUNG GFP$^{pos}$cells/10$^5$ nuclei | 2334 ± 234* | 1523 ± 263*† | 1 ± 1 | 2 ± 2 |
| SOLEUS MUSCLE GFP$^{pos}$cells/10$^5$ nuclei | 0 ± 0 | 14 ± 5 | 0 ± 0 | 0 ± 0 |
| SPLEEN GFP$^{pos}$cells/10$^5$ nuclei | 2978 ± 230* | 4069 ± 346* | 0 ± 0 | 0 ± 0 |

*vs. heart, liver and soleus muscle
vs. liver, lung, soleus muscle, spleen.
†vs. spleen These results show that the c-kit$^{pos}$CSCs have a strong tropism for the damaged myocardium, which is CXCR4-SDF-1 dependent and where the enhanced expression of SDF-1 by the surviving myocardium serves as a positive chemotactic agent.

6.11 c-kit$^{pos}$eCSCs are Necessary and Sufficient for Myocyte Regeneration and Functional Recovery after Severe Diffuse Myocardial Damage To test whether c-kit$^{pos}$eCSCs are necessary and/or sufficient for myocardial anatomical and functional regeneration, 3 days after ISO we eliminated the proliferating eCSCs and their progeny through administration of the anti-mitotic agent 5-flurouracil (5-FU; 10 mg kg$^{-1}$). This regime (ISO+5-FU) ablated eCSC expansion and new CM formation (FIG. 18A-C) resulting in a severe cardiomyopathy (ISO+5-FU induced) (FIG. 18D) with a deficit and significant hypertrophy of the spared CMs, compared to animals treated with ISO alone (ISO+saline), where regeneration was normal (FIG. 26). While all ISO+saline animals survived the acute myocardial insult and fully recovered cardiac function, the ISO+5-FU animals developed heart failure (FIG. 18D and FIG. 26) with increased mortality (4 of 10 ISO+5-FU-treated vs. 0 of 10 for the ISO+saline) at 28 days. These effects were not due to 5-FU toxicity because the same 5-FU regime administered to control animals did not cause any cellular or functional cardiac or extra-cardiac toxic effects (FIG. 26), including in the bone marrow (FIG. 26). However, 5-FU would have targeted other replicating cells together with activated eCSCs. Indeed, at 3 days after ISO when 5-FU started to be administered, the eCSCs represented only 17±3% of total Ki67 positive myocardial cells, while 55±4% were inflammatory cells (i.e. granulocytes and macrophages). A small fraction were cycling cardiac fibroblasts (9±2%), smooth muscle (4±1%) and endothelial (5±2%) cells.

To evaluate the effect, if any, of ablating non-eCSCs on blocking the regenerative response and simultaneously to establish a causal relationship between eCSC activation on one hand and myocardial regeneration and repair on the other, we injected 5×10$^5$ cloned CSCs$^{GFP}$ or the same number of GFP$^{pos}$ cardiac fibroblasts (cFibro) into the tail vein of rats with ISO+5-FU cardiomyopathy, 28 days after ISO. Additionally, to address whether the transplanted cells and their progeny are continuously required to maintain cardiac cell homeostasis and functional recovery, in a separate set of animals we transplanted cells from an eCSC clone expressing GFP together with the herpes simplex virus thymidine kinase (CSC$^{GFP/TK}$). Ganciclovir (GCV) administration produces selective suicide of the transplanted CSC$^{GFP/TK}$ and their progeny (FIG. 27). As an additional control, saline was tail-vein injected into another group of animals. See (FIG. 19A) for the study design.

At 2 months, the surviving rats with ISO+5-FU cardiomyopathy that received either saline or cFibro were indistinguishable and in overt heart failure with a dramatic deficit in c-kit$^{pos}$eCSCs, a lack of CM regeneration and increased CM death and hypertrophy (FIG. 19B-D and FIG. 27). In contrast, 95% of the animals treated with CSCs$^{GFP}$ were alive at 2 months, showed efficient homing and nesting of CSCs$^{GFP}$ into the damaged myocardium which had reconstituted the resident eCSC pool (~90% eCSC chimerism; (FIG. 19D-F and FIG. 27). These CSC$^{GFP}$ chimeric hearts had complete restoration of ventricular volumes and function (FIG. 19B-C, Table 5 and FIG. 27) with ~8% GFP$^{pos}$ CMs (FIG. 19D), indicating that they are the progeny of the transplanted cells. These data in addition to highlighting the homing and regenerative capacity of the CSCs also point to these cells as one of the cell targets of the in vivo direct reprogramming protocols for myocardial regeneration using retroviral vectors encoding CM-determining genes (Qian et al., 2012; Song et al., 2012).

TABLE 5

| Group | LVIDd (mm) | LVIDs (mm) | FS (%) | EF (%) |
|---|---|---|---|---|
| CTRL (56 days) 2 months (n = 5) | 5.12 ± 0.22 | 2.32 ± 0.1 | 54.18 ± 2.91 | 90.5 ± 1.90 |
| ISO + 5FU + saline (56 d) 2 months (n = 5) | 6.34 ± 0.14* | 4.43 ± 0.20* | 30.04 ± 3.04* | 65.61 ± 4.40* |
| ISO + 5FU + cFibro (56 d) 2 months (n = 5) | 6.06 ± 0.18* | 4.24 ± 0.39* | 29.95 ± 4.65* | 65.27 ± 6.31* |
| ISO + 5FU + CSCs$^{GFP}$ (56 d) 2 months (n = 6) | 5.30 ± 0.29# | 2.46 ± 0.17# | 53.32 ± 5.56# | 89.5 ± 3.91# |

TABLE 5-continued

| Group | | | | |
|---|---|---|---|---|
| ISO + 5FU + CSCs$^{GFP/TK}$ (56 d) 2 months (n = 5) | 5.23 ± 0.41# | 2.43 ± 0.28# | 53.65 ± 3.18# | 89.94 ± 2.01# |
| CTRL (84 days) 3 months (n = 5) | 5.26 ± 0.25 | 2.45 ± 0.21 | 53.4 ± 4.22 | 89.7 ± 2.88 |
| ISO (84 d) 3 months (n = 6) | 5.25 ± 0.42 | 2.53 ± 0.31 | 51.7 ± 3.7 | 88.6 ± 2.56 |
| ISO + 5FU + saline (84 d) 3 months (n = 4) | 6.29 ± 0.23* | 4.28 ± 0.26* | 31.0 ± 2.96* | 67.01 ± 4.18* |
| ISO + 5FU + GCV (84 d) 3 months (n = 5) | 6.28 ± 0.22* | 4.47 ± 0.25* | 28.74 ± 4.72* | 63.45 ± 6.61* |
| ISO + 5FU + CSCs$^{GFP}$ + saline (84 d) 3 months (n = 6) | 5.27 ± 0.28 | 2.52 ± 0.34 | 52.33 ± 5.10 | 88.86 ± 3.72 |
| ISO + 5FU + CSCs$^{GFP}$ + GCV (84 d) 3 months (n = 7) | 5.23 ± 0.37 | 2.44 ± 0.18 | 53.10 ± 4.35 | 89.47 ± 2.78 |
| ISO + 5FU + CSCs$^{GFP/TK}$ + saline (84 d) 3 months (n = 5) | 5.37 ± 0.40 | 2.64 ± 0.27 | 50.75 ± 5.41 | 87.71 ± 3.98 |
| ISO + 5FU + CSCs$^{GFP/TK}$ + GCV (84 d) 3 months (n = 6) | 6.29 ± 0.29*¶ | 4.24 ± 0.37*¶ | 32.69 ± 4.13*¶ | 69.23 ± 5.54*¶ |

| Group | LVEDP (mmHg) | LVDevP (mmHg) | dP/dt+ (mmHg/s) | dP/dt− (mmHg/s) |
|---|---|---|---|---|
| CTRL (56 days) 2 months (n = 5) | 1.9 ± 0.6 | 95.8 ± 3.3 | 8705 ± 377 | 8606 ± 440 |
| ISO + 5FU + saline (56 d) 2 months (n = 5) | 21.6 ± 2.1* | 63.8 ± 6.1* | 4927 ± 685* | 4435 ± 816* |
| ISO + 5FU + cFibro (56 d) 2 months (n = 5) | 18.9 ± 2.1* | 65.8 ± 4.5* | 5363 ± 956* | 4840 ± 964* |
| ISO + 5FU + CSCs$^{GFP}$ (56 d) 2 months (n = 6) | 3.3 ± 2.1# | 102.02 ± 2.3# | 8694 ± 699# | 7642 ± 636# |
| ISO + 5FU + CSCs$^{GFP/TK}$ (56 d) 2 months (n = 5) | 4.5 ± 2.9# | 95.8 ± 6.6# | 8310 ± 585# | 7391 ± 577# |
| CTRL (84 days) 3 months (n = 5) | 2.5 ± 1.6 | 94.8 ± 3.2 | 8600.9 ± 383 | 8207 ± 476 |
| ISO (84 d) 3 months (n = 6) | 2.2 ± 2.3 | 98.9 ± 10.6 | 8344 ± 1294 | 7936 ± 1072 |
| ISO + 5FU + saline (84 d) 3 months (n = 4) | 19.3 ± 2.7* | 66.7 ± 2.6* | 5601 ± 512* | 5065 ± 458* |
| ISO + 5FU + GCV (84 d) 3 months (n = 5) | 21.8 ± 2.8 | 62.8 ± 4.9 | 5129 ± 717 | 4506 ± 1036 |
| ISO + 5FU + CSCs$^{GFP}$ + saline (84 d) 3 months (n = 6) | 4.1 ± 3.7 | 107.1 ± 4.5 | 8369 ± 698 | 7686 ± 788 |
| ISO + 5FU + CSCs$^{GFP}$ + GCV (84 d) 3 months (n = 7) | 4.4 ± 3.5 | 101.4 ± 9.4 | 8019 ± 773 | 7286 ± 804 |
| ISO + 5FU + CSCs$^{GFP/TK}$ + saline (84 d) 3 months (n = 5) | 2.9 ± 3.3 | 99.7 ± 6.7 | 8521 ± 719 | 7860 ± 769 |
| ISO + 5FU + CSCs$^{GFP/TK}$ + GCV (84 d) 3 months (n = 6) | 16.9 ± 3.4*¶ | 68.1 ± 4.6*¶ | 5293 ± 1085*¶ | 4291 ± 1090*¶ |

*$p < 0.05$ vs. CTRL
$p < 0.05$ vs. saline and cFibro at 2 months
¶$p < 0.05$ vs. CSCs groups at 3 months
LVIDd = left ventricular internal diameter diastole
LVIDs = left ventricular internal diameter sistole
FS = (left ventricular) fractional shortening
EF = (left ventricular) ejection fraction
LVEDP = left ventricular end-diastolic pressure
LVDevP = left ventricular dveloped pressure
dP/dt+ = positive (maximum) rate of pressure change in the left ventricle
dP/dt− = negative (minimum) rate of pressure change in the left ventricle To rule out that cell fusion was the source of the new GFP$^{pos}$ CMs in the CSCs$^{GFP}$-transplanted animals, cloned male CSCs$^{GFP}$ were injected into female rat recipients with ISO+5FU cardiomyopathy as above. X and Y chromosomes were identified in GFP$^{pos}$ cells and their CM progeny. None of the GFP$^{pos}$ cells had more than one X chromosome ruling out cell fusion as the source of the GFP$^{pos}$ CMs (FIG. 27). Furthermore, cloned c-kit$^{pos}$eCSCs from MerCreMer mice transduced with Red Fluorescence Protein were injected into RYP mice with ISO+5FU cardiomyopathy and chased with tamoxifen before sacrifice. We could not detect any Red-labeled eCSC-derived CMs expressing EYFP, which, if present, would identify cell fusion (FIG. 27).

Figure 19A:
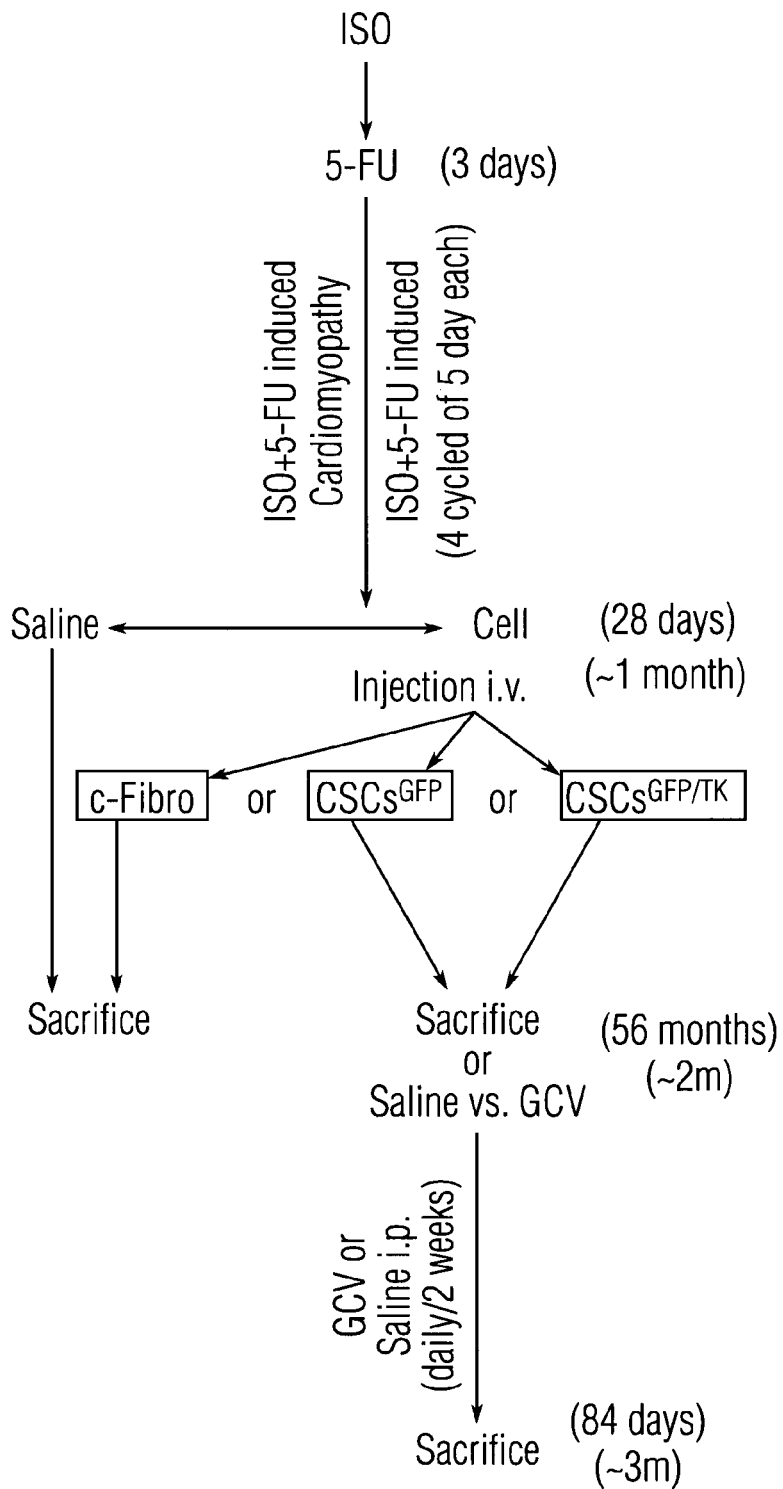
Figure 19B:
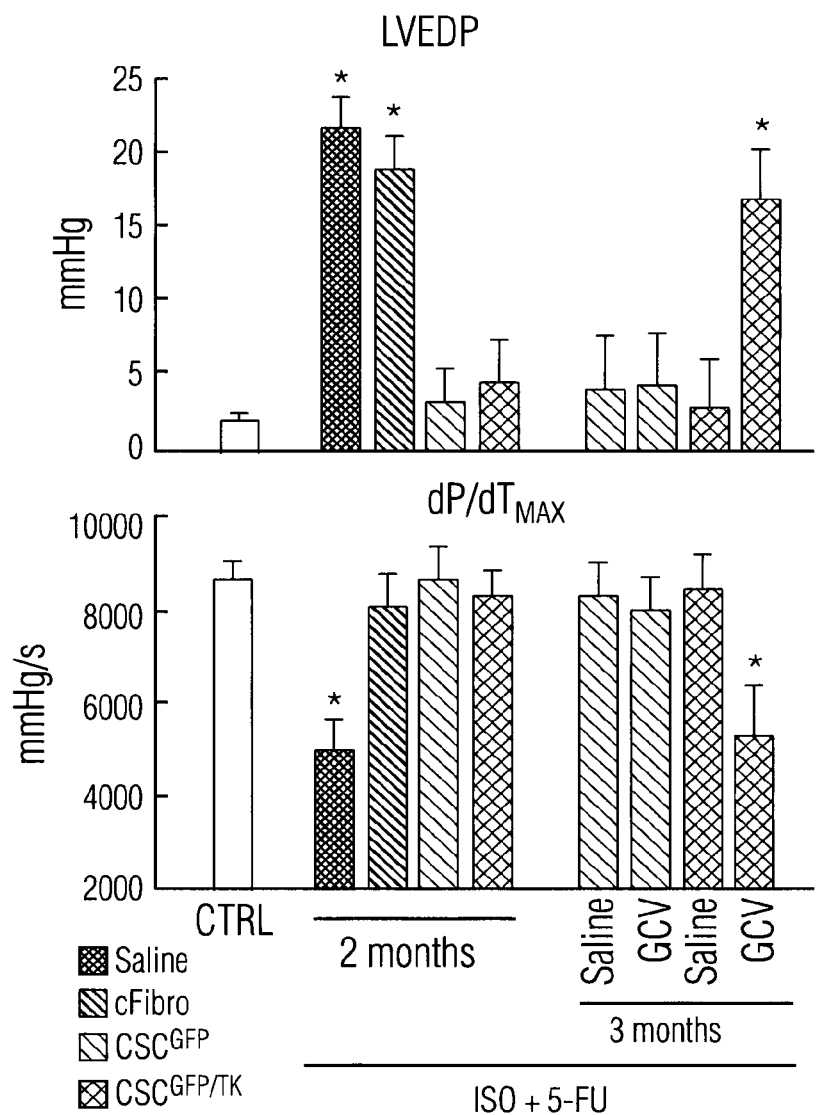
Figure 19C:
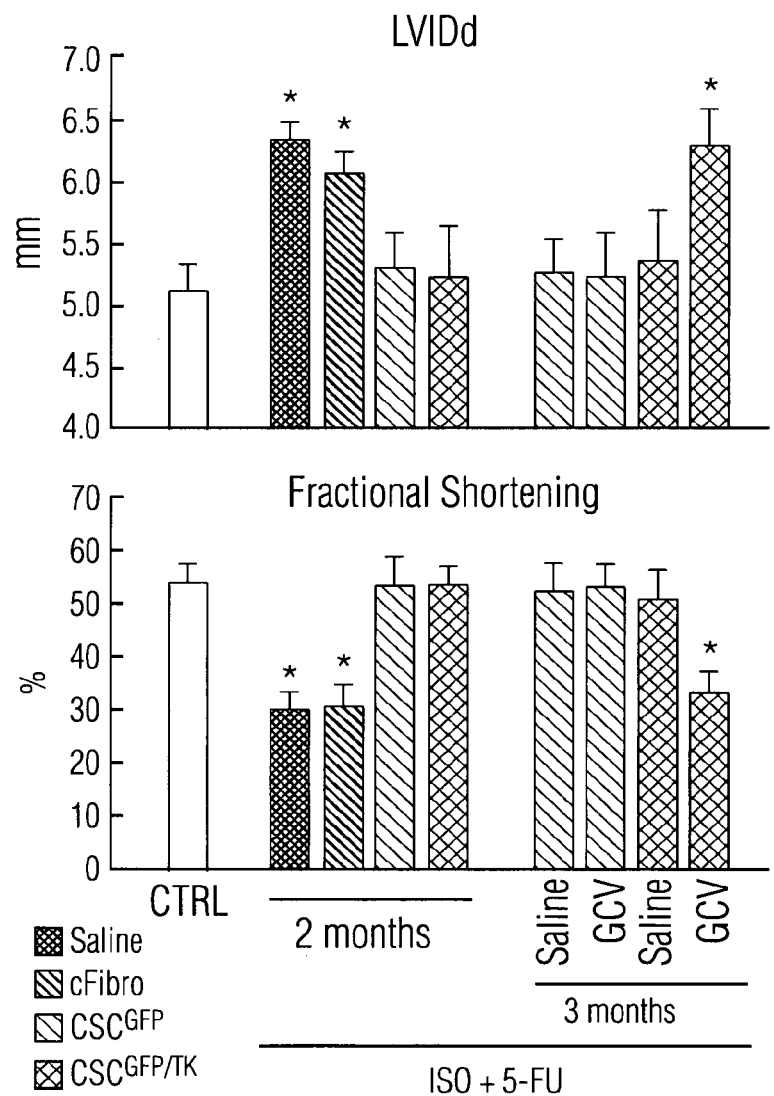
Figure 19D:
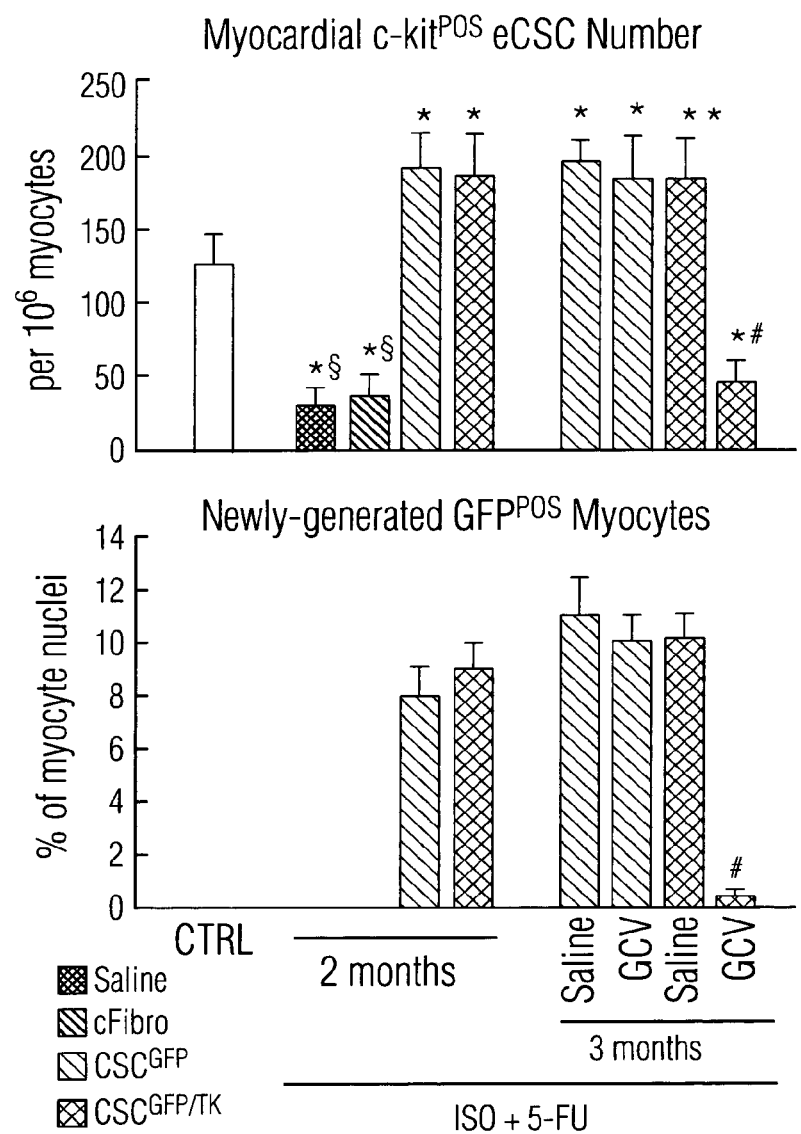
Figure 19E:
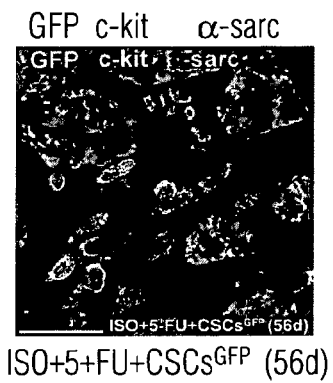
Figure 19F:
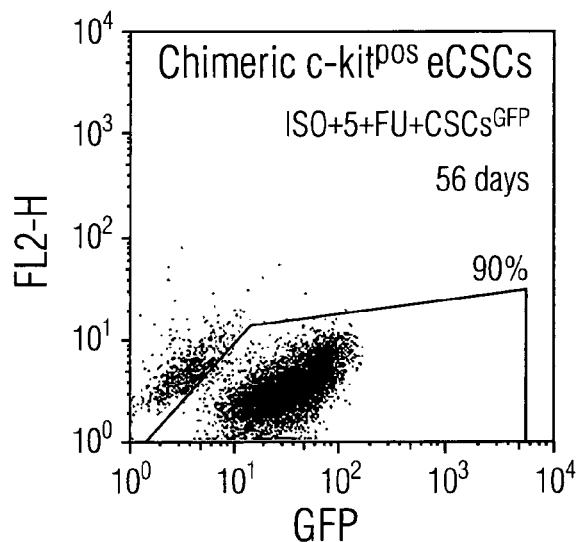
Figure 19G:
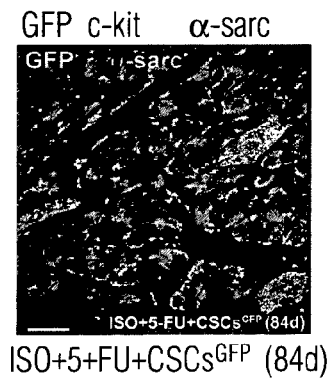
Figure 19H:
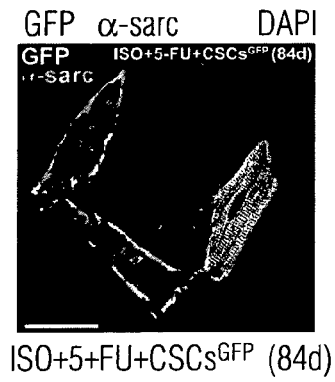
Figures 20A, 20B:
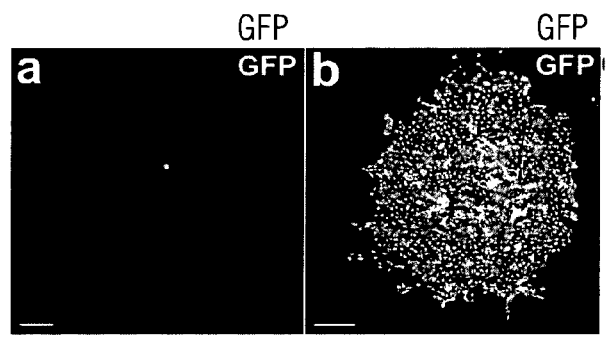
Figure 20C:
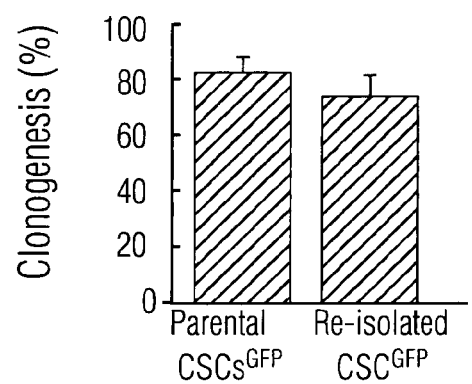
Figure 20D:
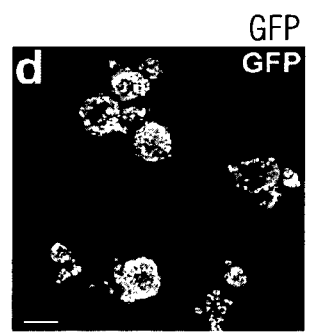
Figure 20E:
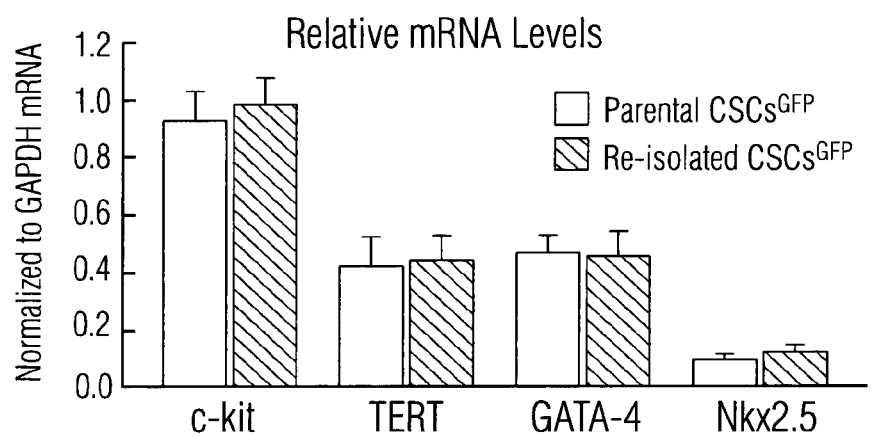
Figure 20F:
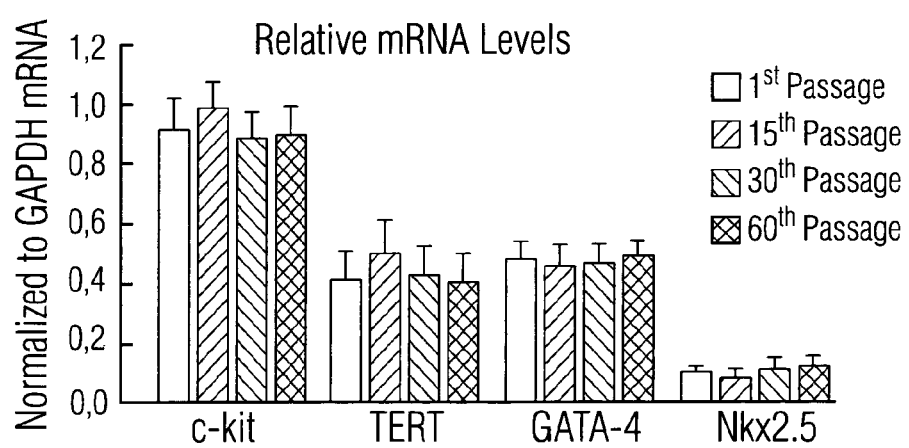
Figures 20G, 20H:
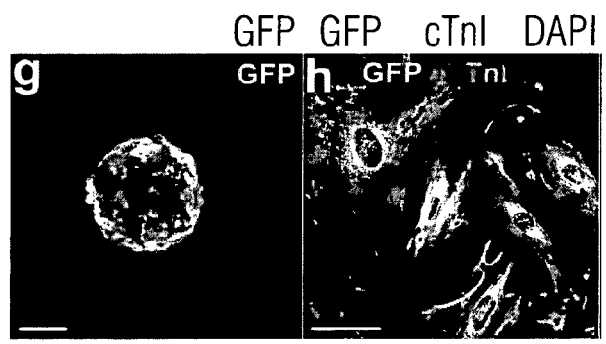
Figures 20I, 20J:
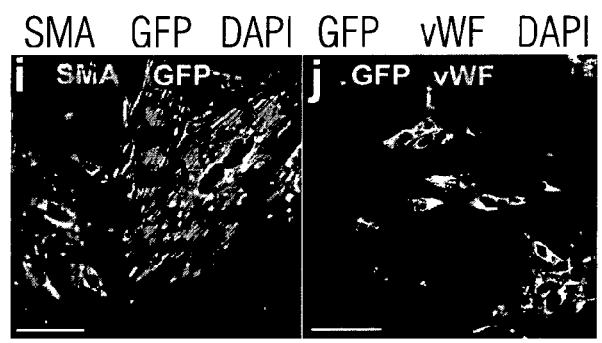
Figure 20K:
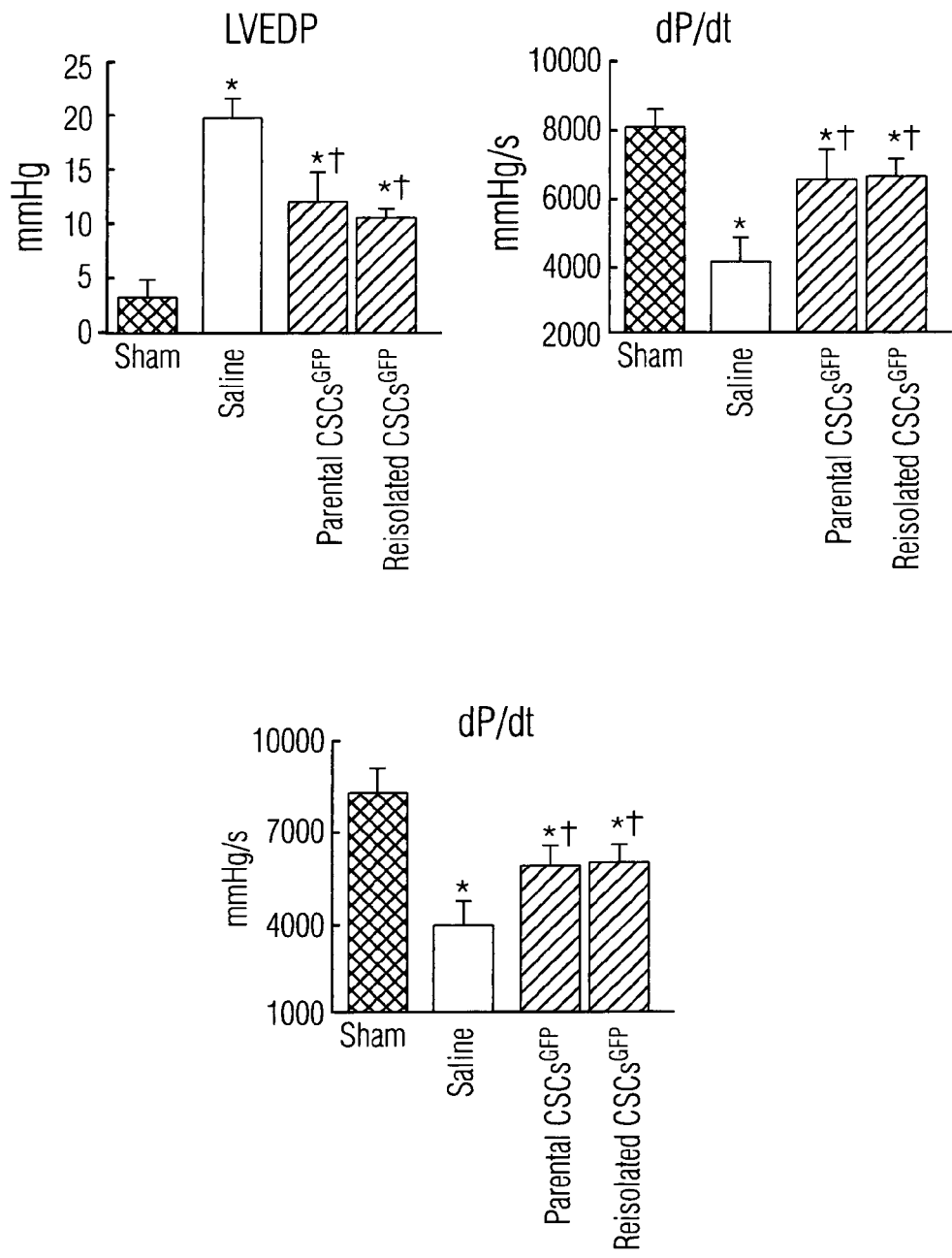
Figure 20L:
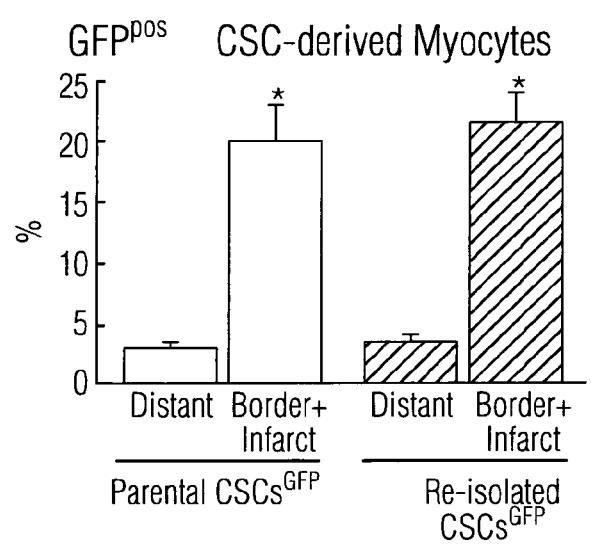
Figures 20M, 20N:
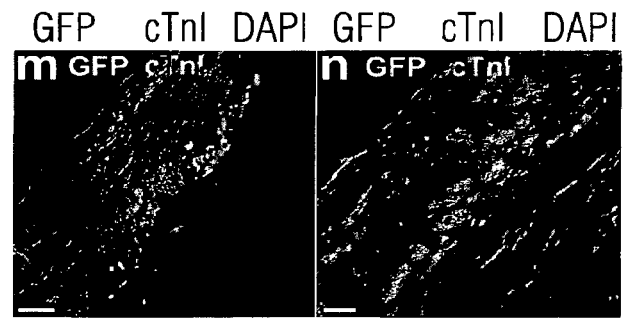
Figures 20O, 20P:
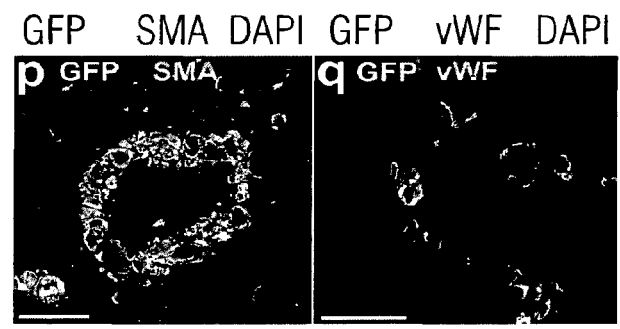

Histological and functional results identical to the injection of exogenous CSCs$^{GFP}$ were obtained in ISO+5FU-induced cardiomyopathic animals by injection of GFP$^{pos}$TK$^{pos}$CSCs (CSCs$^{GFP/TK}$) (FIG. 19B-D, Table 5 and FIG. 27) (FIG. 19B-D, Table 5 and FIG. 27). At 56 days (~2 months), additional animals with ISO+5-FU cardiomyopathy rescued by exogenous CSCs$^{GFP}$ or CSCs$^{GFP/TK}$ were treated with either saline or GCV for two weeks and sacrificed at 84 days (~3 months). At this time point, CSCs$^{GFP}$ and CSCs$^{GFP/TK}$ rats treated with saline showed a fully reconstituted eCSC pool together with complete myocardial regeneration and repair (FIG. 19D, G and FIG. 27). Myocardial immunohistochemistry was corroborated at the single cell level quantifying isolated rod-shaped GFP$^{pos}$ CMs by immunocytochemistry and FACS (FIG. 19H and FIG. 28). CSC-derived GFP$^{pos}$ CMs were still mostly mononucleated but had a size comparable to pre-existing CMs, indicating that the maturation of newly-generated CMs is completed in two months (FIG. 19G and FIG. 28). Furthermore, $CSC^{GFP}$-derived CMs expressed cardiac transcription factors and contractile genes with mRNA levels comparable with normal adult CMs (FIG. 28).

GCV treatment did not cause any histological or functional adverse effects to the rats in the ISO+5-FU+$CSC^{GFP}$ group. In contrast, GCV treatment of ISO+5-FU+$CSCs^{GFP/TK}$ group activated the programmed suicide of $CSCs^{GFP/TK}$ and their progeny, which caused a dramatic reversal of all the recovered cellular and functional parameters (FIG. 19D and FIG. 27). At 3 months, the myocardium was devoid of $CSCs^{GFP/TK}$ and of $GFP^{pos}$ CM progeny (FIG. 19D), which was accompanied by pathologic remodelling, ventricular chamber dilation and hemodynamic deterioration to levels of overt cardiac failure (FIG. 19B, Table 5).

Finally, the reported "bystander effect" of GCV (Yoon et al., 2010) was ruled out by several lines of evidence. First, GCV at a concentration sufficient to kill the $CSCs^{GFP/TK}$ cultured with adult rat ventricular CMs in a 10:1 ratio does not affect survival of the latter (FIG. 28). Second, early time points after GCV administration showed death of only $CSCs^{GFP/TK}$ and $CSCs^{GFP/TK}$-derived CMs and not of the larger spared, $GFP^{neg}$ neighboring CMs (data not shown). Third, GCV-derived metabolites effectively kill cycling cells, while non-cycling terminally differentiated cells are naturally resistant to it.

6.12 Transplanted $CSCs^{GFP}$ Re-Isolated after Having Regenerated the Damaged Myocardium Retain Tissue-Specific Stem Cell Properties To test whether after transplantation some of the engrafted $GFP^{pos}$ cells remain bona fide eCSCs, cells dissociated from the hearts with ISO+5-FU cardiomyopathy rescued by $CSCs^{GFP}$ were FACS-sorted for c-kit and GFP. These c-$kit^{pos}CSCs^{GFP}$ re-isolated from the transplanted hearts exhibited a phenotype indistinguishable from the parental c-$kit^{pos}CSC^{GFP}$ clone originally transplanted (FIG. 20). They were clonogenic, self-renewing, formed typical cardiospheres and differentiated into CMs, endothelial and smooth muscle cells in vitro (FIG. 20A-J). A clone of the re-isolated c-$kit^{pos}CSC^{GFP}$, when transplanted back into rats with ISO+5FU cardiomyopathy, proved indistinguishable from the primary parental clone in their efficiency to replenish the depleted eCSC and CM-pool and reverse the severe cardiac dysfunction (FIG. 29). Furthermore, when these re-isolated cells were transplanted into rats with acute myocardial infarction, they repopulated the ischemic myocardium with new $GFP^{pos}$ CMs and vascular cells, leading to improved LV function (FIG. 20K-Q).

6.13 C-$kit^{pos}CD166^{pos}CD45^{neg}Tryp^{neg}$ Cardiac Stem-Progenitor Cells-CSC Presence/Abundance in the Human and Animal Heart It should be noted that up to date we have concentrated in the distribution of the c-kit CSCs in the adult, both experimental animals and human. Although we have some preliminary data from pre-puberal animals, the results listed below concern only to the adult.

The presence and quantification of the c-kit CSCs in the control animals and in the human is presented as measured from histological sections and quantified by morphometry. Therefore, the values obtained are only approximations. In the mouse, rat, pig and human the abundance of c-kit CSCs is ~1/1500-2000 myocytes, which translates to 1 per every 6000 to 10,000 nuclei since in the adult myocardium only ~1 of every 4 nuclei corresponds to a myocyte. The CSCs can be found in all areas of the heart from the atria to the apex. Their distribution is not uniform. The highest density is found in the atrial appendices and the apex of the (left) ventricle. That is in the areas of the lowest wall tension. In the normal heart ~95% of the c-kit CSCs are quiescent with the remainder in different stages of the cell cycle. The quiescent cells are almost invariable found as single cells close to capillaries, while the one activated and in the cell cycle are normally in groups ranging from 2 to up to 10-12 cells, as expected for cells in the process of amplification before differentiation. In the young adult a small % of the c-kit CSCs show the typical markers of aging, such as p16 expression, short telomeres, and low telomerase activity. The frequency of these "aged" cells increases in direct correlation with the age of the animal and the human. There is also a concomitant increase in the total number of c-kit CSCs with age but because the cells with an "aged phenotype" are not productive, the end result is that with increasing age is despite the increase in absolute number of c-kit CSCs there is a linear decrease in the number of productive CSCs. This phenomenon is confirmed when the clonal efficiency and self-renewal capacity of the CSCs is tested in vitro. C-kit CSCs from young animals and human have a significantly higher cloning and self-renewal capacity which decreases with age to a point that it is less than 25% of the young in the rodents past 22 months and humans over 70 years old.

6.14 Aging of the Cardiac Stem-Progenitor Cell Population in Parallel with the Age of the Organism The data on the isolation and characterization of the rodent and pig CSCs has been described herein. As an example of genetic stability, pig cloned cells isolated in 2005 and used almost continuously since then have still a normal karyotype, and all the characteristics of stem cells, such as expression of multipotency genes, normal telomeres, high clonal efficiency, etc. The isolation and expansion of the human CSCs is described below.

Isolation of human c-kit CSCs from small biopsies obtained either during a surgical procedure (mainly the right atrial appendage), by catheter biopsy (endocardial right and left ventricle) or from a cadaver is routine and successful in almost all the cases. The frequency of isolation of human c-kit CSCs which can be cloned and exhibit long term expansion capability is highly dependent on the age of the donor. The older the donor the lower the clonal efficiency of the c-kit CSCs and, in most cases the lower their capacity to expand which might be exhausted after 20-30 passages. Yet, in almost all donors it is possible to find clones that can be maintained in culture and expanded for long periods of time. From very young donors, and particularly from fetuses, almost all c-kit CSC clones show very strong self-renewal capability, genetic stability and capacity to expansion which in practical terms seems unlimited. The maximum number of cells we have produced starting from a SINGLE cells has been $1 \times 10^{12}$ cells which have normal karyotype, self-renewal and diagnostic markers. The expansion was voluntarily stopped at this point because this level of expansion was sufficient to produce more than 100 doses of the product, each composed of $1 \times 10^8$ human c-kit CSCs. See FIG. 31.

6.15 Allogeneic Cardiac Stem-Progenitor Cells are Well Tolerated and have an Anti-Inflammatory and Immunomodulatory Role The data on the immune response to allogeneic cells was obtained in pigs where the recipients were always Large White (bred to reduce homozygosis) and the injected cells where either from very distant Large White breeders or from Iberian black pigs. The immunological reaction to the two cell types was similar.

Below is shown the measurements of the IgM and IgG antigenic response of three pigs injected with $1\times10^6$ allogeneic c-kit CSCs, blood samples taken at 0, 15 and 30 days later. See FIGS. 33 & 34. On day 30 each animal received a new intracoronary injection of $1\times10^6$ allogeneic c-kit CSCs from the same clone used in the initial injection. Blood samples were collected on day 33, 37, 45 and 60. Because there are no available antibodies against the pig haplotypes the appearance of specific IgM and IgG antibodies against the donor cells was determined in a cell assay where the donor cells where use as targets for the available antibodies en the recipient sera. The amount of IgM and IgG bound to the donor cells was determined using monoclonal antibodies against these two immunoglobulin types. By necessity the results had to be expressed in arbitrary units.

As shown below, there is no significant increase in anti-donor IgM or IgG in response to the first intracoronary injection. The second injection, however, produces a mild to moderate increase of IgM and IgG antibodies against the donor cells, which did not produce any detectable clinical symptoms in the animals or any detected pathological or histological changes in a variety of tissues analyzed after sacrifice at 2 months following the first c-kit CSC administration. It should be pointed out that the cells injected each time where GFP positive and therefore, either the transgene or the vector used might have contributed to the immune response.

These results indicate that the humoral immune response to $1\times10^6$ allogeneic c-kit CSCs in the adult pig is very low and not detectable by the method used. If repeated injections are required the data suggest that for each new administration it might be advisable to use a different donor expressing a different HLA haplotype. In this manner the immune reaction to each administration should be similar to the first.

6.16 Immunomodulatory Properties of the Human c-kit CSCs

The human c-kit CSCs (hCSCs) from all the donors tested so far (n=8) expressed normal levels of the HLA class I and no detectable levels of HLA class II and the co-stimulatory molecules CD40, CD80 and CD 86 (see primary data example below)> they also fail to express CD 275 but express high levels of PD-L1 (CD274). If the cells are stimulated by inflammatory cytokines, such as IFNγ the expression of HLA class I and class II is significantly enhanced together with the expression of PD-L1. However, IFNγ does not induce the expression of the co-stimulatory molecules CD40, CD80 and CD 86 so even in the inflammatory environment the immunogenicity of the hCSCs is very low because of their low profile to be recognized by the allogeneic T cells.

In a one-way mixed lymphocyte cultures the hCSC were able to stimulate the proliferation of CD4+ but not CD8+ T cells and the response was significantly lower than the typical allogeneic PBMC response and very similar to that induced by the hMSCs. This response was not significantly modified by prior treatment of the hCSC with IFNγ. Concordant with the hCSC effect, there is no increase in the supernatant of IFNγ or IL-4 but a significant increase in the anti-inflammatory IL-10. The hCSC do not produce IL-10 which is produced by the allogeneic cells.

These data indicate that that hCSCs can inhibit the T cell response produced by mismatched-MHC molecules even in an inflammatory environment and is in agreement with the finding described herein that stimulation of the endogenous CSCs in acute MI, after damage by ISO overdose or extraneous exercise reduces inflammation and collagen deposition in the damaged myocardium.

Preliminary data suggest that because of the failure of inflammatory molecules to induce the expression of the co-stimulatory molecules the T-cell activation produced by the allogeneic hCSCs do not produce Th 1 or Th2 responses but induce the expression of the immunomodulatory PD-L1.

Taken together, all these data support the observation that the allogeneic hCSCs injected through the coronary artery in the pig after the production of an AMI are eliminated mostly by apoptosis and not by necrosis, which in itself would be pro-inflammatory (See FIG. 35)

6.17 Use of Heterologous Non-Matched Cardiac Stem-Progenitor Cells (CSCs) without Immunosuppression as an Effective Regenerating Agent in a Porcine Model of Acute Myocardial Infarction In humans, transplantation of a variety of cell types post myocardial infarction (MI) has produced modest results. It is postulated that a paracrine mechanism supports cell survival, neo-angiogenesis and possibly endogenous CSC activation. The regenerative properties of c-kit and CD166 positive CD45 and Tryp negative (c-kit+) cardiac stem cells (CSCs) potentially renders them as the best cell type for future effective therapy. However, the time needed for their isolation and ex vivo expansion makes them unavailable for regeneration protocols in acute MI management. In a porcine model, which is similar to human anatomy, we investigated the effects of intracoronary injection of cloned c-kit+ heterologous HLA non-matched porcine CSCs on myocardial remodelling and regeneration after MI.

Animals and Myocardial Infarction—

Female Landrace swine ~2 month of age (25-30 kg) were sedated with telazol (100 mg, I.M.), intubated and maintained in anesthesia with isoflurane (2.5% in $O_2$). In 24 closed-chest animals, a coronary balloon catheter was advanced over a guidewire and positioned in the proximal portion of the left anterior coronary artery (LAD), below the origin of the first perforating artery. Lidocaine (2 mg/kg$^{-1}$) was administered intravenously and the balloon inflated (2.5 mm diameter) for occlusion of 75 mins. After placement of a naked metal stent at the site of the occlusion each animal was injected intra-coronary with 15 ml of the cell suspension in pig serum or just pig serum for the control animals The tip of the injection catheter was placed just distal to the stent and the 15 ml solution injected at a rate of 1 ml/min with a recess of 3 min. after every 5 ml administration.

CSC Administration—

Cloned male EGFP-transduced porcine CSCs, all derived from a single clone were administered intracoronary at differential doses ($5\times10^6$, $5\times10^7$ and $1\times10^8$) in 3 groups of pigs, 30 minutes after coronary reperfusion. Pig serum was injected to 6 control pigs after MI (CTRL). BrdU was administered via osmotic pumps (B. Braun) to track myocardial regeneration. Pigs were sacrificed at 30 min, 1 and 21 days (See FIG. 42).

Cardiac Function Measurements—

Cardiac function was measured by echocardiography, cardiac Magnetic Resonance Imaging (MRI) and intracardiac pressure-volume loop analysis. Regional microvascular resistance was quantified by simultaneous assessment of intracoronary pressure-/and flow velocity parameters.

Three animals died during the induction of ischemia by LAD occlusion as consequence of refractory ventricular fibrillation. One control animal died one week later shortly after induction of general anesthesia presumably because of cardiac failure. Of the survived 14 animals, 5 animals were randomly allocated to 5×107 CSCs, 5 animals to the 1×108 CSCs and the remaining 4 animals to serum alone, serving as controls. One of the control animals was excluded from the analysis since there was no initial decline in cardiac function, a limited troponin rise after MI and only a minor endocardial rim of scar tissue visible by TTC staining. In one of the 5×10$^7$ CSC treated animals, histological analysis was not possible due to a technical error during the fixation process of the tissue samples.

6.18 Allogeneic Cardiac Stem-Progenitor Cell Administration Improves Cardiac Function in Acute MI To test the effects of the allogeneic CSC treatment on cardiac function after MI, PV loop analysis and echocardiography was assessed prior to coronary occlusion, at 1 month (prior to injections in the chronic MI) and at 2 months (1 month after injections) after MI. First, the controls, serum administration without CSCs, were compared against a historical cohort of identical MI procedure 1 month after MI.

There were no differences in any echocardiographic or PV-loop derived parameters. Thus, with no indication that the injection procedure by itself influenced post-MI remodeling, we considered the serum administered animals as negative controls. Fractional area shortening was significantly improved in both the 5×10$^5$ CSC and 1×10$^8$ groups compared to the CTRL animals (Fig; +2.3±1.8% vs +4.2±2.0% vs −2.6±3.6%; p=0.008). Progressive deterioration in left ventricular ejection fraction was reversed in the 1×10$^8$ CSC group (Fig; mean change +2.8±2.7%), compared to CTRL animals (Fig; −5.9±3.8%, p=0.02). However, there were no apparent signs of cardiac dilatation in all groups and LV end diastolic volume did not differ between treatment groups (CTRL vs 5×10$^7$ CSC vs 1×10$^8$; 94.9±10.8 ml vs 94.0±8.9 ml vs 92.4±6.6 ml respectively, p=0.915). With regard to diastolic function of the heart, the ratio of transmitral flow velocity to annular peak diastolic velocity (E/E') was preserved in the CSC treated animals (5×10$^7$ CSC 7.7±0.3; 1×10$^8$ CSC 7.4±1.1), compared to CTRLs (9.3±0.6; p=0.04).

Immunohistochemistry and Confocal Microscopy—

To identify CSCs, transverse sections were stained with antibodies against GFP (Rockland), and the stem cell antigen, c-kit (DAKO). Cycling cells were identified by BrdU and Ki67. Progenitor cells stained positive for c-kit and the transcription factors, Nkx2.5 and Ets-1. Newly formed myocytes were identified with antibodies against BrdU, Ki67 and α-sarcomeric actin. Newly formed capillary structures were detected by staining for BrdU and vWF. Images were acquired using confocal microscopy (Zeiss 510 Meta). The number of CSCs and newly formed cardiac cells (BrdU$^{pos}$ and ki67$^{pos}$) were quantified in the infarct, border and distal regions. The results of the immunohistochemical analysis are shown in FIGS. 36-39.

6.19 Allogeneic Cardiac Stem-Progenitor Cell Administration in Combination with Growth Factors Further Improves Cardiac Function in Acute MI The main effect of allogeneic cardiac stem-progenitor cell administration, either intra-coronary, intra-venous or directly into to damaged myocardium is due to the paracrine effect of the allogeneic cells which have a strong anti-apoptotic and anti-inflammatory effect on the host myocardial cells at risk. In addition, the secreted factor by the activated allogeneic stem-progenitor cells produce the activation of the host's cardiac endogenous stem-progenitor cells which replicate, differentiate and mature into autologous myocytes and microvasculature. Thus, although the stimulus is allogeneic the result is an autologous regeneration.

Two of the most effective factors secreted by the activated stem-progenitor cells are IGF-1 and HGF which by themselves have a strong antiapoptotic and replicative effect on other cells and act synergistically when used together. These two factors also have a synergistic effect when administered with Neuroregulin and/or Periostin. In order to strengthen the regenerative effect of the allogeneic cells we combined those with 2 µg of HGF and 8 µg of IGF-1 added to the cell suspension before its administration intra-coronary to the infarcted animals.

As shown in the table below the effect of the combined therapy is far superior to that of the allogeneic stem-progenitor cells alone.

Table of ventricular function results after administration of allogeneic CSCs together with IGF-1 and HGF

| EDV 2 Mo (ml) | ESV 72 h (ml) | ESV 1 Mo (ml) | ESV 2 Mo (ml) | EF 72 h (%) | EF 1 Mo (%) | EF 2 Mo (%) |
|---|---|---|---|---|---|---|
| 134 | 43 | 82 | 84 | 40 | 33 | 37 |
| 152 | 43 | 80 | 104 | 43 | 37 | 32 |
| 126 | 39 | 67 | 81 | 41 | 38 | 36 |
| 157 | 49 | 102 | 118 | 38 | 28 | 25 |
| 142.3 | 43.5 | 82.8 | 96.8 | 40.5 | 34.0 | 32.5 |
| 14.7 | 4.1 | 14.5 | 17.5 | 2.1 | 4.5 | 5.4 |
| 82 | 37 | 40 | 42 | 43 | 48 | 48 |
| 106 | 44 | 57 | 57 | 44 | 43 | 46 |
| 103 | 40 | 53 | 61 | 43 | 45 | 44 |
| 109 | 42 | 51 | 55 | 42 | 45 | 45 |
| 112 | 46 | 61 | 60 | 41 | 41 | 47 |
| 102.4 | 41.8 | 52.4 | 55.0 | 42.5 | 44.4 | 46.0 |
| 11.9 | 3.5 | 7.9 | 7.6 | 1.1 | 2.6 | 1.6 |

Table.-
The upper panel shows the ventricular function parameters of the control animals injected with porcine serum after the MI. The two lower lines in bold represent the average values of the five animals and the standard deviation, respectively.

The bottom panel shows the ventricular function parameters of the five animals injected after the MI with 1×10$^8$ porcine allogeneic CSCs together with 2 µg of HGF and 8 µg of IGF-1 dissolved in the 15 ml of the CSC suspension. The two lower lines in bold represent the average values of the five animals and the standard deviation, respectively.

6.20 Experimental Procedures

Animals

Experimental procedures were carried out under the British Home Office Animal (Scientific Procedures) Act 1986 and/or approved by the corresponding Institutional Review Boards. Male Wistar adult rats (339±21 g, purchased from Charles River) received a single injection (subcutaneous; s.c.) of 5 mg kg$^{-1}$ isoproterenol (ISO) or saline (CTRL) into the loose skin over the neck and were sacrificed 1, 3, 6, 14 or 28 days later (n=7 per group). CTRL animals (n=7) were treated identically and housed next to the experimental groups, and received an equivalent volume (~0.25 ml) of the saline vehicle only. Animals were housed under controlled conditions of 25° C., 50% relative humidity and a 12 hr light (6:00-18:00) and 12 hr dark cycle, with water and food (containing 18.5% protein) available ad libitum. Animals were injected (intra-peritoneal, i.p.) with 50 mg kg$^{-1}$ of bromodeoxyuridine (BrdU; MP Biomedicals) twice daily or the BrdU (0.6M) was administered continuously using an Alzet osmotic mini pump (Charles River). The latter were implanted subcutaneously in the dorsal region via a small interscapular incision using sterile surgical technique, while the animals were under light isoflurane anaesthesia. LV catheterization was performed to assess hemodynamic parameters at the specified intervals in all animals before sacrifice and heart fixation for histology (see below).

In another set of animals (296±19 g), to test the effects of eCSC ablation on cardiac tissue repair and function after ISO-damage, 5-fluorouracil (5-FU; Sigma) was administered (10 mg kg$^{-1}$) for 4×5 day cycles starting at the 3$^{rd}$ day post ISO injection and animals were sacrificed 7, 14, and 28 days later (n=6, 6 and 4, respectively). In additional ISO injured rats, only saline was administered as control and these animals were accordingly sacrificed at 7, 14, and 28 days after ISO (n=6, 6 and 4, respectively). CTRL rats received saline vehicle (n=5) or 5-FU (n=5). Echocardiography and LV catheterization were performed to assess LV dimensions, cardiac global function and hemodynamic parameters at the specified intervals in all animals before sacrifice and heart fixation for histology (see below).

We generated double transgenic MerCreMer-ZEG mice by crossbreeding cardiomyocyte-specific (Myh6 promoter) MerCreMer [B6129-Tg(Myh6-cre/Esr1)1Jmk/J] mice (Sohal et al., 2001) and Z/EG (B6.Cg-Tg(ACTB-Bgeo/GFP) 21Lbe/J) mice (Hsieh et al., 2007) (the latter purchased from Jackson Laboratory). Mer-CreMer-RYP mice were generated by crossbreeding MerCreMer mice with B6.129X1-Gt (ROSA)26Sortm1(EYFP)Cos/J (also known as R26R-EYFP and hereafter named as RYP) mice. To induce Cre recombination, we injected intraperitoneally 4-OH-tamoxifen (Sigma), dissolved in peanut/sunflower oil (Sigma), either into 8-week-old MerCreMer-ZEG mice daily at a dosage of 0.5 mg per day for 14 days (Hsieh et al., 2007; Loffredo et al., 2011) or into 8-12-week-old MerCreMer-RYP mice daily at a dosage of 20 mg kg$^{-1}$ day$^{-1}$ for 5 days (Qian et al., 2012). Animals were then used 1 week later. Transgenic or wild type mice received a single injection (s.c) of 200 mg kg$^{-1}$ Isoproterenol (ISO) (Brooks & Conrad, 2009; Shao et al. 2012) or saline (CTRL) and were sacrificed at different time points similar to rat experiments. Mice were injected (i.p.) with 35 mg kg$^{-1}$ of BrdU (MP Biomedicals) twice daily. See FIG. 15A for schematic of the experiment design.

Tg$^{c\text{-}kit/GFP}$ mice expressing transgenic green fluorescent protein (GFP) under the control of c-kit promoter (line 3) were generated as previously described (Cairns et al., 2003). ISO injections and BrdU labelling were performed as above described.

Female pigs of the Large White strain of ~2 months of age and 25 to 39 kg of weight were used to generate a myocardial infarction by balloon occlusion followed by re-vascularization. A short time after the infarcted animals were divided into two groups (control and experimental). The control animals received the same volume of pig blood serum through the affected coronary artery than those treated with allogeneic cardiac stem-progenitor cells with or without growth factors released at the point of the Coronary artery Descendent Anterior (CDA) where the balloon occlusion had been produced. This protocol was designed to mimic a procedure that would be similar for the treatment of acute myocardial infarction in humans.

Cell Administration in Pigs:

Female juvenile White pigs were sedated with telazol, intubated and shaved. An intravenous catheter was placed in a peripheral ear vein. The animals were moved to the surgery room, placed onto a support board, and secured to the surgical table with limb bindings. Animals were maintained in anesthesia with isoflurane (2.5% in O2). In closed-chest animals, a coronary balloon catheter was advanced over a guide wire and positioned in the proximal portion of the left anterior coronary artery (LAD), below the origin of the first diagonal artery. Pigs were given 125 UI/kg of heparin before the infarction was induced and then heparin infusion (10 UI/kg/h) during the infarction procedure. To induce infarction, the LAD coronary artery was occluded by balloon inflation (2.5 mm diameter) for 60 mins. For anti-arrhythmic medication, pigs were continuously infused with Amiodarona (Trangorex) (5 mg/kg/h) throughout the procedure, beginning 15 minutes before the infarction. In the case of ventricular extra-systole or ventricular fibrillation, Lidocaine of 1-3 mg/kg was administered intravenously. Pre-operative medication was administered as 75 mg clopidrogel (Plavix) and 250 mg aspirin one day before surgical procedure. Post-operative medication consisted of 75 mg clopidrogel (Plavix) and 125 mg aspirin daily until the sacrifice. 30 minutes after coronary reperfusion, hCSCs were administered in differential doses (ranging from 1 to 200×10$^6$) to pigs through a perfusion balloon catheter advanced immediately distal to the origin of the first diagonal artery 60 minutes after coronary occlusion. hCSCs were administered in 15 ml of PBS over 15 minutes at a rate of 1 ml/min with 1 minute reperfusion every 3 minutes of administration.

Lenti c-Kit/Cre Production and In Vivo Injection—

The c-kit/cre construct was generated starting from a construct encoding the EGFP gene under the c-kit promoter (c-kit/EGFP) (Cairns et al., 2003), by replacing the EGFP gene with the CRE gene. The c-kit/cre plasmid was tested in vitro by correctly and efficiently transducing RYP mouse bone marrow-derived mast cells (data not shown), which express high levels of c-kit. The c-kit/cre construct, the c-kit/EGFP construct, the EGFP gene or the Cre gene (Addgene) was cloned in the self-inactivating HIV-based pLenti vector using the p-Lentiviral-III Expression System (Abmgood, Canada). The derived construct of interest, Lenti-c-kit/cre, was checked for proper insertion and absence of unwanted mutations in c-kit/cre and flanking sequences by cycle sequencing. Lentiviral particles were generated in human embryonic kidney 293-T cells, quantified by testing reverse transcriptase activity and titrated in 293-T cells by flow cytometry. Ultra-high titre virus (>1× 10$^{10}$ transduction units, T.U. per ml) was resuspended in PBS. After verification of high transduction efficiency in cell culture (>90%, see below), small stock aliquots (10 μl) were made and frozen at −80° C. until use. c-kit$^{pos}$ eCSCs, isolated from 8-12 weeks-old male B6.129X1-Gt(ROSA) 26Sortm1(EYFP)Cos/J (RYP) mice (purchased from Jackson Lab) were seeded at 5×10$^5$/well in six-multiwell plates and transduced 24 h later with Lenti/Empty, p-Lenti-Cre, or equivalent amounts of Lenti-c-kit/Cre. In additional experiments, c-kit$^{pos}$ eCSCs, isolated from 8-12 weeks-old male wild type C57BL/6 mice were seeded and transfected as above with p-Lenti-EGFP or Lenti-c-kit/GFP (data not shown). Vector supernatant was replaced with fresh CSC medium 6 h later, and cells were further incubated for 48 h. The efficiency of transduction was determined by flow cytometry.

Murine fibrinogen was PEGylated by BTC-PEG-BTC as previously described (Zhang et al., 2006). Briefly, BTC-PEG-BTC (3400 Da; Nektar, San Carlos, Calif.) was added to fibrinogen (40 mg/mL in tris-buffered saline [TBS], pH 7.8; Sigma) at a molar ratio of 10:1. The reaction was carried out at 37° C. in TBS (Sigma) at pH 7.6 for 20 min. Lenti-empty, Lenti-cre or Lenti-c-kit/cre was immediately added to PEGylated fibrinogen at equal volume. This mixture then underwent gelation by adding a solution of thrombin (20 U/mL in 40 mM calcium chloride; Sigma).

12-week-old male RYP mice were used for the in vivo cre-lox recombination of c-kit$^{pos}$ eCSCs using the Lenti-c-kit/cre encapsulated PEGylated Fibrin hydrogel plus direct intra-myocardial Lenti-c-kit/cre injections (see FIG. 16). To pre-test the feasibility of such strategy, we delivered in RYP mice a Lenti-cre or in wild-type mice a Lenti-GFP, both of them encapsulated in PEGylated Fibrin hydrogel plus direct intra-myocardial injections (see below). Both these tests proved that the two lentiviral vectors could respectively activate the cre-lox recombination in vivo for YFP expression or infect with GFP the apical myocardial cells (data not shown). Specifically, for c-kit$^{pos}$eCSC genetic fate map in vivo experiments, mice were randomized into groups, were anesthetised and under a dissection microscope received a direct apical injection of Lenti-ckit/cre plus treatment with the PEGylated fibrin patch encapsulated with Lenti-c-kit/cre. For direct intra-myocardial injection, the Lenti c-kit/cre (1×10$^{10}$ T.U/ml) was injected (5 μl per injection) into 5 regions of the apex per mouse using a 32-gauge needle. For the lentivirus-encapsulated PEGylated fibrin, the patch was formed in vitro as described above and placed on the surface of the ventricular myocardium shortly after formation. The chest was closed in layers. After surgery, the mice were allowed to recover for timed intervals of 1, 2, and 4 weeks. ISO injury was induced as described above 2 weeks after lenti-c-kit/cre injection. In separate parallel experiments, RYP mice were injected with Lenti-Empty to rule out any aspecific effect of the lentiviral construct per se on cre/lox cell specific in vivo recombination and on c-kit$^{pos}$CSC activation and ensuing new myocyte formation in vivo after ISO injury. The lenti-empty did not give rise to YFP expression in any myocardial (or other organ) cell type and concurrently no newly-formed myocardial cell (BrdU$^{pos}$) was indeed labelled by YFP.

Tail Vein Cell Injections—

Clonogenic c-kit positive CSCs (c-kit$^{pos}$ CSCs) and c-kit negative myocyte-depleted cardiac cells [c-kit$^{neg}$ MDCCs, mainly constituted by cardiac fibroblasts (>70% of MDCC population)] were transfected with a lenti-viral vector encoding the enhanced green fluorescent protein (GFP) under the control of the CMV promoter. Transfection efficiency was tested by flow cytometry and was over 95%.

Male Wistar rats (299±11 g) were injected with ISO or saline as described above. 12 hours later, rats were anaesthetized and 5×10$^5$ GFP-tagged c-kit$^{pos}$ CSCs (CSCs$^{GFP}$; n=15/group) or c-kit$^{neg}$ MDCCs (n=15/group) were injected through the tail vein. 1, 6 and 28 days later, rats were sacrificed and lung, spleen, liver, soleus skeletal muscle and heart were harvested. The number of animals for these determinations were n=5 at 1, 6 and 28 days for both ISO and saline vehicle CTRL groups and c-kit$^{pos}$ CSCs and c-kit$^{neg}$ MDCCs.

To test whether the SDF-1/CXCR-4 axis targets CSCs to injured myocardial areas, c-kit$^{pos}$CSCs were genetically-modified to knock-down the SDF-1 receptor through the transfection of a lentiviral vector carrying a CXCR4 shRNA tagged by GFP (the construct was purchased from Open Biosystems, Thermo Scientific, USA). Efficiency of transfection was verified by flow cytometry (over 90% GFP positive c-kit$^{pos}$ CSCs) and the knock down of CXCR4 was analysed by western blot as shown in FIG. 24. The cells were then named as CXCR4$^{KD}$CSCs$^{GFP}$. 12 hours after ISO injury we injected 5×10$^5$ CXCR4$^{KD}$CSCs$^{GFP}$ through the tail vein into 8 male Wistar rats (288±11 g). As cell controls, we injected 5×10$^5$ CSCs$^{GFP}$ in 8 additional male ISO-injured rats. The two cell types were also injected to 16 additional saline injected control (not injured; CTRL) rats (8 for CSCs$^{GFP}$ and 8 for CXCR4$^{KD}$CSCs$^{GFP}$). In further experiments, 5×10$^5$ CSC$^{GFP}$ were injected as described above in ISO-injured rats treated with an anti-SDF-1 neutralizing antibody (MAB310, R&D Systems, 500 μg) through the tail vein 20 minutes before cell injection and 12 hours later. The anti-SDF-1 dose was based on the available literature (Lin, et al. 2008) and a cursory trial and error. Animals were sacrificed at 24 hours and at 28 days and lung, spleen, liver, soleus skeletal muscle and heart were harvested.

To test the ability of exogenous CSCsGFP to repopulate 5-FU-ablated endogenous CSCs after ISO-damage, 145 male Wistar rats (301±15 g) were injected with ISO (n=130) or saline (n=15) and then 5-FU was administered (10 mg kg$^{-1}$) for 4×5 day cycles starting at the 3$^{rd}$ day post ISO injection (n=110). On the 28$^{th}$ day the animals were injected through the tail vein with either saline (n=30), 5×10$^5$ GFP-tagged c-kit$^{pos}$ CSCs (CSCs$^{GFP}$) (n=20) or 5×10$^5$ GFP-tagged cardiac fibroblasts (n=8). Additional rats (n=20) were transplanted with 5×10$^5$ clonogenic CSCs, which co-expressed GFP and the herpes simplex virus thymidine kinase (CSC$^{GFP/TK}$) after transfection with a lentiviral vector containing the GFP gene under the CMV promoter and the HSV-TK gene with a Puro cassette for puromycin resistance gene (purchased from Open Biosystems, Thermo Scientific, USA). CSC$^{GFP/TK}$ were ~99% positive for GFP (by FACS analysis). Ganciclovir (GCV; to activate the suicide of GFP/TK-transfected cells) was administered (i.p.) at the dose of 50 mg/kg twice daily for 14 days from day 56 to day 70 after ISO. Animals were sacrificed 56 or 84 days after ISO. The groups sacrificed at 56 days and their respective n values were: n=5 for saline vehicle (CTRL), n=5 for ISO+5-FU+Saline, n=5 for ISO+5-FU+cFibro, n=6 for ISO+5-FU+CSCs$^{GFP}$ and n=5 for ISO+5-FU+CSCs$^{GFP/TK}$. The groups sacrificed at 84 days and their respective n values were: n=5 for saline vehicle (CTRL), n=6 for ISO+saline, n=4 for ISO+5-FU+Saline, n=5 for ISO+5-FU+GCV, n=6 for ISO+5-FU+CSCs$^{GFP}$+Saline, n=7 for ISO+5-FU+CSCs$^{GFP}$+GCV, n=5 for ISO+5-FU+CSCs$^{GFP/TK}$+Saline and n=6 for ISO+5-FU+CSCs$^{GFP/TK}$+GCV.

To directly test whether cell fusion was the source of the newly formed fluorescent protein-labeled myocytes in the labelled-CSCs-transplanted animals, a high titer ($1\times10^{10}$ PFU/ml) recombinant human adenovirus type 5 expressing Red Fluorescent Protein (RFP) under the control of CMV promoter (purchased from Vector Biolabs) was efficiently transfected at 100 MOI in a c-kit$^{pos}$eCSC clone from Myh6-MerCreMer mice (FIG. 26). A human Adenovirus Type5 containing an empty CMV promoter (Ad-Empty, from Vector Biolabs) was used for control experiments. ISO (200 mg/kg) was injected in RYP mice (n=16) and 5-FU (15 mg/kg) was injected twice daily i.p. for 4×5 day cycles starting at the 3rd day post ISO injection (similarly to the rat experiments detailed above). On the 28th day the RYP mice with ISO+5FU cardiomyopathy were injected through the tail vein with either saline (n=6) or MerCreMer mice-derived and cloned RFP$^{pos}$eCSCs (n=4). Finally, 4-OH-tamoxifen, dissolved in peanut/sunflower oil, was injected daily at a dosage of 20 mg kg-1 day-1 for 5 days before sacrifice to activate cre recombination in vivo. If CSC-derived myocytes in ISO+5-FU cardiomyopathy in RYP mice treated with RFP$^{pos}$CSCs from MerCreMer mice were the product of cell fusion it was expected that RFP labelled myocytes had turned on YFP label arising from cre recombination of only fused cells. Thus, at 56 day sacrifice, cardiomyocytes were isolated from the heart of the two groups of mice (ISO+5-FU+Saline and ISO+5-FU+CSC$^{RFP}$, n=4 each) and FACS analysis was performed to identify at the single cell level RFP and YFP expression (see below for the detailed methods on myocyte isolation and the FACS analysis).

Myocardial Infarction:

In a group of male Wistar rats (n=15, 308±11 g), myocardial infarction was induced through permanent ligation of left descendant anterior coronary artery as previously described (Beltrami et al., 2003). 30 minutes later, $2\times10^5$ re-isolated and re-cloned c-kit$^{pos}$ GFP-tagged CSCs (re-isolated CSCs$^{GFP}$) from cell chimeric ISO+5-FU+CSCs$^{GFP}$ hearts (see below) (n=5), or just saline (n=5) were transplanted in 2 sites of the border infarct zone (Beltrami et al., 2003). As cell positive controls, parental cloned c-kit$^{pos}$ GFP-tagged CSCs (parental CSCs$^{GFP}$) were similarly injected to another 5 infarcted rats. Finally, 5 additional rats served as sham operated controls (Sham). Animals were then sacrificed 28 days later.

Cardiac Hemodynamics and Echocardiography—

For hemodynamics measurements, rats or mice were anaesthetised with ketamine (50 mg kg$^{-1}$, i.p.) and xylazine (10 mg kg$^{-1}$, i.p.) at the specified time points (see above) and a Millar microtip pressure transducer (Houston, Tex., USA), connected to a chart recorder (PowerLab, ADInstruments, Australia), was advanced into the LV cavity through the right carotid artery. This facilitated evaluation of LV end-diastolic and end-systolic pressures, developed pressure and $^+$dP/dt (contraction) and $^-$dP/dt (relaxation) in the closed chest preparation (Ellison et al., 2007). The numbers of animals for these determinations were as described above.

Echocardiograms were obtained using a Vivid-Q ultrasound system (GE Healthcare) or a VisualSonics Vevo 2100 as previously reported by our laboratory (Waring et al. 2012). Animals were anesthetized with the minimum amount of inhaled isoflurane needed to prevent movement and placed in the supine position. Hair was removed from the chest and LV images were obtained using a 12L-RS transducer (5.0-13.0 MHz) or a MS250 transducer (13-24 MHz) placed parasternally. Parasternal long and short axis views were obtained with both M-mode and two-dimensional echocardiography. LV dimensions (LV end diastolic diameter, LVEDD and LV end systolic diameter, LVESD) were measured perpendicular to the long axis of the ventricle at the mid-chordal level on three consecutive cycles and averaged by two independent observers (I.A. and A.L.) in a blinded fashion. Fractional shortening and LV ejection fraction were accordingly calculated. The numbers of animals for these determinations were as described above.

Tissue Harvesting—

After completion of the hemodynamic and/or echocardiographic measurements, the abdominal aorta was cannulated and the heart arrested in diastole using cadmium chloride ($CdCl_2$). The isolated hearts were perfused with 10% buffered formalin and cut into right and left ventricles, and right and left atria (Ellison et al., 2007). After being weighed, the LV was sectioned into 3 parts, i.e. apical, mid and basal regions, embedded in paraffin and 5 µm cross sections were prepared on a microtome (Leica).

Myocyte Death and Hypertrophy—

Apoptosis was detected on 5 m LV sections using a rabbit anti-caspase 3 Ab (1:200 dilution; R&D systems) which detects the activated caspase 3. In addition, the Terminal deoxynucleotidyltransferase (TdT) assay was also used (Ellison et al., 2007). Apoptotic (caspase 3 or TdT positive) myocytes were identified and quantified (~3000 myocytes were counted per heart and the apoptotic fraction was expressed as a percent of total myocyte nuclei) using light, fluorescent (Nikon E1000M) and confocal microscopy (Zeiss LSM 510).

Myocyte diameter was measured across the nucleus on transverse H&E sections of the sub-endocardium LV wall layer (~500 myocytes/animal were sampled). Myocyte volume was calculated assuming a circular cross-section. The numbers of animals for these determinations were as described above.

Immunohistochemistry on LV Cross Sections—

Table 6 contains the full list of antibodies used and their applications. Antigen retrieval was achieved using Target Retrieval Solution, Citrate pH 6 (DAKO). Newly formed myocytes were detected through double staining for BrdU and/or Ki67 and α-sarcomeric actin. BrdU was detected using an antibody against BrdU (1:50 dilution; Roche) for 45 minutes at 37° C. This antibody was detected with an anti-mouse IgG FITC (1:100 dilution; Jackson Immunoresearch). Ki67 was detected using a rabbit polyclonal antibody against Ki67 (1:50 dilution; Vector Labs) overnight at 4° C. This antibody was detected with an anti-rabbit IgG FITC (488) (1:100 dilution; Jackson Immunoresearch). Myocyte cytoplasm was detected using an antibody against α-sarcomeric actin (1:50 dilution; clone 5C5, Sigma), Myosin heavy chain (1:50 dilution, clone NOQ7.5.4D, Sigma) or cardiac Troponin I (1:50 dilution; rabbit polyclonal, Santa Cruz) for 2 hrs at 37° C. and this was detected with anti-mouse IgM or IgG anti-rabbit IgG Texas Red (1:100 dilution; Jackson Immunoresearch). Cnx43 was detected with a rabbit polyclonal antibody against connexin 43 (1:50 dilution; Abcam) overnight at 4° C. This antibody was detected with an anti-rabbit IgG Cy5 (1:100 dilution; Jackson Immunoresearch). c-kit$^{pos}$ Lin$^{neg}$ eCSCs were detected on LV sections using double staining for c-kit and a lineage depletion cocktail (see below), c-kit was detected with either rabbit polyclonal (1:50 dilution; Santa Cruz) or goat polyclonal (10 µg/ml dilution; R&D Systems) antibody for 2 hrs at 37° C. and this was detected with an anti-rabbit IgG FITC (1:100 dilution; Jackson Immunoresearch) or an anti-goat IgG FITC (1:100 dilution; Jackson Immunoresearch). c-kit$^{pos}$ eCSCs were identified as lineage negative (Lin$^{neg}$) on LV sections, by staining negative following incubation with a cocktail composed of antibodies against the hematopoietic, neural, and skeletal muscle lineages (Beltrami et al., 2003). Myocyte progenitor (c-kit$^{pos}$/GATA4$^{pos}$ or Nkx2.5$^{pos}$) and precursor (c-kit$^{pos}$/GATA4$^{pos}$ or Nkx2.5$^{pos}$/α-sarcomeric actin$^{pos}$) cells were detected through triple staining with c-kit and Nkx2.5 or GATA4 together with α-sarcomeric actin. Nkx2.5 was detected using a goat antibody against Nkx2.5 (10 µg/ml dilution; R&D systems) overnight at 4° C. This antibody was detected with an anti-goat IgG Cy5 (1:100 dilution; Jackson Immunoresearch). GATA4 was detected using a rabbit antibody against GATA4 (1:50 dilution; Santa Cruz) overnight at 4° C. This antibody was detected with an anti-goat IgG Cy5 (1:100 dilution; Jackson Immunoresearch). GFP$^{pos}$ cells were detected using a goat polyclonal or rabbit polyclonal antibody against GFP (1:50 dilution; Rockland Immunochemicals (goat); Abcam (rabbit)) for 1 hr at 37° C. and this was detected with an anti-goat or anti-rabbit IgG FITC (1:100 dilution; Jackson Immunoresearch). GFP positive cardiomyocytes, smooth muscle, fibroblasts and endothelial cells (capillaries) were identified on LV cross sections by double staining for GFP and cTnI (1:50 dilution), or Smooth Muscle Actin (SMA; 1:100 dilution) or vimentin (1:100 dilution) or vWF (1:100 dilution). Secondary Ab incubations were carried out at 37° C. for 1 hr. The nuclei were counterstained with the DNA binding dye, 4,6-diamidino-2-phenylindole (DAPI, Sigma) at 1 µg/ml. Sections were mounted in Vectashield and analysed and scanned using confocal microscopy (Zeiss LSM 510 or 710). Myocardial-produced SDF-1 was detected on LV cross sections by incubation with Abs (see Table 6) for 1 hr at 37° C., and this antibody was detected by fluorescence. GFP and β-gal were also detected on LV cross sections by incubation with Abs (1:100 dilution and see Table 6) for 1 hr at 37° C., and these antibodies were detected by HRP-conjugated 2° Abs and visualised by DAB-substrate histochemistry or fluorescence conjugated 2° Abs and visualised by confocal microscopy.

TABLE 6

List of Antibodies used and their application

| Antigen | Antibody ID | Company | Application |
|---|---|---|---|
| SDF-1 | Rabbit #3740; SC-28876 | Cell Signaling; Santa Cruz Biotech | WB; IH |
| cTnI | H-170 | Santa Cruz Biotech | IH, IF, FC |
| Actin | C-2 | Santa Cruz Biotech | WB |
| c-kit | H-300 | Santa Cruz Biotech | IH, CSC isolation, FC |
| c-kit | AF1356 | R&D systems | IH, CSC isolation, FC |
| c-kit | 2B8 | BD Pharmingen | FC, IF |
| c-kit | 3C1 | Miltenyi | FC, IF |
| Sca-1 | D7 | Miltenyi | FC |
| CXCR4 | Rabbit ab2074 | Abcam | WB |
| Nkx2.5 | Goat AF2444 | R&D systems | IH |
| GATA4 | H-112 | Santa Cruz Biotech | IH, FC |
| α-Sarcomeric Actin | Clone 5C5, IgM | Sigma | IH, FC |
| BrdU | Clone BMG 6H8 | Roche | IH |
| Ki67 | VP-K451 | Vector labs | IH |
| Vimentin | Mouse LN-6 | Sigma | IF |
| CD45 | OX-1 | Bio-Legend | FC |
| CD45 | OX30 | Santa Cruz | CSC isolation, IH |
| CD45 | 30F11.1 | Miltenyi | FC |
| CD34 | RAM34 | eBioscience | FC |
| CD105 | MJ7/18 | Miltenyi | FC |
| Cn43 | Rabbit | Abcam | IH, IF |
| GFP | Goat | Rockland Immunochemicals | IH, IF |
| GFP | Rabbit | Abcam | IH, IF |
| Caspase 3 | Rabbit AF835 | R&D systems | IH |
| vWF | Rabbit AB7356 | Chemicon | IH, IF |
| Smooth Muscle Actin | Mouse A2547 | Sigma | IH, IF |
| MHC | Clone NOQ7.5.4D | Sigma | IH, IF |
| β-galactosidase | Rabbit | Abcam | IH |

IH denotes Immunohistochemistry;
WB denotes Western Blot;
FC denotes Flow Cytometry;
IF denotes cell immunofluorescence.

Quantitative Immunohistochemistry—

The number of c-kit$^{pos}$ Lin$^{neg}$ eCSCs and their committed progeny (GATA4$^{pos}$, Nkx2.5$^{pos}$) and proliferative state (BrdU$^{pos}$, Ki67$^{pos}$) was counted across a total of 3 sections of the LV for each animal at ×100 magnification and expressed as number of positive cells per $10^6$ myocytes, except for BrdU$^{pos}$ and Ki67$^{pos}$ eCSCs which were expressed as percent of c-kit$^{pos}$ eCSCs. The fraction of myocytes labelled by BrdU or Ki67 was measured at ×100 magnification by counting a total of 1500 cardiomyocytes for each layer of the LV wall (sub-endocardium, mid-wall and sub-epicardium), across a total of 4 cross sections from each animal. The number of newly formed cardiomyocytes (i.e. BrdU$^{pos}$ or Ki67$^{pos}$) was expressed as a percent fraction of the cardiomyocyte nuclei. To determine any changes in the size of the newly formed myocytes with time, the diameter of newly formed myocytes (BrdU$^{pos}$) was measured. In the tail vein injected rats, GFP$^{pos}$ cells were counted for each layer of the LV wall (sub-endocardium, mid-wall and sub-epicardium) in 20 fields/layer at 40× magnification. The numbers were expressed per $10^5$ nuclei or per $10^6$ cardiomyocyte nuclei. The GFP$^{pos}$ cells that were Ki67, Nkx2.5 or cTnI positive were expressed as a percentage of total GFP$^{pos}$ cells. The fraction of GFP$^{pos}$ cardiomyocytes was measured at ×100 magnification by counting a total of 1500 cardiomyocytes for each layer of the LV wall across a total of 4 sections for each animal. The number of GFP$^{pos}$ cardiomyocytes was expressed as a percent fraction of the cardiomyocyte nuclei. For the in vivo regeneration myocardial infarction assay, GFP$^{pos}$/cTnI$^{pos}$ myocytes were counted in the border/infarct and distal areas by counting at ×63 magnification a total of 20 fields, and the number of GFP$^{pos}$-CSC-derived cardiomyocytes expressed as a percent fraction of the total number of nuclei.

Fluorescent In Situ Hybridisation (FISH)—

Immunofluorescence was performed on 5 µm LV paraffin embedded-tissue sections to detect GFP$^{pos}$ cardiomyocytes as described above and images of GFP$^{pos}$ cardiomyocytes were acquired. Following Immunofluorescence, FISH was performed using Rat IDetect™ chromosome paint probes (ID Labs, Ontario, Canada) according to the manufacturer's instructions with a few modifications. Cardiac muscle was digested in 0.025% pepsin for 40 min at 37° C. and post-fixed in 4% formaldehyde for 10 min at room temperature. Following dehydration, tissue was immersed in 70% formamide/2×SSC at 72° C. for 5 min to denature cellular DNA. Cy3-conjugated X- and FITC-conjugated Y-chromosome paints were applied to tissue sections, sealed under coverslips and denatured at 70° C. for 5 min before hybridization in a humidified chamber overnight at 37° C. Coverslips were removed and post-hybridisation washes were performed according to the StarFISH chromosome paint protocol (Cambio). Nuclei were stained with DAPI. Sections were analysed and scanned using confocal microscopy (Zeiss LSM 710).

Rat Cardiomyocyte, eCSC and Cardiac Fibroblast Isolation—

Cardiomyocytes and eCSCs were isolated from additional ISO-treated or CTRL adult male Wistar rat (308±9 g) hearts by enzymatic dissociation (Ellison et al., 2007; Waring et al., 2012). Also, $CSC^{GFP}$ were re-isolated from cell chimeric hearts (n=5) at 42 days following ISO+5-FU-treated $CSC^{GFP}$ tail vein injection. Hearts were excised, the aorta cannulated and hung on a retrograde perfusion system. Briefly, this procedure consists of three main steps: 1) A collagenase type II perfusion of the myocardium performed at 37° C. with HEPES-MEM, gassed with 85% $O_2$ and 15% $N_2$. 2) The heart is removed from the apparatus, cut into small pieces and the fragments shaken in re-suspension medium at 37° C. 3) Cardiomyocytes and small cardiac cells are separated by centrifugation and then the myocyte suspension is passed through a BSA size separation gradient for further purification. In particular for qPCR of $GFP^{pos}$ CMs (FIG. 26), fluorescent positive CMs were selected manually by micro-pipette based on the presence of GFP signal under the fluorescent microscope directly after isolation. For isolation of c-$kit^{pos}$ $CD45^{neg}$ cells, first the myocyte-depleted small cardiac cells are treated with an anti-rat CD45 mouse monoclonal antibody (Biolegend). After antibody binding, the CD45 positive cells are depleted from the preparation through indirect anti-mouse IgG microbead sorting (Miltenyi), leaving the $CD45^{neg}$ fraction. From the $CD45^{neg}$ fraction, the c-$kit^{pos}$ cardiac cells are enriched through incubation with a rabbit polyclonal antibody against c-kit (Santa Cruz), followed by indirect anti-rabbit IgG microbead sorting (Miltenyi) (Ellison et al., 2007; Waring et al., 2012). The purity of the preparation was assessed by flow cytometry and cytospin-based cytochemistry (see below). $CD45^{neg}$ c-$kit^{pos}$ freshly isolated cardiac small cells scored negative following incubation with an antibodies' cocktail to identify hematopoietic, neural, and skeletal muscle cell lineages, therefore, being defined as lineage negative ($Lin^{neg}$) (data not shown).

Mouse CSC and Cardiomyocyte Isolation—

The same procedure described above was used to isolate eCSCs from adult mouse hearts but using direct CD45 negative and then c-kit positive anti-mouse microbead sorting (Miltenyi). Adult cardiomyocyte isolation was performed as described with minor modifications (Qian et al., 2012). Briefly, hearts were removed from anesthetized mice and perfused retrogradely via aortic cannulation with a constant flow of 3 ml/min in a Langendorf apparatus. Hearts were perfused at 37° C. for 3 min with supplemented Wittenberg Isolation Medium (WIM) containing (in mM): 116 NaCl, 5.4 KCl, 6.7 MgCl2, 12 glucose, 2 glutamine, 3.5 NaHCO3, 1.5 KH2PO4, 1.0 NaH2PO4, 21 HEPES, with 1.5 nM insulin, essential vitamins (GIBCO), and essential amino acids (GIBCO) (pH 7.4), followed by digestion solution (WIM, supplemented with 0.8-1 mg/ml collagenase II and 10 μM CaCl2) for 8 min. Hearts were then removed from the Langendorf apparatus while intact (with tissues loosely connected). Desired areas (that is, LV or LV apex) were then micro-dissected under the microscope, followed by mechanical dissociation, triturating, and re-suspension in a low-calcium solution (WIM, supplemented with 5 mg/ml BSA, 10 mM taurine, and 150 μM CaCl2). Cardiomyocytes and small cardiac cells were separated by centrifugation and then the CM suspension was passed on a discontinuous Percoll gradient (Sigma) for further purification.

Cell Culture— c-$kit^{pos}$ CSCs were grown in CSC growth medium consisting of Dulbecco's MEM/Ham's F12 (DMEM/F12; Sigma) medium containing 10% ESQ-FBS (Invitrogen), LIF (10 ng/ml; Millipore), bFGF (10 ng/ml; Peprotech), EGF (20 ng/ml; Peprotech), insulin-transferrin-selenite (ITS; Invitrogen), EPO (2.5 U; Sigma) (CSC growth medium), 1% pen-strep (Invitrogen), and 0.1% gentamicin (10 mg/ml liquid, Invitrogen). For cardiosphere generation, c-$kit^{pos}$ CSCs were placed in bacteriological dishes with cardiosphere generation medium (mCSFM) composed of 1:1 ratio of CSC growth medium and Neural Basal Media supplemented with B27 and N2 supplements (Invitrogen). For co-culture assays, $1 \times 10^5$ c-$kit^{pos}$ $CSC^{GFP/TK}$ were co-cultured in 6-well plates with $1 \times 10^6$ Adult Rat Ventricular Cardiomyocytes (ARVM), with fresh media changes every 3 days. Ganciclovir (GCV, $10^{-5}$ M) was added and cells were cultured for 3 and 7 days.

Immunocytochemistry—

Mouse c-$kit^{pos}$ CSCs or c-$kit^{pos}$ CSC-derived cardiospheres were cultured on glass chamber slides (BD Falcon), fixed with 4% PFA for 20 min, and then stained. Cells were stained for GFP (1:50 dilution), cTnI (1:50 dilution), Smooth muscle actin (SMA; 1:100 dilution) and von Willebrand factor (vWF; 1.100 dilution). For cardiomyocyte/$CSC^{GFP/TK}$ co-culture assays, 3× wells/condition were fixed and stained to assess the number of apoptotic (TdT and caspase-3) cardiomyocytes (Kawaguchi et al., 2010). Cardiomyocytes were identified by co-staining for cTnI. The percentage of TdT-positive and caspase-3 positive cardiomyocytes was determined by counting 20 random fields at ×40 magnification for each well. Numbers were expressed as a percentage of TdT- or caspase-3 positive cardiomyocytes relative to the total number of cardiomyocytes counted. FITC or Texas Red-conjugated 2° Abs were used. Nuclei were stained with DAPI. Fluorescence was visualized and images acquired with confocal microscopy (Zeiss LSM 510 or 710). Table 6 lists antibodies used and their applications.

Quantitative RT-PCR (qRT-PCR)—

RNA was extracted using Qiagen RNeasy columns and was reverse transcribed using first strand cDNA synthesis with random or oligo-dT primers (Applied Biosystems). Residual amounts of DNA were removed by on-column DNase treatment using the RNase-Free DNase Set (Qiagen) during the RNeasy procedure. Quantitative RT-PCR was performed using SYBR Green (BioRad) on a MyIQ thermocycler (BioRad). The PCR-reaction included 2 μl of template cDNA, and 300 nM forward and reverse primers. PCR efficiency was evaluated by using a standard curve of five serial dilution points. Data were analysed using BioRad IQ software and mRNA was normalized to the housekeeping gene, GAPDH. Primers were designed using the Primer 3 software and the specific sequences are given in Table 7. All reactions were carried out in triplicate.

TABLE 7 qPCR Primers (Rat primers disclosed as SEQ ID NOS 1-34 and Mouse primers disclosed as SEQ ID NOS 35-56, all respectively, in order of appearance)

| Primer Name | Sequence | Product (bp) | Accession |
|---|---|---|---|
| Rat Primers | | | |
| c-kit forward | GAAAGGGAGGCCCTAATGTC | 259 | NM_022264.1 |
| c-kit reverse | CGTTTGAGCTGTCACAGGAA | | |
| TERT forward | AGTGGTGAACTTCCCTGTGG | 232 | NM_053423 |
| TERT reverse | CAACCGCAAGACTGACAAGA | | |
| Nkx2.5 forward | CGCCCTTCTCAGICAAAGAC | 227 | NM_053651 |
| Nkx2.5 reverse | GAAAGCAGGAGAGCACTTGG | | |

TABLE 7-continued qPCR Primers (Rat primers disclosed as SEQ ID NOS 1-34 and Mouse primers disclosed as SEQ ID NOS 35-56, all respectively, in order of appearance)

| Primer Name | Sequence | Product (bp) | Accession |
|---|---|---|---|
| GATA4 forward | CTGTGCCAACTGCCAGACTA | 165 | NM_144730 |
| GATA4 reverse | AGATTCTTGGGCTTCCGTTT | | |
| cTnI forward | ACGTGGAAGCAAAAGTCACC | 198 | NM_017144 |
| cTnI reverse | CCTTCTTCACCTGCTTGAGG | | |
| α-MHC forward | GGCACAGAAGATGCTGACAA | 117 | NM_017239 |
| α-MHC reverse | CTGCCCCTTGGTGACATACT | | |
| β-MHC forward | TGGCACCGTGGACTACAATA | 145 | NM_017240 |
| β-MHC reverse | TACAGGTGCATCAGCTCCAG | | |
| Cn43 forward | TCCTTGGTGTCTCTCGCTTT | 167 | NM_012567 |
| Cn43 reverse | GAGCAGCCATTGAAGTAGGC | | |
| Isl-1 forward | AGTCCGGAGAGACATGATGG | 207 | NM_017339.3 |
| Isl-1 reverse | ATCTGGGAGCTGAGAGGACA | | |
| MYL-2 forward | GACCCAGATCCAGGAGTTCA | 162 | NM_001035252.2 |
| MYL-2 reverse | ATTGGACCTGGAGCCTCTTT | | |
| GFP forward | ACGTAAACGGCCACAAGTTC | 187 | EU056361.1 |
| GFP reverse | AAGTCGTGCTGCTTCATGTG | | |
| PLN forward | TGACGATCACAGAAGCCAAG | 160 | NM_0022707.1 |
| PLN reverse | GCCGAGCGAGTAAGGTATTG | | |
| RyR-2 forward | TTTCGTGAGCATTAGCAACG | 161 | NM_EU346200.2 |
| RyR-2 reverse | GAGGCACAAAGAGGAACTCG | | |
| ATP2A2 forward | TGCTGGAACTTGTGATCGAG | 191 | NM_017290.1 |
| ATP2A2 reverse | AGCGTTTCTCTCCTGCCATA | | |
| ACTC1 forward | CACGGCATTATCACCAACTG | 240 | NM_019183.1 |
| ACTC1 reverse | AACAATGCCTGTGGTTCTCC | | |
| Mef-2c forward | CGAGATACCCACAACACACG | 175 | XM_003749164.1 |
| Mef-2c reverse | CGCTTGACTGAGGGACTTTC | | |
| GAPDH forward | AGACAGCCGCATCTTCTTGT | 207 | NM_017008.4 |
| GAPDH reverse | CTTGCCGTGGGTAGAGTCAT | | |

Mouse primers

| Primer Name | Sequence | Product (bp) | Accession |
|---|---|---|---|
| c-kit forward | TCATCGAGTGTGATGGGAAA | 222 | NM_001122733.1 |
| c-kit reverse | GGTGACTTGTTTCAGGCACA | | |
| Sca-1 forward | CCATCAATTACCTGCCCCTA | 275 | NM_010738.2 |
| Sca-1 reverse | AAGGTCTGCAGGAGGACTGA | | |
| Abcg-2 forward | TCACTGACCCTTCCATCCTC | 276 | NM_011920.3 |
| Abcg-2 reverse | AATCCGCAGGGTTGTTGTAG | | |
| Tert forward | CTGCAAGGTGGTGTCTGCTA | 254 | NM_009354.1 |
| Tert reverse | CCACGTATGTGTCCATCAGC | | |
| Bmi-1 forward | TGTGTCCTGTGTGGAGGGTA | 139 | NM_007552.4 |
| Bmi-1 reverse | TGGTTTTGTGAACCTGGACA | | |
| GATA-4 forward | TCTCACTATGGGCACAGCAG | 136 | NM_008092.3 |
| GATA-4 reverse | GCGATGTCTGAGTGACAGGA | | |
| Nkx2.5 forward | GCTACAAGTGCAAGCGACAG | 184 | NM_008700 |
| Nkx2.5 reverse | GGGTACGCGTTGTAGCCATA | | |
| Isl-1 forward | ACGTGCTTTGTTAGGGATGG | 108 | NM_021459.4 |
| ISl-1 reverse | CACGAAGTCGTTCTTGCTGA | | |
| GFP forward | ACGTAAACGGCCACAAGTTC | 187 | EU056361.1 |
| GFP reverse | AAGTCGTGCTGCTTCATGTG | | |
| ANP forward | CCTAAGCCCTTGTGGTGTGT | 153 | NM_008725.2 |
| ANP reverse | CAGAGTGGGAGAGGCAAGAC | | |
| GAPDH forward | ACCCAGAAGACTGTGGATGG | 171 | NM_008084.2 |
| GAPDH reverse | CACATTGGGGGTAGGAACAC | | |

Western Blot Analysis—

Immunoblots and immunoprecipitations were carried out using protein lysates obtained from freshly isolated eCSCs, cardiomyocytes or clonogenic CSCs (Torella et al., 2004). Generally, aliquots equivalent of ~50 µg of protein were separated on gradient (6-15%) SDS-polyacrylamide gels. After electrophoresis, proteins were transferred onto nitrocellulose filters, blocked with either 5% dry milk or 5% bovine serum albumin, and incubated with Abs against SDF-1 (Cell Signaling), CXCR4 (Abcam) at dilutions suggested by the manufacturers (See Table 6 for list of Antibodies and their applications). Actin (Santa Cruz) was used as a loading control. Proteins were detected by chemiluminescence using horseradish peroxidase-conjugated 2° Abs and the Chemidoc XRS system (Bio-Rad).

Flow Cytometry—

For cell cycle analysis, freshly isolated c-kit$^{pos}$ CD45$^{neg}$ cardiac cells were incubated with Vybrant DyeCycle stain (Molecular probes). Analysis was performed on FACSCalibur with CellQuest software. Freshly isolated bone marrow cells, peripheral blood cells, total c-kit$^{pos}$ and c-kit$^{pos}$CD45$^{neg}$ cardiac cells were analysed for GFP using a FACScan (BD Biosciences) flow cytometer. Re-isolated c-kit$^{pos}$CSCs$^{GFP}$ were obtained after MACS negative/positive sorting for CD45/c-kit and following GFP (or YFP for mice) sorting using the BD FACSAria cell sorter. Antibodies used are shown in Table 6. Appropriate labeled isotype controls were always used to define the specific gates.

FACS Sorting and Flow Cytometry of Adult Cardiomyocytes—

For the quantification of the number of YFP, GFP or RFP cardiomyocytes, cardiomyocytes were isolated as above described. In preliminary cursory trial experiments to standardize the procedure, it became apparent that fluorescent proteins within cardiomyocytes can be reliably analyzed only in freshly isolated unfixed cardiomyocyte preparations, as fixation/permeabilization of the myocytes leads to leaking of the fluorescent protein. Also, autofluorescence generated by the fixation/permeabilization step makes it virtually impossible to distinguish real fluorescence from negative cardiomyocytes. These problems prevent the quantification of fluorescent proteins in cardiomyocytes by double fluorescence staining of YFP (or GFP or RFP) and a cardiomyocyte marker like cTnI or αSA. So, we gathered data from isolated cardiomyocytes that produced preparations of over 97% of cardiomyocytes from total cardiac cells. These isolated cardiomyocytes were counted and re-suspended to be equally divided in one half for FACS direct YFP (or GFP or RFP in the other related experiments, see below) quantification, while the other half was fixed and FACS quantified for cTnI (or αSA) expression. This combined approach allowed us to reliably quantify the number of YFP$^{pos}$ (GFP$^{pos}$ or RFP$^{pos}$) myocytes. According to the above protocol, RYP mouse hearts were injected with the c-kit/cre lentivirus and then injured by ISO, while saline was used for the controls following the study design. 28 days later, cardiac myocytes were isolated by enzymatic digestion and equally divided for YFP or c-TnI assessment, respectively. In particular, cardiomyocytes were isolated from the entire LV in 6 (3 CTRL and 3 ISO) mice or from just the LV Apex of an additional 6 ISO-treated mice (whereby two cardiomyocyte preparations were combined to have an appropriate cell number for further analysis, so that n=3 was established).

Enzymatically dispersed myocyte preparations resuspended in WYM solution were sorted on a BD FACSAria™ III (BD Biosciences) with a flow rate of 500 cells/s, using a 130 µm nozzle (Diez & Simm, 1998). Cardiomyocytes were sorted based on cell size (high forward and side scatter) and YFP expression. Saline plus lenti-empty injected RYP mice were used as controls.

Phenotypic characterization of unsorted and sorted cardiomyocytes (expression of cTnI or αSA) was performed using commercially available kits (BD Biosciences). Similar procedures were employed for FACS analysis of rat GFP$^{pos}$ cardiomyocytes.

Figure 16J:
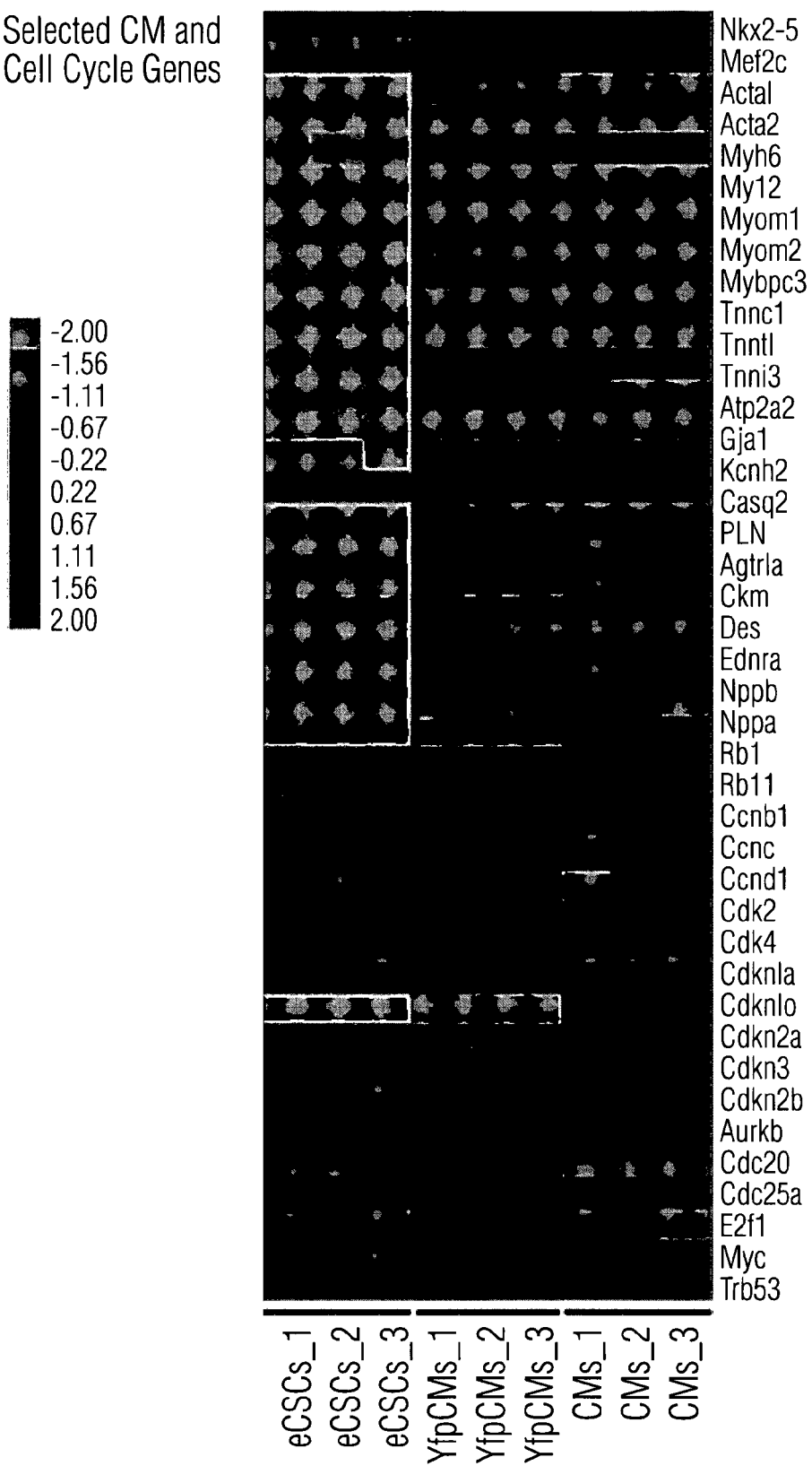

Gene Expression Microarray Analysis Pipeline— c-kit$^{pos}$CD45$^{neg}$ eCSCs and adult cardiomyocytes were isolated from RYP mice as above described (n=3). YFP$^{pos}$ cardiomyocytes were FACS sorted from 6 LV apexes (2 combined in one) of Lenti-c-kit/cre injected RYP mice 28 days after ISO (n=3). mRNA was isolated as above described. Illumina chip (illumina company) were scanned with illumina iScan system. Data were log 2 transformed and normalized using the RSN (Robust Spline Normalization) method (lumi software package) (Du P, 2008). Normalized data were filtered for genes with significant expression levels (log fold change $\geq 1$ or $\leq -1$ and p value <0.005) compared with negative control (eCSCs). Selection for differentially expressed genes was performed on the bases of arbitrary threshold for fold changes plus statistical significance according to the t-test with Benjamini-Hochberg correction. Two-way hierarchical cluster of genes (3774) showed significant modulation in YFP$^{pos}$CMs (also labelled as YfpCMs in FIG. 16) and/or in adult CMs. Gene-wise median-centered normalized intensities (in log 2 space) of c-kit$^{pos}$CD45$^{neg}$ eCSCs, YFP$^{pos}$CMs and CM cells are shown in FIG. 16I and FIG. 16J. The heat map was clustered using centered correlation as the distance metric and complete linkage clustering (Cluster 3.0 software). Functional annotation of significant genes identify by microarray analysis was searched by DAVID Bioinformatics Resources 6.7 (david.abcc.ncifcrf.gov) (Huang da, 2009).

Statistical Analysis—

Data are reported as Mean±S.D. Significance was determined by the analysis of variance (ANOVA). The Bonferroni post hoc method was used to locate the differences. Significance was set at p<0.05.

6.14 Conclusions

The results presented here demonstrate that c-kit$^{pos}$eCSCs behave as true resident, endogenous stem-progenitor cells which are necessary and sufficient for myocardial repair and cellular homeostasis. These results, however, do not rule out the participation of other cardiac stem cell-like populations (Oh et al., 2003; Chong et al., 2011; Smart et al., 2011), or minor contributions by other cells (Senyo et al., 2013). As the c-kit/cre lentivirus strategy labeled ~half of the c-kit$^{pos}$eCSCs in the LV (FIG. 16), these results cannot determine whether the fraction of newly generated EYFP$^{neg}$ CMs were not labelled because of the lentivirus inefficiency in vivo, or because some of them are the progeny of c-kit$^{neg}$ stem-progenitor cells. Nonetheless, the replacement of the eCSC cohort by the progeny of a single CSC convincingly favors the first alternative.

It is generally accepted that in healthy adult tissue most stem cells are quiescent and if they cycle they do so very slowly, providing just enough transient amplifying cells to maintain tissue homeostasis (Orford & Scadden, 2008). In contrast, the quiescent stem cells in response to injury, are rapidly activated, multiply and differentiate to replace the cells lost. In the healthy adult myocardium >90% of the c-kit$^{pos}$eCSCs are quiescent (GO) (FIG. 14). In response to diffuse ISO-injury, most eCSCs enter the cell cycle, replicate and commit to the myocardial cell lineages (FIG. 14), including CMs (FIG. 16). Once the ISO-induced cell loss and cardiac failure have been corrected by the regenerated cells, the number of activated eCSCs diminishes progressively with a concomitant increase of the quiescent cohort (FIG. 14). Thus, the return to myocardial homeostasis is accompanied by the return of activated eCSCs to their quiescent state. This roundtrip from dormancy to activated and back to quiescence has been suggested for other self-renewing organs (Wilson et al., 2008). This toggling between eCSC cycling states might just highlight the important role of these cells in the homeostasis of a tissue essential for organismic survival. Understanding the mechanisms by which cycling eCSCs return to quiescence has clinical implications to exploit the regenerative potential of these cells.

The efficiency of some adult stem cells, such as HSCs and eCSCs, to specifically home to and nest into their tissue of origin is dependent on tissue damage together with depletion of the resident stem-progenitor cells. This is so because the number of tissue niches appears to be limited and non-expandable (Czechowicz et al., 2007). Here we show that the injured myocardium provides a milieu that supports the homing, nesting, survival and differentiation of the CSCs (FIG. 17). However, if after injury the eCSCs are left in the tissue, despite the very effective cardiac homing of the transplanted CSC$^{GFP}$ only a very small number succeed in long-term nesting in the myocardium. This behavior contrasts with a host myocardium which has been depleted of most eCSCs prior to transplantation (FIGS. 18 and 19). Then the empty niches are very efficiently occupied by the CSCs$^{GFP}$ transplanted through the systemic circulation, which not only survive, but differentiate into the four main myocardial cell types and re-constitute the resident eCSC pool (FIG. 19). The sturdiness of the CSCs homing, engraftment and regenerative properties after many passages in culture and cloning (FIG. 20) contrasts with the reported loss of engraftment of ex-vivo expanded HSCs (Guenechea et al., 1999) and skeletal muscle satellite cells (Montarras et al., 2005). Therefore, this robust homing of the eCSCs can be exploited to replace the stem cell population of the myocardium by non-invasive means, as clinically implemented now for the bone marrow. In one embodiment, the homing property of the CSCs can be used for the replacement of the myocardial eCSCs in patients with genetic cardiomyopathies produced by point mutations where the mutated gene could be corrected in vitro followed by that transplantation of the "corrected" CSCs by administration through the systemic circulation.

The HSCs are the best understood adult stem cells and have become the standard for most adult stem cell biology.

Unfortunately, solid tissues have serious experimental limitations over the bone marrow where it is possible to transplant a single genetically tagged HSC and follow its progeny in the host (Rossi et al., 2008). That no such feat is possible in solid tissues has hampered most attempts to define the role of tissue-specific stem-progenitor cells in the regenerative process. So far there is no report of replacing the ablated stem cells with genetically tagged exogenous cells in solid tissues. Such replacement is required to produce a chimeric tissue whose regeneration can be shown to be dependent on the transplanted cells. In the myocardium, the best approximation to the HSC paradigm is transplantation of the progeny of a single cell. The high degree of cell chimerism obtained by transplantation of cloned $CSCs^{GFP}$ and $CSC^{TK/GFP}$ shows that the progeny of a single CSC can reconstitute the 5-FU ablated eCSC cohort and generate a cell chimeric heart with new cardiomyocytes and vascular cells, thereby restoring cardiac function. That the cellular and functional regeneration of the ISO-damaged myocardium is due to the transplanted CSCs is clearly shown by the rapid deterioration of cardiac function when these cells and their progeny are selectively killed by the GCV (FIG. 19).

The data presented here supports the conclusion that the eCSCs are necessary and sufficient for anatomical and functional regeneration of the adult mammalian myocardium.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

REFERENCES

1. Buckingham M, Meilhac S, Zaffran S. Building the mammalian heart from two sources of myocardial cells. Nat Rev Genet. 2005; 6:826-35.
2. Riley P R, Smart N. Vascularizing the heart. Cardiovasc Res. 2011 Jul. 15; 91(2):260-8.
3. Keyte A, Hutson M R. The neural crest in cardiac congenital anomalies. Differentiation. 2012; 84:25-40.
4. Vincent S D, Buckingham M E. How to make a heart: the origin and regulation of cardiac progenitor cells. Curr Top Dev Biol. 2010; 90:1-41.
5. Ellison G M, Nadal-Ginard B, Torella D. Optimizing cardiac repair and regeneration through activation of the endogenous cardiac stem cell compartment. J Cardiovasc Transl Res. 2012; 5:667-77.
6. Hsieh P C, Segers V F, Davis M E, MacGillivray C, Gannon J, Molkentin J D, Robbins J, Lee R T. Evidence from a genetic fate-mapping study that stem cells refresh adult mammalian cardiomyocytes after injury. Nat Med. 2007; 13:970-4.
7. Torella D, Ellison G M, Karakikes I, Nadal-Ginard B. Resident cardiac stem cells. Cell Mol Life Sci. 2007; 64:661-73.
8. Mercola M, Ruiz-Lozano P, Schneider M D. Cardiac muscle regeneration: lessons from development. Genes Dev. 2011; 25:299-309.
9. Noseda M, Peterkin T, Simões F C, Patient R, Schneider M D. Cardiopoietic factors: extracellular signals for cardiac lineage commitment. Circ Res. 2011; 108:129-52.
10. Ellison G M, Torella D, Dellegrottaglie S, Perez-Martinez C, Perez de Prado A, Vicinanza C, Purushothaman S, Galuppo V, Iaconetti C, Waring C D, Smith A, Torella M, Cuellas Ramon C, Gonzalo-Orden J M, Agosti V, Indolfi C, Galiñanes M, Fernandez-Vazquez F, Nadal-Ginard B. Endogenous cardiac stem cell activation by insulin-like growth factor-1/hepatocyte growth factor intracoronary injection fosters survival and regeneration of the infarcted pig heart. J Am Coll Cardiol. 2011; 58:977-86.
11. Yamanaka S, Blau H M. Nuclear reprogramming to a pluripotent state by three approaches. Nature. 2010; 465: 704-12.
12. Beltrami A P, Barlucchi L, Torella D, Baker M, Limana F, Chimenti S, Kasahara H, Rota M, Musso E, Urbanek K, Leri A, Kajstura J, Nadal-Ginard B, Anversa P. Adult cardiac stem cells are multipotent and support myocardial regeneration. Cell. 2003; 114:763-76.
13. Stem Cells In Vitro. Jaiswal N, Haynesworth S E, Caplan A I, Bruder S P. Osteogenic Differentiation of Purified, Culture-Expanded Human Mesenchymal. Journal of Cellular Biochemistry 1997; 64:295-312.
14. Song Z, Cai J, Liu Y, Zhao D, Yong J, Duo S, Song X, Guo Y, Zhao Y, Qin H, Yin X, Wu C, Che J, Lu S, Ding M, Deng H. Efficient generation of hepatocyte-like cells from human induced pluripotent stem cells. Cell Res. 2009; 19:1233-42.
15. Tomita Y, Matsumura K, Wakamatsu Y, Matsuzaki Y, Shibuya I, Kawaguchi H, Ieda M, Kanakubo S, Shimazaki T, Ogawa S, Osumi N, Okano H, Fukuda K. Cardiac neural crest cells contribute to the dormant multipotent stem cell in the mammalian heart. J Cell Biol. 2005; 170:1135-46.
16. Ellison G M, Torella D, Karakikes I, Purushothaman S, Curcio A, Gasparri C, Indolfi C, Cable N T, Goldspink D F, Nadal-Ginard B. Acute beta-adrenergic overload produces myocyte damage through calcium leakage from the ryanodine receptor 2 but spares cardiac stem cells. J Biol Chem. 2007; 282:11397-409.
17. Urbanek K, Torella D, Sheikh F, De Angelis A, Nurzynska D, Silvestri F, Beltrami C A, Bussani R, Beltrami A P, Quaini F, Bolli R, Leri A, Kajstura J, Anversa P. Myocardial regeneration by activation of multipotent cardiac stem cells in ischemic heart failure. Proc Natl Acad Sci USA. 2005; 102:8692-7.
18. Urbanek K, Quaini F, Tasca G, Torella D, Castaldo C, Nadal-Ginard B, Leri A, Kajstura J, Quaini E, Anversa P. Intense myocyte formation from cardiac stem cells in human cardiac hypertrophy. Proc Natl Acad Sci USA. 2003; 100:10440-5.
19. Waring C D, Vicinanza C, Papalamprou A, Smith A J, Purushothaman S, Goldspink D F, Nadal-Ginard B, Torella D, Ellison G M. The adult heart responds to increased workload with physiologic hypertrophy, cardiac stem cell activation, and new myocyte formation. Eur Heart J. 2012 Oct. 25. [Epub ahead of print]
20. Epstein J A. Franklin H. Epstein Lecture. Cardiac development and implications for heart disease. N Engl J Med. 2010; 363:1638-47.
21. Wray J, Hartmann C. WNTing embryonic stem cells. Trends Cell Biol. 2012; 22:159-68.
22. Schuijers J, Clevers H. Adult mammalian stem cells: the role of Wnt, Lgr5 and R-spondins. EMBO J. 2012; 31:2685-96.

23. Oshimori N, Fuchs E. The Harmonies Played by TGF-β in Stem Cell Biology. Cell Stem Cell. 2012; 11:751-64.
24. Cohen E D, Wang Z, Lepore J J, Lu M M, Taketo M M, Epstein D J, Morrisey E E. Wnt/beta-catenin signaling promotes expansion of Isl-1-positive cardiac progenitor cells through regulation of FGF signaling. J Clin Invest. 2007; 117:1794-804.
25. Qyang Y, Martin-Puig S, Chiravuri M, Chen S, Xu H, Bu L, Jiang X, Lin L, Granger A, Moretti A, Caron L, Wu X, Clarke J, Taketo M M, Laugwitz K L, Moon R T, Gruber P, Evans S M, Ding S, Chien K R. The renewal and differentiation of Isl1+ cardiovascular progenitors are controlled by a Wnt/beta-catenin pathway. Cell Stem Cell. 2007; 1:165-79.
26. Kattman S J, Huber T L, Keller G M. Multipotent flk-1+ cardiovascular progenitor cells give rise to the cardiomyocyte, endothelial, and vascular smooth muscle lineages. Dev Cell. 2006; 11:723-32.
27. Klaus A, Müller M, Schulz H, Saga Y, Martin J F, Birchmeier W. Wnt/β-catenin and Bmp signals control distinct sets of transcription factors in cardiac progenitor cells. Proc Natl Acad Sci USA. 2012; 109:10921-6.
28. Messina E, De Angelis L, Frati G, Morrone S, Chimenti S, Fiordaliso F, Salio M, Battaglia M, Latronico M V, Coletta M, Vivarelli E, Frati L, Cossu G, Giacomello A. Isolation and expansion of adult cardiac stem cells from human and murine heart. Circ Res. 2004; 9:911-21.
29. Smits A M, van Vliet P, Metz C H, Korfage T, Sluijter J P, Doevendans P A, Goumans M J. Human cardiomyocyte progenitor cells differentiate into functional mature cardiomyocytes: an in vitro model for studying human cardiac physiology and pathophysiology. Nat Protoc. 2009; 4:232-43.
30. Zaruba M M, Soonpaa M, Reuter S, Field L J. Cardiomyogenic potential of C-kit(+)-expressing cells derived from neonatal and adult mouse hearts. Circulation. 2010; 121:1992-2000.
31. Jesty S A, Steffey M A, Lee F K, Breitbach M, Hesse M, Reining S, Lee J C, Doran R M, Nikitin A Y, Fleischmann B K, Kotlikoff M I. c-kit+ precursors support postinfarction myogenesis in the neonatal, but not adult, heart. Proc Natl Acad Sci USA. 2012; 109:13380-5.
32. Laflamme M A, Chen K Y, Naumova A V, Muskheli V, Fugate J A, Dupras S K, Reinecke H, Xu C, Hassanipour M, Police S, O'Sullivan C, Collins L, Chen Y, Minami E, Gill E A, Ueno S, Yuan C, Gold J, Murry C E. Cardiomyocytes derived from human embryonic stem cells in pro-survival factors enhance function of infarcted rat hearts. Nat Biotechnol. 2007; 25:1015-24.
33. Matsuura K, Nagai T, Nishigaki N, Oyama T, Nishi J, Wada H, Sano M, Toko H, Akazawa H, Sato T, Nakaya H, Kasanuki H, Komuro I. Adult cardiac Sca-1-positive cells differentiate into beating cardiomyocytes. J Biol Chem. 2004; 279: 11384-91
34. Oyama T, Nagai T, Wada H, Naito A T, Matsuura K, Iwanaga K, Takahashi T, Goto M, Mikami Y, Yasuda N, Akazawa H, Uezumi A, Takeda S, Komuro I. Cardiac side population cells have a potential to migrate and differentiate into cardiomyocytes in vitro and in vivo. J Cell Biol. 2007; 176: 329-41.
35. Ellison G M, Waring C D, Vicinanza C, Torella D. Physiological cardiac remodelling in response to endurance exercise training: cellular and molecular mechanisms. Heart. 2012; 98: 5-10.
36. Laugwitz K L, Moretti A, Lam J, Gruber P, Chen Y, Woodard S, Lin L Z, Cai C L, Lu M M, Reth M, Platoshyn O, Yuan J X, Evans S, Chien K R. Postnatal isl1+ cardioblasts enter fully differentiated cardiomyocyte lineages. Nature. 2005; 433:647-53.
37. Chong J J, Chandrakanthan V, Xaymardan M, Asli N S, Li J, Ahmed I, Heffernan C, Menon M K, Scarlett C J, Rashidianfar A, Biben C, Zoellner H, Colvin E K, Pimanda J E, Biankin A V, Zhou B, Pu W T, Prall O W, Harvey R P. Adult cardiac-resident MSC-like stem cells with a proepicardial origin. Cell Stem Cell. 2011; 9:527-40.
38. Kuroda Y, Kitada M, Wakao S, Nishikawa K, Tanimura Y, Makinoshima H, Goda M, Akashi H, Inutsuka A, Niwa A, Shigemoto T, Nabeshima Y, Nakahata T, Nabeshima Y, Fujiyoshi Y, Dezawa M. Unique multipotent cells in adult human mesenchymal cell populations. Proc Natl Acad Sci USA. 2010 May 11; 107(19):8639-43.
39. Beltrami A P, Urbanek K, Kajstura J, Yan S M, Finato N, Bussani R, Nadal-Ginard B, Silvestri F, Leri A, Beltrami C A, Anversa P. Evidence that human cardiac myocytes divide after myocardial infarction. N Engl J Med. 2001; 344:1750-7.
40. Priori S G, Napolitano C, Di Pasquale E, Condorelli G. Induced pluripotent stem cell-derived cardiomyocytes in studies of inherited arrhythmias. J Clin Invest. 2013; 123:84-91.
41. Akashi, Y. J., Goldstein, D. S., Barbaro, G. and Ueyama, T. (2008) Takotsubo cardiomyopathy: a new form of acute, reversible heart failure. Circulation. 118, 2754-2762.
42. Askari, A., Unzek, S., Popovic, Z. B., Goldman, C. K., Forudi, F., Kiedrowski, M., Rovner, A., Ellis, S. G., Thomas, J. D., DiCorleto, P. E. et al. (2003) Effect of stromal-cell-derived factor-1 on stem cell homing and tissue regeneration in ischemic cardiomyopathy. Lancet 362, 697-703.
43. Bergmann, O., Bhardwaj, R. D., Bernard, S., Zdunek, S., Barnabe-Heider, F., Walsh, S., Zupicich, J., Alkass, K., Buchholz, B. A., Druid, H. et al. (2009) Evidence for cardiomyocyte renewal in humans. Science 324, 98-102.
44. Cairns, L. A., Moroni, E., Levantini, E., Giorgetti, A., Klinger, F. G., Ronzoni, S., Tatangelo, L., Tiveron, C., De Felici, M., Dolci, S. et al. (2003) Kit regulatory elements required for expression in developing hematopoietic and germ cell lineages. Blood 102, 3954-3962.
45. Czechowicz, A., Kraft, D., Weissman, I. L. and Bhattacharya, D. (2007) Efficient transplantation via antibody-based clearance of hematopoietic stem cell niches. Science 318, 1296-1299.
46. Dong, F., Harvey, J., Finan, A., Weber, K., Agarwal, U., and Penn, M. S. (2012) Myocardial CXCR4 expression is required for mesenchymal stem cell mediated repair following acute myocardial infarction. Circulation 126, 314-24.
47. Ellison, G. M., Torella, D., Karakikes, I. and Nadal-Ginard B. (2007a) Myocyte death and renewal: modern concepts of cardiac cellular homeostasis. Nat Clin Pract Cardiovasc Med 4 Suppl 1, S52-59.
48. Ellison, G. M., Galuppo, V., Vicinanza, C., Aquila, I., Waring, C. D., Leone, A., Indolfi, C. and Torella, D. (2010) Cardiac stem and progenitor cell identification: different markers for the same cell? Front Biosci (Schol Ed). 2, 641-652.
49. Guenechea, G., Segovia, J. C., Albella, B., Lamana, M., Ramírez, M., Regidor, C., Fernández, M. N. and Bueren, J. A. (1999) Delayed engraftment of nonobese diabetic/severe combined immunodeficient mice transplanted with ex vivo-expanded human CD34(+) cord blood cells. Blood 93, 1097-1105.

50. Jesty, S. A., Steffey, M. A., Lee, F. K., Breitbach, M., Hesse, M., Reining, S., Lee, J. C., Doran, R. M., Nikitin, A. Y., Fleischmann, B. K. et al. (2012) c-kit+ precursors support postinfarction myogenesis in the neonatal, but not adult, heart. Proc Natl Acad Sci USA. 109, 13380-13385.

51. Kajstura, J., Rota, M., Cappetta, D., Ogórek, B., Arranto, C., Bai, Y., Ferreira-Martins, J., Signore, S., Sanada, F., Matsuda, A. et al. (2012) Cardiomyogenesis in the aging and failing human heart. Circulation 126, 1869-18681.

52. Loffredo, F. S., Steinhauser, M. L., Gannon, J. and Lee, R. T. (2011) Bone marrow-derived cell therapy stimulates endogenous cardiomyocyte progenitors and promotes cardiac repair. Cell Stem Cell 8, 389-398.

53. Lompré, A. M., Nadal-Ginard, B. and Mahdavi, V. (1984) Expression of the cardiac ventricular alpha- and beta-myosin heavy chain genes is developmentally and hormonally regulated. J Biol Chem. 259, 6437-6446.

54. Montarras, D., Morgan, J., Collins, C., Relaix, F., Zaffran, S., Cumano, A., Partridge, T. and Buckingham, M. (2005) Direct isolation of satellite cells for skeletal muscle regeneration. Science 309, 2064-2067.

55. Oh, H., Bradfute, S. B., Gallardo, T. D., Nakamura, T., Gaussin, V., Mishina, Y., Pocius, J., Michael, L. H., Behringer, R. R., Garry, D. J. et al. (2003) Cardiac progenitor cells from adult myocardium: homing, differentiation, and fusion after infarction. Proc Natl Acad Sci USA. 100, 12313-12318.

56. Orford, K. W. and Scadden, D. T. (2008) Deconstructing stem cell self-renewal: genetic insights into cell-cycle regulation. Nat Rev Genet. 9, 115-128.

57. Orlic, D., Kajstura, J., Chimenti, S., Jakoniuk, I., Anderson, S. M., Li, B., Pickel, J., McKay, R., Nadal-Ginard, B., Bodine, D. M. et al. (2001) Bone marrow cells regenerate infarcted myocardium. Nature 410, 701-705.

58. Qian, L., Huang, Y., Spencer, C. I., Foley, A., Vedantham, V., Liu, L., Conway, S. J., Fu, J. D. and Srivastava, D. (2012) In vivo reprogramming of murine cardiac fibroblasts into induced cardiomyocytes. Nature 485, 593-598.

59. Rossi, D. J., Jamieson, C. H., and Weissman, I. L. (2008). Stems cells and the pathways to aging and cancer. Cell. 132, 681-696.

60. Sata, M., Saiura, A., Kunisato, A., Tojo, A., Okada, S., Tokuhisa, T., Hirai, H., Makuuchi, M., Hirata, Y. and Nagai, R. (2002) Hematopoietic stem cells differentiate into vascular cells that participate in the pathogenesis of atherosclerosis. Nat. Med. 8, 403-409.

61. Schneider, J. W., Gu, W., Zhu, L., Mahdavi, V., and Nadal-Ginard, B. (1994) Reversal of terminal differentiation mediated by p107 in Rb-/- muscle cells. Science. 264, 1467-71.

62. Senyo, S. E., Steinhauser, M. L., Pizzimenti, C. L., Yang, V. K., Cai, L., Wang, M., Wu, T. D., Guerquin-Kern, J. L., Lechene, C. P., and Lee, R. T. (2013) Mammalian heart renewal by pre-existing cardiomyocytes. Nature. 493, 433-6.

63. Smart, N., Bollini, S., Dubé, K. N., Vieira, J. M., Zhou, B., Davidson, S., Yellon, D., Riegler, J., Price, A. N., Lythgoe, M. F. et al. (2011) De novo cardiomyocytes from within the activated adult heart after injury. Nature 474, 640-644.

64. Song, K., Nam, Y. J., Luo, X., Qi, X., Tan, W., Huang, G. N., Acharya, A., Smith, C. L., Tallquist, M. D., Neilson, E. G. et al. (2012) Heart repair by reprogramming non-myocytes with cardiac transcription factors. Nature 485, 599-604.

65. Takeuchi, J. K. and Bruneau, B. G. (2009) Directed transdifferentiation of mouse mesoderm to heart tissue by defined factors. Nature 459, 708-711.

66. Tallini, Y. N., Greene, K. S., Craven, M., Spealman, A., Breitbach, M., Smith, J., Fisher, P. J., Steffey, M., Hesse, M., Doran, R. M. et al. (2009) c-kit expression identifies cardiovascular precursors in the neonatal heart. Proc Natl Acad Sci USA 106, 1808-1813.

67. Vincent, S. D. and Buckingham, M. E. (2010) How to make a heart: the origin and regulation of cardiac progenitor cells. Curr Top Dev Biol. 90, 1-41.

68. Waring, C. D., Vicinanza, C., Papalamprou, A., Smith, A. J., Purushothaman, S., Goldspink, D. F., Nadal-Ginard, B., Torella, D. and Ellison, G. M. (2012) The adult heart responds to increased workload with physiologic hypertrophy, cardiac stem cell activation, and new myocyte formation. Eur Heart J. [Epub ahead of print]. doi: 10.1093/eurheartj/ehs338.

69. Weissman, I. L. (2000). Translating stem and progenitor cell biology to the clinic: barriers and opportunities. Science 287, 1442-1446.

70. Wilson, A., Laurenti, E., Oser, G., van der Wath, R. C., Blanco-Bose, W., Jaworski, M., Offner, S., Dunant, C. F., Eshkind, L., Bockamp, E. et al. (2008) Hematopoietic stem cells reversibly switch from dormancy to self-renewal during homeostasis and repair. Cell 135, 1118-1129.

71. Yoon C. H., Koyanagi, M., Iekushi, K., Seeger, F., Urbich, C., Zeiher, A. M. and Dimmeler, S. (2010) Mechanism of improved cardiac function after bone marrow mononuclear cell therapy: role of cardiovascular lineage commitment. Circulation. 121, 2001-2011.

72. Zaruba, M. M., Soonpaa, M., Reuter, S. and Field, L. J. (2010) Cardiomyogenic potential of C-kit(+)-expressing cells derived from neonatal and adult mouse hearts. Circulation 121, 1992-2000.

73. Zhang, G., Wang, X., Wang, Z., Zhang, J. and Suggs, L. (2006). A PEGylated fibrin patch for mesenchymal stem cell delivery. Tissue Eng. 12, 9-19.

74. Brooks, W. W. and Conrad, C. H. (2009) Isoproterenol-induced myocardial injury and diastolic dysfunction in mice: structural and functional correlates. Comp Med. 59, 339-343.

75. Diez, C., and Simm, A. (1998) Gene expression in rod shaped cardiac myocytes, sorted by flow cytometry. Cardiovasc Res. 40, 530-7.

76. Du P, Kibbe W A, and Lin S M (2008) lumi: a pipeline for processing Illumina microarray. *Bioinformatics* 24, 1547-1548.

77. Huang da W, Sherman B T, and Lempicki R A (2009) Systematic and integrative analysis of large gene lists using DAVID bioinformatics resources. Nat Protoc 4, 44-57.

78. Kawaguchi, N., Smith, A. J., Waring, C. D., Hasan, M. K., Miyamoto, S., Matsuoka, R. and Ellison, G. M. (2010) c-kit$^{pos}$ GATA-4 high rat cardiac stem cells foster adult cardiomyocyte survival through IGF-1 paracrine signalling. PLoS One. 5, e14297.

79. Lin, H. H., Chen, Y. H., Chang, P. F., Lee, Y. T., Yet, S. F., and Chau, L. Y. (2008) Heme oxygenase-1 promotes neovascularization in ischemic heart by coinduction of VEGF and SDF-1. *J Mol Cell Cardiol.* 45, 44-55.

80. Sohal, D. S., Nghiem, M., Crackower, M. A., Witt, S. A., Kimball, T. R., Tymitz, K. M., Penninger, J. M. and Molkentin, J. D. (2001) Temporally regulated and tissue-specific gene manipulations in the adult and embryonic heart using a tamoxifen-inducible Cre protein. Circ Res 89, 20-25.
81. Shao, Y., Redfors, B., Ståhlman, M., Täng, M. S., Miljanovic, A., Möllmann, H., Troidl, C., Szardien, S., Hamm, C., Nef, H. et al. (2013) A mouse model reveals an important role for catecholamine-induced lipotoxicity in the pathogenesis of stress-induced cardiomyopathy. Eur J Heart Fail. 15, 9-22.
82. Torella, D., Rota, M., Nurzynska, D., Musso, E., Monsen, A., Shiraishi, I., Zias, E., Walsh, K., Rosenzweig, A., Sussman, M. A. et al. (2004) Cardiac stem cell and myocyte aging, heart failure, and insulin-like growth factor-1 overexpression. Circ Res. 94, 514-524.

The invention claimed is:

1. A method for promoting autologous cardiac tissue regeneration in a subject with cardiac tissue damage comprising administering to the subject a therapeutically effective amount of allogeneic adult cardiac stem-progenitor cells that express c-Kit and CD166 and lack detectable expression of CD45, CD34, CD31, Tryptase and Wilms Tumor-1 in the absence of an immunosuppressive agent to promote subject-mediated autologous regeneration of cardiac tissue, assessing left ventricular ejection fraction in the subject after administration of the allogeneic adult cardiac stem-progenitor cells, wherein the allogeneic adult cardiac stem-progenitor cells optionally express one or more markers selected from the group consisting of CD90, PDGFrα, CXCR4, Nestin, CD146, Flk-1, Klf-4, Nanog and Sox-2;

wherein the allogeneic adult cardiac stem-progenitor cells lack detectable expression of Oct-4 protein;

wherein the therapeutically effective amount comprises $1 \times 10^7$ to $1 \times 10^8$ cells; and wherein autologous cardiac tissue regeneration in the subject comprises preventing deterioration of the left ventricular ejection fraction that is observed in an untreated control subject with cardiac tissue damage.

2. The method of claim 1, wherein the subject exhibits myocardium damage and the allogeneic adult cardiac stem-progenitor cells are administered intra-coronary or directly into the cardiac tissue of the subject, wherein the allogeneic adult cardiac stem-progenitor cells spontaneously home and nest to the damaged myocardium of the subject.

3. The method of claim 1, further comprising treating a deficit of endogenous cardiac stem-progenitor cells in the subject via peripheral circulation.

4. The method of claim 1, wherein the allogeneic adult cardiac stem-progenitor cells are administered together with at least one of IGF-1, Wnt3a, FGF-2, HGF, neuroregulin, or periostin.

5. The method of claim 1, further comprising ameliorating fractional shortening in the subject.

6. The method of claim 1, further comprising forming new capillary structures in the subject.

7. The method of claim 1, further comprising improving at least one parameter of diastolic heart function in the subject.

8. The method of claim 1, wherein the subject has cardiac tissue damage caused by one or more of myocardial infarction, stroke, hypotension, cardiac arrest, ischemia, inflammation, radiation damage, or heart-lung bypass.

9. A method for promoting cardiac tissue regeneration in a subject with a defect in endogenous stem-progenitor cells comprising administering to the subject via peripheral circulation, a therapeutically effective amount of cardiac stem-progenitor cells that express c-Kit and CD166 and lack detectable expression of CD45, CD34, CD31, Tryptase and Wilms Tumor 1 in the absence of an immunosuppressive agent, thereby promoting subject-mediated regeneration of cardiac tissue, assessing left ventricular ejection fraction in the subject after administration of the cardiac stem-progenitor cells, wherein the cardiac stem-progenitor cells optionally express one or more markers selected from the group consisting of CD90, PDGFrα, CXCR4, Nestin, CD146, Flk-1, Klf-4, Nanog and Sox-2;

wherein the cardiac stem-progenitor cells lack detectable expression of Oct-4 protein;

wherein the therapeutically effective amount comprises $1 \times 10^7$ to $1 \times 10^8$ cells; and wherein an increase in left ventricular ejection fraction after administration of the cardiac stem-progenitor cells compared to that observed in an untreated control subject with a defect in endogenous stem-progenitor cells corresponds to cardiac tissue regeneration in the subject.

10. The method of claim 9, wherein the cardiac stem-progenitor cells are administered together with at least one of IGF-1, Wnt3a, FGF-2, HGF, neuroregulin, or periostin.

11. The method of claim 10, wherein the cells are administered through intracoronary injection with a catheter or directly into the myocardium of the subject either trans-endocardically or trans-epicardically.

12. The method of claim 9, wherein the cardiac stem-progenitor cells are HLA matched or allogeneic.

13. The method of claim 9, wherein the defect in the endogenous stem-progenitor cells of the subject is mediated by exposure to a cardiotoxic drug, optionally wherein the cardiotoxic drug is Herceptin, Doxorubicin, a tyrosine kinase receptor inhibitor or an anthracycline.

14. The method of claim 9, wherein the defect in the endogenous stem-progenitor cells of the subject is caused by a mutation in a gene encoding a sarcomeric protein.

15. The method of claim 9, further comprising ameliorating progressive deterioration in left ventricular ejection fraction in the subject or forming new capillary structures in the subject.

16. The method of claim 9, further comprising improving at least one parameter of diastolic heart function in the subject.

17. A method for promoting autologous cardiac tissue regeneration in a subject with cardiac tissue damage comprising:
administering to the subject a therapeutically effective amount of IGF-1, HGF, and allogeneic adult cardiac stem-progenitor cells that express c-Kit and CD166 and lack detectable expression of CD45, CD34, CD31, Tryptase and Wilms Tumor-1 in the absence of an immunosuppressive agent to promote subject-mediated autologous regeneration of cardiac tissue,
assessing left ventricular ejection fraction in the subject after administration of the allogeneic adult cardiac stem-progenitor cells,
wherein the allogeneic adult cardiac stem-progenitor cells optionally express one or more markers selected from the group consisting of CD90, PDGFrα, CXCR4, Nestin, CD146, Flk-1, Klf-4, Nanog and Sox-2,
wherein the allogeneic adult cardiac stem-progenitor cells lack detectable expression of Oct-4 protein;
wherein the therapeutically effective amount comprises $1\times10^7$ to $1\times10^8$ cells; and
wherein an increase in left ventricular ejection fraction after administration of the allogeneic adult cardiac stem-progenitor cells compared to that observed in an untreated control subject with cardiac tissue damage corresponds to autologous cardiac tissue regeneration in the subject.

* * * * *

SEQUENCE LISTING

<160> NUMBER OF SEQ ID NOS: 56

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gaaagggagg ccctaatgtc                                                    20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cgtttgagct gtcacaggaa                                                    20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
agtggtgaac ttccctgtgg                                                    20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
caaccgcaag actgacaaga                                                    20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgcccttctc agtcaaagac                                                    20

-continued

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gaaagcagga gagcacttgg                                                  20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctgtgccaac tgccagacta                                                  20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agattcttgg gcttccgttt                                                  20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acgtggaagc aaaagtcacc                                                  20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccttcttcac ctgcttgagg                                                  20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggcacagaag atgctgacaa                                                  20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctgccccttg gtgacatact                                                20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tggcaccgtg gactacaata                                                20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tacaggtgca tcagctccag                                                20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tccttggtgt ctctcgcttt                                                20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gagcagccat tgaagtaggc                                                20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
agtccggaga gacatgatgg                                                20

<210> SEQ ID NO 18

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
atctgggagc tgagaggaca                                            20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gacccagatc caggagttca                                            20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
attggacctg gagcctcttt                                            20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
acgtaaacgg ccacaagttc                                            20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aagtcgtgct gcttcatgtg                                            20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tgacgatcac agaagccaag                                            20

<210> SEQ ID NO 24
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gccgagcgag taaggtattg                                              20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tttcgtgagc attagcaacg                                              20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gaggcacaaa gaggaactcg                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tgctggaact tgtgatcgag                                              20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
agcgtttctc tcctgccata                                              20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cacggcatta tcaccaactg                                              20

<210> SEQ ID NO 30
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 30
aacaatgcct gtggttctcc                                               20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31 cgagatacccc acaacacacg                                              20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cgcttgactg agggactttc                                               20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
agacagccgc atcttcttgt                                               20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cttgccgtgg gtagagtcat                                               20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tcatcgagtg tgatgggaaa                                               20

<210> SEQ ID NO 36
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 36
ggtgacttgt ttcaggcaca                                              20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ccatcaatta cctgcccta                                               20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
aaggtctgca ggaggactga                                              20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tcactgaccc ttccatcctc                                              20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
aatccgcagg gttgttgtag                                              20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ctgcaaggtg gtgtctgcta                                              20

<210> SEQ ID NO 42
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 42
ccacgtatgt gtccatcagc                                               20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tgtgtcctgt gtggagggta                                               20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tggttttgtg aacctggaca                                               20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tctcactatg ggcacagcag                                               20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gcgatgtctg agtgacagga                                               20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gctacaagtg caagcgacag                                               20

<210> SEQ ID NO 48
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 48
gggtacgcgt tgtagccata                                               20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
acgtgctttg ttagggatgg                                               20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cacgaagtcg ttcttgctga                                               20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
acgtaaacgg ccacaagttc                                               20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
aagtcgtgct gcttcatgtg                                               20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
cctaagccct tgtggtgtgt                                               20

<210> SEQ ID NO 54
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 54
cagagtggga gaggcaagac                                                  20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
acccagaaga ctgtggatgg                                                  20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
cacattgggg gtaggaacac                                                  20
```